United States Patent
Chan et al.

(10) Patent No.: US 12,329,456 B2
(45) Date of Patent: Jun. 17, 2025

(54) EYE TRACKING USING ASPHERIC CORNEA MODEL

(71) Applicant: Magic Leap, Inc., Plantation, FL (US)

(72) Inventors: Richmond B. Chan, Arlington Heights, IL (US); Wenyi Zhao, Weston, FL (US); Bing Wu, Davie, FL (US)

(73) Assignee: Magic Leap, Inc., Plantation, FL (US)

( * ) Notice: Subject to any disclaimer, the term of this patent is extended or adjusted under 35 U.S.C. 154(b) by 0 days.

(21) Appl. No.: 18/647,957

(22) Filed: Apr. 26, 2024

(65) Prior Publication Data

US 2024/0358255 A1 Oct. 31, 2024

Related U.S. Application Data

(63) Continuation of application No. 18/004,979, filed as application No. PCT/US2021/041618 on Jul. 14, 2021.

(Continued)

(51) Int. Cl.
*A61B 3/113* (2006.01)
*G06F 3/01* (2006.01)

(52) U.S. Cl.
CPC .............. *A61B 3/113* (2013.01); *G06F 3/013* (2013.01)

(58) Field of Classification Search
CPC ....... A61B 3/1113; A61B 3/107; G06F 3/013; G02B 2027/0134; G02B 2027/0138;
(Continued)

(56) References Cited

U.S. PATENT DOCUMENTS

| 6,850,221 B1 | 2/2005 | Tickle |
| D514,570 S | 2/2006 | Ohta |

(Continued)

FOREIGN PATENT DOCUMENTS

| EP | 3669753 A1 | 6/2020 |
| JP | 2011081807 A | 4/2011 |

(Continued)

OTHER PUBLICATIONS

Nagamatsu, Takashi, et al. Gaze Estimation Method Involving Corneal Reflection-Based Modeling of the Eye as a General Surface of Revolution about the Optical Axis of the Eye, IEICE Trans. Inf. & Syst., vol. E95-D, No. 6, Jun. 2012, pp. 1656-1667. (Year: 2012).*

(Continued)

*Primary Examiner* — Brent D Castiaux
(74) *Attorney, Agent, or Firm* — Tobias Intellectual Property Law, PLLC

(57) ABSTRACT

A display system can include a head-mounted display configured to project light to an eye of a user to display virtual image content at different amounts of divergence and collimation. The display system can include an inward-facing imaging system possibly comprising a plurality of cameras that image the user's eye and glints thereon and processing electronics that are in communication with the inward-facing imaging system and that are configured to obtain an estimate of a center of cornea of the user's eye using data derived from the glint images. The display system may use spherical and aspheric cornea models to estimate a location of the corneal center of the user's eye.

19 Claims, 65 Drawing Sheets

Related U.S. Application Data

(60) Provisional application No. 63/140,202, filed on Jan. 21, 2021, provisional application No. 63/139,750, filed on Jan. 20, 2021, provisional application No. 63/052,392, filed on Jul. 15, 2020.

(58) Field of Classification Search
CPC .... G02B 2027/0178; G02B 2027/0187; G02B 27/0093; G02B 27/0172; G06T 7/246; G06T 7/73; G06T 2207/30201
See application file for complete search history.

(56) References Cited

U.S. PATENT DOCUMENTS

| | | | |
|---|---|---|---|
| 8,950,867 | B2 | 2/2015 | Macnamara |
| 8,953,899 | B2 | 2/2015 | Wu et al. |
| 9,081,426 | B2 | 7/2015 | Armstrong |
| 9,215,293 | B2 | 12/2015 | Miller |
| D752,529 | S | 3/2016 | Loretan et al. |
| 9,310,559 | B2 | 4/2016 | Macnamara |
| 9,348,143 | B2 | 5/2016 | Gao et al. |
| 9,354,445 | B1 | 5/2016 | Weaver et al. |
| D758,367 | S | 6/2016 | Natsume |
| D759,657 | S | 6/2016 | Kujawski et al. |
| 9,417,452 | B2 | 8/2016 | Schowengerdt et al. |
| 9,470,906 | B2 | 10/2016 | Kaji et al. |
| 9,547,174 | B2 | 1/2017 | Gao et al. |
| 9,671,566 | B2 | 6/2017 | Abovitz et al. |
| D794,288 | S | 8/2017 | Beers et al. |
| 9,740,006 | B2 | 8/2017 | Gao |
| 9,791,700 | B2 | 10/2017 | Schowengerdt |
| D805,734 | S | 12/2017 | Fisher et al. |
| 9,851,563 | B2 | 12/2017 | Gao et al. |
| 9,857,591 | B2 | 1/2018 | Welch et al. |
| 9,874,749 | B2 | 1/2018 | Bradski et al. |
| 11,315,288 | B2 | 4/2022 | Farmer et al. |
| 11,998,275 | B2 | 6/2024 | Chan et al. |
| 2006/0028436 | A1 | 2/2006 | Armstrong |
| 2007/0081123 | A1 | 4/2007 | Lewis |
| 2009/0028423 | A1 | 1/2009 | Sandstrom et al. |
| 2011/0069277 | A1 | 3/2011 | Blixt et al. |
| 2011/0085139 | A1 | 4/2011 | Blixt et al. |
| 2012/0113223 | A1 | 5/2012 | Hilliges et al. |
| 2012/0127062 | A1 | 5/2012 | Bar-Zeev et al. |
| 2012/0127320 | A1 | 5/2012 | Balogh |
| 2012/0162549 | A1 | 6/2012 | Gao et al. |
| 2012/0182334 | A1 | 7/2012 | Ranieri et al. |
| 2013/0050642 | A1 | 2/2013 | Lewis et al. |
| 2013/0082922 | A1 | 4/2013 | Miller |
| 2013/0117377 | A1 | 5/2013 | Miller |
| 2013/0125027 | A1 | 5/2013 | Abovitz |
| 2013/0208234 | A1 | 8/2013 | Lewis |
| 2013/0242262 | A1 | 9/2013 | Lewis |
| 2013/0300635 | A1 | 11/2013 | White et al. |
| 2014/0003762 | A1 | 1/2014 | Macnamara |
| 2014/0071539 | A1 | 3/2014 | Gao |
| 2014/0177023 | A1 | 6/2014 | Gao et al. |
| 2014/0218468 | A1 | 8/2014 | Gao et al. |
| 2014/0267420 | A1 | 9/2014 | Schowengerdt et al. |
| 2014/0267771 | A1 | 9/2014 | Lawler |
| 2014/0306866 | A1 | 10/2014 | Miller et al. |
| 2014/0313423 | A1 | 10/2014 | Johnson et al. |
| 2014/0347548 | A1 | 11/2014 | Wu et al. |
| 2015/0016777 | A1 | 1/2015 | Abovitz et al. |
| 2015/0098620 | A1 | 4/2015 | Wu et al. |
| 2015/0103306 | A1 | 4/2015 | Kaji et al. |
| 2015/0104101 | A1 | 4/2015 | Bryant et al. |
| 2015/0136990 | A1 | 5/2015 | Blixt et al. |
| 2015/0178939 | A1 | 6/2015 | Bradski et al. |
| 2015/0205126 | A1 | 7/2015 | Schowengerdt |
| 2015/0222883 | A1 | 8/2015 | Welch |
| 2015/0222884 | A1 | 8/2015 | Cheng |
| 2015/0241959 | A1 | 8/2015 | Abovitz et al. |
| 2015/0264299 | A1 | 9/2015 | Leech et al. |
| 2015/0268415 | A1 | 9/2015 | Schowengerdt et al. |
| 2015/0296203 | A1 | 10/2015 | Lucente et al. |
| 2015/0302652 | A1 | 10/2015 | Miller et al. |
| 2015/0309263 | A2 | 10/2015 | Abovitz et al. |
| 2015/0309316 | A1 | 10/2015 | Osterhout et al. |
| 2015/0326570 | A1 | 11/2015 | Publicover et al. |
| 2015/0346490 | A1 | 12/2015 | TeKolste et al. |
| 2015/0346495 | A1 | 12/2015 | Welch et al. |
| 2016/0011419 | A1 | 1/2016 | Gao |
| 2016/0026253 | A1 | 1/2016 | Bradski et al. |
| 2016/0029883 | A1 | 2/2016 | Cox |
| 2016/0085301 | A1 | 3/2016 | Lopez |
| 2016/0131902 | A1 | 5/2016 | Ambrus et al. |
| 2016/0270656 | A1 | 9/2016 | Samec et al. |
| 2016/0344957 | A1 | 11/2016 | Kaehler |
| 2016/0370605 | A1 | 12/2016 | Ain-Kedem |
| 2017/0053165 | A1 | 2/2017 | Kaehler |
| 2017/0053166 | A1 | 2/2017 | Amayeh et al. |
| 2017/0091996 | A1 | 3/2017 | Wei et al. |
| 2017/0109936 | A1 | 4/2017 | Powderly et al. |
| 2017/0115483 | A1 | 4/2017 | Aleem et al. |
| 2017/0122725 | A1 | 5/2017 | Yeoh et al. |
| 2017/0263007 | A1* | 9/2017 | Cavin ................ G06V 40/18 |
| 2017/0276934 | A1 | 9/2017 | Sarkar et al. |
| 2018/0018515 | A1 | 1/2018 | Spizhevoy et al. |
| 2018/0096503 | A1 | 4/2018 | Kaehler et al. |
| 2018/0131853 | A1 | 5/2018 | Pellman et al. |
| 2018/0183986 | A1 | 6/2018 | Smith et al. |
| 2018/0246320 | A1 | 8/2018 | Rana et al. |
| 2018/0275410 | A1 | 9/2018 | Yeoh et al. |
| 2018/0276467 | A1 | 9/2018 | Kaehler |
| 2018/0278843 | A1 | 9/2018 | Smith et al. |
| 2018/0278924 | A1 | 9/2018 | Schowengerdt et al. |
| 2018/0314416 | A1 | 11/2018 | Powderly et al. |
| 2018/0335629 | A1 | 11/2018 | Cheng et al. |
| 2019/0018485 | A1 | 1/2019 | Aleem et al. |
| 2019/0042842 | A1 | 2/2019 | Cavin et al. |
| 2019/0108383 | A1 | 4/2019 | Klingström et al. |
| 2019/0181169 | A1 | 6/2019 | Tadmor et al. |
| 2019/0181171 | A1 | 6/2019 | Tadmor et al. |
| 2019/0222830 | A1 | 7/2019 | Edwin et al. |
| 2019/0243448 | A1 | 8/2019 | Miller et al. |
| 2019/0302882 | A1 | 10/2019 | Blixt et al. |
| 2019/0324276 | A1 | 10/2019 | Edwin et al. |
| 2020/0225744 | A1* | 7/2020 | Lindén ................ A61B 3/113 |
| 2020/0241635 | A1 | 7/2020 | Cohen |
| 2020/0372678 | A1 | 11/2020 | Farmer et al. |
| 2021/0157401 | A1 | 5/2021 | Abele et al. |
| 2023/0210365 | A1 | 7/2023 | Chan et al. |

FOREIGN PATENT DOCUMENTS

| | | |
|---|---|---|
| JP | 2019512726 A | 5/2019 |
| KR | 20110038588 A | 4/2011 |
| WO | 2017079329 A1 | 5/2017 |
| WO | 2017079333 A1 | 5/2017 |
| WO | 2020023542 A1 | 1/2020 |
| WO | 2020023672 A1 | 1/2020 |
| WO | 2020236827 A1 | 11/2020 |
| WO | 2021011686 A1 | 1/2021 |
| WO | 2022015847 A1 | 1/2022 |

OTHER PUBLICATIONS

Nagamatsu et al., Gaze Estimation Method based on an Aspherical Model of the Cornea: Surface of Revolution about the Optical Axis of the Eye, Proceedings of The 27th Annual International Conference on Mobile Computing and Networking, ACM, New York, NY, USA, Mar. 22, 2010 (Mar. 22, 2010), pp. 255-258. (Year: 2010).*
ARToolKit: https://web.archive.org/web/20051013062315/http://www.hitl.washington.edu:80/artoolkit/documentation/hardware.htm, archived Oct. 13, 2005.
Azuma, "A Survey of Augmented Reality," Teleoperators and Virtual Environments 6, (Aug. 4, 1997), pp. 355-385. https://web.archive.org/web/20010604100006/http://www.cs.unc.edu/ azuma/ARpresence.pdf.

(56) References Cited

OTHER PUBLICATIONS

Azuma, "Predictive Tracking for Augmented Realty," TR95-007, Department of Computer Science, UNC-Chapel Hill, NC, Feb. 1995.
Bimber, et al., "Spatial Augmented Reality-Merging Real and Virtual Worlds," 2005 https://web.media.mit.edu/raskar/book/BimberRaskarAugmentedRealityBook.pdf.
Geisler David et al: "Real-time 3D Glint Detection in Remote Eye Tracking Based on Bayesian Inference", 2018 IEEE International Conference on Robotics and Automation (ICRA), IEEE, May 21, 2018 (May 21, 2018), pp. 7119-7126, XP033403294, DOI: 10.1109/ICRA.2018.8460800 [retrieved on Sep. 10, 2018].
International Preliminary Report on Patentability for PCT Application No. PCT/US2021/041618, dated Jan. 17, 2023.
International Search Report and Written Opinion for PCT Application No. PCT/US2021/041618, dated Oct. 28, 2021.
Jacob, "Eye Tracking in Advanced Interface Design," Human-Computer Interaction Lab Naval Research Laboratory, Washington, D.C. / paper/ in Virtual Environments and Advanced Interface Design, ed. by W. Barfield and T.A. Furness, pp. 258-288, Oxford University Press, New York (1995).
Nair, et al., "RIT-Eyes: Rendering of near-eye images for eye-tracking applications," Proceedings of ACM Conference, Washington DC, USA, Jul. 17 (Conference '17), 10 pages.
Tanriverdi and Jacob, "Interacting With Eye Movements in Virtual Environments," Department of Electrical Engineering and Computer Science, Tufts University, Medford, MA—paper/Proc. AMC CHI 2000 Human Factors in Computing Systems Conference, pp. 265-272, Addison-Wesley/ACM Press (2000).
Nagamatsu et al., Gaze Estimation Method based on an Aspherical Model of the Cornea: Surface of Revolution about the Optical Axis of the Eye, Proceedings of The 27th Annual International Conference on Mobile Computing and Networking, ACM, New York, NY, USA, Mar. 22, 2010 (Mar. 22, 2010), pp. 255-258.
KR2023-7004641 Office Action dated Nov. 12, 2024.
Nagamatsu, Takashi, et al. Gaze Estimation Method Involving Corneal Reflection-Based Modeling of the Eye as a General Surface of Revolution about the Optical Axis of the Eye, IEICE Trans. Inf. & Syst., vol. E95-D, No. 6, Jun. 2012, pp. 1656-1667.
EP21841770.7 Extended European Search Report dated Jun. 25, 2024.

* cited by examiner

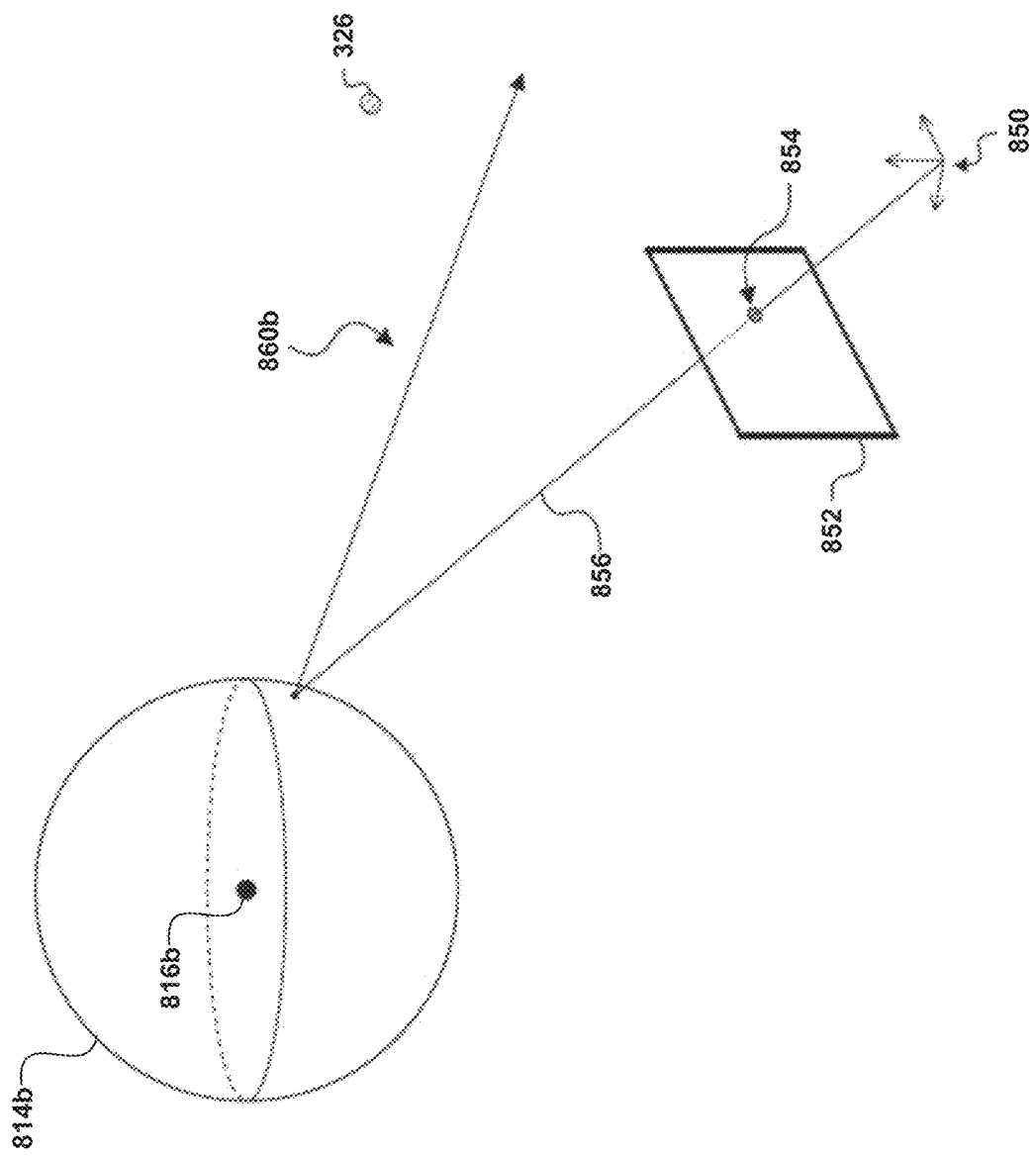

EYE TRACKING USING ASPHERIC CORNEA MODEL

CROSS-REFERENCE TO RELATED APPLICATIONS

This application is a continuation of U.S. application Ser. No. 18/004,979 filed on Jan. 10, 2023 titled "EYE TRACKING USING ASPHERIC CORNEA MODEL", which is a National Stage Entry of International Application No. PCT/US2021/041618 filed on Jul. 14, 2021, which claims priority from U.S. Provisional Application No. 63/052,392 filed on Jul. 15, 2020 titled "EYE TRACKING USING ASPHERIC CORNEA MODEL", U.S. Provisional Application No. 63/139,750 filed on Jan. 20, 2021 titled "EYE TRACKING USING ASPHERIC CORNEA MODEL", and U.S. Provisional Application No. 63/140,202 filed on Jan. 21, 2021 titled "EYE TRACKING USING ASPHERIC CORNEA MODEL". The entire contents of each of the above-listed applications are hereby incorporated by reference into this application.

This application is related to U.S. application Ser. No. 16/250,931, which is titled "EYE CENTER OF ROTATION DETERMINATION, DEPTH PLANE SELECTION, AND RENDER CAMERA POSITIONING IN DISPLAY SYSTEMS," and was filed on Jan. 17, 2019, and the corresponding U.S. Patent Publication 2019/0243448 A1 that was published on Aug. 8, 2019, and U.S. Patent Publication 2018/0018515 A1, which is titled "IRIS BOUNDARY ESTIMATION USING CORNEA CURVATURE" and was published on Jan. 18, 2018, which are hereby incorporated by reference into this application. The aforementioned patent application as well as the International Application No. PCT/US2020/042178, which is titled "EYE CENTER OF ROTATION DETERMINATION WITH ONE OR MORE EYE TRACKING CAMERAS" and was filed on Jul. 15, 2020, and the corresponding International Publication WO 2021/011686 that was published on Jan. 21, 2021, are each hereby expressly incorporated by reference herein in their entirety for all purposes.

FIELD

The present disclosure relates to display systems, virtual reality, and augmented reality imaging and visualization systems and, more particularly, to eye tracking using a center of rotation of an eye calculated using cornea data.

BACKGROUND

Modern computing and display technologies have facilitated the development of systems for so called "virtual reality", "augmented reality", or "mixed reality" experiences, wherein digitally reproduced images or portions thereof are presented to a user in a manner wherein they seem to be, or may be perceived as, real. A virtual reality, or "VR", scenario typically involves presentation of digital or virtual image information without transparency to other actual real-world visual input; an augmented reality, or "AR", scenario typically involves presentation of digital or virtual image information as an augmentation to visualization of the actual world around the user; a mixed reality, or "MR", related to merging real and virtual worlds to produce new environments where physical and virtual objects co-exist and interact in real time. As it turns out, the human visual perception system is very complex, and producing a VR, AR, or MR technology that facilitates a comfortable, natural-feeling, rich presentation of virtual image elements amongst other virtual or real-world imagery elements is challenging. Systems and methods disclosed herein address various challenges related to VR, AR and MR technology.

SUMMARY

Various examples of depth plane selection in a mixed reality system are disclosed.

A display system can be configured to project light to an eye of a user to display virtual image content in a vision field of said user. The user's eye may have a cornea, an iris, a pupil, a lens, a retina, and an optical axis extending through said lens, pupil, and cornea. The display system can include a frame configured to be supported on a head of the user, a head-mounted display disposed on the frame, said display configured to project light into said user's eye to display virtual image content to the user's vision field at different amounts of at least one of divergence and collimation and thus the displayed virtual image content appears to originate from different depths at different periods of time, one or more eye tracking cameras configured to image the user's eye, and processing electronics in communication with the display and the one or more eye tracking cameras, the processing electronics configured to obtain an estimate of a center of rotation of said eye based on images of said eye obtained with said one or more eye tracking cameras.

The processing electronic may additionally estimate location of a center of corneal curvature of the said eye using a spherical and/or an aspherical model of said cornea. In some cases, the processing electronics uses said spherical and/or aspherical models in numerical calculations to determine a value (e.g., a three-dimensional location such as an x, y, z location described by one or more coordinates such as x, y, z or r, $\theta$, $\varphi$, etc., with respect to a reference frame or coordinate system) or an estimate or a location of a center of curvature of the cornea based on the location of the glint reflections in images produced by said one or more cameras, locations of the one or more tracking cameras and the locations of the emitters that produced said respective glint reflections. In some implementations, the location of the center of curvature of the cornea may be determined with respect to reference frame or coordinate system of the eye camera or a fixed reference frame with a respect a head-mounted display.

Various examples of display systems that project light to one or more eyes of a user to display virtual image content in a vision field of said user are described herein such as the examples enumerated below:

Example 1: A display system configured to project light to an eye of a user to display virtual image content in a vision field of said user, said display system comprising: a frame configured to be supported on a head of the user; a head-mounted display disposed on the frame, said display configured to project light into said user's eye to display virtual image content to the user's vision field; first and second eye tracking cameras configured to image the user's eye; a plurality of light emitters; and processing electronics in communication with the display and the first and second eye tracking cameras, the processing electronics configured to: receive images of the user's eye captured by the first and second eye tracking cameras, glint reflections of the different light emitters observable in said images of the eye captured by the first and second eye tracking cameras; and estimate a location of said center of corneal curvature of the user's eye based on the location of the glint reflections in said images produced by both said first and second eye tracking camera and based on the location of both the first and second eye tracking cameras and the locations of the emitters that produced said respective glint reflections.

Example 2: A display system configured to project light to an eye of a user to display virtual image content in a vision field of said user, said display system comprising: a frame configured to be supported on a head of the user; a head-mounted display disposed on the frame, said display configured to project light into said user's eye to display virtual image content to the user's vision field; first and second eye tracking cameras configured to image the user's eye; a plurality of light emitters; and processing electronics in communication with the display and the first and second eye tracking cameras, the processing electronics configured to: receive images of the user's eye captured by the first and second eye tracking cameras, glint reflections of the different light emitters observable in said images of the eye captured by the first and second eye tracking cameras; and estimate a location of said center of rotation of the user's eye based on the location of the glint reflections in said images produced by both said first and second eye tracking camera and based on said the location of both the first and second eye tracking cameras and the locations of the emitters that produced said glint reflections for multiple eye poses.

Example 3: A method of determining one or more parameters associated with an eye for rendering virtual image content in a display system configured to project light to an eye of a user to display the virtual image content in a vision field of said user, said eye having a cornea, said method comprising: with a plurality of eye tracking cameras configured to image the eye of the user and a plurality of light emitters disposed with respect to said eye to form glints thereon, capturing a plurality of images of the eye of the user, said images comprising a plurality of glints; and obtaining an estimate of a center of rotation of said eye based on the plurality of glints, wherein obtaining an estimate of the center of rotation of said eye comprises: determining a plurality of estimates of the center of corneal curvature of the user's eye based on the plurality of glints; generating a three-dimensional surface from the plurality of estimates of the center of the corneal curvature; and determining the estimate of the center of rotation of the user's eye using the three-dimensional surface.

Example 4: A display system configured to project light to an eye of a user to display virtual image content in a vision field of said user, said display system comprising: a frame configured to be supported on a head of the user; a head-mounted display disposed on the frame, said display configured to project light into said user's eye to display virtual image content; first and second eye tracking cameras configured to image the user's eye; and processing electronics in communication with the display and the first and second eye tracking cameras, the processing electronics configured to: receive multiple pairs of captured images of the user's eye from the first and second eye tracking cameras; for pairs of images received from the first and second eye tracking cameras, respectively, obtain an estimate of a center of corneal curvature of the user's eye based at least in part on the respective pair of captured images; determine a three-dimensional surface based on the estimated centers of corneal curvature of the user's eye obtained based on the multiple pairs of captured images of the user's eye received from the respective first and second eye tracking cameras; and identify a center of curvature of the 3D surface to obtain an estimate of a center of rotation of the user's eye.

Example 5: A display system configured to project light to an eye of a user to display virtual image content in a vision field of said user, said display system comprising: a frame configured to be supported on a head of the user; a head-mounted display disposed on the frame, said display configured to project light into said user's eye to display virtual image content to the user's vision field; an eye tracking camera configured to image the user's eye; a plurality of light emitters; and processing electronics in communication with the display and the eye tracking camera, the processing electronics configured to: receive images of the user's eye captured by the eye tracking camera at a first and second location, glint reflections of the different light emitters observable in said images of the eye captured by the eye tracking camera; and estimate a location of said center of corneal curvature of the user's eye based on the location of the glint reflections in said images produced by said eye tracking camera and based on the location of the eye tracking camera and the locations of the emitters that produced said respective glint reflections.

Example 6: A display system configured to project light to an eye of a user to display virtual image content in a vision field of said user, said display system comprising: a frame configured to be supported on a head of the user; a head-mounted display disposed on the frame, said display configured to project light into said user's eye to display virtual image content to the user's vision field; an eye tracking camera configured to image the user's eye; a plurality of light emitters; and processing electronics in communication with the display and the eye tracking camera, the processing electronics configured to: receive images of the user's eye captured by the eye tracking camera at a first camera and second location, glint reflections of the different light emitters observable in said images of the eye captured by the eye tracking camera; and estimate a location of said center of rotation of the user's eye based on the location of the glint reflections in said images produced by said eye tracking camera and based on said first and second location of the eye tracking camera and the locations of the emitters that produced said glint reflections for multiple eye poses.

Example 7: A method of determining one or more parameters associated with an eye for rendering virtual image content in a display system configured to project light to an eye of a user to display the virtual image content in a vision field of said user, said eye having a cornea, said method comprising: with an eye tracking camera configured to image the eye of the user and a plurality of light emitters disposed with respect to said eye to form glints thereon, capturing a plurality of images of the eye of the user, said images comprising a plurality of glints; and obtaining an estimate of a center of rotation of said eye based on the plurality of glints, wherein obtaining an estimate of the center of rotation of said eye comprises: determining a plurality of estimates of the center of corneal curvature of the user's eye based on the plurality of glints; generating a three-dimensional surface from the plurality of estimates of the center of the corneal curvature; and determining the estimate of the center of rotation of the user's eye using the three-dimensional surface.

Example 8: A display system configured to project light to an eye of a user to display virtual image content in a vision field of said user, said display system comprising: a frame configured to be supported on a head of the user; a head-mounted display disposed on the frame, said display configured to project light into said user's eye to display virtual image content; an eye tracking camera configured to image the user's eye; and processing electronics in communication with the display and the eye tracking camera, the processing electronics configured to: receive multiple pairs of captured images of the user's eye from the eye tracking camera; for pairs of images received from the eye tracking camera, respectively, obtain an estimate of a center of corneal curvature of the user's eye based at least in part on the respective pair of captured images; determine a three-dimensional surface based on the estimated centers of corneal curvature of the user's eye obtained based on the multiple pairs of captured images of the user's eye received from the eye tracking camera; and identify a center of curvature of the 3D surface to obtain an estimate of a center of rotation of the user's eye.

Example 9: A display system configured to project light to an eye of a user to display virtual image content in a vision field of said user, said display system comprising: a frame configured to be supported on a head of the user; a head-mounted display disposed on the frame, said display configured to project light into said user's eye to display virtual image content to the user's vision field; at least one eye tracking camera configured to image the user's eye; a plurality of light emitters; and processing electronics in communication with the display and the eye tracking camera, the processing electronics configured to: receive images of the user's eye captured by the at least one eye tracking camera at a first and second location, glint reflections of the different light emitters observable in said images of the eye captured by the eye tracking camera; and estimate a location of said center of corneal curvature of the user's eye based on the location of the glint reflections in said images produced by said at least one eye tracking camera and based on the location of the at least one eye tracking camera and the locations of the emitters that produced said respective glint reflections.

Example 10: A display system configured to project light to an eye of a user to display virtual image content in a vision field of said user, said eye having a cornea and a pupil, said display system comprising: a frame configured to be supported on a head of the user; a head-mounted display disposed on the frame, said display configured to project light into said user's eye to display virtual image content to the user's vision field; one or more eye tracking cameras configured to image the user's eye; a plurality of light emitters; and processing electronics in communication with the display and the one or more eye tracking cameras, the processing electronics configured to: receive images of the user's eye captured by the one or more eye tracking cameras, glint reflections of the different light emitters observable in said images of the eye captured by the one or more tracking cameras; and estimate a location of a center of curvature of said cornea of the user's eye based at least in part on the location of the glint reflections in said images produced by said one or more eye tracking camera, wherein said processing electronics uses an aspheric model of said cornea in numerical calculations to estimate said location of said center of corneal curvature of the user's eye.

Example 11: A display system configured to project light to an eye of a user to display virtual image content in a vision field of said user, said eye having a cornea and a pupil, said display system comprising: a frame configured to be supported on a head of the user; a head-mounted display disposed on the frame, said display configured to project light into said user's eye to display virtual image content to the user's vision field; one or more eye tracking cameras configured to image the user's eye; a plurality of light emitters; and processing electronics in communication with the display and the one or more eye tracking cameras, the processing electronics configured to: receive images of the user's eye captured by the one or more eye tracking cameras, glint reflections of the different light emitters observable in said images of the eye captured by the one or more tracking cameras; and estimate a first parameter of the user's eye based on the location of the glint reflections in said images produced by said one or more eye tracking camera, wherein said processing electronics uses an aspheric model of said cornea in numerical calculations to estimate said first parameter of the user's eye.

Any of the above Examples or Additional Examples can be combined. Additionally, any of the above Examples or Additional Examples can be integrated with a head mounted display. In addition, any of the above Examples or Additional Examples can be implemented with a single depth plane and/or with one or more variable depth planes (e.g., one or more elements with variable focusing power that provide accommodation cues that vary over time).

Furthermore, apparatus and methods for determining a variety of values, parameters, etc., such as, but not limited to, anatomical, optical, and geometric features, locations, and orientations, etc., are disclosed herein. Examples of such parameters include, for example, the center of rotation of the eye, the center of curvature of the cornea, the center of the pupil, the boundary of the pupil, the center of the iris, the boundary of the iris, the boundary of the limbus, the optical axis of the eye, the visual axis of the eye, the center of perspective, but are not limited to these. Determinations of such values, parameters, etc., as recited herein include estimations thereof and need not necessarily coincide precisely with the actual values. For example, determinations of the center of rotation of the eye, the center of curvature of the cornea, the center or boundary of the pupil or iris, the boundary of the limbus, the optical axis of the eye, the visual axis of the eye, the center of perspective, etc., may be estimations, approximations, or values close to, but not the same as, the actual (e.g., anatomical, optical, or geometric) values or parameters. In some cases, for example, root mean square estimation techniques are used to obtain estimates of such values. As an example, certain techniques described herein relate to identifying a location or point at which rays or vectors intersect. Such rays or vectors, however, may not intersect. In this example, the location or point may be estimated. For example, the location or point may be determined based on root mean square, or other, estimation techniques (e.g., the location or point may be estimated to be close to or the closest to the rays or vectors). Other processes may also be used to estimate, approximate or otherwise provide a value that may not coincide with the actual value. Accordingly, the term determining and estimating, or determined and estimated, are used interchangeably herein. Reference to such determined values may therefore include estimates, approximations, or values close to the actual value. Accordingly, reference to determining a parameter or value above, or elsewhere herein should not be limited precisely to the actual value but may include estimations, approximations or values close thereto.

Details of one or more implementations of the subject matter described in this specification are set forth in the accompanying drawings and the description below. Other features, aspects, and advantages will become apparent from the description, the drawings, and the claims. Neither this summary nor the following detailed description purports to define or limit the scope of the inventive subject matter.

BRIEF DESCRIPTION OF THE DRAWINGS

FIGS. 8C-8E illustrate example stages of locating a user's corneal center with an eye tracking module in a wearable system.

FIGS. 19A-1 and 19A-2 illustrate an example surface fit to selected estimated cornea centers.

FIGS. 19B-1 and 19B-2 shows example surface normal vectors that may be normal to a surface fitted to estimated cornea centers.

FIGS. 19C-1 and 19C-2 illustrate an estimated CoR region based on points of intersection of the surface normal vectors.

FIGS. 19D-1 and 19D-2, illustrate an example surface fit to another selection of cornea centers.

Figure 1:
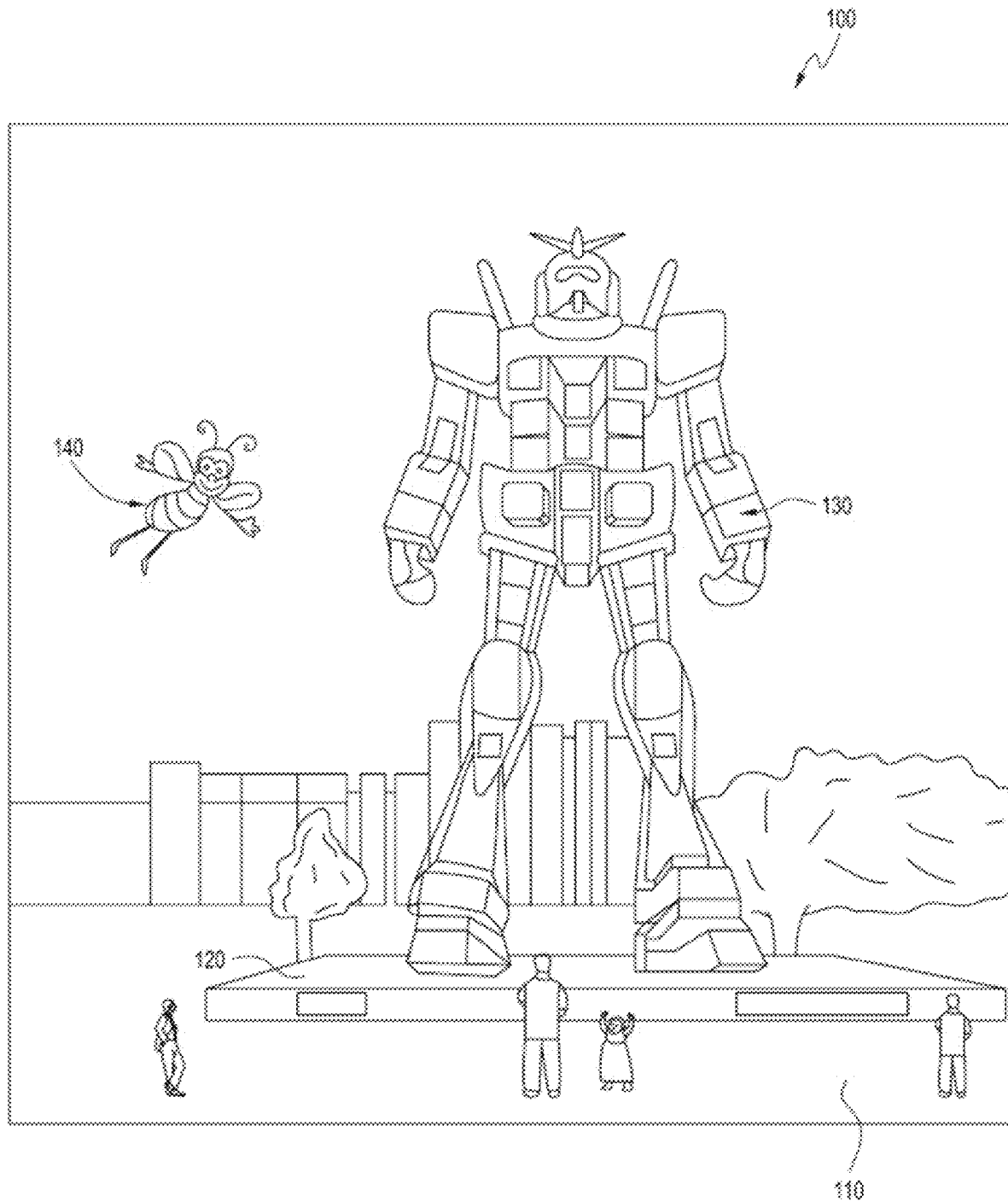
FIG. 1 depicts an illustration of a mixed reality scenario with certain virtual reality objects, and certain physical objects viewed by a person.

Throughout the drawings, reference numbers may be re-used to indicate correspondence between referenced elements. The drawings are provided to illustrate example embodiments described herein and are not intended to limit the scope of the disclosure.

DETAILED DESCRIPTION

Reference will now be made to the drawings, in which like reference numerals refer to like parts throughout. Unless indicated otherwise, the drawings are schematic not necessarily drawn to scale.

A. Examples of 3D Display of a Wearable System

A wearable system (also referred to herein as an augmented reality (AR) system) can be configured to present 2D or 3D virtual images to a user. The images may be still images, frames of a video, or a video, in combination or the like. At least a portion of the wearable system can be implemented on a wearable device that can present a VR, AR, or MR environment, alone or in combination, for user interaction. The wearable device can be used interchangeably as an AR device (ARD). Further, for the purpose of the present disclosure, the term "AR" is used interchangeably with the term "MR".

FIG. 1 depicts an illustration of a mixed reality scenario with certain virtual reality objects, and certain physical objects viewed by a person. In FIG. 1, an MR scene 100 is depicted wherein a user of an MR technology sees a real-world park-like setting 110 featuring people, trees, buildings in the background, and a concrete platform 120. In addition to these items, the user of the MR technology also perceives that he "sees" a robot statue 130 standing upon the real-world platform 120, and a cartoon-like avatar character 140 flying by which seems to be a personification of a bumble bee, even though these elements do not exist in the real world.

In order for the 3D display to produce a true sensation of depth, and more specifically, a simulated sensation of surface depth, it may be desirable for each point in the display's visual field to generate an accommodative response corresponding to its virtual depth. If the accommodative response to a display point does not correspond to the virtual depth of that point, as determined by the binocular depth cues of convergence and stereopsis, the human eye may experience an accommodation conflict, resulting in unstable imaging, harmful eye strain, headaches, and, in the absence of accommodation information, almost a complete lack of surface depth.

VR, AR, and MR experiences can be provided by display systems having displays in which images corresponding to a plurality of depth planes are provided to a viewer. The images may be different for each depth plane (e.g., provide slightly different presentations of a scene or object) and may be separately focused by the viewer's eyes, thereby helping to provide the user with depth cues based on the accommodation of the eye required to bring into focus different image features for the scene located on different depth plane or based on observing different image features on different depth planes being out of focus. As discussed elsewhere herein, such depth cues provide credible perceptions of depth.

Figure 2:
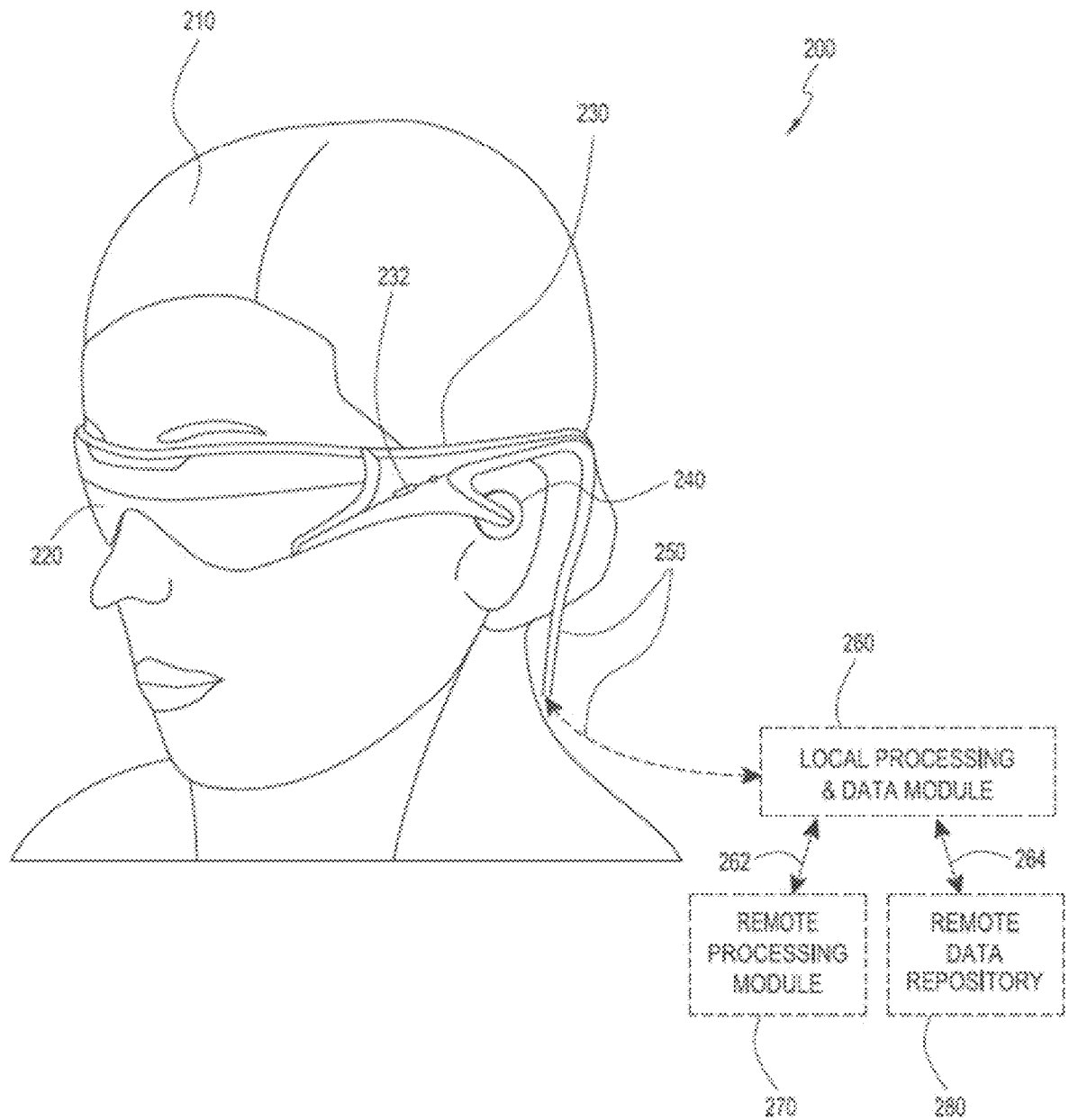
FIG. 2 schematically illustrates an example of a wearable system.

FIG. 2 illustrates an example of wearable system 200 which can be configured to provide an AR/VR/MR scene. The wearable system 200 can also be referred to as the AR system 200. The wearable system 200 includes a display 220, and various mechanical and electronic modules and systems to support the functioning of display 220. The display 220 may be coupled to a frame 230, which is wearable by a user, wearer, or viewer 210. The display 220 can be positioned in front of the eyes of the user 210. The display 220 can present AR/VR/MR content to a user. The display 220 can comprise a head mounted display (HMD) that is worn on the head of the user.

In some embodiments, a speaker 240 is coupled to the frame 230 and positioned adjacent the ear canal of the user (in some embodiments, another speaker, not shown, is positioned adjacent the other ear canal of the user to provide for stereo/shapeable sound control). The display 220 can include an audio sensor (e.g., a microphone) 232 for detecting an audio stream from the environment and capture ambient sound. In some embodiments, one or more other audio sensors, not shown, are positioned to provide stereo sound reception. Stereo sound reception can be used to determine the location of a sound source. The wearable system 200 can perform voice or speech recognition on the audio stream.

The wearable system 200 can include an outward-facing imaging system 464 (shown in FIG. 4) which observes the world in the environment around the user. The wearable system 200 can also include an inward-facing imaging system 462 (shown in FIG. 4) which can track the eye movements of the user. The inward-facing imaging system may track either one eye's movements or both eyes' movements. The inward-facing imaging system 462 may be attached to the frame 230 and may be in electrical communication with the processing modules 260 or 270, which may process image information acquired by the inward-facing imaging system to determine, e.g., the pupil diameters or orientations of the eyes, eye movements or eye pose of the user 210. The inward-facing imaging system 462 may include one or more cameras. For example, at least one camera may be used to image each eye. The images acquired by the cameras may be used to determine pupil size or eye pose for each eye separately, thereby allowing presentation of image information to each eye to be dynamically tailored to that eye.

As an example, the wearable system 200 can use the outward-facing imaging system 464 or the inward-facing imaging system 462 to acquire images of a pose of the user. The images may be still images, frames of a video, or a video.

The display 220 can be operatively coupled 250, such as by a wired lead or wireless connectivity, to a local data processing module 260 which may be mounted in a variety of configurations, such as fixedly attached to the frame 230, fixedly attached to a helmet or hat worn by the user, embedded in headphones, or otherwise removably attached to the user 210 (e.g., in a backpack-style configuration, in a belt-coupling style configuration).

The local processing and data module 260 may comprise a hardware processor, as well as digital memory, such as non-volatile memory (e.g., flash memory), both of which may be utilized to assist in the processing, caching, and storage of data. The data may include data a) captured from sensors (which may be, e.g., operatively coupled to the frame 230 or otherwise attached to the user 210), such as image capture devices (e.g., cameras in the inward-facing imaging system or the outward-facing imaging system), audio sensors (e.g., microphones), inertial measurement units (IMUs), accelerometers, compasses, global positioning system (GPS) units, radio devices, or gyroscopes; or b) acquired or processed using remote processing module 270 or remote data repository 280, possibly for passage to the display 220 after such processing or retrieval. The local processing and data module 260 may be operatively coupled by communication links 262 or 264, such as via wired or wireless communication links, to the remote processing module 270 or remote data repository 280 such that these remote modules are available as resources to the local processing and data module 260. In addition, remote processing module 280 and remote data repository 280 may be operatively coupled to each other.

In some embodiments, the remote processing module 270 may comprise one or more processors configured to analyze and process data or image information. In some embodiments, the remote data repository 280 may comprise a digital data storage facility, which may be available through the internet or other networking configuration in a "cloud" resource configuration. In some embodiments, all data is stored and all computations are performed in the local processing and data module, allowing fully autonomous use from a remote module.

B. Example Components of a Wearable System

Figure 3:
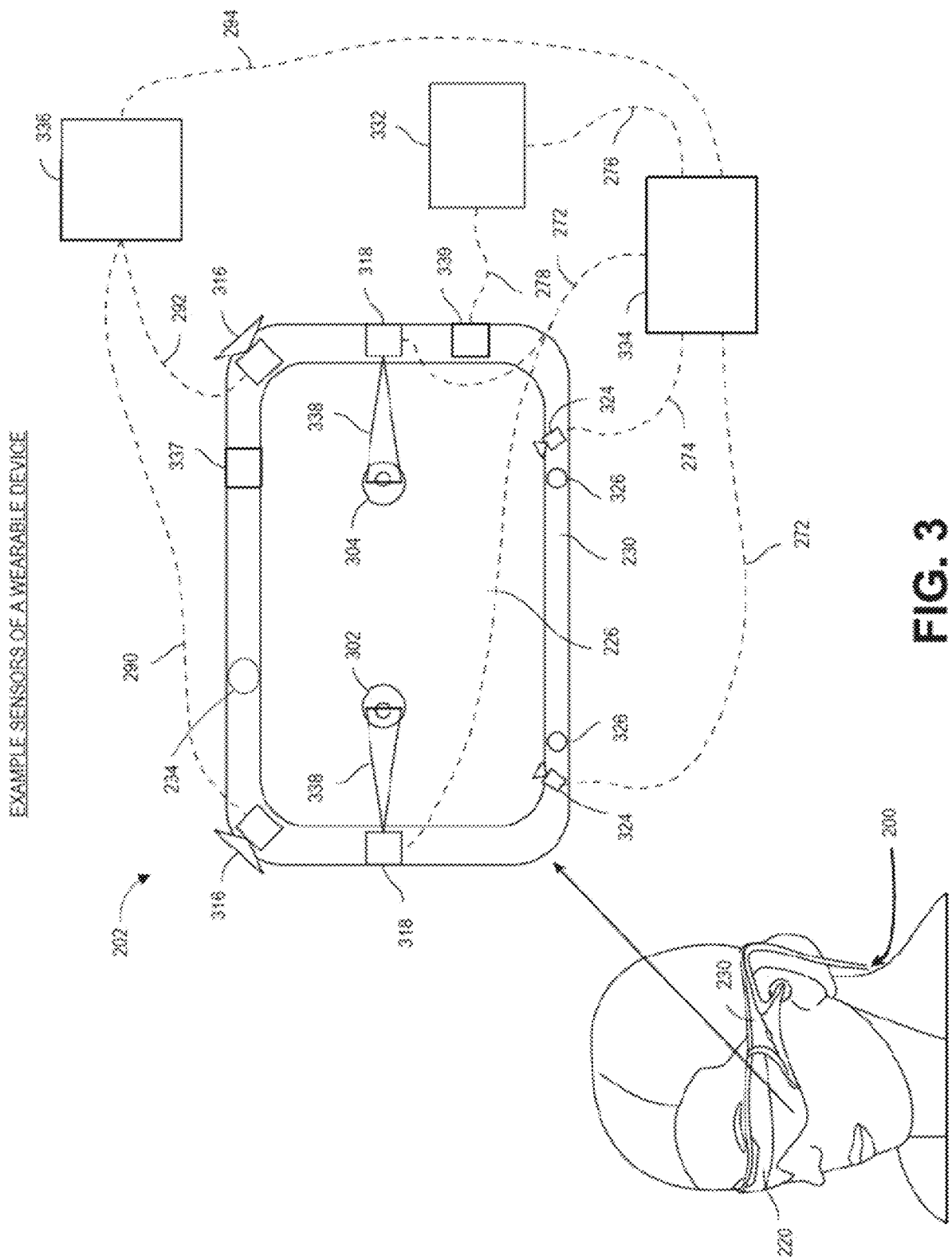
FIG. 3 schematically illustrates example components of a wearable system.

FIG. 3 schematically illustrates example components of a wearable system. FIG. 3 shows a wearable system 200 which can include a display 220 and a frame 230. A blown-up view 202 schematically illustrates various components of the wearable system 200. In certain implements, one or more of the components illustrated in FIG. 3 can be part of the display 220. The various components alone or in combination can collect a variety of data (such as e.g., audio or visual data) associated with the user of the wearable system 200 or the user's environment. It should be appreciated that other embodiments may have additional or fewer components depending on the application for which the wearable system is used. Nevertheless, FIG. 3 provides a basic idea of some of the various components and types of data that may be collected, analyzed, and stored through the wearable system.

FIG. 3 shows an example wearable system 200 which can include the display 220. The display 220 can comprise a display lens 226 that may be mounted to a user's head or a housing or frame 230, which corresponds to the frame 230. The display lens 226 may comprise one or more transparent mirrors positioned by the housing 230 in front of the user's eyes 302, 304 and may be configured to bounce projected light 338 into the eyes 302, 304 and facilitate beam shaping, while also allowing for transmission of at least some light from the local environment. The wavefront of the projected light beam 338 may be bent or focused to coincide with a desired focal distance of the projected light. As illustrated, two wide-field-of-view machine vision cameras 316 (also referred to as world cameras) can be coupled to the housing 230 to image the environment around the user. These cameras 316 can be dual capture visible light/non-visible (e.g., infrared) light cameras. The cameras 316 may be part of the outward-facing imaging system 464 shown in FIG. 4. Image acquired by the world cameras 316 can be processed by the pose processor 336. For example, the pose processor 336 can implement one or more object recognizers 708 to identify a pose of a user or another person in the user's environment or to identify a physical object in the user's environment.

With continued reference to FIG. 3, a pair of scanned-laser shaped-wavefront (e.g., for depth) light projector modules with display mirrors and optics configured to project light 338 into the eyes 302, 304 are shown. The depicted view also shows two miniature infrared cameras 324 paired with infrared light sources 326 (such as light emitting diodes "LED"s), which are configured to be able to track the eyes 302, 304 of the user to support rendering and user input. The cameras 324 may be part of the inward-facing imaging system 462 shown in FIG. 4. The wearable system 200 can further feature a sensor assembly 339, which may comprise X, Y, and Z axis accelerometer capability as well as a magnetic compass and X, Y, and Z axis gyro capability, preferably providing data at a relatively high frequency, such as 200 Hz. The sensor assembly 339 may be part of the IMU described with reference to FIG. 2 The depicted system 200 can also comprise a head pose processor 336, such as an ASIC (application specific integrated circuit), FPGA (field programmable gate array), or ARM processor (advanced reduced-instruction-set machine), which may be configured to calculate real or near-real time user head pose from wide field of view image information output from the capture devices 316. The head pose processor 336 can be a hardware processor and can be implemented as part of the local processing and data module 260 shown in FIG. 2.

The wearable system can also include one or more depth sensors 234. The depth sensor 234 can be configured to measure the distance between an object in an environment to a wearable device. The depth sensor 234 may include a laser scanner (e.g., a lidar), an ultrasonic depth sensor, or a depth sensing camera. In certain implementations, where the cameras 316 have depth sensing ability, the cameras 316 may also be considered as depth sensors 234.

Also shown is a processor 332 configured to execute digital or analog processing to derive pose from the gyro, compass, or accelerometer data from the sensor assembly 339. The processor 332 may be part of the local processing and data module 260 shown in FIG. 2. The wearable system 200 as shown in FIG. 3 can also include a position system such as, e.g., a GPS 337 (global positioning system) to assist with pose and positioning analyses. In addition, the GPS may further provide remotely-based (e.g., cloud-based) information about the user's environment. This information may be used for recognizing objects or information in user's environment.

The wearable system may combine data acquired by the GPS 337 and a remote computing system (such as, e.g., the remote processing module 270, another user's ARD, etc.) which can provide more information about the user's environment. As one example, the wearable system can determine the user's location based on GPS data and retrieve a world map (e.g., by communicating with a remote processing module 270) including virtual objects associated with the user's location. As another example, the wearable system 200 can monitor the environment using the world cameras 316 (which may be part of the outward-facing imaging system 464 shown in FIG. 4). Based on the images acquired by the world cameras 316, the wearable system 200 can detect objects in the environment (e.g., by using one or more object recognizers). The wearable system can further use data acquired by the GPS 337 to interpret the characters.

The wearable system 200 may also comprise a rendering engine 334 which can be configured to provide rendering information that is local to the user to facilitate operation of the scanners and imaging into the eyes of the user, for the user's view of the world. The rendering engine 334 may be implemented by a hardware processor (such as, e.g., a central processing unit or a graphics processing unit). In some embodiments, the rendering engine is part of the local processing and data module 260. The rendering engine 334 can be communicatively coupled (e.g., via wired or wireless links) to other components of the wearable system 200. For example, the rendering engine 334, can be coupled to the eye cameras 324 via communication link 274, and be coupled to a projecting subsystem 318 (which can project light into user's eyes 302, 304 via a scanned laser arrangement in a manner similar to a retinal scanning display) via the communication link 272. The rendering engine 334 can also be in communication with other processing units such as, e.g., the sensor pose processor 332 and the image pose processor 336 via links 276 and 294 respectively.

The cameras 324 (e.g., mini infrared cameras) may be utilized to track the eye pose to support rendering and user input. Some example eye poses may include where the user is looking or at what depth he or she is focusing (which may be estimated with eye vergence). The GPS 337, gyros, compass, and accelerometers 339 may be utilized to provide coarse or fast pose estimates. One or more of the cameras 316 can acquire images and pose, which in conjunction with data from an associated cloud computing resource, may be utilized to map the local environment and share user views with others.

The example components depicted in FIG. 3 are for illustration purposes only. Multiple sensors and other functional modules are shown together for case of illustration and description. Some embodiments may include only one or a subset of these sensors or modules. Further, the locations of these components are not limited to the positions depicted in FIG. 3. Some components may be mounted to or housed within other components, such as a belt-mounted component, a hand-held component, or a helmet component. As one example, the image pose processor 336, sensor pose processor 332, and rendering engine 334 may be positioned in a beltpack and configured to communicate with other components of the wearable system via wireless communication, such as ultra-wideband, Wi-Fi, Bluetooth, etc., or via wired communication. The depicted housing 230 preferably is head-mountable and wearable by the user. However, some components of the wearable system 200 may be worn to other portions of the user's body. For example, the speaker 240 may be inserted into the ears of a user to provide sound to the user.

Regarding the projection of light 338 into the eyes 302, 304 of the user, in some embodiment, the cameras 324 may be utilized to measure where the centers of a user's eyes are geometrically verged to, which, in general, coincides with a position of focus, or "depth of focus", of the eyes. A 3-dimensional surface of all points the eyes verge to can be referred to as the "horopter". The focal distance may take on a finite number of depths, or may be infinitely varying. Light projected from the vergence distance appears to be focused to the subject eye 302, 304, while light in front of or behind the vergence distance is blurred. Examples of wearable devices and other display systems of the present disclosure are also described in U.S. Patent Publication No. 2016/0270656, which is incorporated by reference herein in its entirety.

The human visual system is complicated and providing a realistic perception of depth is challenging. Viewers of an object may perceive the object as being three-dimensional due to a combination of vergence and accommodation. Vergence movements (e.g., rolling movements of the pupils toward or away from each other to converge the lines of sight of the eyes to fixate upon an object) of the two eyes relative to each other are closely associated with focusing (or "accommodation") of the lenses of the eyes. Under normal conditions, changing the focus of the lenses of the eyes, or accommodating the eyes, to change focus from one object to another object at a different distance will automatically cause a matching change in vergence to the same distance, under a relationship known as the "accommodation-vergence reflex." Likewise, a change in vergence will trigger a matching change in accommodation, under normal conditions. Display systems that provide a better match between accommodation and vergence may form more realistic and comfortable simulations of three-dimensional imagery.

Further spatially coherent light with a beam diameter of less than about 0.7 millimeters can be correctly resolved by the human eye regardless of where the eye focuses. Thus, to create an illusion of proper focal depth, the eye vergence may be tracked with the cameras 324, and the rendering engine 334 and projection subsystem 318 may be utilized to render all objects on or close to the horopter in focus, and all other objects at varying degrees of defocus (e.g., using intentionally-created blurring). Preferably, the system 220 renders to the user at a frame rate of about 60 frames per second or greater. As described above, preferably, the cameras 324 may be utilized for eye tracking, and software may be configured to pick up not only vergence geometry but also focus location cues to serve as user inputs. Preferably, such a display system is configured with brightness and contrast suitable for day or night use.

In some embodiments, the display system preferably has latency of less than about 20 milliseconds for visual object alignment, less than about 0.1 degree of angular alignment, and about 1 arc minute of resolution, which, without being limited by theory, is believed to be approximately the limit of the human eye. The display system 220 may be integrated with a localization system, which may involve GPS elements, optical tracking, compass, accelerometers, or other data sources, to assist with position and pose determination; localization information may be utilized to facilitate accurate rendering in the user's view of the pertinent world (e.g., such information would facilitate the glasses to know where they are with respect to the real world).

In some embodiments, the wearable system 200 is configured to display one or more virtual images based on the accommodation of the user's eyes. Unlike prior 3D display approaches that force the user to focus where the images are being projected, in some embodiments, the wearable system is configured to automatically vary the focus of projected virtual content to allow for a more comfortable viewing of one or more images presented to the user. For example, if the user's eyes have a current focus of 1 m, the image may be projected to coincide with the user's focus. If the user shifts focus to 3 m, the image is projected to coincide with the new focus. Thus, rather than forcing the user to a predetermined focus, the wearable system 200 of some embodiments allows the user's eye to a function in a more natural manner.

Such a wearable system 200 may eliminate or reduce the incidences of eye strain, headaches, and other physiological symptoms typically observed with respect to virtual reality devices. To achieve this, various embodiments of the wearable system 200 are configured to project virtual images at varying focal distances, through one or more variable focus elements (VFEs). In one or more embodiments, 3D perception may be achieved through a multi-plane focus system that projects images at fixed focal planes away from the user. Other embodiments employ variable plane focus, wherein the focal plane is moved back and forth in the z-direction to coincide with the user's present state of focus.

In both the multi-plane focus systems and variable plane focus systems, wearable system 200 may employ eye tracking to determine a vergence of the user's eyes, determine the user's current focus, and project the virtual image at the determined focus. In other embodiments, wearable system 200 comprises a light modulator that variably projects, through a fiber scanner, or other light generating source, light beams of varying focus in a raster pattern across the retina. Thus, the ability of the display of the wearable system 200 to project images at varying focal distances not only cases accommodation for the user to view objects in 3D, but may also be used to compensate for user ocular anomalies, as further described in U.S. Patent Publication No. 2016/0270656, which is incorporated by reference herein in its entirety. In some other embodiments, a spatial light modulator may project the images to the user through various optical components. For example, as described further below, the spatial light modulator may project the images onto one or more waveguides, which then transmit the images to the user.

C. Waveguide Stack Assembly

Figure 4:
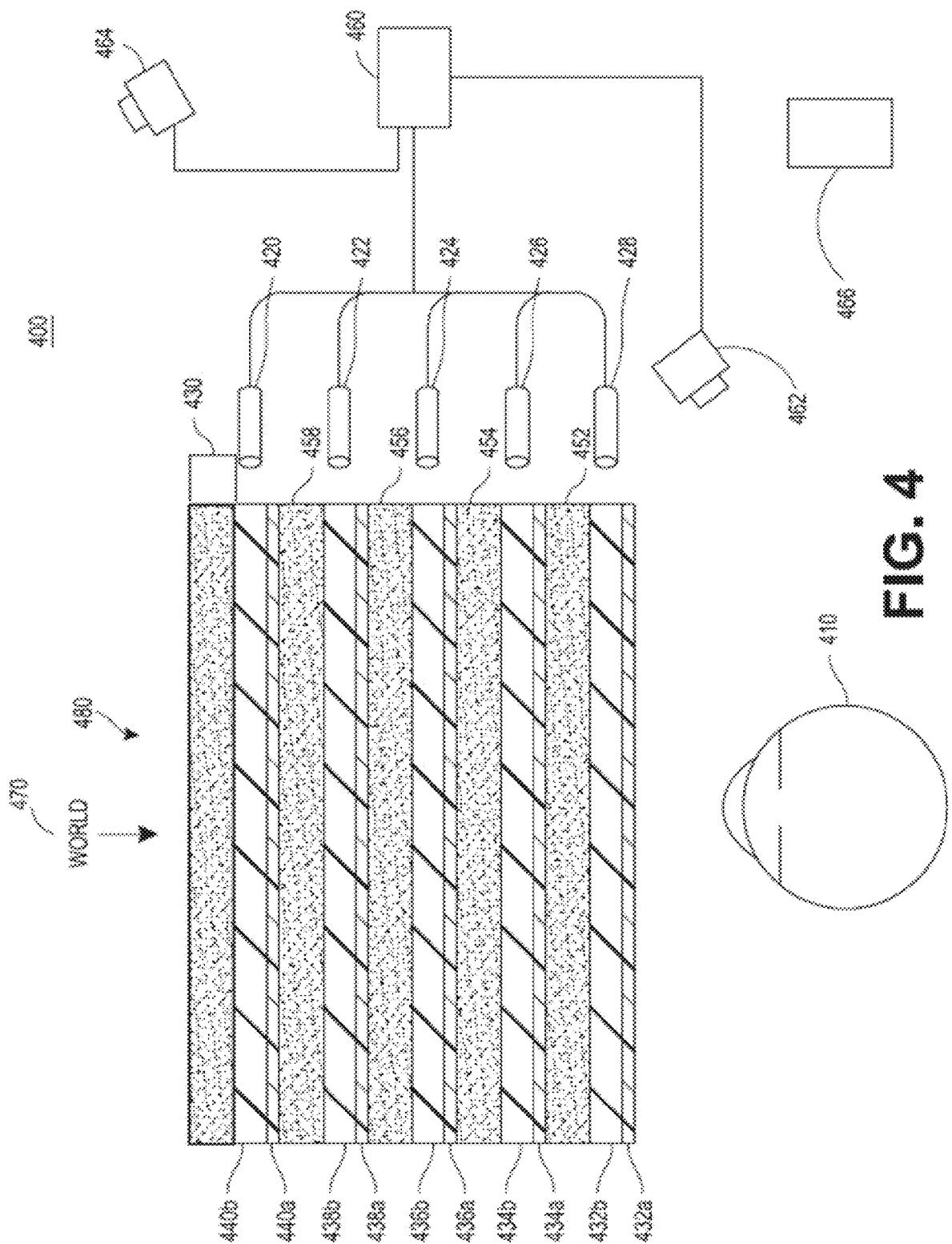
FIG. 4 schematically illustrates an example of a waveguide stack of a wearable device for outputting image information to a user.

FIG. 4 illustrates an example of a waveguide stack for outputting image information to a user. A wearable system 400 includes a stack of waveguides, or stacked waveguide assembly 480 that may be utilized to provide three-dimensional perception to the eye/brain using a plurality of waveguides 432b, 434b, 436b, 438b, 4400b. In some embodiments, the wearable system 400 may correspond to wearable system 200 of FIG. 2, with FIG. 4 schematically showing some parts of that wearable system 200 in greater detail. For example, in some embodiments, the waveguide assembly 480 may be integrated into the display 220 of FIG. 2.

With continued reference to FIG. 4, the waveguide assembly 480 may also include a plurality of features 458, 456, 454, 452 between the waveguides. In some embodiments, the features 458, 456, 454, 452 may be lenses. In other embodiments, the features 458, 456, 454, 452 may not be lenses. Rather, they may simply be spacers (e.g., cladding layers or structures for forming air gaps).

The waveguides 432b, 434b, 436b, 438b, 440b or the plurality of lenses 458, 456, 454, 452 may be configured to send image information to the eye with various levels of wavefront curvature or light ray divergence. Each waveguide level may be associated with a particular depth plane and may be configured to output image information corresponding to that depth plane. Image injection devices 420, 422, 424, 426, 428 may be utilized to inject image information into the waveguides 440b, 438b, 436b, 434b, 432b, each of which may be configured to distribute incoming light across each respective waveguide, for output toward the eye 410. Light exits an output surface of the image injection devices 420, 422, 424, 426, 428 and is injected into a corresponding input edge of the waveguides 440b, 438b, 436b, 434b, 432b. In some embodiments, a single beam of light (e.g., a collimated beam) may be injected into each waveguide to output an entire field of cloned collimated beams that are directed toward the eye 410 at particular angles (and amounts of divergence) corresponding to the depth plane associated with a particular waveguide.

In some embodiments, the image injection devices 420, 422, 424, 426, 428 are discrete displays that each produce image information for injection into a corresponding waveguide 440b, 438b, 436b, 434b, 432b, respectively. In some other embodiments, the image injection devices 420, 422, 424, 426, 428 are the output ends of a single multiplexed display which may, e.g., pipe image information via one or more optical conduits (such as fiber optic cables) to each of the image injection devices 420, 422, 424, 426, 428.

A controller 460 controls the operation of the stacked waveguide assembly 480 and the image injection devices 420, 422, 424, 426, 428. The controller 460 includes programming (e.g., instructions in a non-transitory computer-readable medium) that regulates the timing and provision of image information to the waveguides 440b, 438b, 436b, 434b, 432b. In some embodiments, the controller 460 may be a single integral device, or a distributed system connected by wired or wireless communication channels. The controller 460 may be part of the processing modules 260 or 270 (illustrated in FIG. 2) in some embodiments.

The waveguides 440b, 438b, 436b, 434b, 432b may be configured to propagate light within each respective waveguide by total internal reflection (TIR). The waveguides 440b, 438b, 436b, 434b, 432b may each be planar or have another shape (e.g., curved), with major top and bottom surfaces and edges extending between those major top and bottom surfaces. In the illustrated configuration, the waveguides 440b, 438b, 436b, 434b, 432b may each include light extracting optical elements 440a, 438a, 436a, 434a, 432a that are configured to extract light out of a waveguide by redirecting the light, propagating within each respective waveguide, out of the waveguide to output image information to the eye 410. Extracted light may also be referred to as outcoupled light, and light extracting optical elements may also be referred to as outcoupling optical elements. An extracted beam of light is outputted by the waveguide at locations at which the light propagating in the waveguide strikes a light redirecting element. The light extracting optical elements (440a, 438a, 436a, 434a, 432a) may, for example, be reflective or diffractive optical features. While illustrated disposed at the bottom major surfaces of the waveguides 440b, 438b, 436b, 434b, 432b for case of description and drawing clarity, in some embodiments, the light extracting optical elements 440a, 438a, 436a, 434a, 432a may be disposed at the top or bottom major surfaces, or may be disposed directly in the volume of the waveguides 440b, 438b, 436b, 434b, 432b. In some embodiments, the light extracting optical elements 440a, 438a, 436a, 434a, 432a may be formed in a layer of material that is attached to a transparent substrate to form the waveguides 440b, 438b, 436b, 434b, 432b. In some other embodiments, the waveguides 440b, 438b, 436b, 434b, 432b may be a monolithic piece of material and the light extracting optical elements 440a, 438a, 436a, 434a, 432a may be formed on a surface or in the interior of that piece of material.

With continued reference to FIG. 4, as discussed herein, each waveguide 440b, 438b, 436b, 434b, 432b is configured to output light to form an image corresponding to a particular depth plane. For example, the waveguide 432b nearest the eye may be configured to deliver collimated light, as injected into such waveguide 432b, to the eye 410. The collimated light may be representative of the optical infinity focal plane. The next waveguide up 434b may be configured to send out collimated light which passes through the first lens 452 (e.g., a negative lens) before it can reach the eye 410. First lens 452 may be configured to create a slight convex wavefront curvature so that the eye/brain interprets light coming from that next waveguide up 434b as coming from a first focal plane closer inward toward the eye 410 from optical infinity. Similarly, the third up waveguide 436b passes its output light through both the first lens 452 and second lens 454 before reaching the eye 410. The combined optical power of the first and second lenses 452 and 454 may be configured to create another incremental amount of wavefront curvature so that the eye/brain interprets light coming from the third waveguide 436b as coming from a second focal plane that is even closer inward toward the person from optical infinity than was light from the next waveguide up 434b.

The other waveguide layers (e.g., waveguides 438b, 440b) and lenses (e.g., lenses 456, 458) are similarly configured, with the highest waveguide 440b in the stack sending its output through all of the lenses between it and the eye for an aggregate focal power representative of the closest focal plane to the person. To compensate for the stack of lenses 458, 456, 454, 452 when viewing/interpreting light coming from the world 470 on the other side of the stacked waveguide assembly 480, a compensating lens layer 430 may be disposed at the top of the stack to compensate for the aggregate power of the lens stack 458, 456, 454, 452 below. (Compensating lens layer 430 and the stacked waveguide assembly 480 as a whole may be configured such that light coming from the world 470 is conveyed to the eye 410 at substantially the same level of divergence (or collimation) as the light had when it was initially received by the stacked waveguide assembly 480.) Such a configuration provides as many perceived focal planes as there are available waveguide/lens pairings. Both the light extracting optical elements of the waveguides and the focusing aspects of the lenses may be static (e.g., not dynamic or electro-active). In some alternative embodiments, either or both may be dynamic using electro-active features.

With continued reference to FIG. 4, the light extracting optical elements 440*a*, 438*a*, 436*a*, 434*a*, 432*a* may be configured to both redirect light out of their respective waveguides and to output this light with the appropriate amount of divergence or collimation for a particular depth plane associated with the waveguide. As a result, waveguides having different associated depth planes may have different configurations of light extracting optical elements, which output light with a different amount of divergence depending on the associated depth plane. In some embodiments, as discussed herein, the light extracting optical elements 440*a*, 438*a*, 436*a*, 434*a*, 432*a* may be volumetric or surface features, which may be configured to output light at specific angles. For example, the light extracting optical elements 440*a*, 438*a*, 436*a*, 434*a*, 432*a* may be volume holograms, surface holograms, and/or diffraction gratings. Light extracting optical elements, such as diffraction gratings, are described in U.S. Patent Publication No. 2015/0178939, published Jun. 25, 2015, which is incorporated by reference herein in its entirety.

In some embodiments, the light extracting optical elements 440*a*, 438*a*, 436*a*, 434*a*, 432*a* are diffractive features that form a diffraction pattern, or "diffractive optical element" (also referred to herein as a "DOE"). Preferably, the DOE has a relatively low diffraction efficiency so that only a portion of the light of the beam is deflected away toward the eye 410 with each intersection of the DOE, while the rest continues to move through a waveguide via total internal reflection. The light carrying the image information can thus be divided into a number of related exit beams that exit the waveguide at a multiplicity of locations and the result is a fairly uniform pattern of exit emission toward the eye 304 for this particular collimated beam bouncing around within a waveguide.

In some embodiments, one or more DOEs may be switchable between "on" state in which they actively diffract, and "off" state in which they do not significantly diffract. For instance, a switchable DOE may comprise a layer of polymer dispersed liquid crystal, in which microdroplets comprise a diffraction pattern in a host medium, and the refractive index of the microdroplets can be switched to substantially match the refractive index of the host material (in which case the pattern does not appreciably diffract incident light) or the microdroplet can be switched to an index that does not match that of the host medium (in which case the pattern actively diffracts incident light).

In some embodiments, the number and distribution of depth planes or depth of field may be varied dynamically based on the pupil sizes or orientations of the eyes of the viewer. Depth of field may change inversely with a viewer's pupil size. As a result, as the sizes of the pupils of the viewer's eyes decrease, the depth of field increases such that one plane that is not discernible because the location of that plane is beyond the depth of focus of the eye may become discernible and appear more in focus with reduction of pupil size and commensurate with the increase in depth of field. Likewise, the number of spaced apart depth planes used to present different images to the viewer may be decreased with the decreased pupil size. For example, a viewer may not be able to clearly perceive the details of both a first depth plane and a second depth plane at one pupil size without adjusting the accommodation of the eye away from one depth plane and to the other depth plane. These two depth planes may, however, be sufficiently in focus at the same time to the user at another pupil size without changing accommodation.

In some embodiments, the display system may vary the number of waveguides receiving image information based upon determinations of pupil size or orientation, or upon receiving electrical signals indicative of particular pupil size or orientation. For example, if the user's eyes are unable to distinguish between two depth planes associated with two waveguides, then the controller 460 (which may be an embodiment of the local processing and data module 260) can be configured or programmed to cease providing image information to one of these waveguides. Advantageously, this may reduce the processing burden on the system, thereby increasing the responsiveness of the system. In embodiments in which the DOEs for a waveguide are switchable between the on and off states, the DOEs may be switched to the off state when the waveguide does receive image information.

In some embodiments, it may be desirable to have an exit beam meet the condition of having a diameter that is less than the diameter of the eye of a viewer. However, meeting this condition may be challenging in view of the variability in size of the viewer's pupils. In some embodiments, this condition is met over a wide range of pupil sizes by varying the size of the exit beam in response to determinations of the size of the viewer's pupil. For example, as the pupil size decreases, the size of the exit beam may also decrease. In some embodiments, the exit beam size may be varied using a variable aperture.

The wearable system 400 can include an outward-facing imaging system 464 (e.g., a digital camera) that images a portion of the world 470. This portion of the world 470 may be referred to as the field of view (FOV) of a world camera and the imaging system 464 is sometimes referred to as an FOV camera. The FOV of the world camera may or may not be the same as the FOV of a viewer 210 which encompasses a portion of the world 470 the viewer 210 perceives at a given time. For example, in some situations, the FOV of the world camera may be larger than the viewer 210 of the viewer 210 of the wearable system 400. The entire region available for viewing or imaging by a viewer may be referred to as the field of regard (FOR). The FOR may include $4\pi$ steradians of solid angle surrounding the wearable system 400 because the wearer can move his body, head, or eyes to perceive substantially any direction in space. In other contexts, the wearer's movements may be more constricted, and accordingly the wearer's FOR may subtend a smaller solid angle. Images obtained from the outward-facing imaging system 464 can be used to track gestures made by the user (e.g., hand or finger gestures), detect objects in the world 470 in front of the user, and so forth.

The wearable system 400 can include an audio sensor 232, e.g., a microphone, to capture ambient sound. As described above, in some embodiments, one or more other audio sensors can be positioned to provide stereo sound reception useful to the determination of location of a speech source. The audio sensor 232 can comprise a directional microphone, as another example, which can also provide such useful directional information as to where the audio source is located. The wearable system 400 can use information from both the outward-facing imaging system 464 and the audio sensor 230 in locating a source of speech, or to determine an active speaker at a particular moment in time, etc. For example, the wearable system 400 can use the voice recognition alone or in combination with a reflected image of the speaker (e.g., as seen in a mirror) to determine the identity of the speaker. As another example, the wearable system 400 can determine a position of the speaker in an environment based on sound acquired from directional microphones. The wearable system 400 can parse the sound coming from the speaker's position with speech recognition algorithms to determine the content of the speech and use voice recognition techniques to determine the identity (e.g., name or other demographic information) of the speaker.

The wearable system 400 can also include an inward-facing imaging system 466 (e.g., a digital camera), which observes the movements of the user, such as the eye movements and the facial movements. The inward-facing imaging system 466 may be used to capture images of the eye 410 to determine the size and/or orientation of the pupil of the eye 304. The inward-facing imaging system 466 can be used to obtain images for use in determining the direction the user is looking (e.g., eye pose) or for biometric identification of the user (e.g., via iris identification). In some embodiments, at least one camera may be utilized for each eye, to separately determine the pupil size or eye pose of each eye independently, thereby allowing the presentation of image information to each eye to be dynamically tailored to that eye. In some other embodiments, the pupil diameter or orientation of only a single eye 410 (e.g., using only a single camera per pair of eyes) is determined and assumed to be similar for both eyes of the user. The images obtained by the inward-facing imaging system 466 may be analyzed to determine the user's eye pose or mood, which can be used by the wearable system 400 to decide which audio or visual content should be presented to the user. The wearable system 400 may also determine head pose (e.g., head position or head orientation) using sensors such as IMUs, accelerometers, gyroscopes, etc.

The wearable system 400 can include a user input device 466 by which the user can input commands to the controller 460 to interact with the wearable system 400. For example, the user input device 466 can include a trackpad, a touchscreen, a joystick, a multiple degree-of-freedom (DOF) controller, a capacitive sensing device, a game controller, a keyboard, a mouse, a directional pad (D-pad), a wand, a haptic device, a totem (e.g., functioning as a virtual user input device), and so forth. A multi-DOF controller can sense user input in some or all possible translations (e.g., left/right, forward/backward, or up/down) or rotations (e.g., yaw, pitch, or roll) of the controller. A multi-DOF controller which supports the translation movements may be referred to as a 3DOF while a multi-DOF controller which supports the translations and rotations may be referred to as 6DOF. In some cases, the user may use a finger (e.g., a thumb) to press or swipe on a touch-sensitive input device to provide input to the wearable system 400 (e.g., to provide user input to a user interface provided by the wearable system 400). The user input device 466 may be held by the user's hand during the use of the wearable system 400. The user input device 466 can be in wired or wireless communication with the wearable system 400.

D. Other Components of the Wearable System

In many implementations, the wearable system may include other components in addition or in alternative to the components of the wearable system described above. The wearable system may, for example, include one or more haptic devices or components. The haptic devices or components may be operable to provide a tactile sensation to a user. For example, the haptic devices or components may provide a tactile sensation of pressure or texture when touching virtual content (e.g., virtual objects, virtual tools, other virtual constructs). The tactile sensation may replicate a feel of a physical object which a virtual object represents, or may replicate a feel of an imagined object or character (e.g., a dragon) which the virtual content represents. In some implementations, haptic devices or components may be worn by the user (e.g., a user wearable glove). In some implementations, haptic devices or components may be held by the user.

The wearable system may, for example, include one or more physical objects which are manipulatable by the user to allow input or interaction with the wearable system. These physical objects may be referred to herein as totems. Some totems may take the form of inanimate objects, such as for example, a piece of metal or plastic, a wall, a surface of table. In certain implementations, the totems may not actually have any physical input structures (e.g., keys, triggers, joystick, trackball, rocker switch). Instead, the totem may simply provide a physical surface, and the wearable system may render a user interface so as to appear to a user to be on one or more surfaces of the totem. For example, the wearable system may render an image of a computer keyboard and trackpad to appear to reside on one or more surfaces of a totem. For example, the wearable system may render a virtual computer keyboard and virtual trackpad to appear on a surface of a thin rectangular plate of aluminum which serves as a totem. The rectangular plate does not itself have any physical keys or trackpad or sensors. However, the wearable system may detect user manipulation or interaction or touches with the rectangular plate as selections or inputs made via the virtual keyboard or virtual trackpad. The user input device 466 (shown in FIG. 4) may be an embodiment of a totem, which may include a trackpad, a touchpad, a trigger, a joystick, a trackball, a rocker or virtual switch, a mouse, a keyboard, a multi-degree-of-freedom controller, or another physical input device. A user may use the totem, alone or in combination with poses, to interact with the wearable system or other users.

Examples of haptic devices and totems usable with the wearable devices, HMD, and display systems of the present disclosure are described in U.S. Patent Publication No. 2015/0016777, which is incorporated by reference herein in its entirety.

E. Example of an Eye Image

Figures 5, 5A:
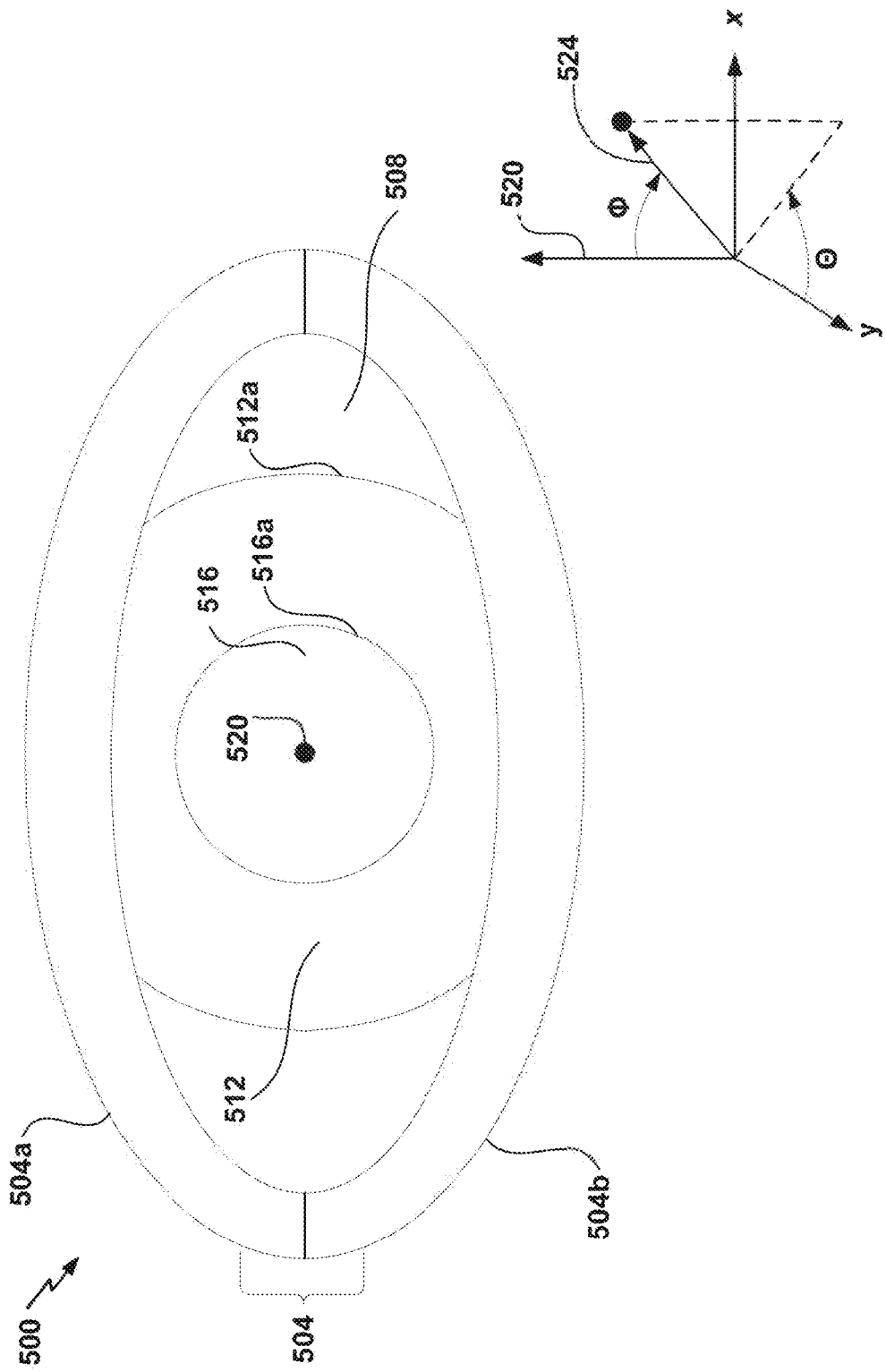
FIG. 5 schematically illustrates an example of an eye.
FIG. 5A schematically illustrates an example coordinate system for determining an eye pose of an eye

FIG. 5 illustrates an image of an eye 500 with eyelids 504, sclera 508 (the "white" of the eye), iris 512, and pupil 516. Curve 516*a* shows the pupillary boundary between the pupil 516 and the iris 512, and curve 512a shows the limbic boundary between the iris 512 and the sclera 508. The eyelids 504 include an upper eyelid 504a and a lower eyelid 504b. The eye 500 is illustrated in a natural resting pose (e.g., in which the user's face and gaze are both oriented as they would be toward a distant object directly ahead of the user). The natural resting pose of the eye 500 can be indicated by a natural resting direction 520, which is a direction orthogonal to the surface of the eye 500 when in the natural resting pose (e.g., directly out of the plane for the eye 500 shown in FIG. 5) and in this example, centered within the pupil 516.

As the eye 500 moves to look toward different objects, the eye pose will change relative to the natural resting direction 520. The current eye pose can be determined with reference to an eye pose direction 524, which is a direction orthogonal to the surface of the eye (and centered in within the pupil 516) but oriented toward the object at which the eye is currently directed. With reference to an example coordinate system shown in FIG. 5A, the pose of the eye 500 can be expressed as two angular parameters indicating an azimuthal deflection and a zenithal deflection of the eye pose direction 524 of the eye, both relative to the natural resting direction 520 of the eye. For purposes of illustration, these angular parameters can be represented as θ (azimuthal deflection, determined from a fiducial azimuth) and ¢ (zenithal deflection, sometimes also referred to as a polar deflection). In some implementations, angular roll of the eye around the eye pose direction 524 can be included in the determination of eye pose, and angular roll can be included in the following analysis. In other implementations, other techniques for determining the eye pose can be used, for example, a pitch, yaw, and optionally roll system.

An eye image can be obtained from a video using any appropriate process, for example, using a video processing algorithm that can extract an image from one or more sequential frames. The pose of the eye can be determined from the eye image using a variety of eye-tracking techniques. For example, an eye pose can be determined by considering the lensing effects of the cornea on light sources that are provided. Any suitable eye tracking technique can be used for determining eye pose.

F. Example of an Eye Tracking System

Figure 6:
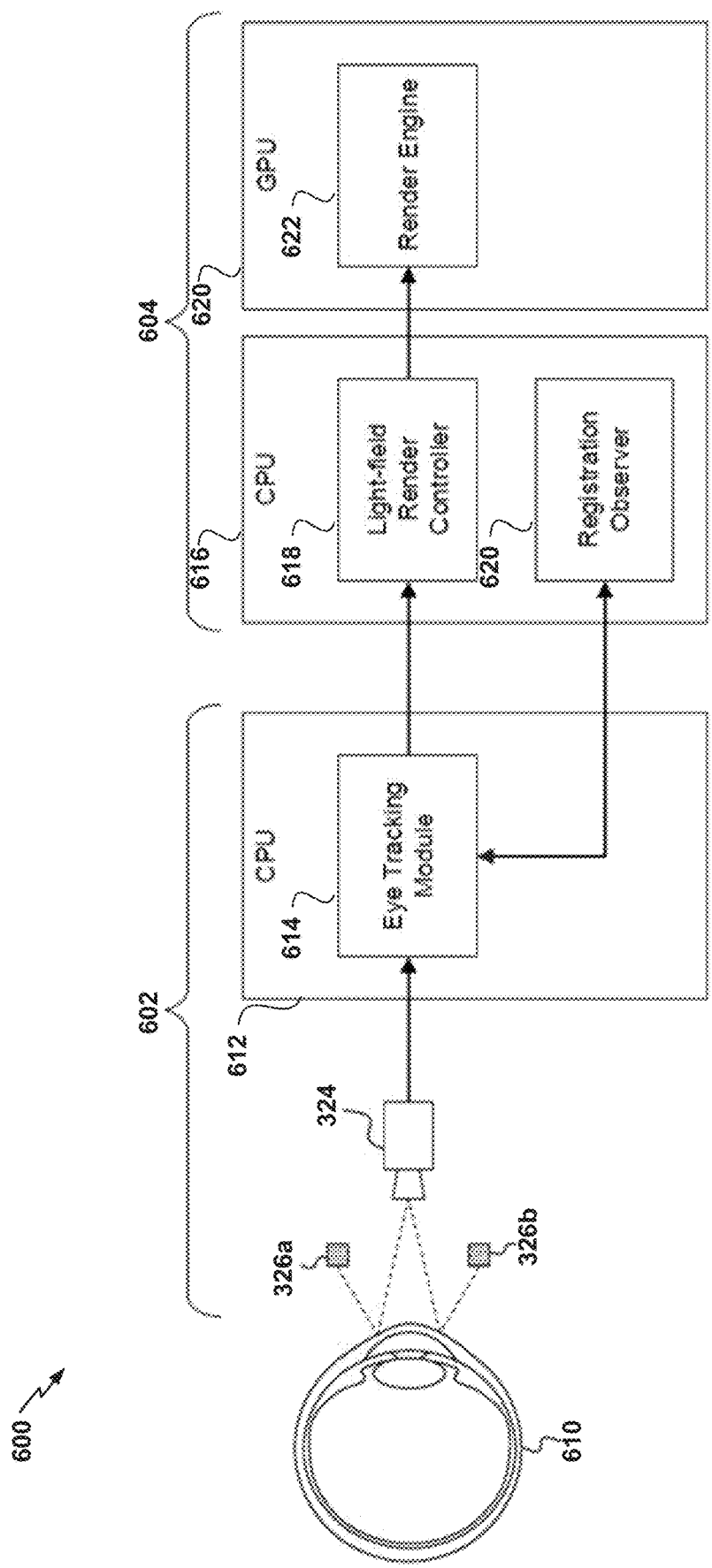
FIG. 6 is a schematic diagram of a wearable system that includes an eye tracking system.

FIG. 6 illustrates a schematic diagram of a wearable system 600 that includes an eye tracking system. The wearable system 600 may, in at least some embodiments, include components located in a head-mounted unit 602 and components located in a non-head-mounted unit 604. Non-head mounted unit 604 may be, as examples, a belt-mounted component, a hand-held component, a component in a backpack, a remote component, etc. Incorporating some of the components of the wearable system 600 in non-head-mounted unit 604 may help to reduce the size, weight, complexity, and cost of the head-mounted unit 602. In some implementations, some or all of the functionality described as being performed by one or more components of head-mounted unit 602 and/or non-head mounted 604 may be provided by way of one or more components included elsewhere in the wearable system 600. For example, some or all of the functionality described below in association with a CPU 612 of head-mounted unit 602 may be provided by way of a CPU 616 of non-head mounted unit 604, and vice versa. In some examples, some or all of such functionality may be provided by way of peripheral devices of wearable system 600. Furthermore, in some implementations, some or all of such functionality may be provided by way of one or more cloud computing devices or other remotely-located computing devices in a manner similar to that which has been described above with reference to FIG. 2.

As shown in FIG. 6, wearable system 600 can include an eye tracking system including a camera 324 that captures images of a user's eye 610. If desired, the eye tracking system may also include light sources 326a and 326b (such as light emitting diodes "LED"s). The light sources 326a and 326b may generate glints (e.g., reflections off of the user's eyes that appear in images of the eye captured by camera 324). The positions of the light sources 326a and 326b relative to the camera 324 may be known and, as a consequence, the positions of the glints within images captured by camera 324 may be used in tracking the user's eyes (as will be discussed in more detail below in connection with FIG. 7). In at least one embodiment, there may be one light source 326 and one camera 324 associated with a single one of the user's eyes 610. In another embodiment, there may be one light source 326 and one camera 324 associated with each of a user's eyes. 610. In yet other embodiments, there may be one or more cameras 324 and one or more light sources 326 associated with one or each of a user's eyes 610. As a specific example, there may be two light sources 326a and 326b and one or more cameras 324 associated with each of a user's eyes 610. As another example, there may be three or more light sources such as light sources 326a and 326b and one or more cameras 324 associated with each of a user's eyes 610. In some implementations described herein, two or more cameras may be employed for imaging a given eye.

Eye tracking module 614 may receive images from eye tracking camera(s) 324 and may analyze the images to extract various pieces of information. As examples, the eye tracking module 614 may detect the user's eye poses, a three-dimensional position of the user's eye relative to the eye tracking camera 324 (and to the head-mounted unit 602), the direction one or both of the user's eyes 610 are focused on, the user's vergence depth (e.g., the depth from the user at which the user is focusing on), the positions of the user's pupils, the positions of the user's cornea and/or cornea sphere, the center of rotation of one or each of the user's eyes, and the center of perspective of one or each of the user's eyes or any combination thereof. The eye tracking module 614 may extract such information using techniques described below in connection with FIGS. 7-11. As shown in FIG. 6, eye tracking module 614 may be a software module implemented using a CPU 612 in a head-mounted unit 602.

Although one camera 324 is shown in FIG. 6 imaging an eye, in some implementation such as discussed herein a plurality of cameras may image an eye and be used for measurements such as corneal center and/or center of rotation measurements or otherwise used for eye tracking or other purposes.

Data from eye tracking module 614 may be provided to other components in the wearable system. As example, such data may be transmitted to components in a non-head-mounted unit 604 such as CPU 616 including software modules for a light-field render controller 618 and a registration observer 620.

Render controller 618 may use information from eye tracking module 614 to adjust images displayed to the user by render engine 622 (e.g., a render engine that may be a software module in GPU 620 and that may provide images to display 220). As an example, the render controller 618 may adjust images displayed to the user based on the user's center of rotation or center of perspective. In particular, the render controller 618 may use information on the user's center of perspective to simulate a render camera (e.g., to simulate collecting images from the user's perspective) and may adjust images displayed to the user based on the simulated render camera.

A "render camera," which is sometimes also referred to as a "pinhole perspective camera" (or simply "perspective camera") or "virtual pinhole camera" (or simply "virtual camera"), is a simulated camera for use in rendering virtual image content possibly from a database of objects in a virtual world. The objects may have locations and orientations relative to the user or wearer and possibly relative to real objects in the environment surrounding the user or wearer. In other words, the render camera may represent a perspective within render space from which the user or wearer is to view 3D virtual contents of the render space (e.g., virtual objects). The render camera may be managed by a render engine to render virtual images based on the database of virtual objects to be presented to said eye. The virtual images may be rendered as if taken from the perspective the user or wearer. For example, the virtual images may be rendered as if captured by a pinhole camera (corresponding to the "render camera") having a specific set of intrinsic parameters (e.g., focal length, camera pixel size, principal point coordinates, skew/distortion parameters, etc.), and a specific set of extrinsic parameters (e.g., translational components and rotational components relative to the virtual world). The virtual images are taken from the perspective of such a camera having a position and orientation of the render camera (e.g., extrinsic parameters of the render camera). It follows that the system may define and/or adjust intrinsic and extrinsic render camera parameters. For example, the system may define a particular set of extrinsic render camera parameters such that virtual images may be rendered as if captured from the perspective of a camera having a specific location with respect to the user's or wearer's eye so as to provide images that appear to be from the perspective of the user or wearer. The system may later dynamically adjust extrinsic render camera parameters on-the-fly so as to maintain registration with said specific location. Similarly, intrinsic render camera parameters may be defined and dynamically adjusted over time. In some implementations, the images are rendered as if captured from the perspective of a camera having an aperture (e.g., pinhole) at a specific location with respect to the user's or wearer's eye (such as the center of perspective or center of rotation, or elsewhere).

In some embodiments, the system may create or dynamically reposition and/or reorient one render camera for the user's left eye, and another render camera for the user's right eye, as the user's eyes are physically separated from one another and thus consistently positioned at different locations. It follows that, in at least some implementations, virtual content rendered from the perspective of a render camera associated with the viewer's left eye may be presented to the user through an eyepiece on the left side of a head-mounted display (e.g., head-mounted unit 602), and that virtual content rendered from the perspective of a render camera associated with the user's right eye may be presented to the user through an eyepiece on the right side of such a head-mounted display. Further details discussing the creation, adjustment, and use of render cameras in rendering processes are provided in U.S. patent application Ser. No. 15/274,823, entitled "METHODS AND SYSTEMS FOR DETECTING AND COMBINING STRUCTURAL FEA- TURES IN 3D RECONSTRUCTION," which is expressly incorporated herein by reference in its entirety for all purposes.

In some examples, one or more modules (or components) of the system 600 (e.g., light-field render controller 618, render engine 620, etc.) may determine the position and orientation of the render camera within render space based on the position and orientation of the user's head and eyes (e.g., as determined based on head pose and eye tracking data, respectively). That is, the system 600 may effectively map the position and orientation of the user's head and eyes to particular locations and angular positions within a 3D virtual environment, place and orient render cameras at the particular locations and angular positions within the 3D virtual environment, and render virtual content for the user as it would be captured by the render camera. Further details discussing real world to virtual world mapping processes are provided in U.S. patent application Ser. No. 15/296,869, entitled "SELECTING VIRTUAL OBJECTS IN A THREE-DIMENSIONAL SPACE," which is expressly incorporated herein by reference in its entirety for all purposes. As an example, the render controller 618 may adjust the depths at which images are displayed by selecting which depth plane (or depth planes) are utilized at any given time to display the images. In some implementations, such a depth plane switch may be carried out through an adjustment of one or more intrinsic render camera parameters. For example, the light-field render controller 618 may adjust the focal lengths of render cameras when executing a depth plane switch or adjustment. As described in further detail below, depth planes may be switched based on the user's determined vergence or fixation depth.

Registration observer 620 may use information from eye tracking module 614 to identify whether the head-mounted unit 602 is properly positioned on a user's head. As an example, the eye tracking module 614 may provide eye location information, such as the positions of the centers of rotation of the user's eyes, indicative of the three-dimensional position of the user's eyes relative to camera 324 and head-mounted unit 602 and the eye tracking module 614 may use the location information to determine if display 220 is properly aligned in the user's field of view, or if the head-mounted unit 602 (or headset) has slipped or is otherwise misaligned with the user's eyes. As examples, the registration observer 620 may be able to determine if the head-mounted unit 602 has slipped down the user's nose bridge, thus moving display 220 away and down from the user's eyes (which may be undesirable), if the head-mounted unit 602 has been moved up the user's nose bridge, thus moving display 220 closer and up from the user's eyes, if the head-mounted unit 602 has been shifted left or right relative the user's nose bridge, if the head-mounted unit 602 has been lifted above the user's nose bridge, or if the head-mounted unit 602 has been moved in these or other ways away from a desired position or range of positions. In general, registration observer 620 may be able to determine if head-mounted unit 602, in general, and displays 220, in particular, are properly positioned in front of the user's eyes. In other words, the registration observer 620 may determine if a left display in display system 220 is appropriately aligned with the user's left eye and a right display in display system 220 is appropriately aligned with the user's right eye. The registration observer 620 may determine if the head-mounted unit 602 is properly positioned by determining if the head-mounted unit 602 is positioned and oriented within a desired range of positions and/or orientations relative to the user's eyes.

In at least some embodiments, registration observer 620 may generate user feedback in the form of alerts, messages, or other content. Such feedback may be provided to the user to inform the user of any misalignment of the head-mounted unit 602, along with optional feedback on how to correct the misalignment (such as a suggestion to adjust the head-mounted unit 602 in a particular manner).

Example registration observation and feedback techniques, which may be utilized by registration observer 620, are described in U.S. patent application Ser. No. 15/717,747, filed Sep. 27, 2017 and U.S. Provisional Patent Application No. 62/644,321, filed Mar. 16, 2018, both of which are incorporated by reference herein in their entirety.

G. Example of an Eye Tracking Module

Figure 7A:
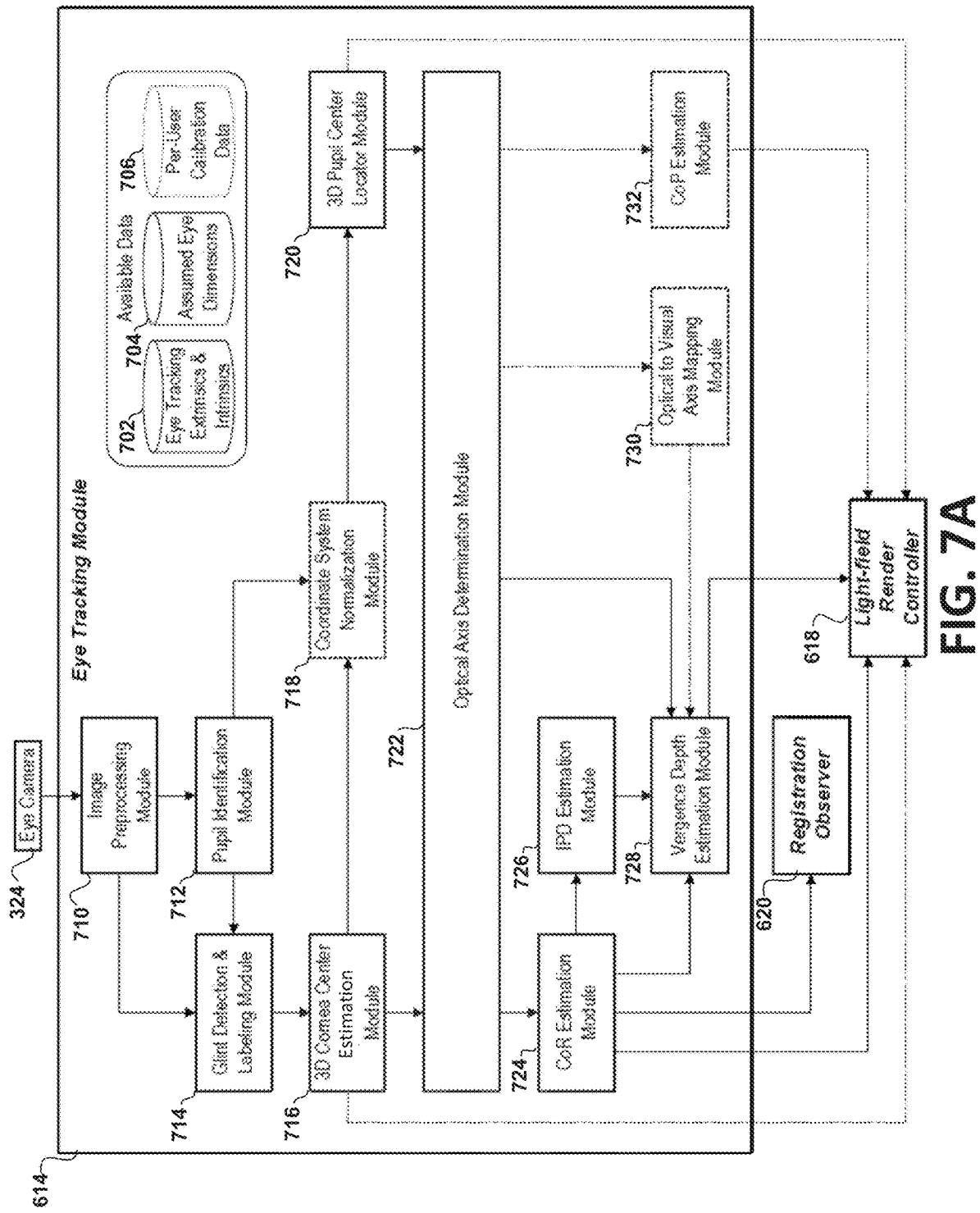
FIG. 7A is a block diagram of an example eye tracking module that may be used in a wearable system that includes an eye tracking system.

A detailed block diagram of an example eye tracking module 614 is shown in FIG. 7A. As shown in FIG. 7A, eye tracking module 614 may include a variety of different submodules, may provide a variety of different outputs, and may utilize a variety of available data in tracking the user's eyes. As examples, eye tracking module 614 may utilize available data including eye tracking extrinsics and intrinsics, such as the geometric arrangements of the eye tracking camera 324 relative to the light sources 326 and the head-mounted-unit 602; assumed eye dimensions 704 such as a typical distance of approximately between a user's center of cornea curvature and the average center of rotation of the user's eye (which may be, e.g., 5.7 or 5.7 mm #1 mm or approximately thereto) or a distance between a user's center of cornea curvature and the center of pupil (which may be, e.g., 4.7 or 4.7 mm+1 mm or approximately thereto), or typical distances between a user's center of rotation and center of perspective; and per-user calibration data 706 such as a particular user's interpupillary distance. Additional examples of extrinsics, intrinsics, and other information that may be employed by the eye tracking module 614 are described in U.S. patent application Ser. No. 15/497,726, filed Apr. 26, 2017, which is incorporated by reference herein in its entirety.

Image preprocessing module 710 may receive images from an eye camera such as eye camera 324 and may perform one or more preprocessing (e.g., conditioning) operations on the received images. As examples, image preprocessing module 710 may apply a Gaussian blur to the images, may down sample the images to a lower resolution, may applying an unsharp mask, may apply an edge sharpening algorithm, or may apply other suitable filters that assist with the later detection, localization, and labelling of glints, a pupil, or other features in the images from eye camera 324. The image preprocessing module 710 may apply a low-pass filter or a morphological filter such as an open filter, which can remove high-frequency noise such as from the pupillary boundary 516a (see FIG. 5), thereby removing noise that can hinder pupil and glint determination. The image preprocessing module 710 may output preprocessed images to the pupil identification module 712 and to the glint detection and labeling module 714.

Pupil identification module 712 may receive preprocessed images from the image preprocessing module 710 and may identify regions of those images that include the user's pupil. The pupil identification module 712 may, in some embodiments, determine the coordinates of the position, or coordinates, of the center, or centroid, of the user's pupil in the eye tracking images from camera 324. In at least some embodiments, pupil identification module 712 may identify contours in eye tracking images (e.g., contours of pupil iris boundary), identify contour moments (e.g., centers of mass), apply a starburst pupil detection and/or a canny edge detection algorithm, reject outliers based on intensity values, identify sub-pixel boundary points, correct for eye-camera distortion (e.g., distortion in images captured by eye camera 324), apply a random sample consensus (RANSAC) iterative algorithm to fit an ellipse to boundaries in the eye tracking images, apply a tracking filter to the images, and identify sub-pixel image coordinates of the user's pupil centroid. The pupil identification module 712 may output pupil identification data (which may indicate which regions of the preprocessing images module 712 identified as showing the user's pupil) to glint detection and labeling module 714. The pupil identification module 712 may provide the 2D coordinates of the user's pupil (e.g., the 2D coordinates of the centroid of the user's pupil) within each eye tracking image to glint detection module 714. In at least some embodiments, pupil identification module 712 may also provide pupil identification data of the same sort to coordinate system normalization module 718.

Pupil detection techniques, which may be utilized by pupil identification module 712, are described in U.S. Patent Publication No. 2017/0053165, published Feb. 23, 2017 and in U.S. Patent Publication No. 2017/0053166, published Feb. 23, 2017, each of which is incorporated by reference herein in its entirety.

Glint detection and labeling module 714 may receive preprocessed images from module 710 and pupil identification data from module 712. Glint detection module 714 may use this data to detect and/or identify glints (e.g., reflections off of the user's eye of the light from light sources 326) within regions of the preprocessed images that show the user's pupil. As an example, the glint detection module 714 may search for bright regions within the eye tracking image, sometimes referred to herein as "blobs" or local intensity maxima, that are in the vicinity of the user's pupil. In at least some embodiments, the glint detection module 714 may rescale (e.g., enlarge) the pupil ellipse to encompass additional glints. The glint detection module 714 may filter glints by size and/or by intensity. The glint detection module 714 may also determine the 2D positions of each of the glints within the eye tracking image. In at least some examples, the glint detection module 714 may determine the 2D positions of the glints relative to the user's pupil, which may also be referred to as the pupil-glint vectors. Glint detection and labeling module 714 may label the glints and output the preprocessing images with labeled glints to the 3D cornea center estimation module 716. Glint detection and labeling module 714 may also pass along data such as preprocessed images from module 710 and pupil identification data from module 712. In some implementations, the glint detection and labeling module 714 may determine which light source (e.g., from among a plurality of light sources of the system including infrared light sources 326a and 326b) produced each identified glint. In these examples, the glint detection and labeling module 714 may label the glints with information identifying the associated light source and output the preprocessing images with labeled glints to the 3D cornea center estimation module 716.

Pupil and glint detection, as performed by modules such as modules 712 and 714, can use any suitable techniques. As examples, edge detection can be applied to the eye image to identify glints and pupils. Edge detection can be applied by various edge detectors, edge detection algorithms, or filters. For example, a Canny Edge detector can be applied to the image to detect edges such as in lines of the image. Edges may include points located along a line that correspond to the local maximum derivative. For example, the pupillary boundary 516a (see FIG. 5) can be located using a Canny edge detector. With the location of the pupil determined, various image processing techniques can be used to detect the "pose" of the pupil 116. Determining an eye pose of an eye image can also be referred to as detecting an eye pose of the eye image. The pose can also be referred to as the gaze, pointing direction, or the orientation of the eye. For example, the pupil may be looking leftwards towards an object, and the pose of the pupil could be classified as a leftwards pose. Other methods can be used to detect the location of the pupil or glints. For example, a concentric ring can be located in an eye image using a Canny Edge detector. As another example, an integro-differential operator can be used to find the pupillary or limbus boundaries of the iris. For example, the Daugman integro-differential operator, the Hough transform, or other iris segmentation techniques can be used to return a curve that estimates the boundary of the pupil or the iris.

3D cornea center estimation module 716 may receive preprocessed images including detected glint data and pupil identification data from modules 710, 712, 714. 3D cornea center estimation module 716 may use these data to estimate the 3D position of the user's cornea. In some embodiments, the 3D cornea center estimation module 716 may estimate the 3D position of an eye's center of cornea curvature or a user's corneal sphere, e.g., the center of an imaginary sphere having a surface portion generally coextensive with the user's cornea. The 3D cornea center estimation module 716 may provide data indicating the estimated 3D coordinates of the corneal sphere and/or user's cornea to the coordinate system normalization module 718, the optical axis determination module 722, and/or the light-field render controller 618. Further details of the operation of the 3D cornea center estimation module 716 are provided herein in connection with FIGS. 11-16C. Example techniques for estimating the positions of eye features such as a cornea or corneal sphere, which may be utilized by 3D cornea center estimation module 716 and other modules in the wearable systems of the present disclosure are discussed in U.S. patent application Ser. No. 15/497,726, filed Apr. 26, 2017, which is incorporated by reference herein in its entirety.

Coordinate system normalization module 718 may optionally (as indicated by its dashed outline) be included in eye tracking module 614. Coordinate system normalization module 718 may receive data indicating the estimated 3D coordinates of the center of the user's cornea (and/or the center of the user's corneal sphere) from the 3D cornea center estimation module 716 and may also receive data from other modules. Coordinate system normalization module 718 may normalize the eye camera coordinate system, which may help to compensate for slippages of the wearable device (e.g., slippages of the head-mounted component from its normal resting position on the user's head, which may be identified by registration observer 620). Coordinate system normalization module 718 may rotate the coordinate system to align the z-axis (e.g., the vergence depth axis) of the coordinate system with the cornea center (e.g., as indicated by the 3D cornea center estimation module 716) and may translate the camera center (e.g., the origin of the coordinate system) to a predetermined distance away from the cornea center such as 30 mm (e.g., module 718 may enlarge or shrink the eye tracking image depending on whether the eye camera 324 was determined to be nearer or further than the predetermined distance). With this normalization process, the eye tracking module 614 may be able to establish a consistent orientation and distance in the eye tracking data, relatively independent of variations of headset positioning on the user's head. Coordinate system normalization module 718 may provide 3D coordinates of the center of the cornea (and/or corneal sphere), pupil identification data, and preprocessed eye tracking images to the 3D pupil center locator module 720.

3D pupil center locator module 720 may receive data, in the normalized or the unnormalized coordinate system, including the 3D coordinates of the center of the user's cornea (and/or corneal sphere), pupil location data, and preprocessed eye tracking images. 3D pupil center locator module 720 may analyze such data to determine the 3D coordinates of the center of the user's pupil in the normalized or unnormalized eye camera coordinate system. The 3D pupil center locator module 720 may determine the location of the user's pupil in three-dimensions based on the 2D position of the pupil centroid (as determined by module 712), the 3D position of the cornea center (as determined by module 716), assumed eye dimensions 704 such as the size of the a typical user's corneal sphere and the typical distance from the cornea center to the pupil center, and optical properties of eyes such as the index of refraction of the cornea (relative to the index of refraction of air) or any combination of these. Techniques for estimating the positions of eye features such as a pupil, which may be utilized by 3D pupil center locator module 720 and other modules in the wearable systems of the present disclosure are discussed in U.S. patent application Ser. No. 15/497,726, filed Apr. 26, 2017, which is incorporated by reference herein in its entirety.

Optical axis determination module 722 may receive data from modules 716 and 720 indicating the 3D coordinates of the center of the user's cornea and the user's pupil. Based on such data, the optical axis determination module 722 may identify a vector from the position of the cornea center (e.g., from the center of the corneal sphere) to the center of the user's pupil, which may define the optical axis of the user's eye. Optical axis determination module 722 may provide outputs specifying the user's optical axis to modules 724, 728, 730, and 732, as examples.

Center of rotation (CoR) estimation module 724 may receive data from module 722 including parameters of the optical axis of the user's eye (e.g., data indicating the direction of the optical axis in a coordinate system with a known relation to the head-mounted unit 602). For example, CoR estimation module 724 may estimate the center of rotation of a user's eye. The center of rotation may indicate a point around which the user's eye rotates when the user eye rotates left, right, up, and/or down. While eyes may not rotate perfectly around a singular point, assuming a singular point may be sufficient. In at least some embodiments, CoR estimation module 724 may estimate an eye's center of rotation by moving from the center of the pupil (identified by module 720) or the center of curvature of the cornea (as identified by module 716) toward the retina along the optical axis (identified by module 722) a particular distance. This particular distance may be an assumed eye dimension 704. As one example, the particular distance between the center of curvature of the cornea and the CoR may be, e.g., 5.7 mm or 4.7 mm, 5.7 mm±1 mm or approximately thereto. This distance may be varied for a particular user based on any relevant data including the user's age, sex, vision prescription, other relevant characteristics, etc.

In at least some embodiments, the CoR estimation module 724 may refine its estimate of the center of rotation of each of the user's eyes over time. As an example, as time passes, the user will eventually rotate their eyes (to look somewhere else, at something closer, further, or sometime left, right, up, or down) causing a shift in the optical axis of each of their eyes. CoR estimation module 724 may then analyze two (or more) optical axes identified by module 722 and locate the 3D point of intersection of those optical axes. The CoR estimation module 724 may then determine the center of rotation lies at that 3D point of intersection. Such a technique may provide for an estimate of the center of rotation, with an accuracy that improves over time.

Various techniques may be employed to increase the accuracy of the CoR estimation module 724 and the determined CoR positions of the left and right eyes. As an example, the CoR estimation module 724 may estimate the CoR by finding the average point of intersection of optical axes determined for various different eye poses over time. As additional examples, module 724 may filter or average estimated CoR positions over time, may calculate a moving average of estimated CoR positions over time, and/or may apply a Kalman filter and known dynamics of the eyes and eye tracking system to estimate the CoR positions over time. In some implementations, a least-squares approach may be taken to determine one or more points of intersection of optical axes. In such implementations, the system may, at a given point in time, identify a location at which the sum of the squared distances to a given set of optical axes is reduced or minimized as the point of optical axes intersection. As a specific example, module 724 may calculate a weighted average of determined points of optical axes intersection and assumed CoR positions (such as 5.7 mm or 4.7 mm, or 5.7 mm±1 mm from an eye's center of cornea curvature or approximately thereto), such that the determined CoR may slowly drift from an assumed CoR position (e.g., 4.7 mm or 5.7 mm, or 5.7 mm±1 mm behind an eye's center of cornea curvature or approximately thereto) to a slightly different location within the user's eye over time as eye tracking data for the user is obtain and thereby enables per-user refinement of the CoR position.

Under ideal conditions, the 3D position of the true CoR of a user's eye relative to the HMD should change a negligible or minimal amount over time as the user moves their eye (e.g., as the user's eye rotates around its center of rotation). In other words, for a given set of eye movements, the 3D position of the true CoR of the user's eye (relative to the HMD) should hypothetically vary less over time than any other point along the optical axis of the user's eye. As such, it follows that the further away a point along the optical axis is from the true CoR of the user's eye, the more variation or variance its 3D position will exhibit over time as the user moves their eye. In some embodiments, the CoR estimation module 724 and/or other submodules of eye tracking module 614 may make use of this statistical relationship to improve CoR estimation accuracy. In such embodiments, the CoR estimation module 724 and/or other submodules of eye tracking module 614 may refine their estimates of the CoR 3D position over time by identifying variations of its CoR estimates having a low variation (e.g., low variance or standard deviation).

As a first example and in embodiments where the CoR estimation module 724 estimates CoR based on intersection of multiple different optical axes (each associated with the user looking in a different direction), the CoR estimation module 724 may make use of this statistical relationship (that the true CoR should have a low variance) by introducing common offsets to the direction of each of the optical axes (e.g., shifting each axis by some uniform amount) and determining if the offset optical axes intersect with each other in an intersection point having a low variation, e.g., low variance or standard deviation. This may correct for minor systemic errors in calculating the directions of the optical axes and help to refine the estimated position of the CoR to be closer to the true CoR.

As a second example and in embodiments where the CoR estimation module 724 estimates CoR by moving along an optical axis (or other axis) by a particular distance (e.g., such as the distance between the center of curvature of the cornea and the CoR), the system may vary, optimize, tune, or otherwise adjust the particular distance between the center of curvature of the cornea and the CoR over time (for example, for a large group of images of the eye captured at different times) in a manner so as to reduce or minimize the variation, for example, variance and/or standard deviation of the estimated CoR position. For example, if the CoR estimation module 724 initially uses a particular distance value of 4.7 mm or 5.7 mm or 5.7 mm±1 mm or approximately thereto (from the center of curvature of the cornea and along the optical axis) to obtain CoR position estimates, but the true CoR of a given user's eye may be positioned 4.9 mm behind the eye's center of cornea curvature (along the optical axis), then an initial set of CoR position estimates obtained by the CoR estimation module 724 may exhibit a relatively high amount of variation, e.g., variance or standard deviation. In response to detecting such a relatively high amount of variation (e.g., variance or standard deviation), the CoR estimation module 724 may look for and identify one or more points along the optical axis having a lower amount of variation (e.g., variance or standard deviation), may identify the 4.9 mm distance as having the lowest variation (e.g., variance or standard deviation), and may thus adjust the particular distance value utilized to 4.9 mm.

The CoR estimation module 724 may look for alternative CoR estimations having lower variation (e.g., variance and/or standard deviation) in response to detecting that a current CoR estimate has a relatively high amount of variation (e.g., variance or standard deviation) or may look for alternative CoR estimations having lower variation (e.g. variance or standard deviation) as a matter of course after obtaining initial CoR estimates. In some examples, such an optimization/adjustment can happen gradually over time, while in other examples, such an optimization/adjustment can be made during an initial user calibration session. In examples where such a procedure is conducted during a calibration procedure, the CoR estimation module 724 may not initially subscribe/adhere to any assumed particular distance, but may rather collect a set of eye tracking data over time, perform statistical analysis on the set of eye tracking data, and determine the particular distance value yielding CoR position estimates with the least possible amount (e.g., global minima) of variation (e.g. variance or standard deviation) based on the statistical analysis.

Interpupillary distance (IPD) estimation module 726 may receive data from CoR estimation module 724 indicating the estimated 3D positions of the centers of rotation of the user's left and right eyes. IPD estimation module 726 may then estimate a user's IPD by measuring the 3D distance between the centers of rotation of the user's left and right eyes. In general, the distance between the estimated CoR of the user's left eye and the estimated CoR of the user's right eye may be roughly equal to the distance between the centers of a user's pupils, when the user is looking at optical infinity (e.g., the optical axes of the user's eyes are substantially parallel to one another), which is the typical definition of interpupillary distance (IPD). A user's IPD may be used by various components and modules in the wearable system. As example, a user's IPD may be provided to registration observer 620 and used in assessing how well the wearable device is aligned with the user's eyes (e.g., whether the left and right display lenses are properly spaced in accordance with the user's IPD). As another example, a user's IPD may be provided to vergence depth estimation module 728 and be used in determining a user's vergence depth. Module 726 may employ various techniques, such as those discussed in connection with CoR estimation module 724, to increase the accuracy of the estimated IPD. As examples, IPD estimation module 724 may apply filtering, averaging over time, weighted averaging including assumed IPD distances, Kalman filters, etc. as part of estimating a user's IPD in an accurate manner.

Vergence depth estimation module 728 may receive data from various modules and submodules in the eye tracking module 614 (as shown in connection with FIG. 7A). In particular, vergence depth estimation module 728 may employ data indicating estimated 3D positions of pupil centers (e.g., as provided by module 720 described above), one or more determined parameters of optical axes (e.g., as provided by module 722 described above), estimated 3D positions of centers of rotation (e.g., as provided by module 724 described above), estimated IPD (e.g., Euclidean distance(s) between estimated 3D positions of centers of rotations) (e.g., as provided by module 726 described above), and/or one or more determined parameters of optical and/or visual axes (e.g., as provided by module 722 and/or module 730 described below). Vergence depth estimation module 728 may detect or otherwise obtain a measure of a user's vergence depth, which may be the distance from the user at which the user's eyes are focused. As examples, when the user is looking at an object three feet in front of them, the user's left and right eyes have a vergence depth of three feet; and, while when the user is looking at a distant landscape (e.g., the optical axes of the user's eyes are substantially parallel to one another such that the distance between the centers of the user's pupils may be roughly equal to the distance between the centers of rotation of the user's left and right eyes), the user's left and right eyes have a vergence depth of infinity. In some implementations, the vergence depth estimation module 728 may utilize data indicating the estimated centers of the user's pupils (e.g., as provided by module 720) to determine the 3D distance between the estimated centers of the user's pupils. The vergence depth estimation module 728 may obtain a measure of vergence depth by comparing such a determined 3D distance between pupil centers to estimated IPD (e.g., Euclidean distance(s) between estimated 3D positions of centers of rotations) (e.g., as indicated by module 726 described above). In addition to the 3D distance between pupil centers and estimated IPD, the vergence depth estimation module 728 may utilize known, assumed, estimated, and/or determined geometries to calculate vergence depth. As an example, module 728 may combine 3D distance between pupil centers, estimated IPD, and 3D CoR positions in a trigonometric calculation to estimate (e.g., determine) a user's vergence depth. Indeed, an evaluation of such a determined 3D distance between pupil centers against estimated IPD may serve to indicate a measure of the user's current vergence depth relative to optical infinity. In some examples, the vergence depth estimation module 728 may simply receive or access data indicating an estimated 3D distance between the estimated centers of the user's pupils for purposes of obtaining such a measure of vergence depth. In some embodiments, the vergence depth estimation module 728 may estimate vergence depth by comparing a user's left and right optical axis. In particular, vergence depth estimation module 728 may estimate vergence depth by locating the distance from a user at which the user's left and right optical axes intersect (or where projections of the user's left and right optical axes on a plane such as a horizontal plane intersect). Module 728 may utilize a user's IPD in this calculation, by setting the zero depth to be the depth at which the user's left and right optical axes are separated by the user's IPD. In at least some embodiments, vergence depth estimation module 728 may determine vergence depth by triangulating eye tracking data together with known or derived spatial relationships.

In some embodiments, vergence depth estimation module 728 may estimate a user's vergence depth based on the intersection of the user's visual axes (instead of their optical axes), which may provide a more accurate indication of the distance at which the user is focused on. In at least some embodiments, eye tracking module 614 may include optical to visual axis mapping module 730. As discussed in further detail in connection with FIG. 10, a user's optical and visual axes are generally not aligned. A visual axis is the axis along which a person is looking, while an optical axis is defined by the center of that person's lens and pupil, and may go through the center of the person's retina. In particular, a user's visual axis is generally defined by the location of the user's fovea, which may be offset from the center of a user's retina, thereby resulting in different optical and visual axis. In at least some of these embodiments, eye tracking module 614 may include optical to visual axis mapping module 730. Optical to visual axis mapping module 730 may correct for the differences between a user's optical and visual axis and provide information on the user's visual axis to other components in the wearable system, such as vergence depth estimation module 728 and light-field render controller 618. In some examples, module 730 may use assumed eye dimensions 704 including a typical offset of approximately 5.2° inwards (nasally, towards a user's nose) between an optical axis and a visual axis. In other words, module 730 may shift a user's left optical axis (nasally) rightwards by 5.2° towards the nose and a user's right optical axis (nasally) leftwards by 5.2° towards the nose in order to estimate the directions of the user's left and right visual axes. In other examples, module 730 may utilize per-user calibration data 706 in mapping optical axes (e.g., as indicated by module 722 described above) to visual axes. As additional examples, module 730 may shift a user's optical axes nasally by between 4.0° and 6.5°, by between 4.5° and 6.0°, by between 5.0° and 5.4°, etc., or any ranges formed by any of these values. In some arrangements, the module 730 may apply a shift based at least in part upon characteristics of a particular user such as their age, sex, vision prescription, or other relevant characteristics and/or may apply a shift based at least in part upon a calibration process for a particular user (e.g., to determine a particular user's optical-visual axis offset). In at least some embodiments, module 730 may also shift the origins of the left and right optical axes to correspond with the user's CoP (as determined by module 732) instead of the user's CoR.

Optional center of perspective (CoP) estimation module 732, when provided, may estimate the location of the user's left and right centers of perspective (CoP). A CoP may be a useful location for the wearable system and, in at least some embodiments, is a position just in front of a pupil. In at least some embodiments, CoP estimation module 732 may estimate the locations of a user's left and right centers of perspective based on the 3D location of a user's pupil center, the 3D location of a user's center of cornea curvature, or such suitable data or any combination thereof. As an example, a user's CoP may be approximately 5.01 mm in front of the center of cornea curvature (e.g., 5.01 mm from the corneal sphere center in a direction that is towards the eye's cornea and that is along the optical axis) and may be approximately 2.97 mm behind the outer surface of a user's cornea, along the optical or visual axis. A user's center of perspective may be just in front of the center of their pupil. As examples, a user's CoP may be less than approximately 2.0 mm from the user's pupil, less than approximately 1.0 mm from the user's pupil, or less than approximately 0.5 mm from the user's pupil or any ranges between any of these values. As another example, the center of perspective may correspond to a location within the anterior chamber of the eye. As other examples, the CoP may be between 1.0 mm and 2.0 mm, about 1.0 mm, between 0.25 mm and 1.0 mm, between 0.5 mm and 1.0 mm, or between 0.25 mm and 0.5 mm from the user's pupil.

The center of perspective described herein (as a potentially desirable position for a pinhole of a render camera and an anatomical position in a user's eye) may be a position that serves to reduce and/or eliminate undesired parallax shifts. In particular, the optical system of a user's eye is very roughly equivalent to theoretical system formed by a pinhole in front of a lens, projecting onto a screen, with the pinhole, lens, and screen roughly corresponding to a user's pupil/iris, lens, and retina, respectively. Moreover, it may be desirable for there to be little or no parallax shift when two point light sources (or objects) at different distances from the user's eye are rigidly rotated about the opening of the pinhole (e.g., rotated along radii of curvature equal to their respective distance from the opening of the pinhole). Thus, it would seem that the CoP should be located at the center of the pupil of an eye (and such a CoP may be used in some embodiments). However, the human eye includes, in addition to the lens and pinhole of the pupil, a cornea that imparts additional optical power to light propagating toward the retina). Thus, the anatomical equivalent of the pinhole in the theoretical system described in this paragraph may be a region of the user's eye positioned between the outer surface of the cornea of the user's eye and the center of the pupil or iris of the user's eye. For instance, the anatomical equivalent of the pinhole may correspond to a region within the anterior chamber of a user's eye. For various reasons discussed herein, it may be desired to set the CoP to such a position within the anterior chamber of the user's eye.

As discussed above, eye tracking module 614 may provide data, such as estimated 3D positions of left and right eye centers of rotation (CoR), vergence depth, left and right eye optical axis, 3D positions of a user's eye, 3D positions of a user's left and right centers of cornea curvature, 3D positions of a user's left and right pupil centers, 3D positions of a user's left and right center of perspective, a user's IPD, etc., to other components, such as light-field render controller 618 and registration observer 620, in the wearable system. Eye tracking module 614 may also include other submodules that detect and generate data associated with other aspects of a user's eye. As examples, eye tracking module 614 may include a blink detection module that provides a flag or other alert whenever a user blinks and a saccade detection module that provides a flag or other alert whenever a user's eye saccades (e.g., quickly shifts focus to another point).

Other methods of eye tracking and determining the center of rotation are possible. Accordingly, the eye tracking module 614 may be different. In various implementations of eye tracking modules described below, for example, estimates of center of rotation are determined based on a plurality of center of corneal curvature values. In some implementations, for example, as discussed with reference to FIGS. 17A-19D, the eye tracking module 614 may estimate an eye's center of rotation by determining a convergence or intersection among surface normal vectors of a surface fitted to a plurality of center of curvatures of the cornea possibly for different eye poses. Nevertheless, one or more features from the eye tracking module 614 described above or elsewhere herein may be included in other implementations of eye tracking modules.

H. Example of a Render Controller

Figure 7B:
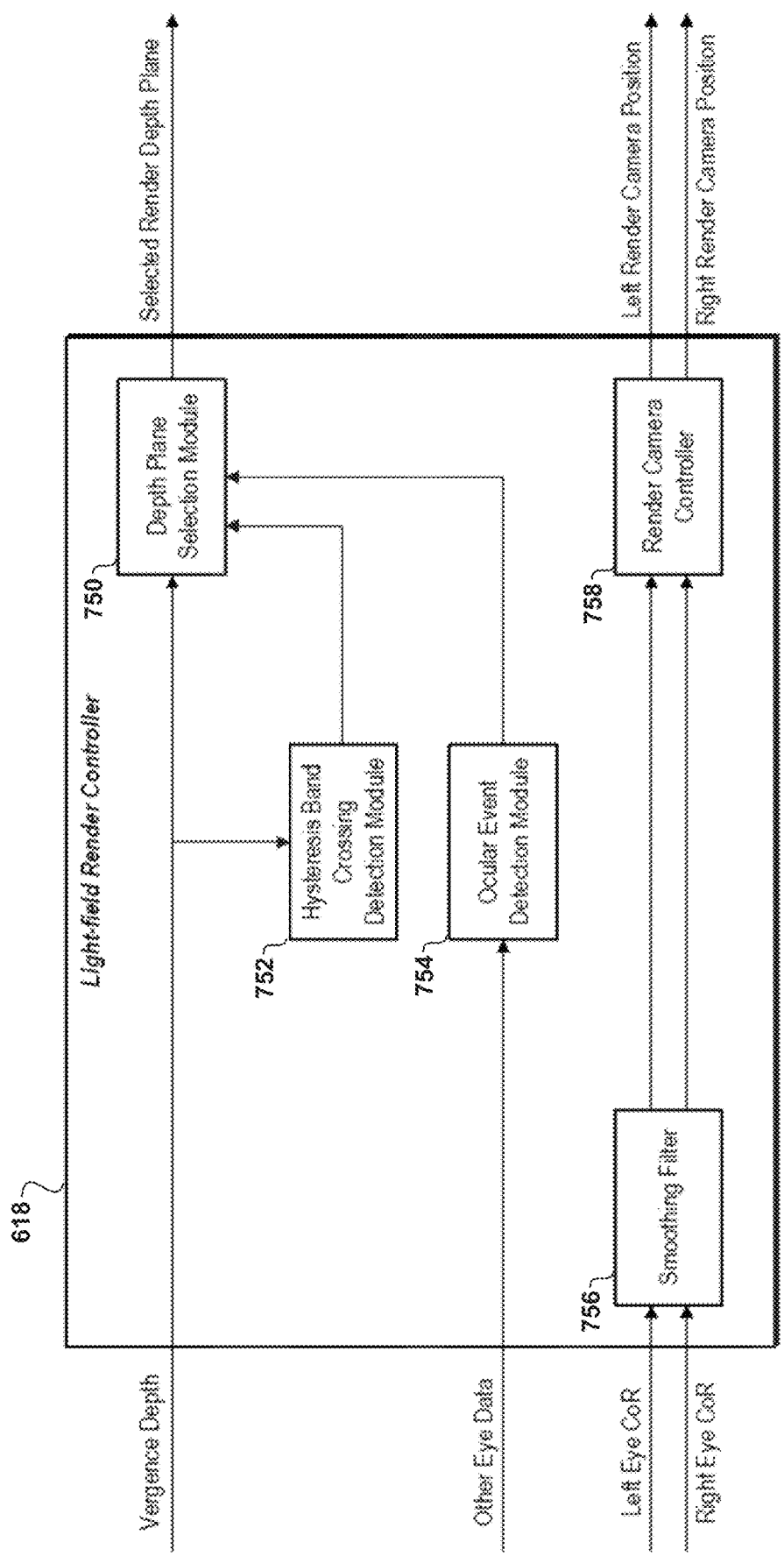
FIG. 7B is a block diagram of a render controller in a wearable system.

A detailed block diagram of an example light-field render controller 618 is shown in FIG. 7B. As shown in FIGS. 6 and 7B, render controller 618 may receive eye tracking information from eye tracking module 614 and may provide outputs to render engine 622, which may generate images to be displayed for viewing by a user of the wearable system. As examples, render controller 618 may receive a vergence depth, left and right eye centers of rotation (and/or centers of perspective), and other eye data such as blink data, saccade data, etc.

Depth plane selection module 750 may receive vergence depth information and other eye data and, based on such data, may cause render engine 622 to convey content to a user with a particular depth plane (e.g., at a particular accommodation or focal distance). As discussed in connection with FIG. 4, a wearable system may include a plurality of discrete depth planes formed by a plurality of waveguides, each conveying image information with a varying level of wavefront curvature. In some embodiments, a wearable system may include one or more variable depth planes, such as an optical element that conveys image information with a level of wavefront curvature that varies over time. In these and other embodiments, depth plane selection module 750 may cause render engine 622 to convey content to a user at a selected depth (e.g., cause render engine 622 to direct display 220 to switch depth planes), based in part of the user's vergence depth. In at least some embodiments, depth plane selection module 750 and render engine 622 may render content at different depths and also generate and/or provide depth plane selection data to display hardware such as display 220. Display hardware such as display 220 may perform an electrical depth plane switching in response to depth plane selection data (which may be control signals) generated by and/or provided by modules such as depth plane selection module 750 and render engine 622.

In general, it may be desirable for depth plane selection module 750 to select a depth plane matching the user's current vergence depth, such that the user is provided with accurate accommodation cues. However, it may also be desirable to switch depth planes in a discreet and unobtrusive manner. As examples, it may be desirable to avoid excessive switching between depth planes and/or it may be desire to switch depth planes at a time when the user is less likely to notice the switch, such as during a blink or eye saccade.

Hysteresis band crossing detection module 752 may help to avoid excessive switching between depth planes, particularly when a user's vergence depth fluctuates at the midpoint or transition point between two depth planes. In particular, module 752 may cause depth plane selection module 750 to exhibit hysteresis in its selection of depth planes. As an example, modules 752 may cause depth plane selection module 750 to switch from a first farther depth plane to a second closer depth plane only after a user's vergence depth passes a first threshold. Similarly, module 752 may cause depth plane selection module 750 (which may in turn direct displays such as display 220) to switch to the first farther depth plane only after the user's vergence depth passes a second threshold that is farther from the user than the first threshold. In the overlapping region between the first and second thresholds, module 750 may cause depth plane selection module 750 to maintain whichever depth plane is currently select as the selected depth plane, thus avoiding excessive switching between depth planes.

Ocular event detection module 750 may receive other eye data from the eye tracking module 614 of FIG. 7A and may cause depth plane selection module 750 to delay some depth plane switches until an ocular event occurs. As an example, ocular event detection module 750 may cause depth plane selection module 750 to delay a planned depth plane switch until a user blink is detected; may receive data from a blink detection component in eye tracking module 614 that indicates when the user is currently blinking; and, in response, may cause depth plane selection module 750 to execute the planned depth plane switch during the blink event (such by causing module 750 to direct display 220 to execute the depth plane switch during the blink event). In at least some embodiments, the wearable system may be able to shift content onto a new depth plane during a blink event such that the user is unlikely to perceive the shift. As another example, ocular event detection module 750 may delay planned depth plane switches until an eye saccade is detected. As discussed in connection with eye blinks, such as an arrangement may facilitate the discretely shifting of depth planes.

If desired, depth plane selection module 750 may delay planned depth plane switches only for a limited period of time before executing the depth plane switch, even in the absence of an ocular event. Similarly, depth plane selection module 750 may execute a depth plane switch when the user's vergence depth is substantially outside of a currently-selected depth plane (e.g., when the user's vergence depth has exceeded a predetermined threshold beyond the regular threshold for a depth plane switch), even in the absence of an ocular event. These arrangements may help ensure that ocular event detection module 754 does not indefinitely delay depth plane switches and does not delay depth plane switches when a large accommodation error is present.

Render camera controller 758 may provide information to render engine 622 indicating where the user's left and right eyes are. Render engine 622 may then generate content by simulating cameras at the positions of the user's left and right eyes and generating content based on the perspectives of the simulated cameras. As discussed above, the render camera is a simulated camera for use in rendering virtual image content possibly from a database of objects in a virtual world. The objects may have locations and orientations relative to the user or wearer and possibly relative to real objects in the environment surrounding the user or wearer. The render camera may be included in a render engine to render virtual images based on the database of virtual objects to be presented to said eye. The virtual images may be rendered as if taken from the perspective the user or wearer. For example, the virtual images may be rendered as if captured by a camera (corresponding to the "render camera") having an aperture, lens, and detector viewing the objects in the virtual world. The virtual images are taken from the perspective of such a camera having a position of the "render camera." For example, the virtual images may be rendered as if captured from the perspective of a camera having a specific location with respect to the user's or wearer's eye so as to provide images that appear to be from the perspective of the user or wearer. In some implementations, the images are rendered as if captured from the perspective of a camera having an aperture at a specific location with respect to the user's or wearer's eye (such as the center of perspective or center of rotation as discussed herein, or elsewhere).

Render camera controller 758 may determine the positions of the left and right cameras based on the left and right eye centers of rotation (CoR), determined by CoR estimation module 724, and/or based on the left and right eye centers of perspective (CoP), determined by CoP estimation module 732. In some embodiments, render camera controller 758 may switch between the CoR and CoP locations based on various factors. As examples, the render camera controller 758 may, in various modes, register the render camera to the CoR locations at all times, register the render camera to the CoP locations at all times, toggle or discretely switch between registering the render camera to the CoR locations and registering the render camera to the CoP locations over time based on various factors, or dynamically register the render camera to any of a range of different positions along the optical (or visual) axis between the CoR and CoP locations over time based on various factors. The CoR and CoP positions may optionally pass through smoothing filter 756 (in any of the aforementioned modes for render camera positioning) which may average the CoR and CoP locations over time to reduce noise in these positions and prevent jitter in the render simulated render cameras.

In at least some embodiments, the render camera may be simulated as a pinhole camera with the pinhole disposed at the position of the estimated CoR or CoP identified by eye tracking module 614. As the CoP is offset from the CoR, the location of the render camera and its pinhole both shift as the user's eye rotates, whenever the render camera's position is based on a user's CoP. In contrast, whenever the render camera's position is based on a user's CoR, the location of the render camera's pinhole does not move with eye rotations, although the render camera (which is behind the pinhole) may, in some embodiments, move with eye rotation. In other embodiments where the render camera's position is based on a user's CoR, the render camera may not move (e.g., rotate) with a user's eye.

I. Example of Differences Between Optical and Visual Axes

Figure 7C:
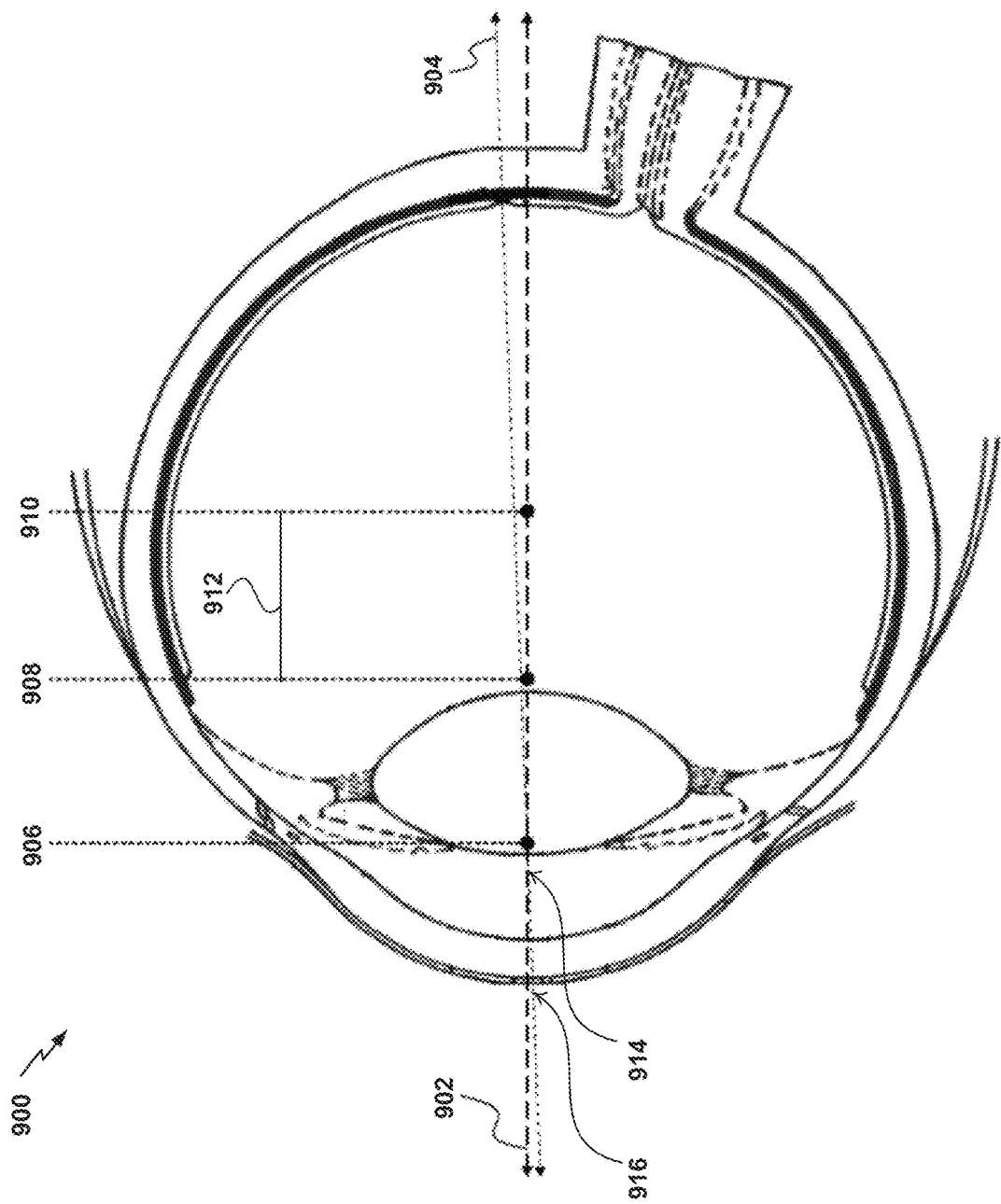
FIG. 7C illustrates an example of an eye including the eye's optical and visual axes and the eye's center of rotation.

As discussed in connection with optical to visual mapping module 730 of FIG. 7A, a user's optical and visual axes are generally not aligned, due in part to a user's visual axis being defined by their fovea and that fovea are not generally in the center of a person's retina. Thus, when a person desires to concentrate on a particular object, the person aligns their visual axis with that object to ensure that light from the object falls on their fovea while their optical axis (defined by the center of their pupil and center of curvature of their cornea) is actually slightly offset from that object. FIG. 7C is an example of an eye 900 illustrating the eye's optical axis 902, the eye's visual axis 904, and the offset between these axes. Additionally, FIG. 7C illustrates the eye's pupil center 906, the eye's center of cornea curvature 908, and the eye's average center of rotation (CoR) 910. In at least some populations, the eye's center of cornea curvature 908 may lie approximately 4.7 mm or 5.7 mm, or 5.7 mm±1 mm in front, as indicated by dimension 912, of the eye's average center of rotation (CoR) 910 or approximately thereto. Additionally, the eye's center of perspective 914 may lie approximately 5.01 mm in front of the eye's center of cornea curvature 908, about 2.97 mm behind the outer surface 916 of the user's cornea, and/or just in front of the user's pupil center 906 (e.g., corresponding to a location within the anterior chamber of eye 900). As additional examples, dimension 912 may be between 2.0 mm and 8.0 mm, between 3.0 and 7.0 mm, between 4.0 and 6.0 mm, between 4.5 and 5.0 mm, between, between 4.6 and 4.8 mm, between 5.0 and 6.0 mm, or between 5.6 and 5.8 mm, between 5.5 and 6.0 mm or any ranges between any values and any values in any of these ranges. The eye's center of perspective (CoP) 914 may be a useful location for the wearable system as, in at least some embodiments, registering a render camera at the CoP may help to reduce or eliminate parallax artifacts.

FIG. 7C also illustrates a location within a human eye 900 with which the pinhole of a render camera can be aligned. As shown in FIG. 7C, the pinhole of a render camera may be registered with a location 914 along the optical axis 902 or visual axis 904 of the human eye 900 closer to the outer surface of the cornea than both (a) the center of the pupil or iris 906 and (b) the center of cornea curvature 908 of the human eye 900. For example, as shown in FIG. 7C, the pinhole of a render camera may be registered with a location 914 along the optical axis 902 of the human eye 900 that is about 2.97 millimeters rearward from the outer surface of the cornea 916 and about 5.01 millimeters forward from the center of cornea curvature 908. The location 914 of the pinhole of the render camera and/or the anatomical region of the human eye 900 to which the location 914 corresponds can be seen as representing the center of perspective of the human eye 900. The optical axis 902 of the human eye 900 as shown in FIG. 7C represents the most direct line through the center of cornea curvature 908 and the center of the pupil or iris 906. The visual axis 904 of the human eye 900 differs from the optical axis 902, as it represents a line extending from the fovea of the human eye 900 to the center of the pupil or iris 906.

J. Example of Locating the Center of Cornea Using a Single Camera

In some implementations, the 3D cornea center estimation module 716 may estimate the center of the cornea based on the measured position of one or more glints generated by one or more light sources on one or more images captured by a single camera. The 3D cornea center estimation module 716 illustrated above in FIG. 7A, for example, may provide an estimate the center of curvature of the cornea based on one or more images obtained from a single eye tracking camera. In some implementations, a spherical eye model may be used. This spherical model may model the shape or curvature of the cornea based on a surface having a spherical shape or curvature.

Figure 8A:
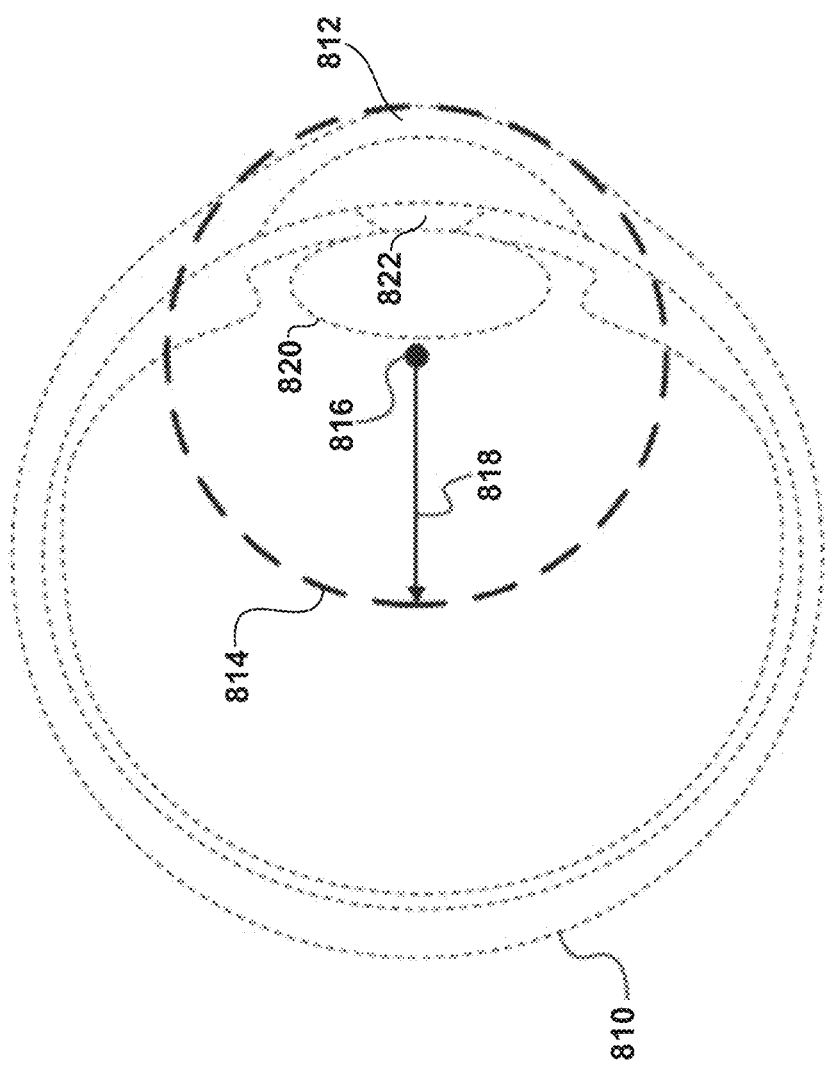
FIG. 8A is a schematic diagram of an eye showing the eye's corneal sphere.

FIG. 8A is a schematic diagram of an eye showing the eye's corneal sphere. As shown in FIG. 8A, a user's eye 810 may have a cornea 812, a pupil 822, and a lens 820. The cornea 812 may have an approximately spherical shape, shown by corneal sphere 814. Corneal sphere 814 may have a center point 816, also referred to as a corneal center, and a radius 818. The semispherical cornea of a user's eye may curve around the corneal center 816.

FIGS. 8B-8E illustrate an example of locating a user's corneal center 816 using 3D cornea center estimation module 716 and eye tracking module 614.

Figure 8B:
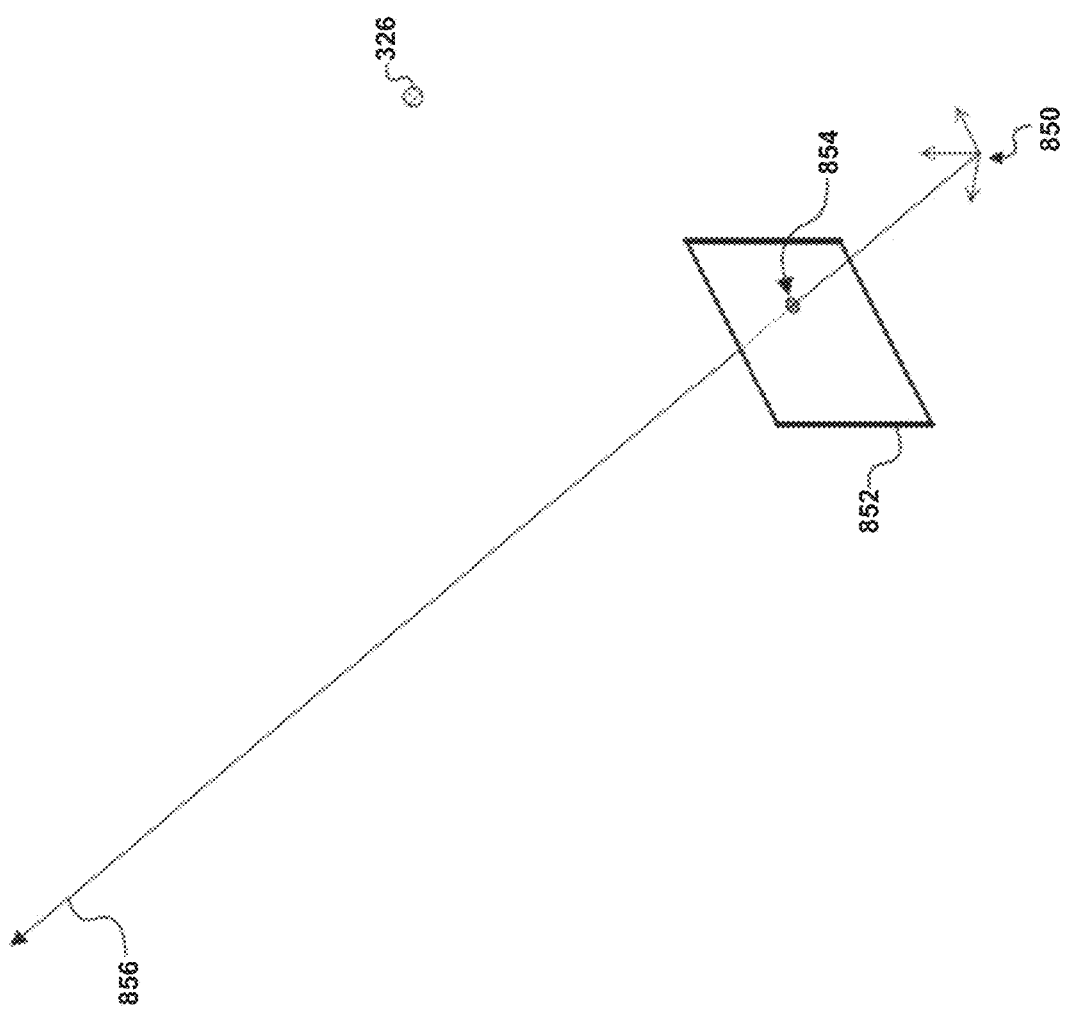
FIG. 8B illustrates an example corneal glint detected by an eye tracking camera.

As shown in FIG. 8B, 3D cornea center estimation module 716 may receive an eye tracking image 852 that includes a corneal glint 854. The 3D cornea center estimation module 716 may then simulate, in an eye camera coordinate system 850, the known 3D positions of the eye camera 324 and light source 326 (which may be based on data in eye tracking extrinsics and intrinsics database 702, assumed eye dimensions database 704, and/or per-user calibration data 706) in order to cast a ray 856 in the eye camera coordinate system. In at least some implementations, the eye camera coordinate system 850 may have its origin at the 3D position of the eye tracking camera 324.

Figure 8C:
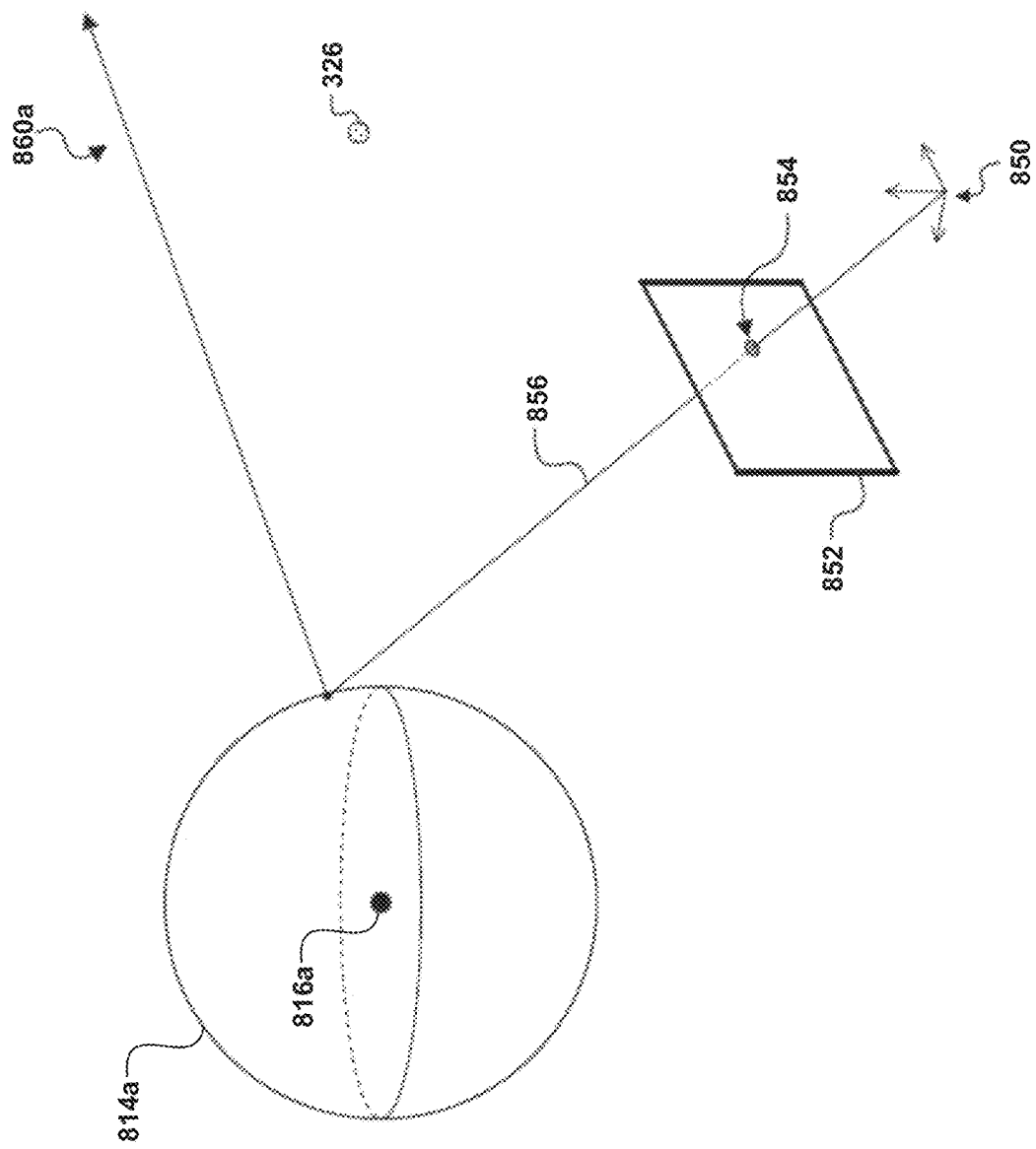

In FIG. 8C, 3D cornea center estimation module 716 simulates a corneal sphere 814a (which may be based on assumed eye dimensions from database 704) and corneal curvature center 816a at a first position. The 3D cornea center estimation module 716 may then check to see whether the corneal sphere 814a would properly reflect light from the light source 326 to the glint position 854. As shown in FIG. 8C, the first position is not a match as the ray 860a does not intersect light source 326.

Similarly in FIG. 8D, 3D cornea center estimation module 716 simulates a corneal sphere 814b and corneal curvature center 816b at a second position. The 3D cornea center estimation module 716 then checks to see whether the corneal sphere 814b properly reflects light from the light source 326 to the glint position 854. As shown in FIG. 8D, the second position is also not a match.

Figure 8E:
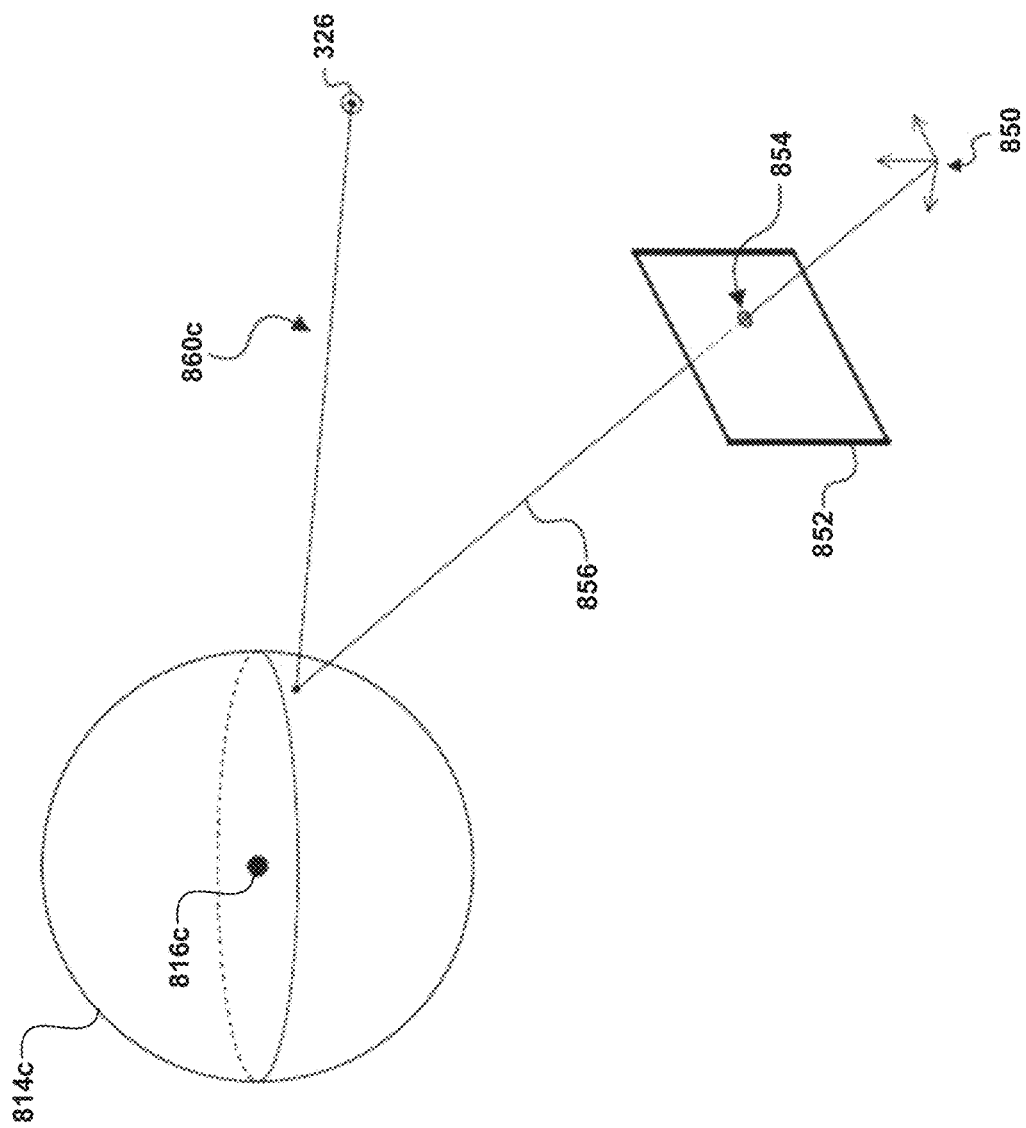

As shown in FIG. 8E, the 3D cornea center estimation module 716 eventually is able to determine the correct position of the corneal sphere is corneal sphere 814c and corneal curvature center 816c. The 3D cornea center estimation module 716 confirms the illustrated position is correct by checking that light from source 326 will properly reflect off of the corneal sphere and be imaged by camera 324 at the correct location of glint 854 on image 852. With this arrangement and with the known 3D positions of the light source 326, the camera 324, and the optical properties of the camera (focal length, etc.), the 3D cornea center estimation module 716 can determine the 3D location of the cornea's center of curvature 816 (e.g., relative to the wearable system).

The processes described herein in connection with at least FIGS. 8C-8E may effectively be an iterative, repetitious, and/or an optimization process to identify the 3D position of the user's cornea center. As such, any of a plurality of techniques (e.g., iterative, optimization techniques, etc.) may be used to efficiently and quickly prune or reduce the search space of possible positions. Moreover, in some implementations, the system may include two, three, four, or more light sources such as light source 326 and some or all of these light sources may be disposed at different positions, resulting in multiple glints such as glint 854 located at different positions on image 852 and multiple rays such as ray 856 having different origins and directions. Such designs may enhance the accuracy of the 3D cornea center estimation module 716, as the module 716 may seek to identify a cornea position that results in some or all of the glints and rays being properly reflected between their respective light sources and their respective positions on image 852. In other words and in these implementations, the positions of some or all of the light sources may be relied upon in the 3D cornea position determination (e.g., iterative, optimization techniques, etc.) processes of FIGS. 8B-8E. In some implementations, the system may determine a vector or ray along which the center of the cornea resides before performing optimization processes (i.e., a 2D cornea center position). In such implementations, the 3D cornea center estimation module 716 may only search for cornea positions along such a vector, which may serve to provide computational and/or time savings when performing optimization or other processes for determining estimates of the center of corneal curvature. In at least some of these implementations, before determining such a vector, the system may initially (i) define a first plane between the origin of the eye camera coordinate system 850, a first light source (e.g., light source 326a), and a first glint (e.g., glint 854a) produced by the first light source, and (ii) define a second plane between the origin of the eye camera coordinate system 850, a second light source (e.g., light source 326b), and a second glint (e.g., glint 854b) produced by the second light source. The system may then simply calculate the cross product of the first plane and the second plane to determine the vector or ray along which the center of the cornea resides (i.e., the 2D cornea center position). Variations of the approaches as well as other methods and configurations may potentially be employed.

K. Example Wearable Device Configuration

Figure 9A:
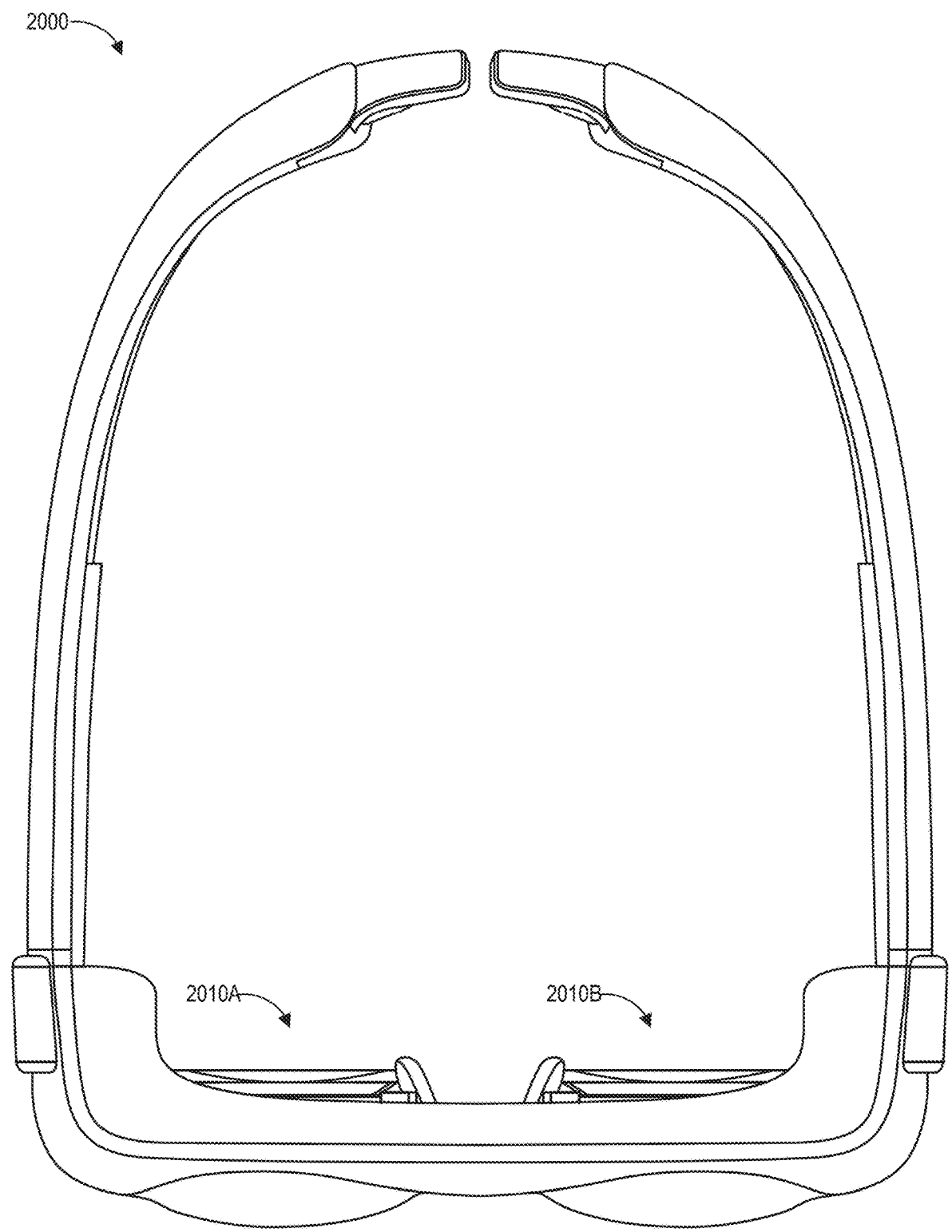
FIGS. 9A-E illustrate views of an example configuration of a wearable system for capturing eye image data for use by an eye tracking module.

FIGS. 9A-E illustrate an example configuration of components of an example wearable device 2000 for capturing eye image data for use by an eye tracking module 614. For example, as illustrated in FIG. 9A, a wearable device 2000 may be part of a wearable system, such as described above with reference to FIGS. 2-4. The wearable device 2000 may include a left eye piece 2010A and a right eyepiece 2010B. The left eyepiece 2010A may be able to image a user's left eye and the right eyepiece 2010B may be able to image a user's right eye.

Figure 9B:
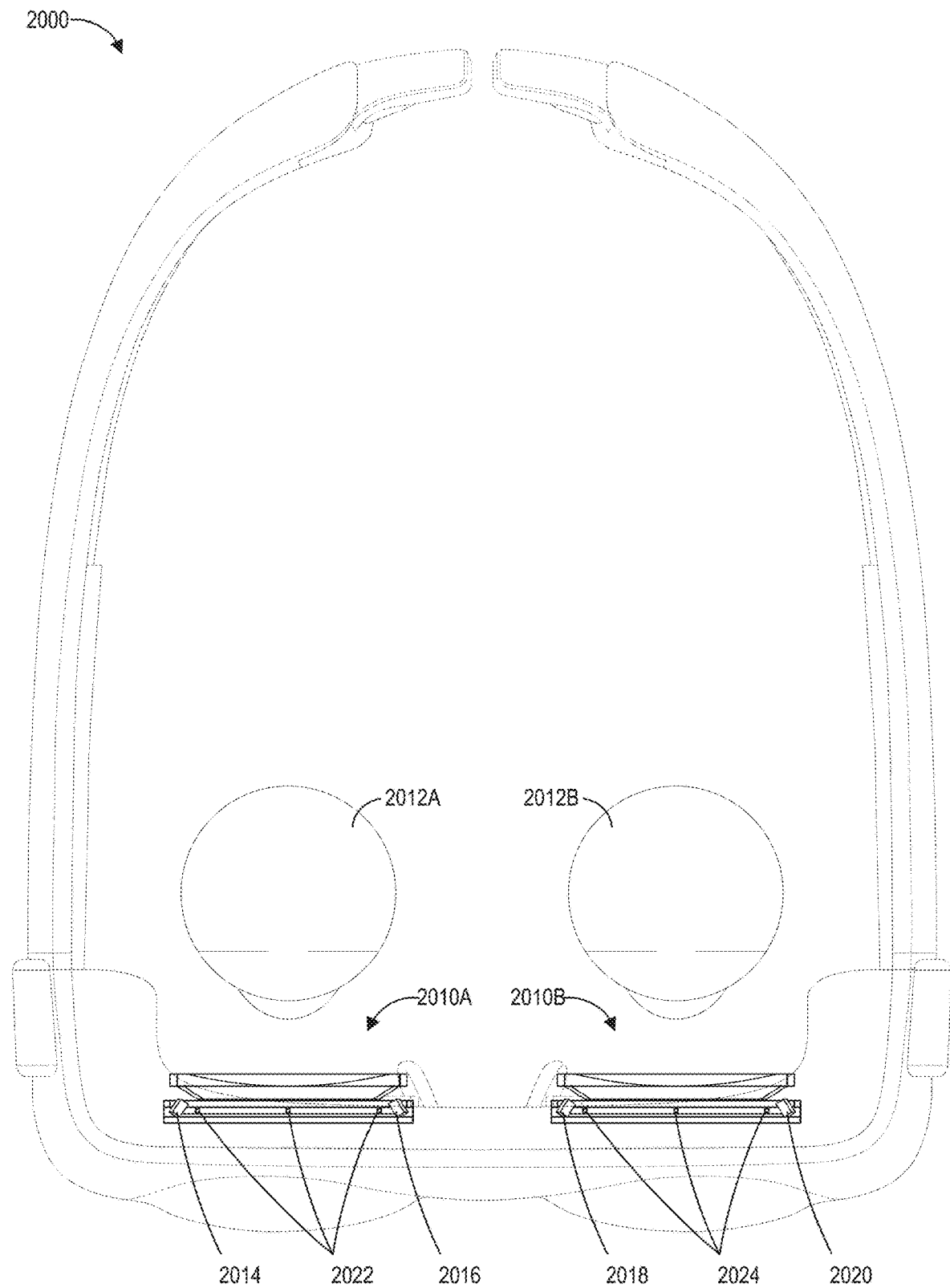

As illustrated in FIG. 9B, the left eyepiece 2010A may include one or more illumination sources 2022. Similarly, the right eyepiece 2010B may include one or more illumination sources 2024. For example, there may be four illumination sources 2022 and four illumination sources 2024. The illumination sources 2022 may be positioned within a left eyepiece 2010A to emit light towards a user's left eye 2012A. The illumination sources 2022 may be positioned so as not to obstruct the user's view through the left eyepiece 2010A. For example, the illumination sources 2022 may be positioned around a rim of a display within the left eyepiece 2010A so as not to obstruct a user's view through the display. Similarly, the illumination sources 2024 may be positioned within a right eyepiece 2010B to emit light towards a user's right eye 2012B. The illumination sources 2024 may be positioned so as not to obstruct the user's view through the right eyepiece 2010B. For example, the illumination sources 20204 may be positioned around a rim of a display within the right eyepiece 2010B so as not to obstruct a user's view through the display. The illumination sources 2022, 2024 may emit light in visible or non-visible light. For example, the illumination sources 2022, 2024 may be infrared (IR) LEDs. Alternatively, the illumination sources may be located or configured differently.

As illustrated in FIG. 9B, the left eye piece 2010A may include a left eye imaging system. The left eye imaging system can include one or more inward-facing cameras (2014, 2016). For example, the left eye imaging system can include a left eye tracking camera 2014 for the left eyepiece 2010A and a right eye tracking camera 2016 for the left eyepiece 2010A located to the left and right of each other, respectively, possibly left and right of center of the left eyepiece, respectively. Similarly, the right eye piece 2010B may include a right eye imaging system. The right eye imaging system can include one or more inward-facing cameras (2018, 2020). For example, the right eye imaging system can include a left eye tracking camera 2018 for the right eyepiece 2010B and a right eye tracking camera 2020 for the right eyepiece 2010B located to the left and right of each other, respectively, possibly left and right of center of the right eyepiece, respectively. The one or more cameras in the left eye tracking system 2010A and the one or more cameras in the right eye tracking system 2010B may be situated within the wearable device 2000 so as to unobtrusively capture images of the user's eye(s). Other configurations are possible.

Figure 9C:
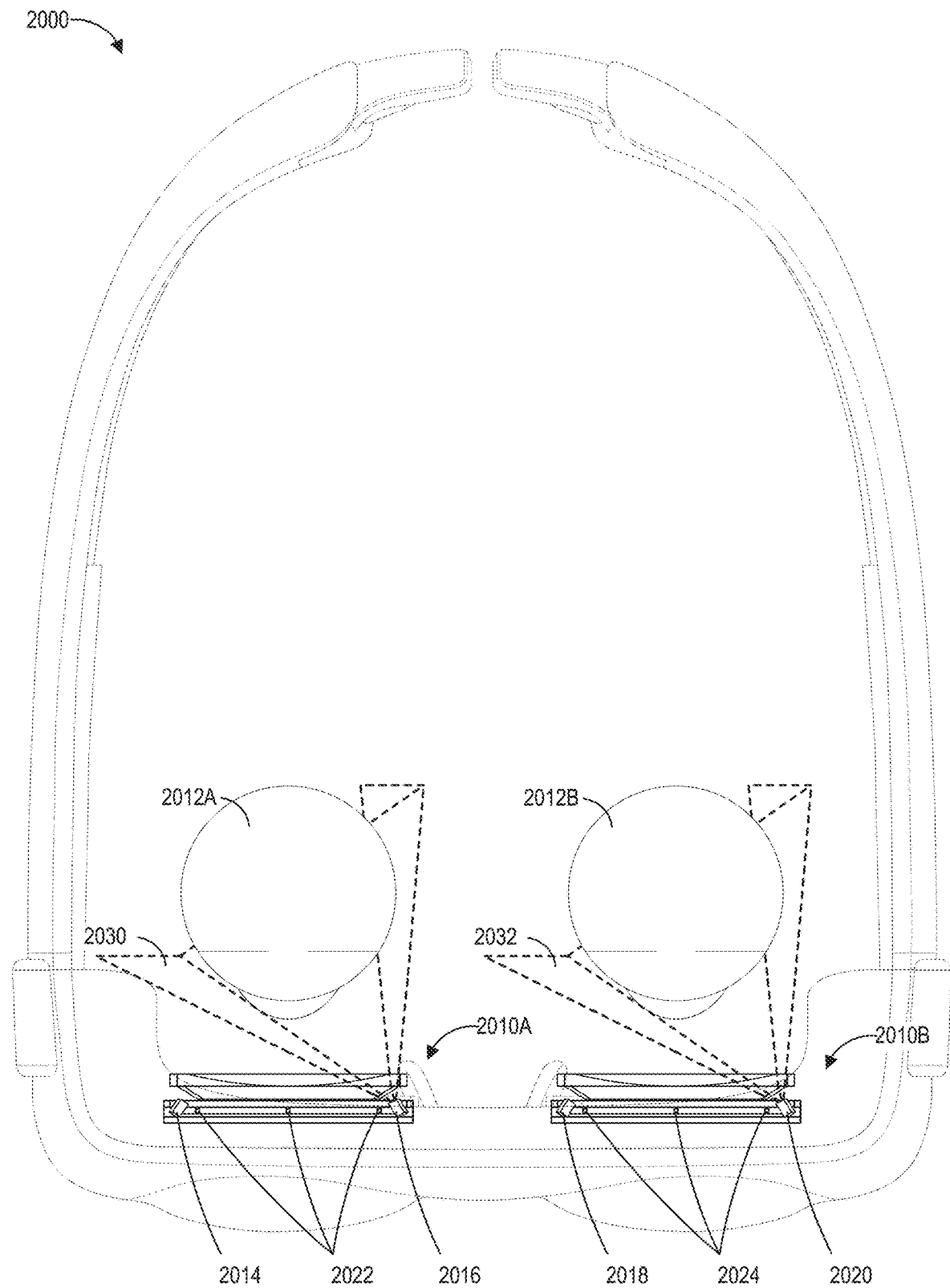
Figure 9D:
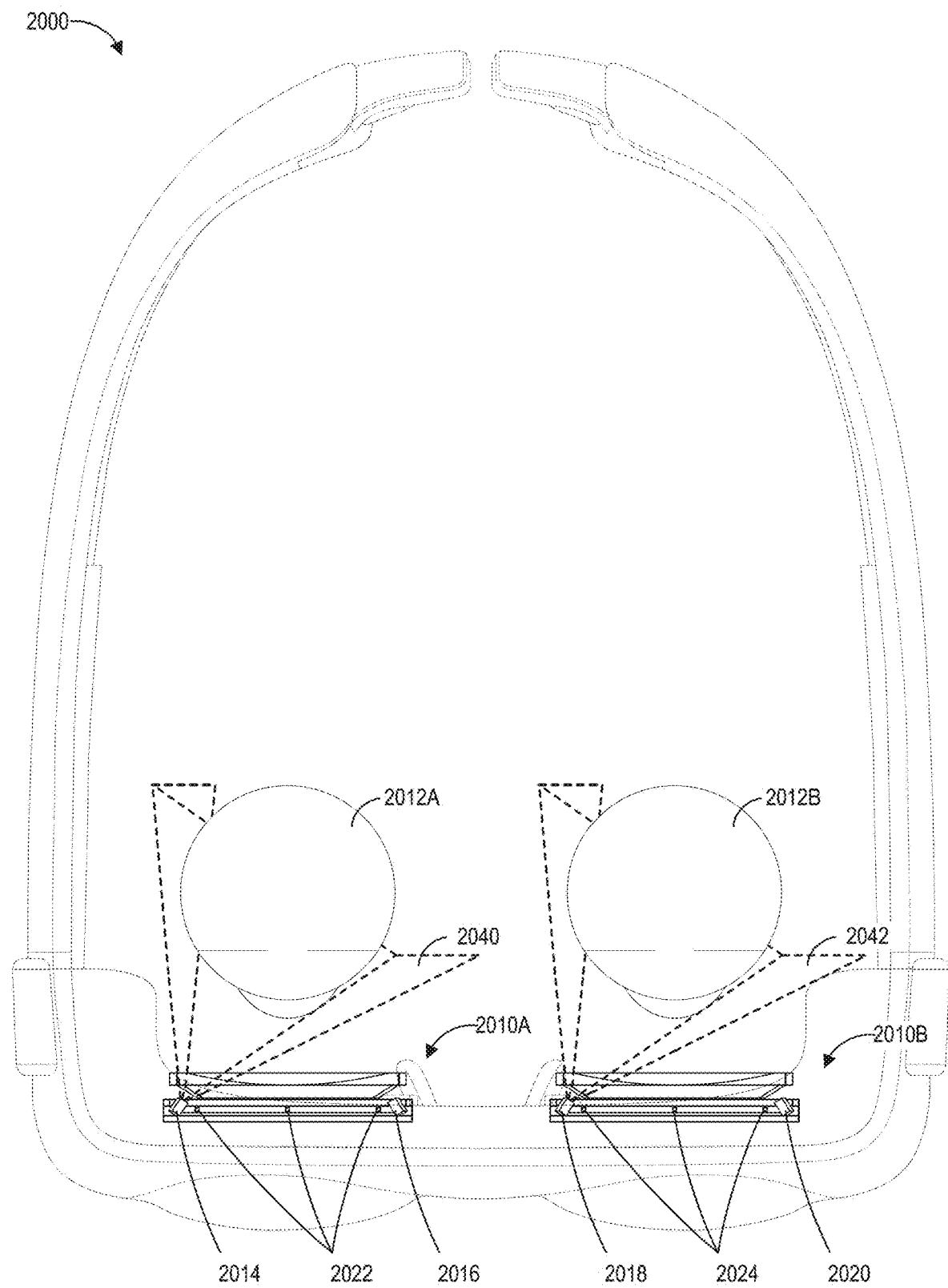
Figure 9E:
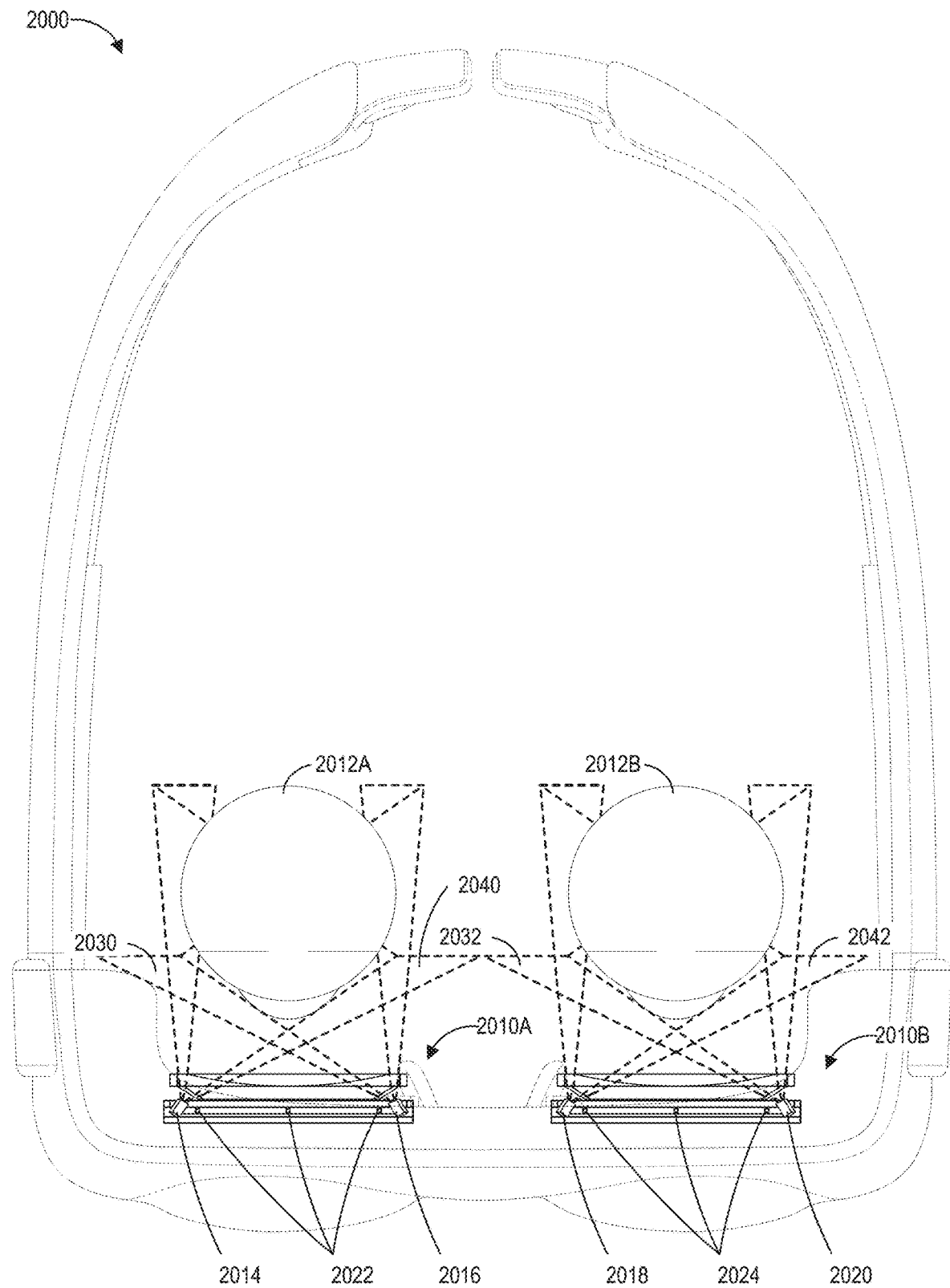

The fields of view of the imaging system for the left eyepiece 2010A can be capable of imaging all or a useful portion of the user's left eye 2012A in many different eye pose positions (and may not necessarily image the right eye or a portion thereof useful for eye tracking). Similarly, the fields of view of the imaging system for the right eyepiece 2010B can be capable of imaging all or a useful portion of the user's right eye 2012B in many different eye pose positions (and may not necessarily image the left eye or a portion thereof useful for eye tracking). For example, a user may be able move their eye up to 50 degrees from center gaze in any direction during normal movement. The imaging systems may be situated to collectively image substantially all of the full range of motion (e.g., of 50 degrees) of the user's eyes during their normal movement. FIG. 9C illustrates an example field of view 2030 of the right eye tracking camera 2016 of the left eye piece 2010A and an example field of view 2032 of the right eye tracking camera 2020 of the right eye piece 2010B. FIG. 9D illustrates an example field of view 2040 of the right eye tracking camera 2014 of the left eye piece 2010A and an example field of view 2042 of the right eye tracking camera 2018 of the right eye piece 2010B. FIG. 9E illustrates how fields of view 2030 and 2040 from the left eye tracking camera 2014 and right eye tracking camera 2016 of the left eyepiece 2010A respectively can overlap so as to image substantially all of the user's left eye 2012A. Additionally, FIG. 9E illustrates how fields of view 2040 and 2042 from the left eye tracking camera 2018 and right eye tracking camera 2020 of the right eyepiece 2010B respectively can overlap so as to image substantially all of the user's right eye 2012B. Variations are possible. For example, the number and locations of the cameras can be different. Other types of imaging systems may also be used.

L. Example of Locating a Center of Rotation with an Eye Tracking System

In order to simplify an eye tracking system (or processes within an eye tracking module 614), it may be desirable to reduce the number of variables required to determine a Center of Rotation (CoR) of the human eye. Advantageously, reducing the number of variables used to determine a CoR can also improve eye tracking accuracy. For example, since the CoR may be used to determine a gaze vector for use in eye tracking, increased error in the CoR may result in less accurate eye tracking. Error in the CoR may result from errors introduced during determination of variables used for calculating the CoR. For example, a CoR calculation may involve extracting a pupil disk center and modeling a corneal sphere. Both of those processes may introduce error and contribute to inaccuracy. Thus, it may be advantageous to extract a CoR using a limited number of variables.

Described herein are systems and methods for extracting a CoR primarily or entirely from corneal data. Advantageously, due to similar reasons as those discussed above, the present system can improve accuracy of an eye tracking system. For example, the present system may require few assumptions, thus reducing the potential for introduction of error. Additionally or in the alternative to improved accuracy, the present system can improve other aspects of an eye tracking system. For example, the present system may rely on shorter eye exposure to illumination sources. The shorter eye exposure can reduce risks associated with prolonged eye exposure to an illumination source, reduce illumination power consumption, and provide high ambient light rejection. In another example, the present system may not require a large field of view. The reduced field of view requirement can allow for greater flexibility in hardware design of a wearable system.

Figure 10:
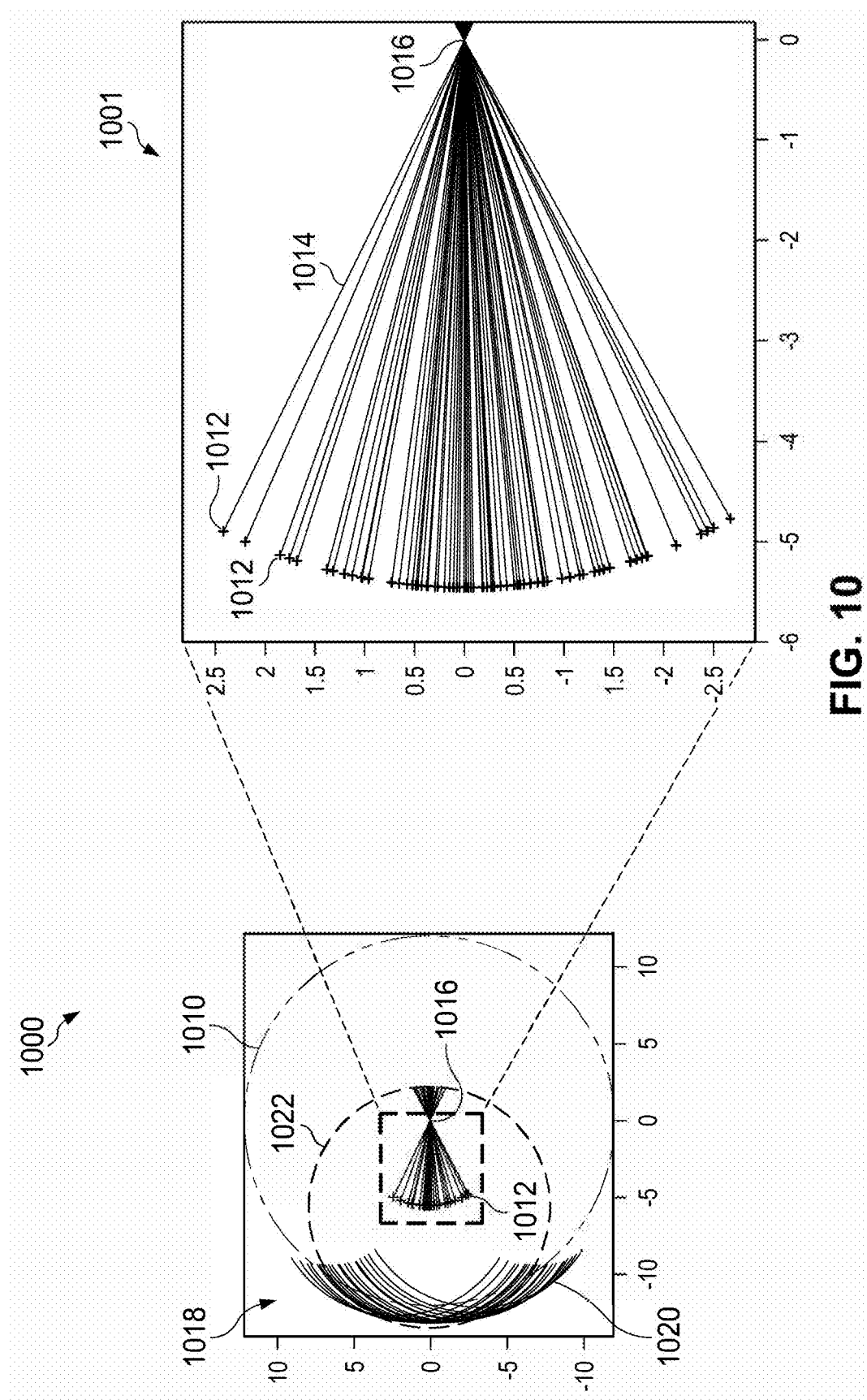
FIG. 10 shows a graphical illustration of an example Center of Rotation (CoR) determination process that may be performed by an eye tracking module.

In some examples, the Center of Rotation (CoR) of a human eye can be extracted from corneal data. FIG. 10 shows a graphical illustration of an example CoR extraction system 1000 that may be performed by an eye tracking module 614. For example, a wearable system may generate two or more glints on the cornea 1020 of a user's eye 1010 using an illumination system comprising a one or more illumination sources. In various implementations, the illumination system comprises a plurality of separate regions where light is output. These regions may correspond to separated light emitters or light sources. A glint detection and labeling module 714 may extract the glint location(s) on the cornea 1020 of the eye 1010. As described below, a 3D cornea center estimation module 716 may determine an approximate corneal curvature 1018 based on the glint locations and calculate an estimated center 1012 of that approximated corneal curvature 1018. Different eye poses may provide different approximated corneal curvatures 1018 and associated estimated centers of corneal curvature 1012. A CoR estimation module 724 may determine an estimated CoR based on a plurality of estimated centers of corneal curvature 1012 by fitting a surface to the estimated centers 1012 and determining a region 1016 of convergence or intersection of a set of surface normal vectors 1014 normal to the surface. An estimated CoR may be obtained from this region 1016, for example, the estimated COR may be at or within this region 1016.

Optionally, the CoR estimate(s) may be further checked using the eye tracking module 614. For example, as described in more detail below, if the CoR was moving with respect to the device during usage of a wearable device, new measurements of the cornea center 1012 may be tested by measuring the distance between the newly calculated cornea center 1012 and the surface fitted to the set of calculated cornea centers 1012. If the distance is too large, the eye tracking module 614 may pause eye tracking or switch to a different method of determining the CoR or a different eye tracking method. In some examples, the switch may be temporary until enough data is collected to reduce overall error.

Advantageously, the CoR extraction 1000 may employ a few assumptions. For example, the CoR extraction 1000 may assume that the glint extraction is accurate, that the geometry of the eye 1010 is known, that the radius of the cornea (or two radii in the case of cornea astigmatism) is known, or that the data is collected during normal or random motion of the user's gaze.

M. Example Eye Tracking Environment

As discussed above, the CoR may be determined from a plurality of estimated centers of corneal curvature 1012. For example, a surface may be fit to the estimated centers of corneal curvature 1012 and a plurality of surface normal vectors 1014 normal to this surface may be obtained. A region 1016 of convergence of a set of these surface normal vectors 1014 may be identified. An estimated CoR may be obtained from this region of convergence 1016, for example, the estimated CoR may be at or within this region 1016.

Figure 11:
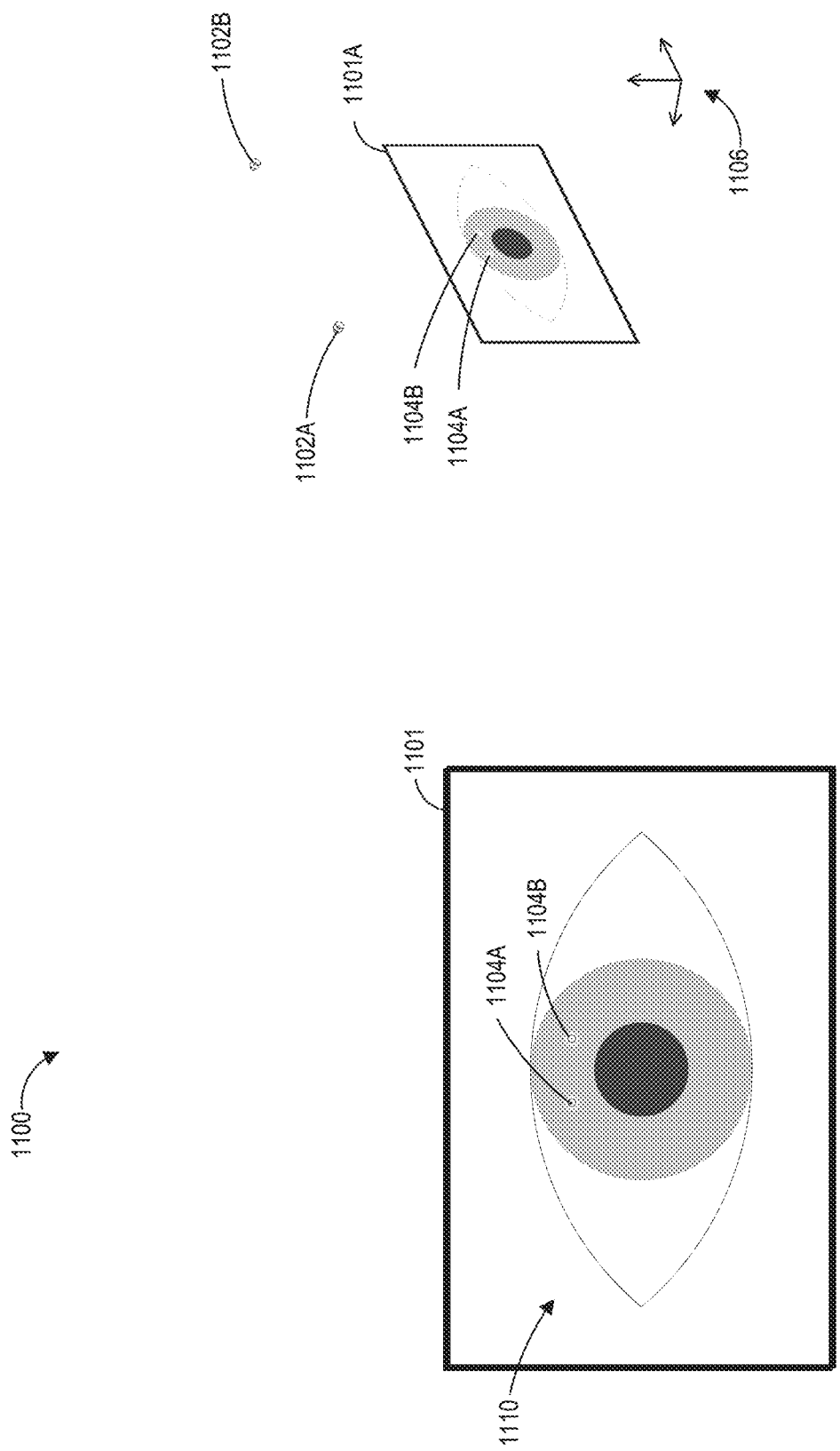
FIG. 11 shows example images of glints on any eye used by the eye tracking module for determining an estimated center of rotation.

To obtain the plurality of estimated centers of corneal curvature 1012, glints may be produced on the eye using illumination sources and imaged by a camera such as described above. FIG. 11 shows example images of glints on any eye used by the eye tracking module for determining an estimated center of rotation. For example, as discussed above, a wearable system may include an imaging system. The imaging system may image a user's eye 1110 to produce an eye image 1101. The wearable system may include one or more illumination source(s) 1102 that comprise spatially separate regions that output light. Accordingly, light from the illumination source(s) 1102 may produce one or more glint(s) 1104 on the user's eye 1110 that are reflections of these spatially separate regions radiating light.

The imaging system of the wearable system may be part of an eye tracking assembly (for example, as shown in FIGS. 9A-E). The imaging system may include one or more cameras. For example, the imaging system can include a single camera at a location 1106 in relation to a user's eye 1110. In another example, the imaging system can include multiple cameras that may be located at different locations in relation to the user's eye 1110.

The illumination source(s) 1102 can include one or more light sources such as light emitting diodes (LEDs). The illumination source(s) may emit light in visible or non-visible light (for example, infrared (IR) light). For example, the illumination source(s) 1102 can be infrared (IR) LEDs. The illumination source(s) 1102 can be part of an eye tracking assembly (for example, as illustrated in FIGS. 9A-E).

The illuminations source(s) 1102 may produce one or more specular reflections 1104 on the cornea of a user's eye 1110. The specular reflections 1104 may also be referred to as glints. For example, there may be two illumination sources (1102A, 1102B). The illumination source(s) may be configured to produce two or more discrete glints (1104A, 1104B) on the user's eye 1110. FIG. 11 shown an image of user's eye with the glints thereon. FIG. 11 also shows a view of the camera 1106 (represented by the origin of the coordinate system) in comparison to the location of the eye 1110 and the glints 1104A, 1104B thereon as well as with respect to the illumination sources 1102A, 1102B at their relative locations.

Figure 12A:
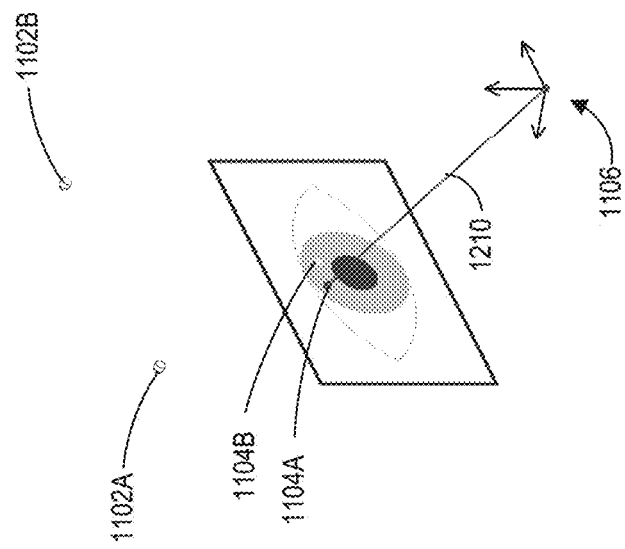
FIGS. 12A-D illustrate steps in an example determination of a first plane that includes the locations of a first glint, the camera capturing the image of the glint, and the source of illumination producing the first glint.
Figure 12A:
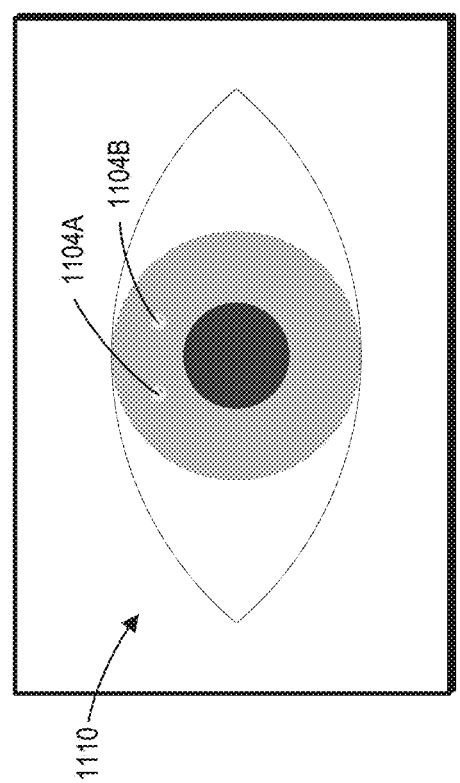
Figure 12B:
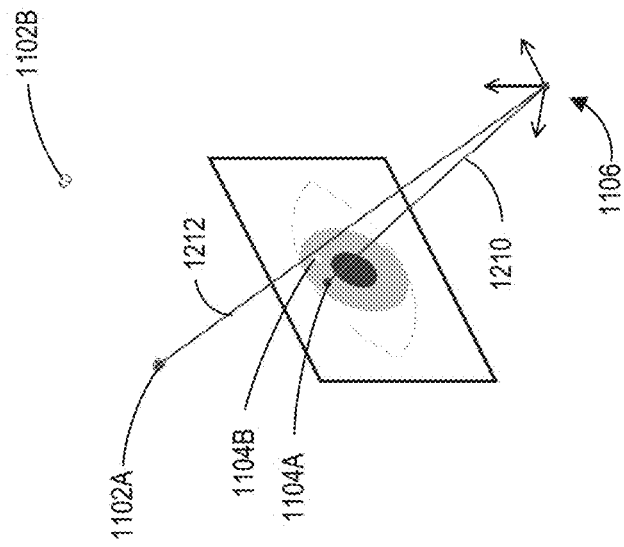
Figure 12B:
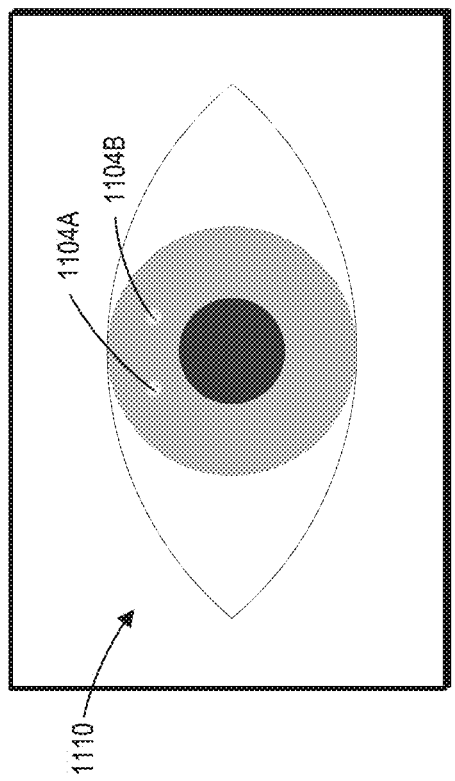
Figure 12C:
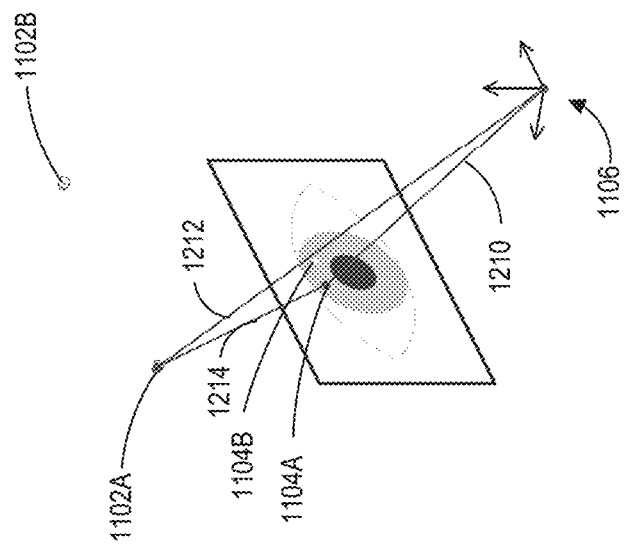
Figure 12C:
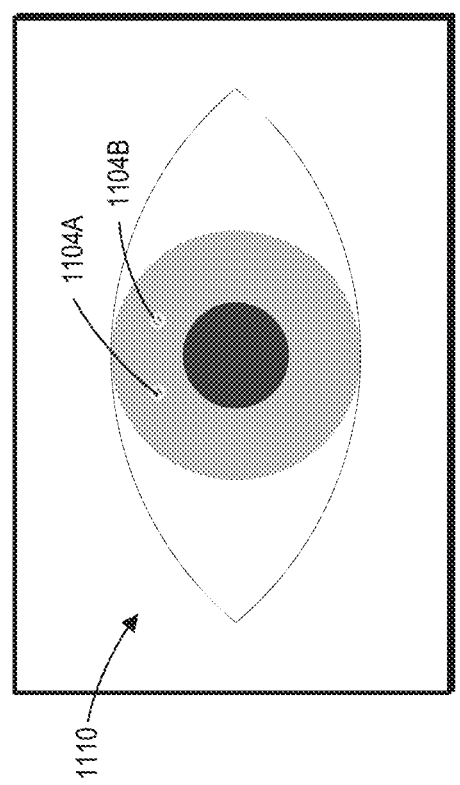
Figure 12D:
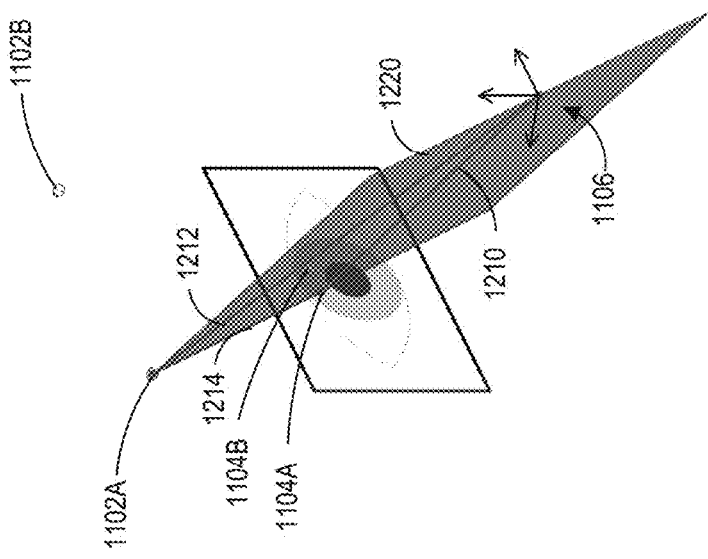
Figure 12D:
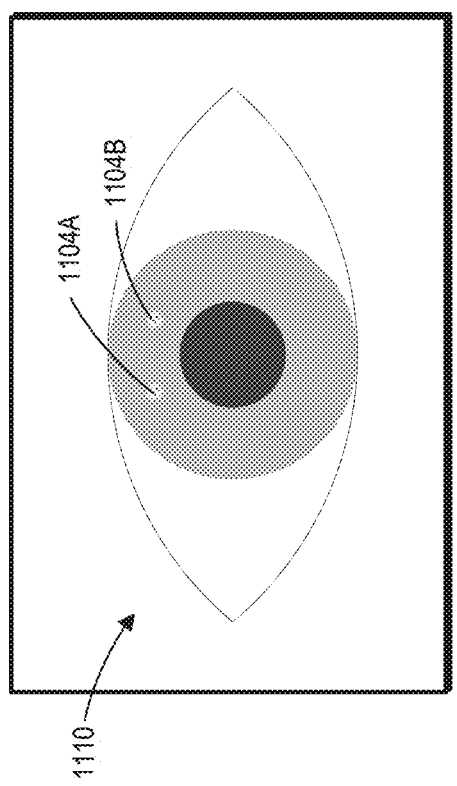
Figure 13A:
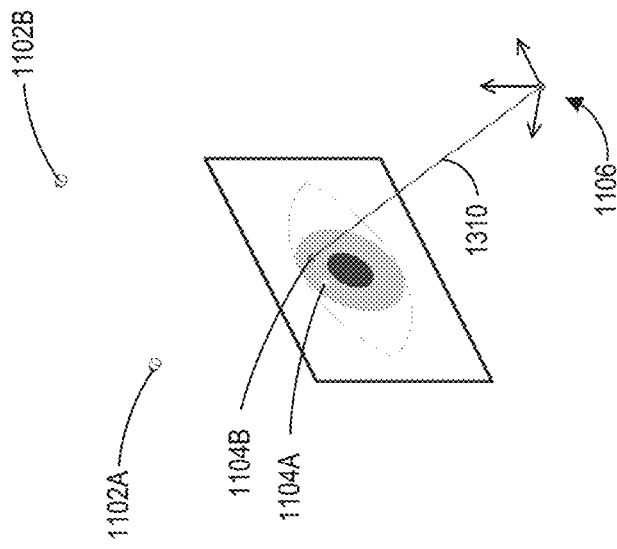
FIGS. 13A-D illustrate steps in an example determination of a second plane that includes the locations of a second glint, the camera, and the source of illumination producing the second glint.
Figure 13A:
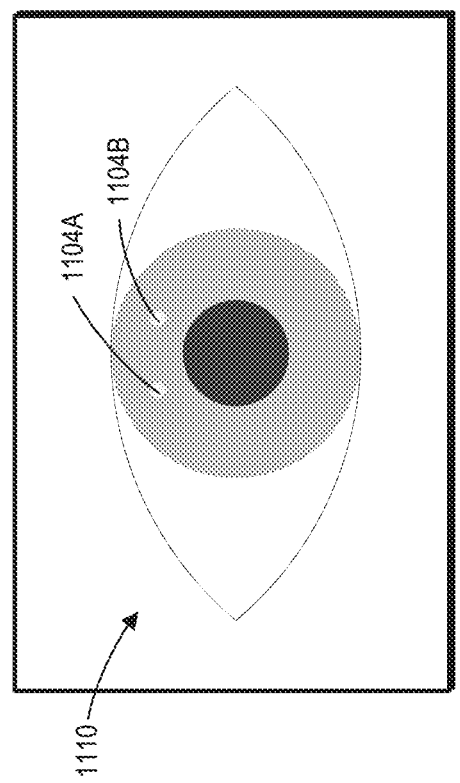
Figure 13B:
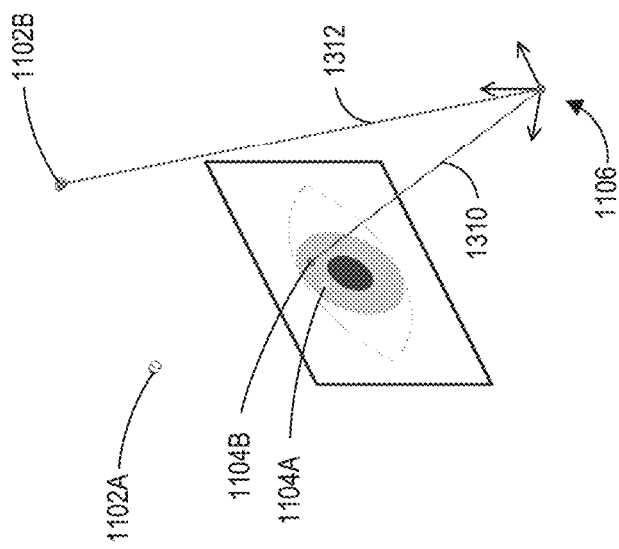
Figure 13B:
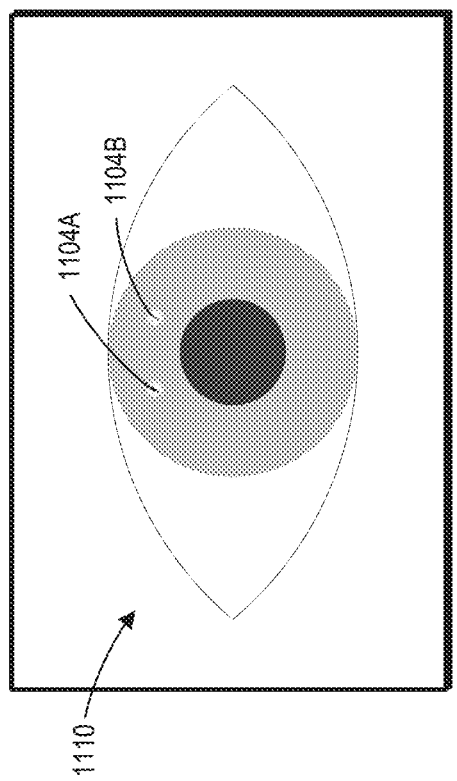
Figure 13C:
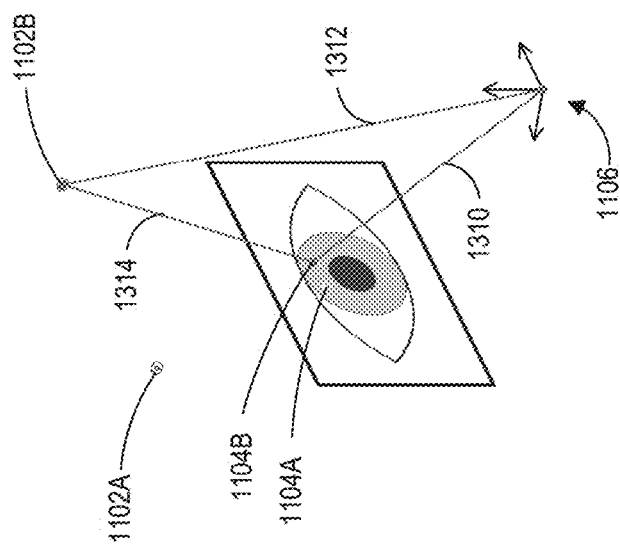
Figure 13C:
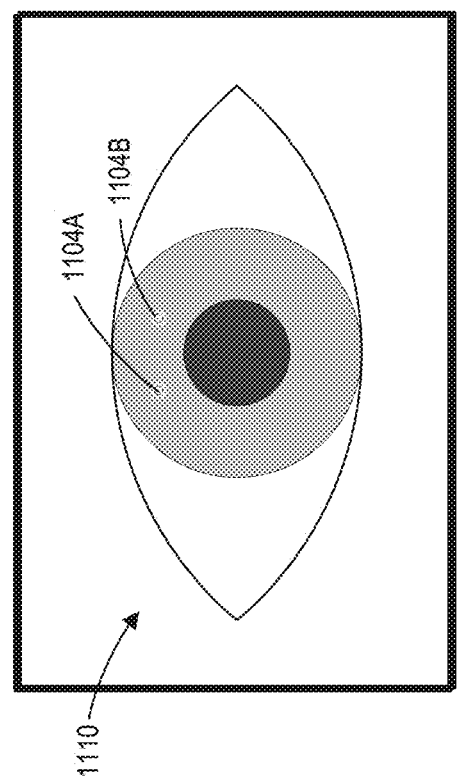
Figure 13D:
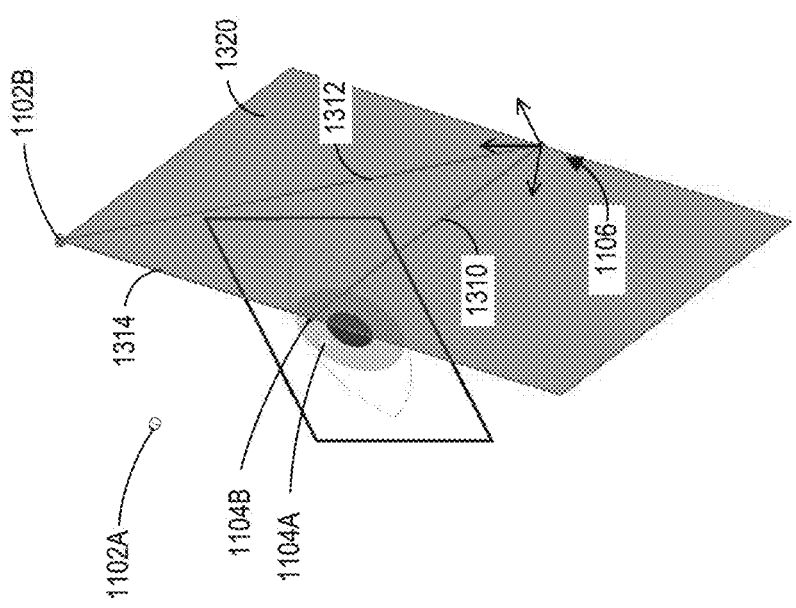
Figure 13D:
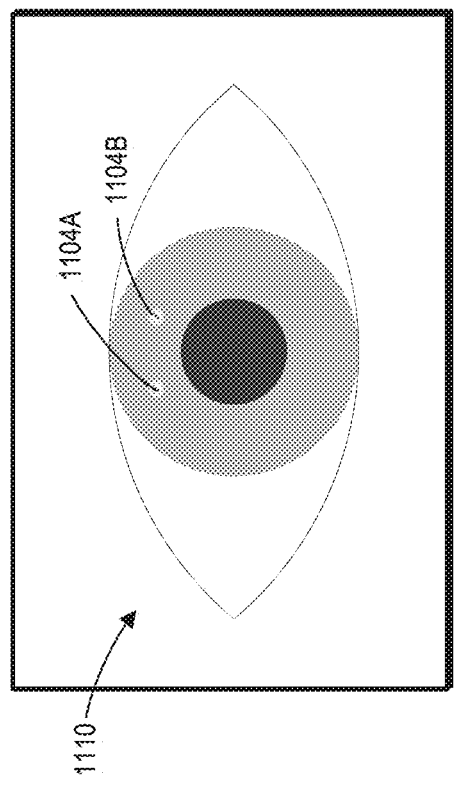
Figure 14A:
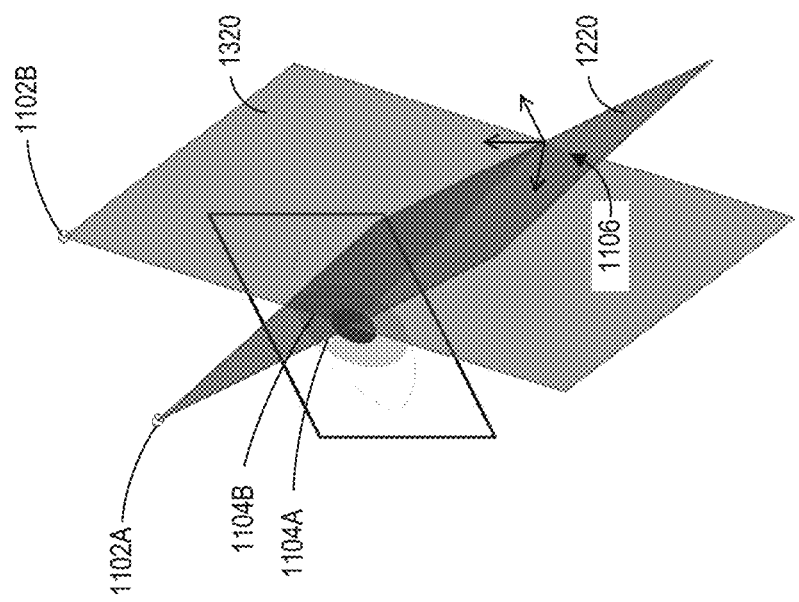
FIGS. 14A-C illustrate the intersection between the first plane of FIGS. 12A-D and the second plane of FIGS. 13A-D. This intersection corresponds to a vector along which the cornea center may lie.
Figure 14A:
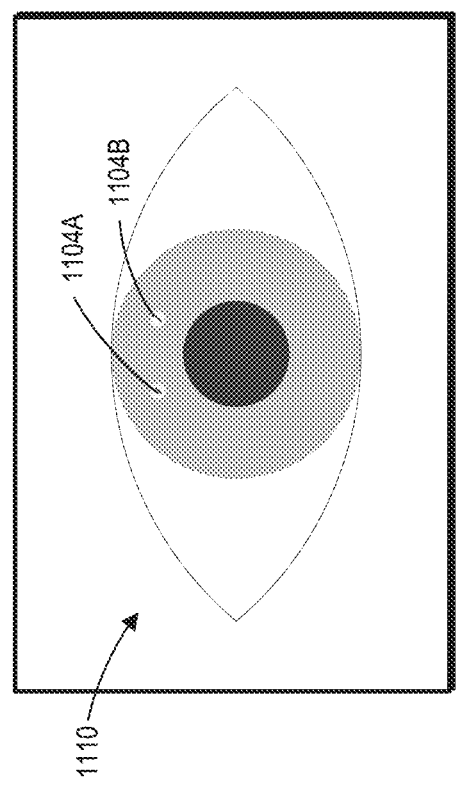
Figure 14B:
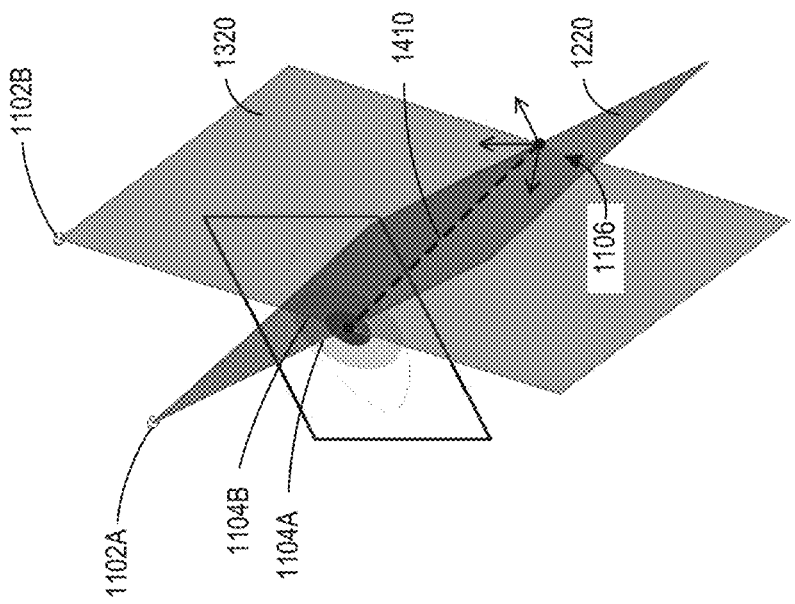
Figure 14B:
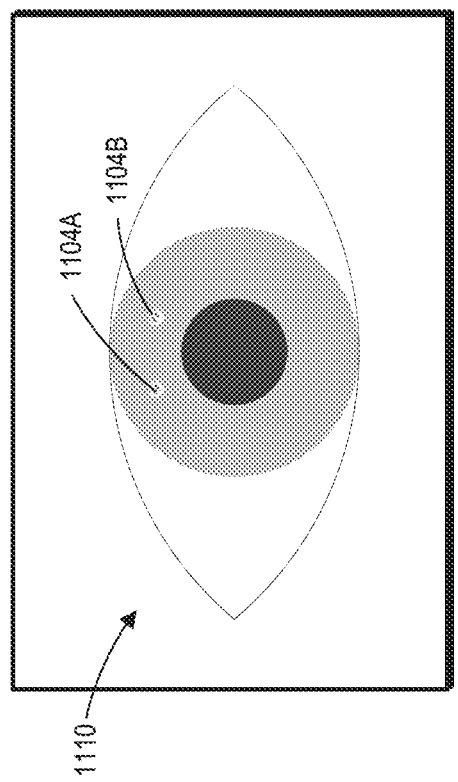
Figure 14C:
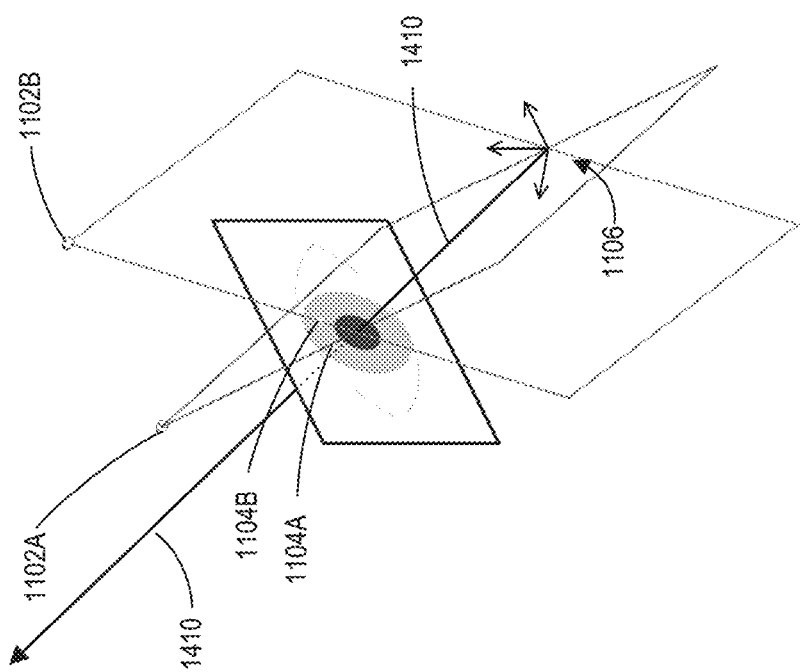
Figure 14C:
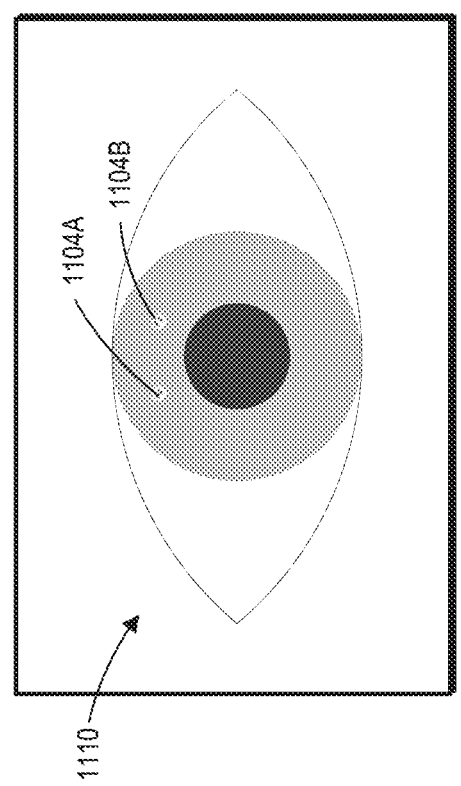

N. Example Extraction of a Vector Along Which a Cornea Center is Located Using a Single Camera As discussed above, a camera at location 1106 may image glints 1104A, 1104B on a user's eye 1110 that are produced by illumination sources 1102A, 1102B. FIGS. 12A-D, a first plane 1220 that includes the location of a glint 1104A, the camera capturing the image of the glint at location 1106, and the source of illumination 1102A producing the glint can be determined. In particular, a module may determine a first plane 1220 that includes a first illumination source 1102A and a first glint 1104A. Similarly, as illustrated in FIGS. 13A-D, a second plane 1320 that includes the locations of a glint 1104B, the camera capturing the image of the glint at location 1106, and the source of illumination 1102B producing the glint can be determined. In particular, the module 716 may determine a second plane 1320 based on a second illumination source 1102B and a second glint 1104B. As illustrated in FIGS. 14A-C, the module 716 may determine the intersection between the first plane 1220 and second plane 1320. The intersection between the first plane 1220 and second plane 1320 may define a vector 1410 directed along where the cornea center is located. As shown in FIGS. 14A-C, this vector 1410 may also extend along a direction that includes the location 1106 of the camera.

In some implementations, the module 716 may determine a first plane 1220 by determining a set of lines 1210, 1212, 1214 between a first illumination source 1102A, a first glint 1104A, and camera location 1106. As illustrated in FIG. 12A, the module 716 may determine a first line 1210 extending between the camera location 1106 and the location in an image plane 1101A of a first glint 1104A that may be produced by a first illumination source 1102A. As illustrated in FIG. 12B, the module 716 may determine a second line 1212 extending between the camera location 1106 and the location of the illumination source 1102A that produced the first glint 1104A. As illustrated in FIG. 12C, the module 716 may determine a third line 1214 cast between the location in the image plane 1101A of the illumination sources 1102A and the first glint 1104A. As illustrated in FIG. 12D, any two of these lines 1210, 1210, and 1214 may define a plane 1220 in which a cornea center may lie.

Similarly, in some implementations, the module 716 may determine a second plane 1320 by determining a set of lines 1310, 1312, 1314 between a second illumination source 1102B, a second glint 1104B, and camera location 1106. As illustrated in FIG. 13A, the module 716 may determine a first line 1310 extending between the camera location 1106 and the location in the image plane 1101A of a second glint 1104B that may be produced by a second illumination source 1102B. As illustrated in FIG. 13B, The module 716 may determine a second line 1313 extending between the camera location 1106 and the location of the second illumination source 1102B that produced the second glint 1104A. As illustrated in FIG. 13C, the module 716 may determine a third line 1314 extending between the location in the image plane 1101A of the second glint 1104B and the second illumination source 1102B. As illustrated in FIG. 13D, the lines 1310, 1310, and 1314 may define a plane 1320 in which a cornea center may lic.

In some implementations, however, the first plane 1220 can be determined directly from the locations of the first illumination source 1102A and the first glint 1104A, as well as the camera location 1106 without necessarily separately defining the lines 1210, 1210, and 1214. Similarly, the second plane 1320 can be determined directly from the locations of the second illumination source 1102B and the second glint 1104B, as well as the camera location 1106 without necessarily separately defining the lines 1310, 1310, and 1314

The module 716 may identify an intersection between first and second planes 1220 and 1320. As illustrated in FIGS. 14A and 14B, the intersection of first plane 1220 and second plane 1320 may define a vector 1410 with an origin at the camera location 1106 or otherwise extending along a direction that may include the camera location. As shown in FIG. 14C, the vector 1410 may point towards a cornea center location.

The module 716 may repeat the estimation process multiple times to generate one or more cornea vectors 1410. For example, the module 716 may determine a first plane 1220 with which to define the vector based on a first illumination source 1102A and a first glint 1104A with multiple different camera locations 1106. The camera locations 1106 can be varied in relation to a user's eye 1110 (for example, with respect to a distance to the user's eye 1110 or horizontal or vertical position with respect to the eye or any combination thereof) or with respect to the location of an illumination source (1102A, 1102B). The module 716 may determine vectors 1410 for one or more of the camera locations 1106. The module 716 may then determine the cornea center from an intersection of two or more vectors as described above. If the two or more vectors do not intersect, then the cornea center may be interpolated or otherwise extrapolated from the vector data. Additionally or alternatively, the eye tracking module 614 may collect and analyze more data to determine the cornea center.

The module 716 may repeat the estimation process while varying one or more parameters associated with an eye tracking environment 1100. For example, the module 716 may repeat the process with different camera locations or for different gaze directions of the user's eye. The eye tracking module 614 may utilize gaze targets to ensure that a user maintains their eye pose while a parameter is varied. For example, the eye tracking module 614 may estimate one or more vectors 1410 while the user directs their gaze at the gaze targets while varying a parameter, such as the location 1106 of the camera or location of an illumination source 1102. Additionally or alternatively, the eye tracking module 614 may estimate one or more vectors 1410 while the user naturally moves their gaze during use of the wearable device. For example, the eye tracking module 614 may capture data associated with different parameters during natural movement of the user's eye.

The repeated estimation process may result in multiple vectors 1410 pointing to a cornea center associated with a particular eye pose. The module 716 may determine an intersection or region of convergence of the multiple vectors 1410 to generate an estimated center of corneal curvature.

Figure 15A:
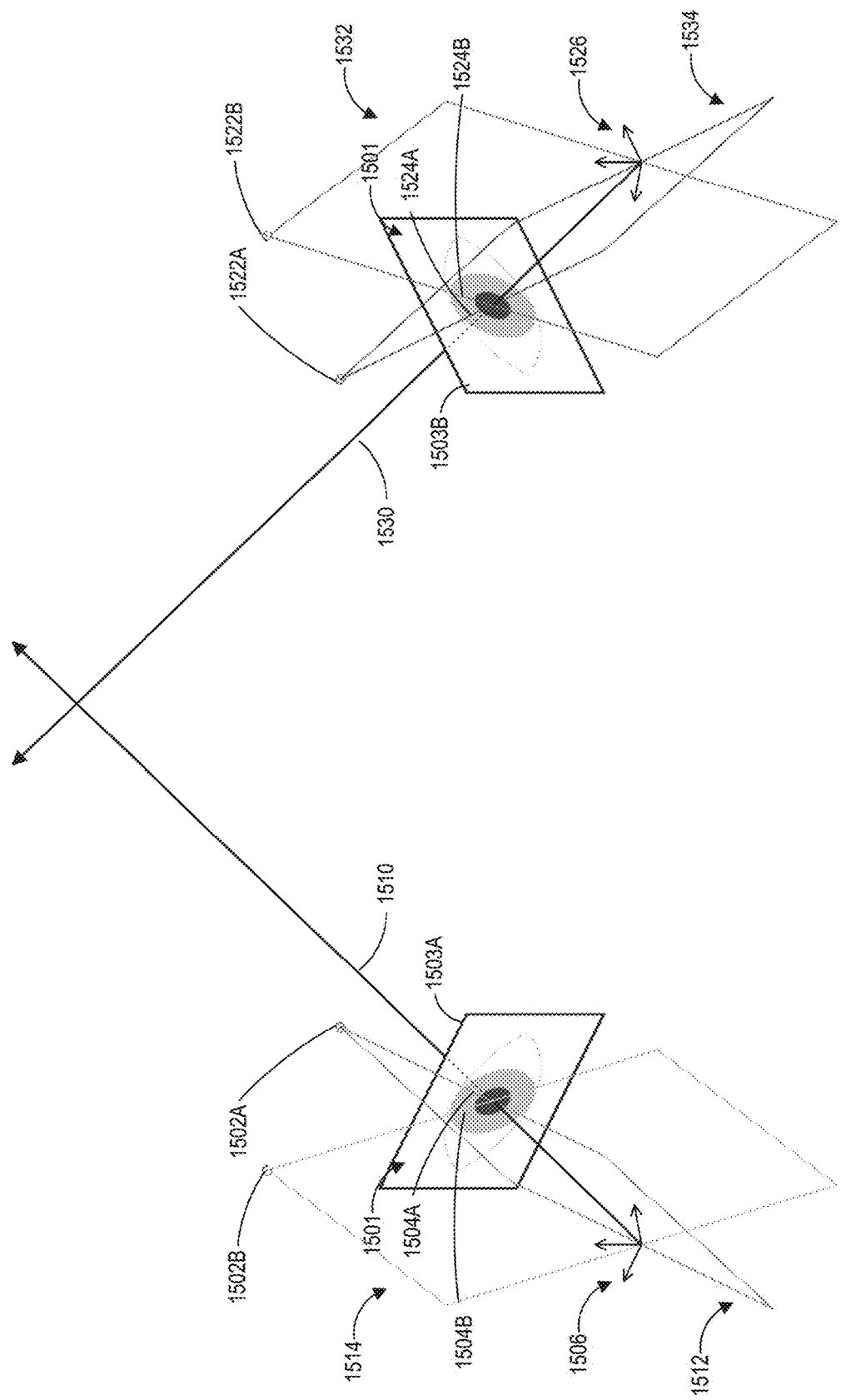
FIGS. 15A-15B illustrate a plurality of vector along which the cornea center may lie obtained using multiple cameras. These vectors may converge or intersect at a location corresponding to or close to the corneal center.
Figure 15B:
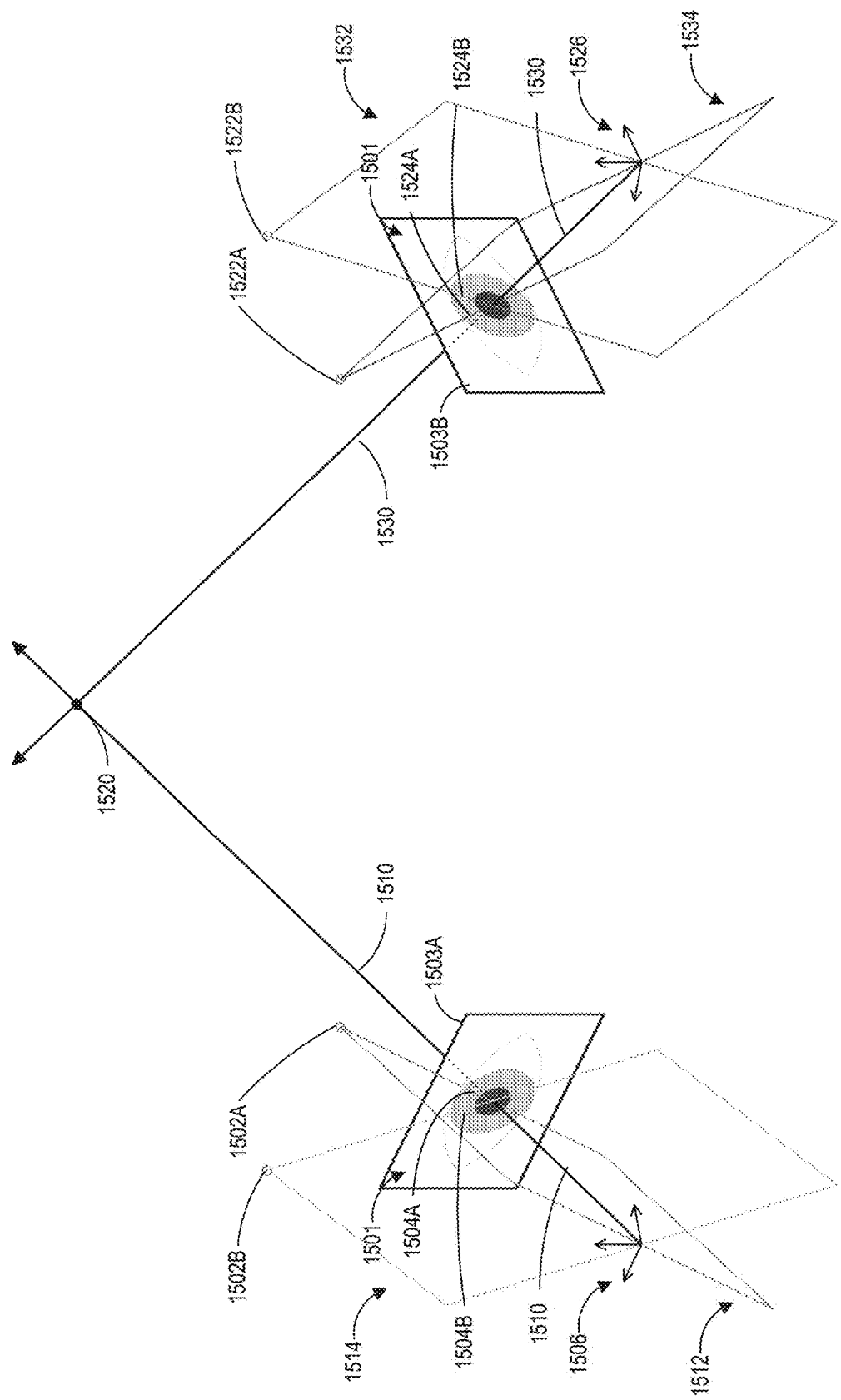

O. Example Extraction of a Vector Along Which a Cornea Center is Located Using a Multiple Cameras In various implementations, multiple cameras may be employed to image the eye and images from the multiple cameras may be used to determine the center of curvature of the cornea of that eye. In particular, the module 716 may determine vectors (1510, 1530) along which the cornea center may be located. FIGS. 15A-16C illustrate steps in an example process for determining such a vector with multiple cameras. For example, as illustrated in FIG. 15A, a first camera at a first location 1506 may image glints 1504A, 1504B on a user's eye 1501 that are produced by illumination sources 1502A, 1502B and a second camera at a location 1526 may image glints 1524A, 1524B on a user's eye 1501 that are produced by illumination sources 1522A, 1522B. The module 716 may determine a first vector 1510 based on data associated with the first camera at location 1506 and illumination sources 1502A, 1502B and may determine a second vector 1530 associated with the second camera at location 1526 illumination sources 1522A, 1522B. As illustrated in FIG. 15B, the module 716 may estimate a cornea center 1520 by determining a convergence or intersection between the first vector 1510 and second vector 1530.

To obtain the first vectors 1510, the module 716 may identify a first plane 1512 by determining a set of lines (not shown) between a first illumination source 1502A, a first glint location 1504A in an image plane 1503A, and a first camera at first location 1506. The module 716 may determine a second plane 1514 by determining a set of lines (not shown) between a second illumination source 1502B, a second glint location 1504B in an image plane 1503A, and a second camera location 1506. The module 716 may determine a vector 1510 by determining an intersection between these first and second planes 1512 and 1514. The intersection of these planes 1512 and 1514 may define a vector 1510 with an origin at the camera location 1506 that point towards a cornea center of curvature location.

In some implementations, however, the first plane 1512 can be determined directly from the locations of the first illumination source 1502A, the first glint 1504A, and the first camera 1106 without necessarily separately defining one or more lines. Similarly, the second plane 1514 can be determined directly from the locations of the second illumination source 1502B, the second glint 1504B, and the first camera 1506 without necessarily separately defining one or more lines.

A module 716 may similarly determine a first plane 1532 by determining a set of lines (not shown) between a first illumination source 1522A, a first glint location 1524A in an image plane 1503B, and a first camera at location 1526. The module 716 may determine a second plane 1534 by determining a set of lines (not shown) between a second illumination source 1522B, a second glint location 1524B in an image plane 1503B, and camera location 1526. The module 716 may determine a second vector 1530 by determining an intersection between these first and second planes 1532 and 1534. The intersection of the planes 1532 and 1534 may define a vector 1530 with an origin at the camera location 1526 that may point towards a cornea center of curvature location. In some implementations, however, the first plane 1532 can be determined directly from the locations of the first illumination source 1522A, the first glint 1524A, and the second camera 1526 without necessarily separately defining one or more lines. Similarly, the second plane 1534 can be determined directly from the locations of the second illumination source 1522B, the second glint 1524B, and the second camera 1526 without necessarily separately defining one or more lines.

As illustrated in FIG. 15B, the module 716 may determine a cornea center of curvature location based on the these first and second vectors 1510 and 1530. For example, the module 716 may determine a convergence or intersection 1520 of these vectors 1510 and 1530. The convergence or intersection 1520 may correspond to an approximate cornea center location. If the vectors 1510 and 1530 do not intersect, then the cornea center of curvature may be interpolated or otherwise extrapolated from the vector data. Additionally or alternatively, the eye tracking module 614 may collect and analyze more data to determine the cornea center of curvature 1520.

Figure 16A:
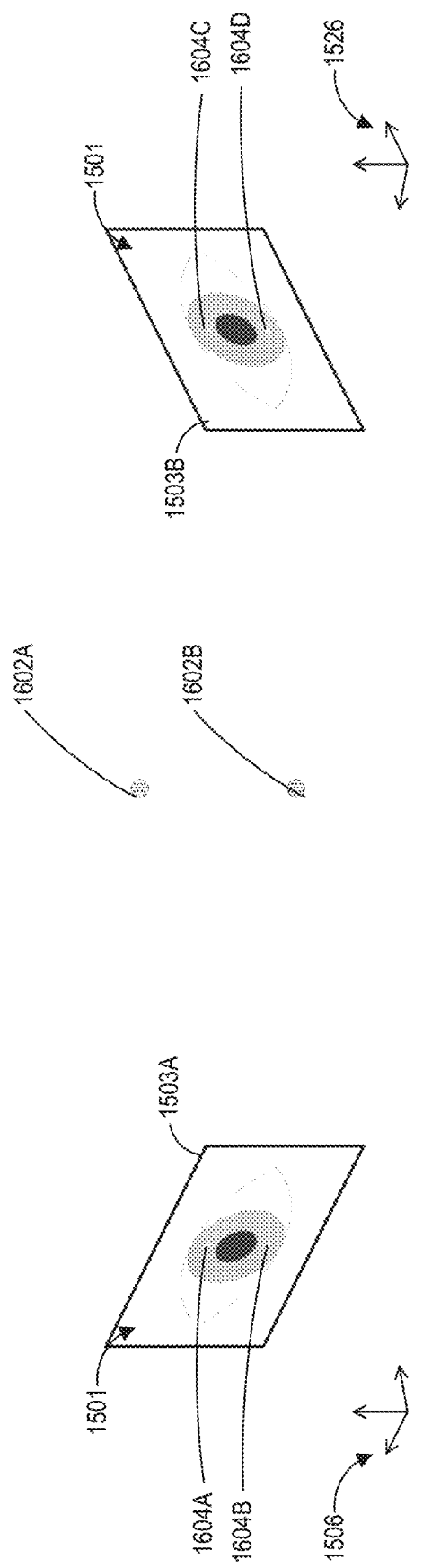
FIGS. 16A-16C illustrate example steps in an example determination of a vectors along which the cornea center may lie using shared illumination sources between multiple cameras.
Figure 16B:
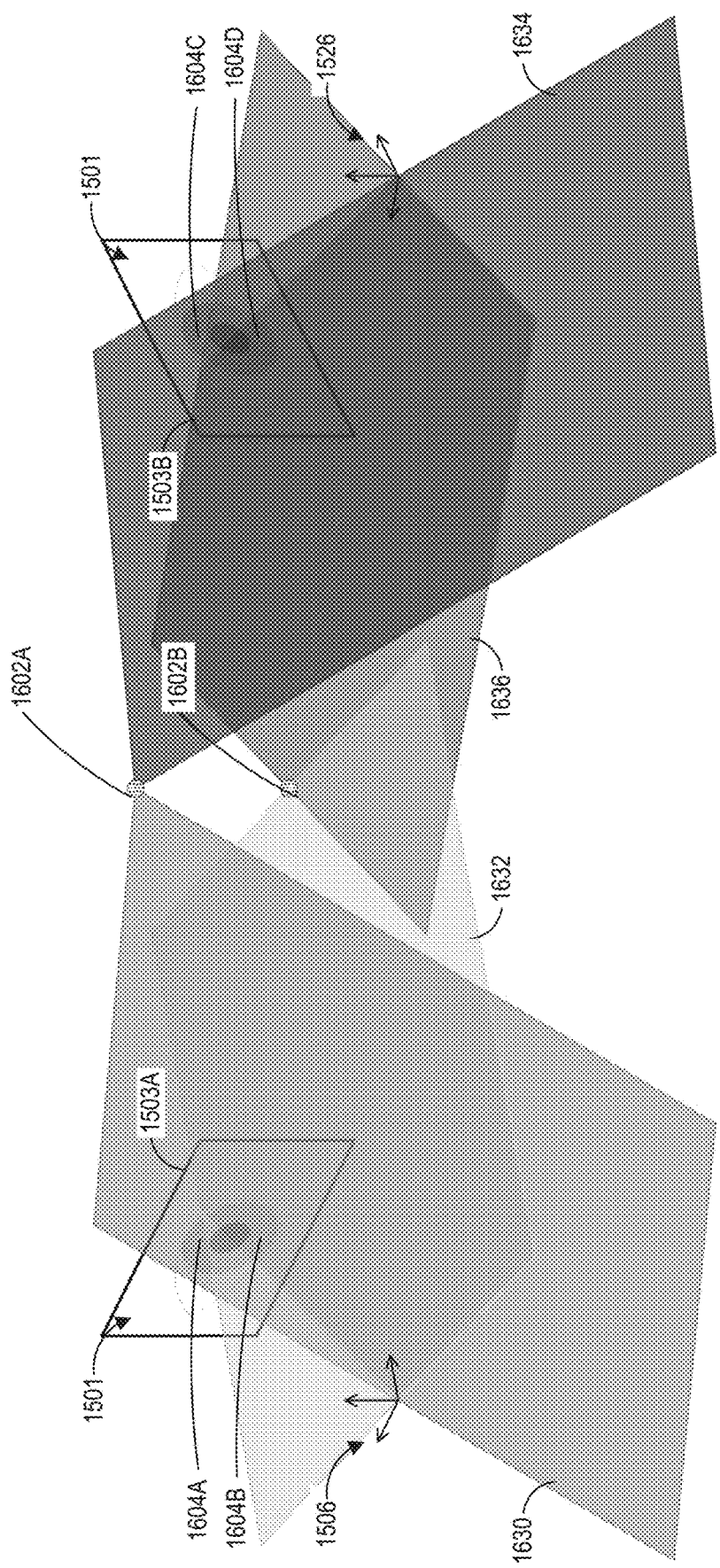
Figure 16C:
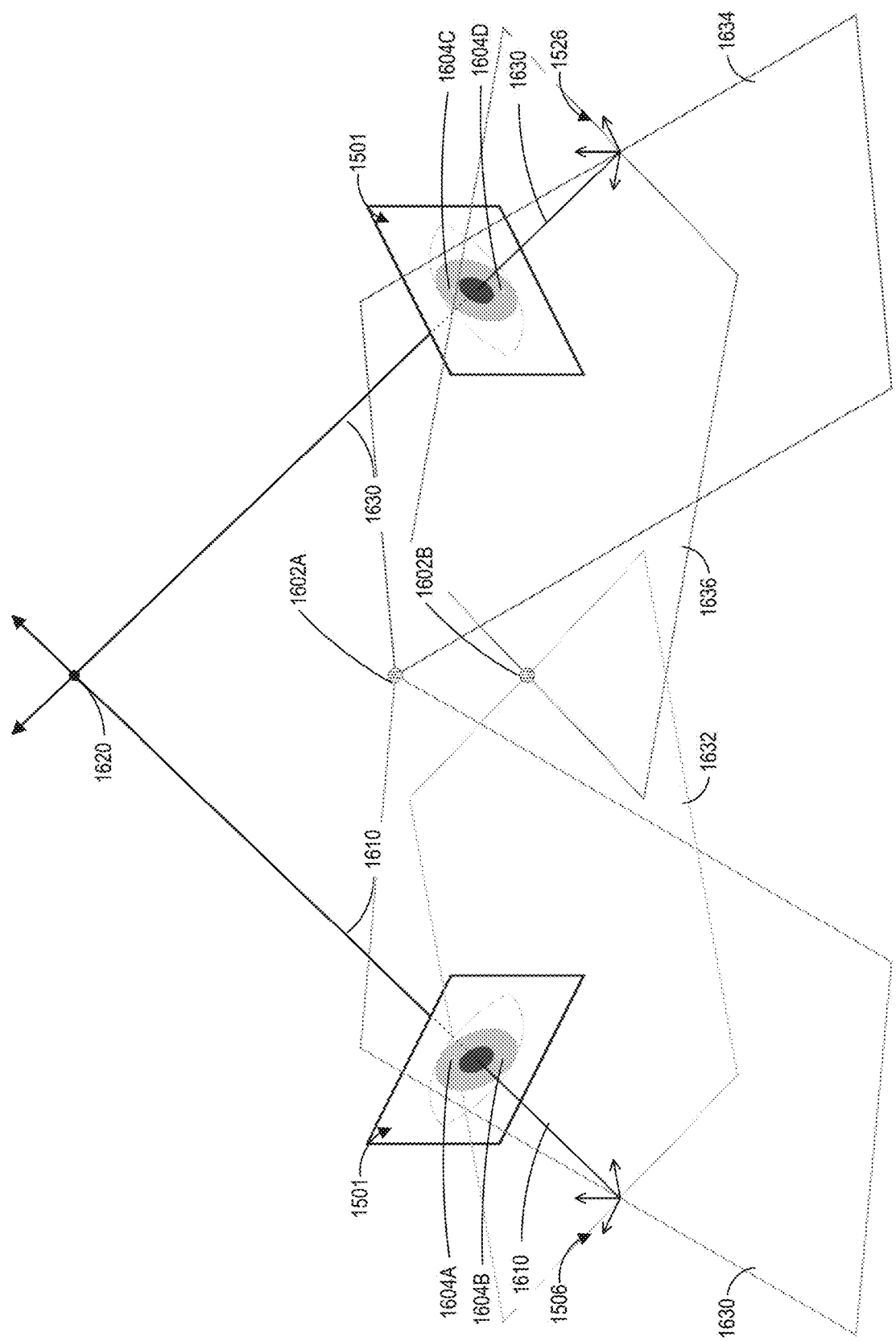

FIGS. 16A-16C illustrate another example process for determining corneal center of curvature using multiple cameras. As illustrated in FIG. 16A, a wearable system may have a set of shared illumination sources 1602A, 1602B that may be used with multiple eye cameras. The shared illumination sources 1602A, 1602B may be in addition or in the alternative to a set of separate illumination sources associated with one or more cameras. The set of shared illumination sources 1602A, 1602B may produce glints 1604A, 1604B, 1604C, 1604D on a user's eye.

As illustrated in FIG. 16B, a module 716 may determine a set of planes using the shared illumination sources 1602A, 1602B. For example, the module 716 may determine a first plane 1630 by determining a set of lines (not shown) between a first illumination source 1602A, a first glint location 1604A in an image plane 1503A, and a first camera at location 1506. The module 716 may determine a second plane 1632 by determining a set of lines (not shown) between a second illumination source 1602B, a second glint location 1604B in a first image plane 1503A, and first camera location 1506.

In some implementations, however, the first plane 1630 can be determined directly from the locations of the first illumination source 1602A, the first glint 1604A in the first image plane 1503A, and the first camera 1506 without necessarily separately defining one or more lines. Similarly, the second plane 1632 can be determined directly from the locations of the second illumination source 1602B, the second glint 1604B, and the first camera 1506 without necessarily separately defining one or more lines.

The module 716 may determine a different first plane 1634 by determining a set of lines (not shown) between the first illumination source 1602A, a first glint location 1604C in an image plane 1503B, and a second camera at location 1526. The module 716 may determine a separate different plane 1636 by determining a set of lines (not shown) between the second illumination source 1602B, a second glint location 1604D in a second image plane 1503B, and second camera location 1526.

In some implementations, however, the different first plane 1634 can be determined directly from the locations of the first illumination source 1602A, the first glint 1604C in the image plane 1503B, and the second camera 1526 without necessarily separately defining one or more lines. Similarly, the different second plane 1636 can be determined directly from the locations of the second illumination source 1602B, the second glint 1604D, and the second camera 1526 without necessarily separately defining one or more lines.

As illustrated in FIG. 16C, the module 614 may determine an intersection between planes 1630 and 1632 to determine a vector 1610. The intersection of the planes 1630 and 1632 may define the vector 1610 with an origin at the camera location 1506 that may point towards a cornea center location. Similarly, the module 614 may determine an intersection between planes 1634 and 1636 to determine a vector 1630. The intersection of the planes 1634 and 1636 may define the vector 1630 with an origin at the camera location 1526 that may point towards a cornea center location.

With continued reference to FIG. 16C, the module 716 may determine a cornea center of curvature location based on the vectors 1610 and 1630. For example, the module 716 may determine a convergence or intersection 1620 of the first and second vectors 1610 and 1630. The convergence or intersection 1620 may correspond to an approximate cornea center of curvature location. If the first and second vectors 1610 and 1630 do not intersect, then the cornea center of curvature may be interpolated or otherwise extrapolated from the vector data. Additionally or alternatively, the eye tracking module 614 may collect and analyze more data to determine the cornea center of curvature.

The module 716 may repeat the estimation process for multiple gaze directions of the user's eye. For example, a wearable system may display one or more gaze targets at which a user may direct their gaze. The eye tracking module 614 may estimate one or more vectors 1410 while the user directs their gaze at the gaze targets. Additionally or alternatively, the eye tracking module 614 may estimate one or more vectors 1410 while the user naturally moves their gaze during use of the wearable device. For example, the eye tracking module 614 may capture data associated with different parameters during natural movement of the user's eye. As described below, the data captured at different eye poses or gaze vectors of the user's eye may be used to calculate multiple cornea centers, which may be used by a CoR estimation module 724 to estimate a CoR.

P. Estimating Center of Rotation

A Center of Rotation (CoR) estimation module 724 may determine an estimated center of rotation based on the estimated centers of corneal curvature 1012. For example, the CoR estimation module 724 may fit a surface to one or more estimated cornea centers of curvature and determine a set of surface normal vectors normal to the fit surface. The surface normal vectors may converge or intersect at a point or region that may correspond to the estimated CoR.

To determine a surface, the module 614 may analyze multiple eye images. For example, a wearable system may image the user's eye 1501 (for example, with the inward facing imaging system 462) while the user's eye 1501 is in one or more eye poses. In some implementations, the module 614 may prompt the one or more eye poses or gaze directions through the display of gaze targets on a display of a wearable device. Additionally or alternatively, the module 614 may collect data associated with one or more eye poses that occur naturally during use of a wearable device.

Figure 17A:
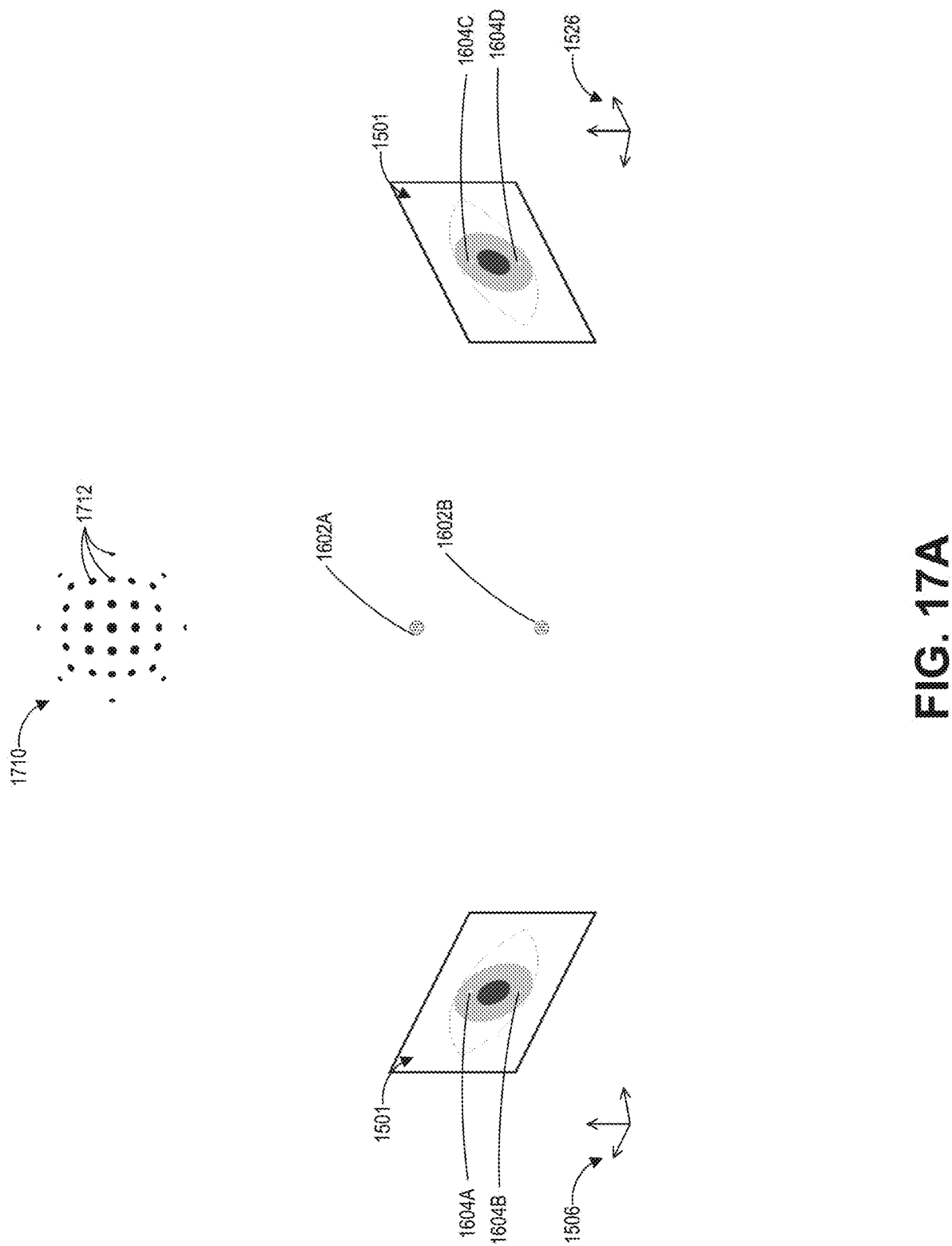
FIGS. 17A-17B show estimation of a 3D surface based on calculated cornea centers.
Figure 17B:
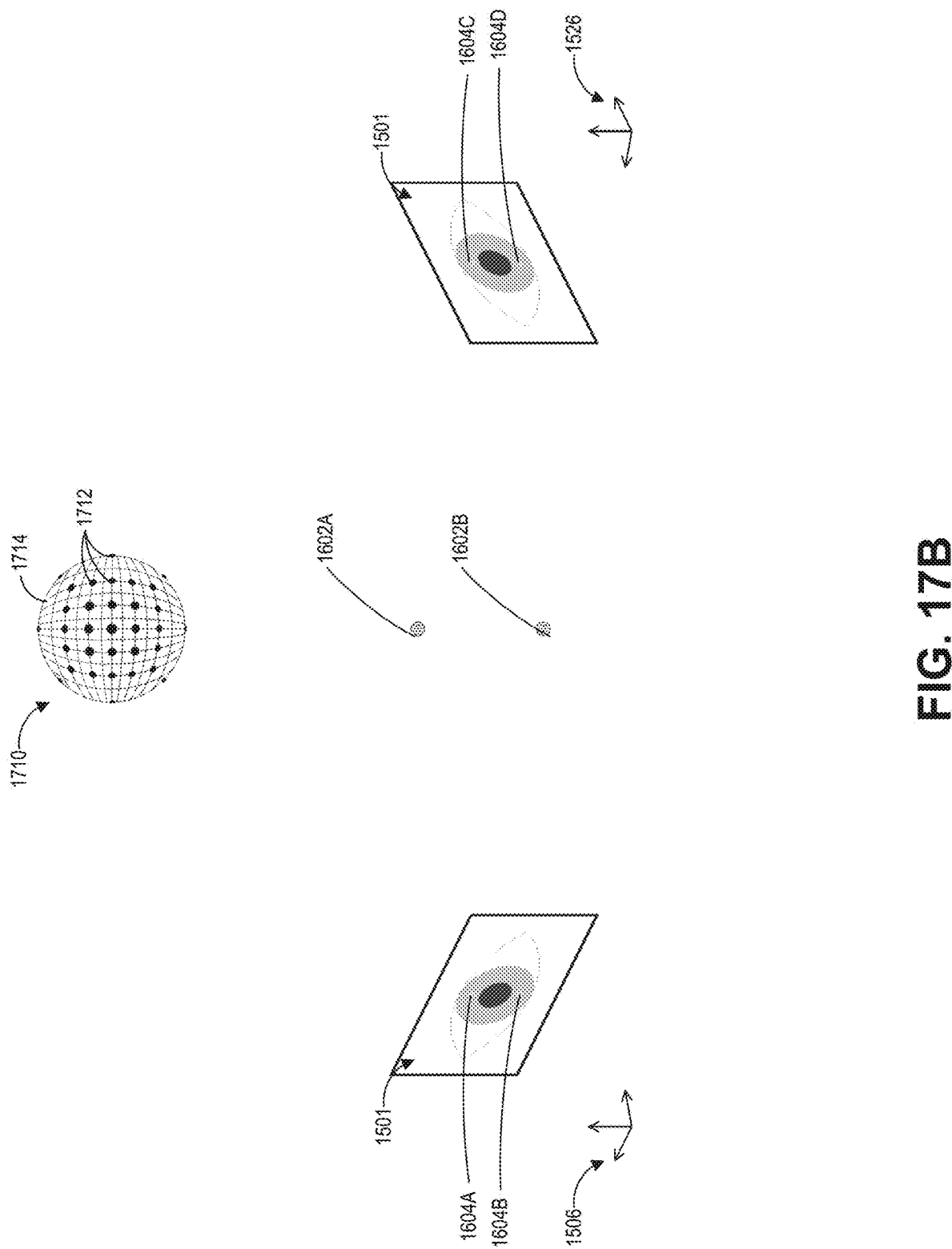

As illustrated in FIGS. 17A and 17B, a module 614 may determine multiple cornea centers of curvature 1712 based on data collected by the wearable system while the user's eye is in one or more eye poses. For example, the module 614 may perform a cornea center of curvature estimation process as described above with one or more camera as part of module 716 multiple times (e.g., for different gaze directions or eye poses of a user's eye 1501). The output of the cornea center estimation processes of module 716 may include multiple estimated cornea centers of curvature 1712.

The multiple cornea centers of curvature 1712 may be situated within a region 1710 of three dimensional (3D) space. The region 1710 may fall within the corneal sphere 1022. Without subscribing to any particular scientific theory, the multiple cornea centers of curvature 1712 may approximately align within the region 1710 according to a shape of the corneal curvature 1018. For example, the multiple cornea centers of curvature 1712 may align within the region 1710 so as to outline a shape substantially parallel to or substantially the same as the shape of the cornea 1020. In cases where the cornea is substantially spherical, the multiple cornea centers 1712 may approximately follow a cornea curvature 1018 at a distance approximately equivalent to the radius of the cornea. In cases of astigmatism (or where the cornea is not substantially spherical), the multiple cornea centers 1712 may approximately follow a cornea curvature 1018 at distances approximately equivalent to one or more radii of the corneal geometry.

In various implementations, the module 614 may determine if the multiple cornea centers 1712 fall within a determined margin of an expected distance to the center of the corneal sphere 1022 from a surface of the cornea 1022. For example, a corneal sphere 1022 may be spherical or astigmatic (e.g., have a geometry other than a spherical shape). An expected distance may correspond to a distance to a center of the corneal sphere 1022 geometry. For example, where the corneal geometry is spherical, the expected distance may be the radius of the corneal sphere 1022. If a cornea center 1712 falls outside of the determined margin, the module 614 may reduce the contribution of the outlier in further analysis. For example, the module 614 may exclude the outlying data point from further analysis. Additionally or alternatively, if a threshold number of cornea centers 1712 falls outside of the determined margin, the module 614 may stop analysis until further data is acquired or switch to a different method of determining center of rotation.

As shown in FIG. 17B, a module 724 may fit a 3D surface 1714 to the multiple cornea centers 1712. The module 724 may fit a 3D surface, for example, using regression analysis. The module 724 may utilize a suitable surface or curve fitting technique to determine the fit. The module 724 may use, for example, polynomial regression to fit the cornea centers 1712 to a low order polynomial 3D surface 1714. In another example, the module 724 may apply a geometric fit to the cornea centers 1712 (e.g. a total least squares fit). In some examples, the surface 1714 may have a similar curvature to the corneal curvature 1018. In other examples, the surface 1714 may have a shape different from the corneal curvature 1018.

Figure 18A:
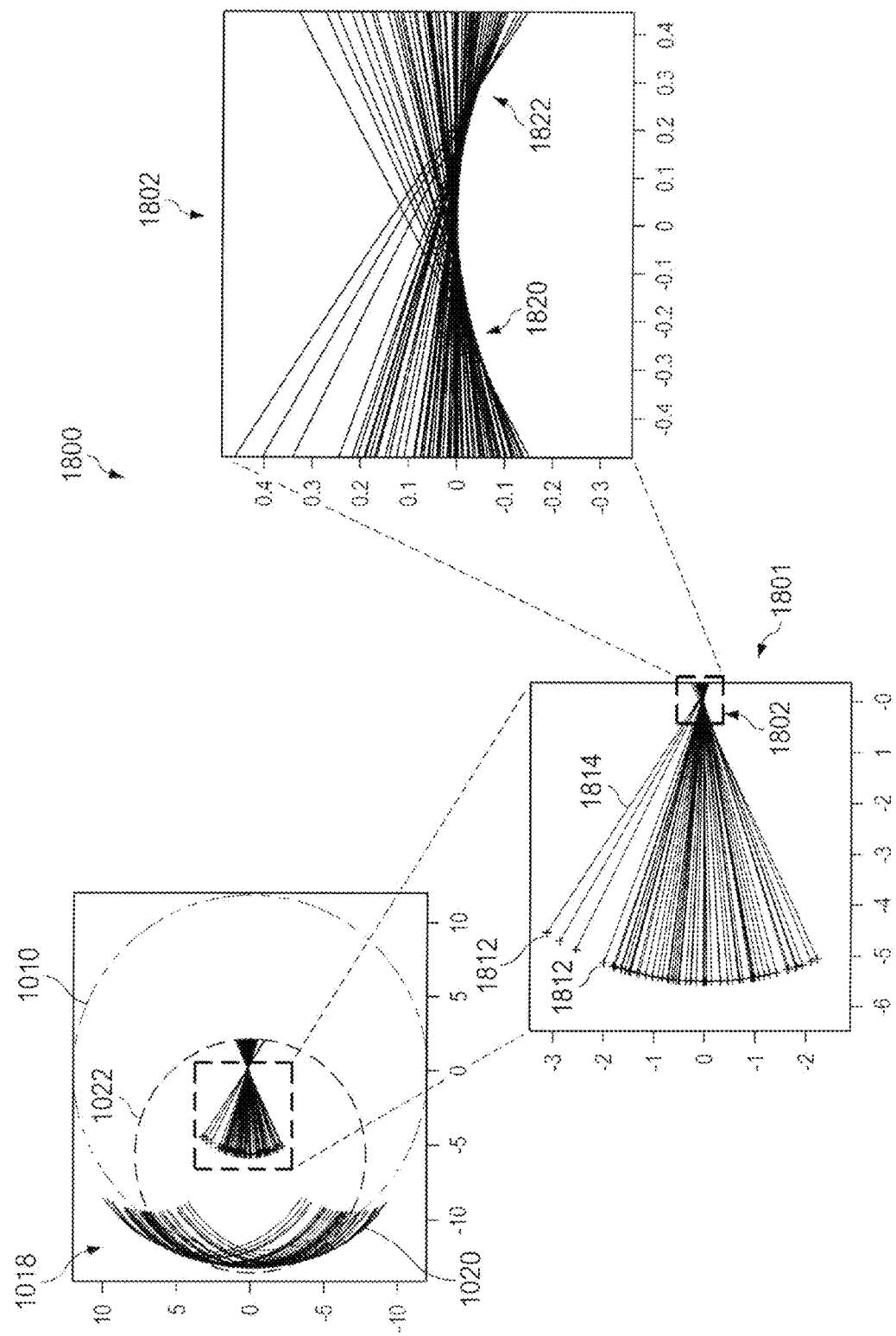
FIGS. 18A and 18B show an example estimation of center of rotation at the convergence of a plurality of surface normal vectors normal to the 3D surface calculated based on the corneal centers.

The module 724 may determine a set of surface normal vectors that are normal to the surface 1714. FIG. 18A illustrates an example calculation 1800 of a CoR (or eye ball center "EBC") using surface normal vectors 1814. For example, a module 716 may determine a set of estimated cornea centers 1812. The module 724 may fit a surface 1714 (as shown in FIG. 17B) to the estimated cornea centers 1812. The module 724 may then determine one or more surface normal vectors 1814 that are normal to the surface 1714. The surface normal vectors 1814 may originate from the estimated centers of corneal curvature 1812. For example, the module 724 may determine a surface normal vector 1814 for each estimated center of corneal curvature 1812 used to determine the surface 1714. Less surface normal may be used in certain implementations. Additionally or alternatively, the surface normal vectors 1814 may originate from other points on the surface 1714.

The module 724 may determine a region of convergence 1802 of the surface normal vectors 1814. For example, as illustrated in inset 1801 of FIG. 18A, some or all of the surface normal vectors 1814 may converge or intersect in a region 1802 of 3D space. The region of 1802 of 3D space may be a point of intersection or a volume of 3D space (for example, volume 1920 in FIGS. 19C and 19D) where the normal vectors intersect and/or converge. The volume of 3D space may be centered around a median point of intersection or convergence of the surface normal vectors 1814. The volume of 3D space may be large enough to encompass a majority of intersection points.

The region of convergence 1802 can include different areas of convergence or intersection corresponding to different gaze directions or eye poses. For example, the region of convergence 1802 can include a sub-region 1820 corresponding to a first gaze direction (e.g., a bottom gaze) and a sub-region 1822 corresponding to a second gaze direction (e.g., a top gaze). In some examples, the sub-regions 1820, 1822 can correspond to an approximated CoR associated with a region of the display of a wearable device. For example, a first sub-region 1820 can correspond to an upper region of the display and a second sub-region 1822 can correspond to a lower region of the display.

The module 724 may determine a CoR by analyzing the region of convergence 1802. For example, the module 724 may determine a CoR by determining the mode or median of convergence or intersection points of the vectors 1814. Additionally or alternatively, the module 724 may determine a CoR by first determining gaze based convergence or intersection points, such as the mode or median of convergence or intersection points of vectors 1814 in sub-regions 1820, 1822, and then determining a mode or median based on those gazebased convergence or intersection points. Additionally or alternatively, the module 724 may perform a different analysis of the convergence or intersection points to determine a CoR. For example, the module 724 may utilize a machine learning algorithm to determine a CoR.

Figure 18B:
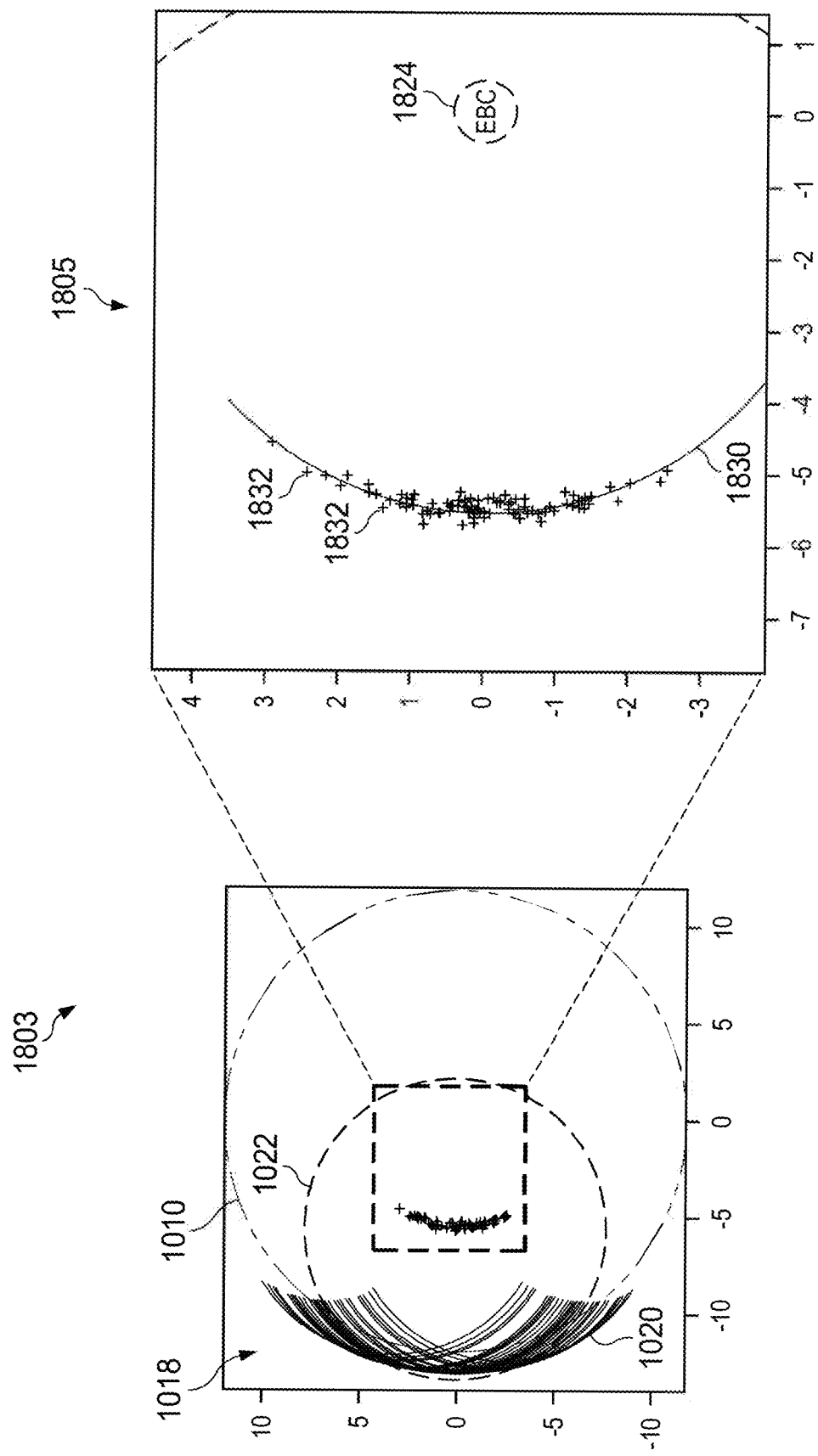

In some examples, variation in the calculated cornea centers of curvature may result in a broader region of convergence 1824 as opposed to a single point of intersection. FIG. 18B illustrates an example CoR calculation 1803 with a region 1824. For example, calculated cornea centers of curvature 1832 may be noisy with respect to a fitted 3D surface 1830. The noisy cornea centers 1832 may result in a region 1824 in which a CoR or eye ball center (EBC) is likely to be based on the intersection of vectors (not shown) with an origin at the cornea centers 1832. In some implementations, the module 614 may use the region 1824 in calculating a gaze direction. For example, the module 614 may determine a CoR as the center of the region 1824 or some other location within or on or otherwise based on the region 1824.

Figures 1, 19A:
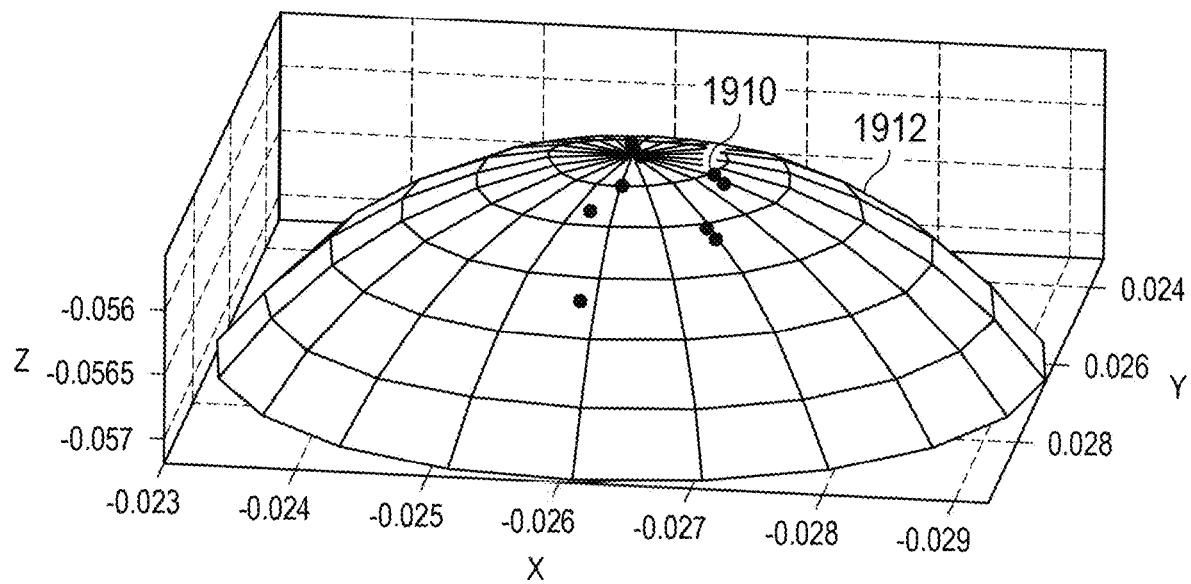
Figures 2, 19A:
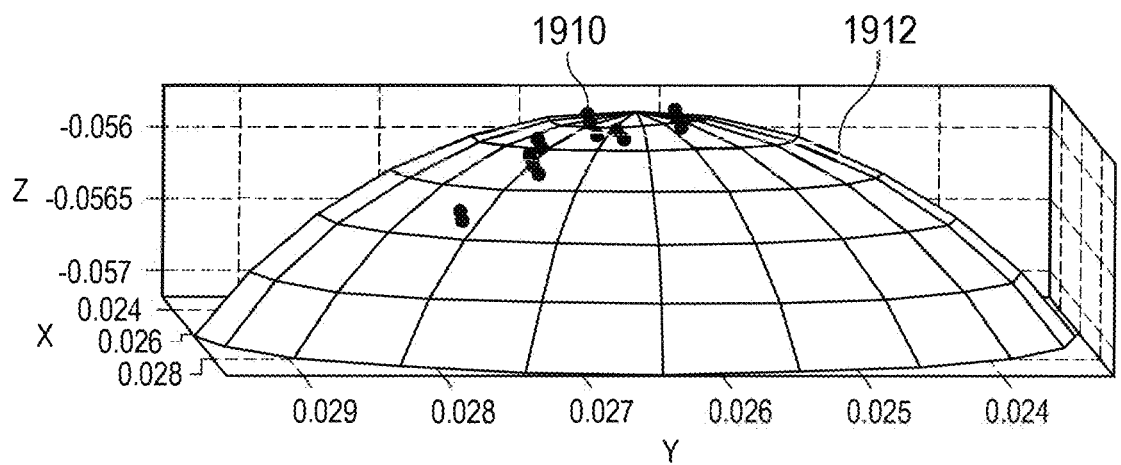
Figures 1, 19B:
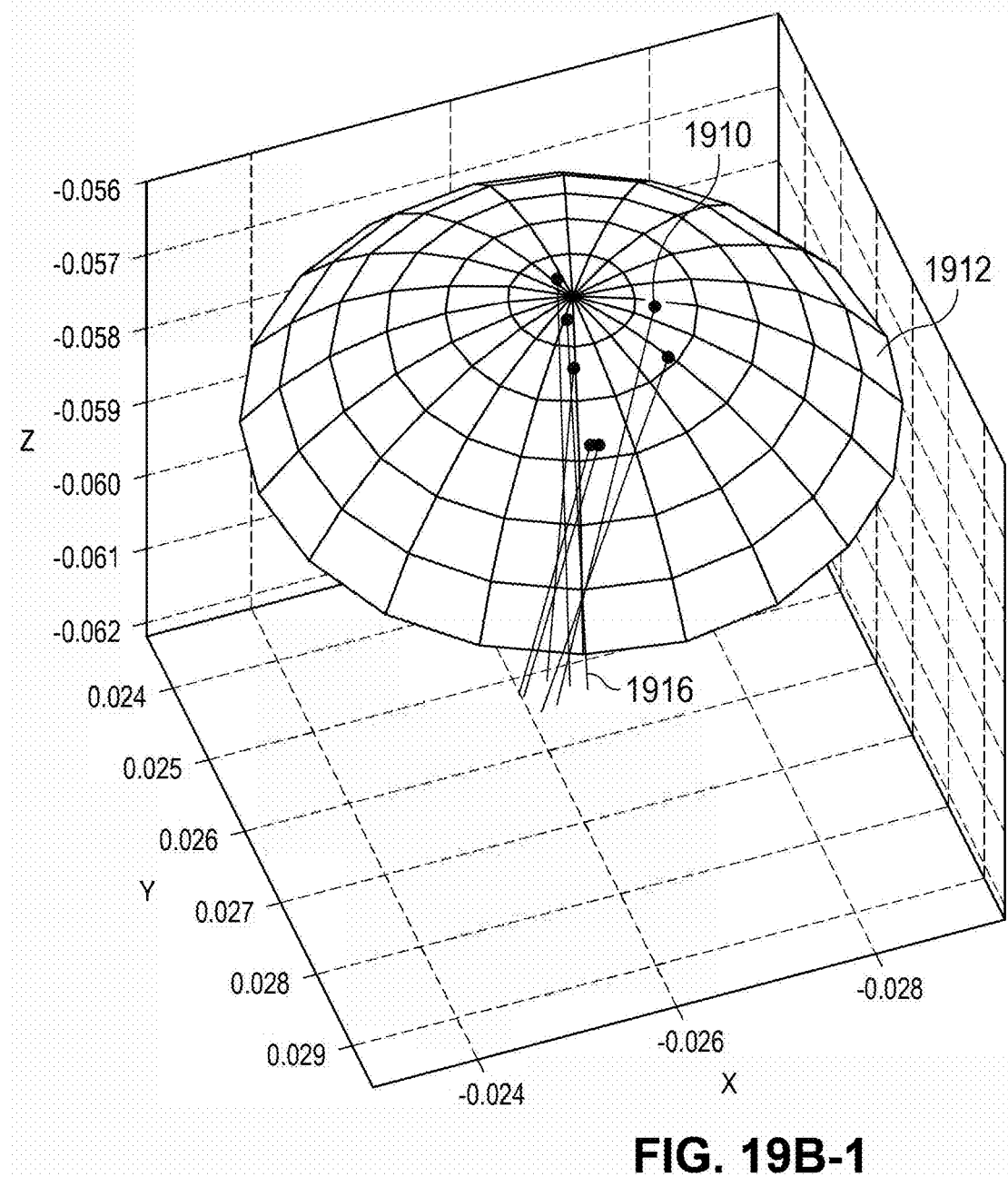
Figures 2, 19B:
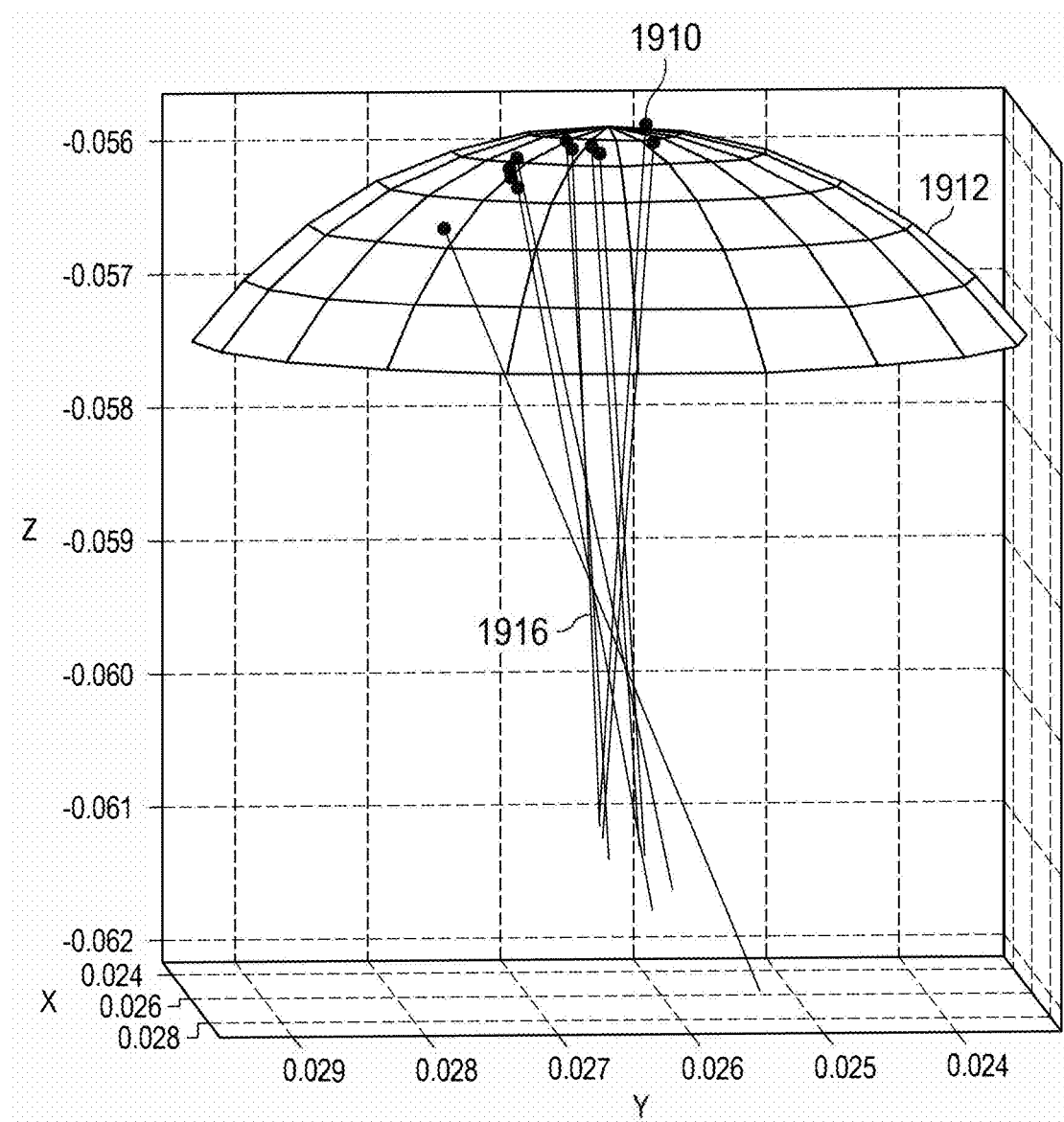
Figures 1, 19C:
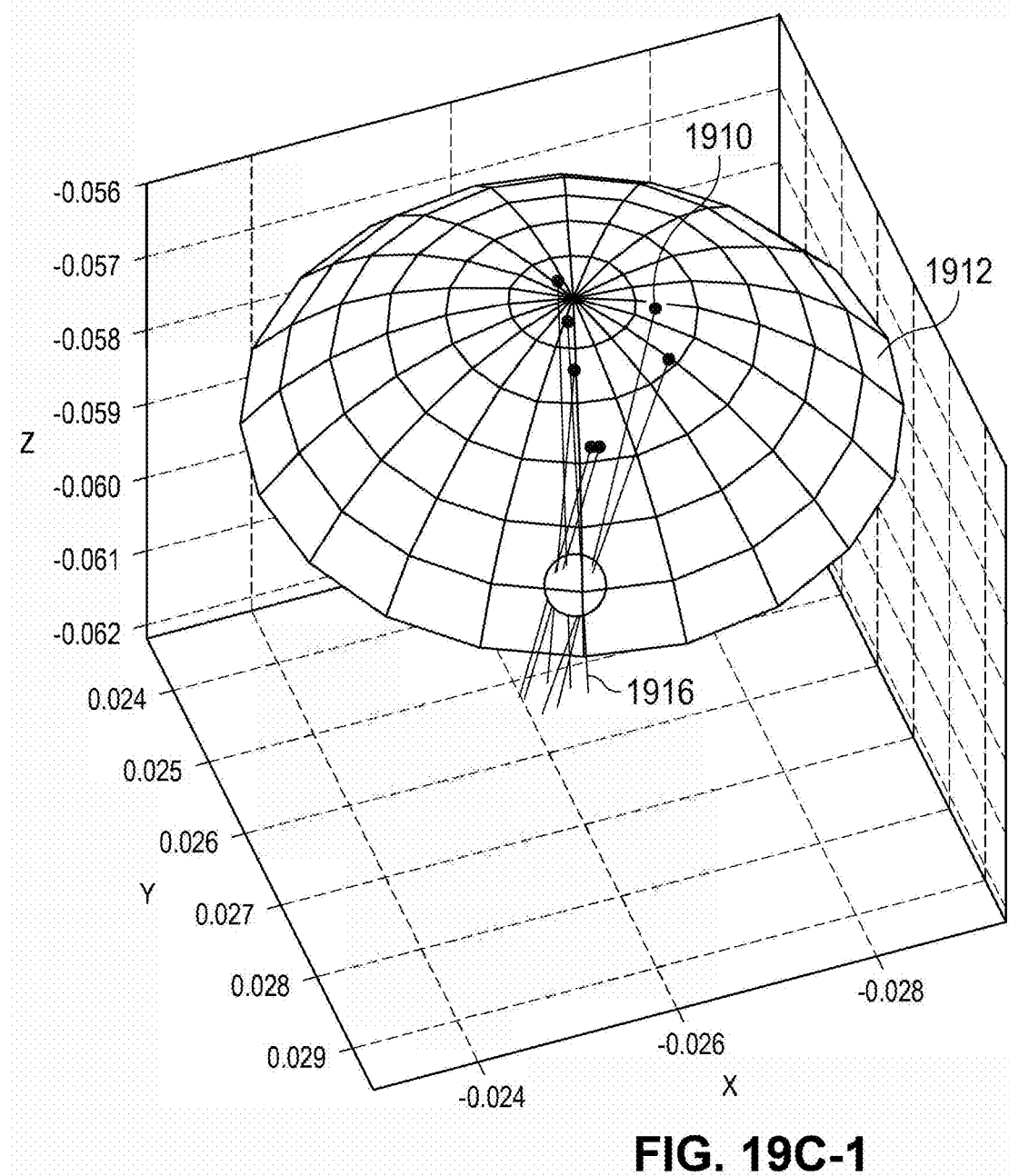
Figures 2, 19C:
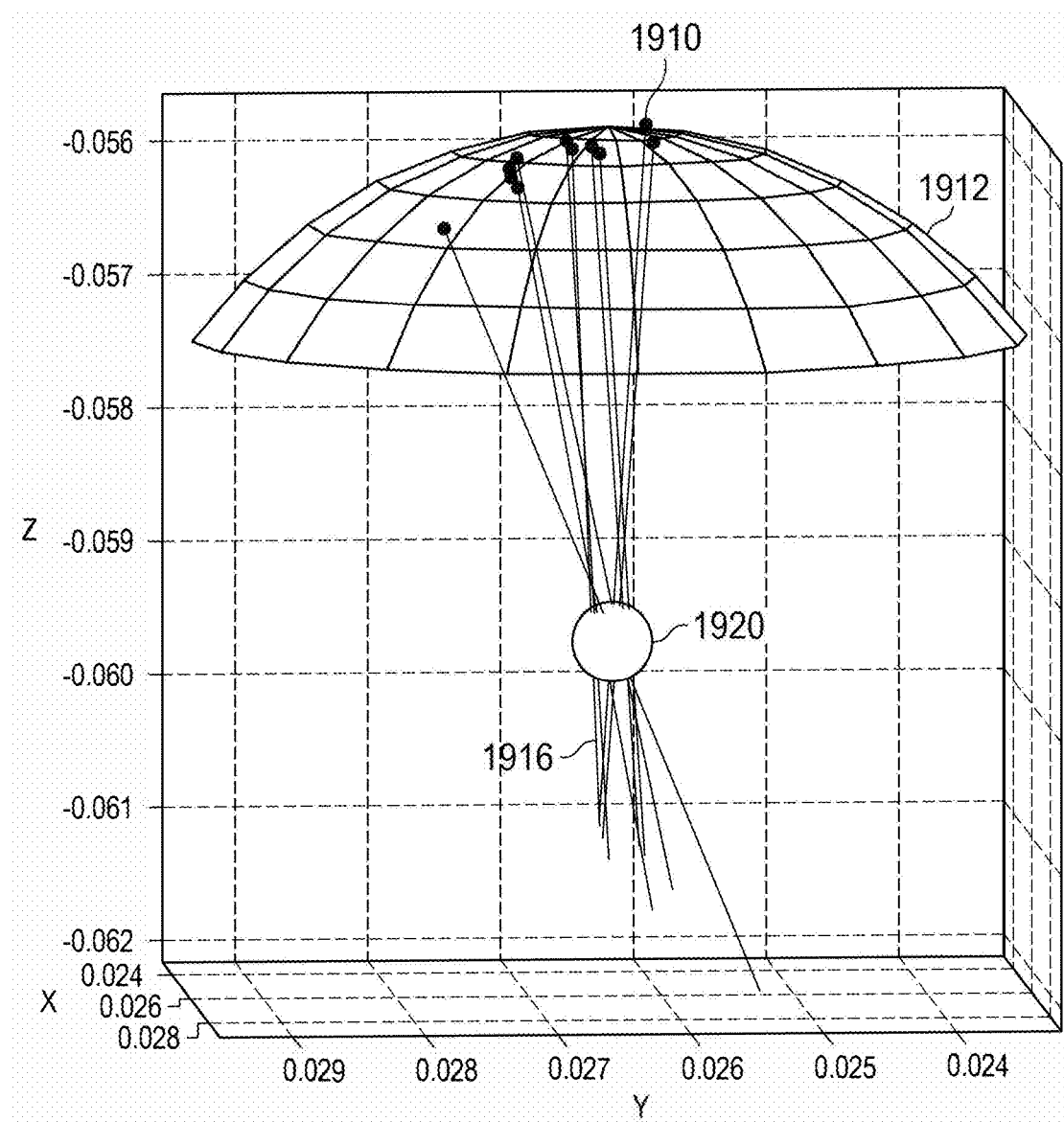
Figures 1, 19D:
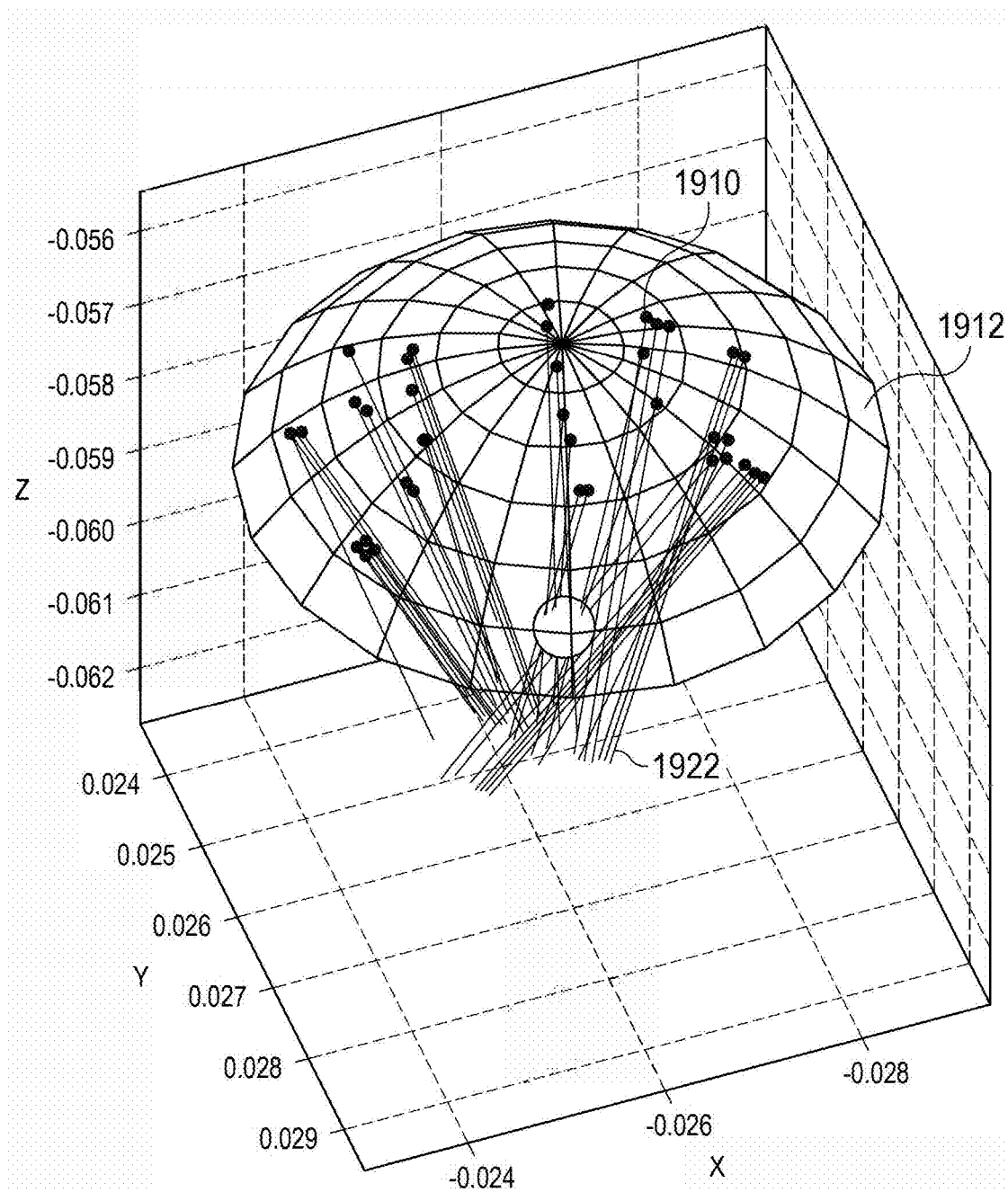
Figures 2, 19D:
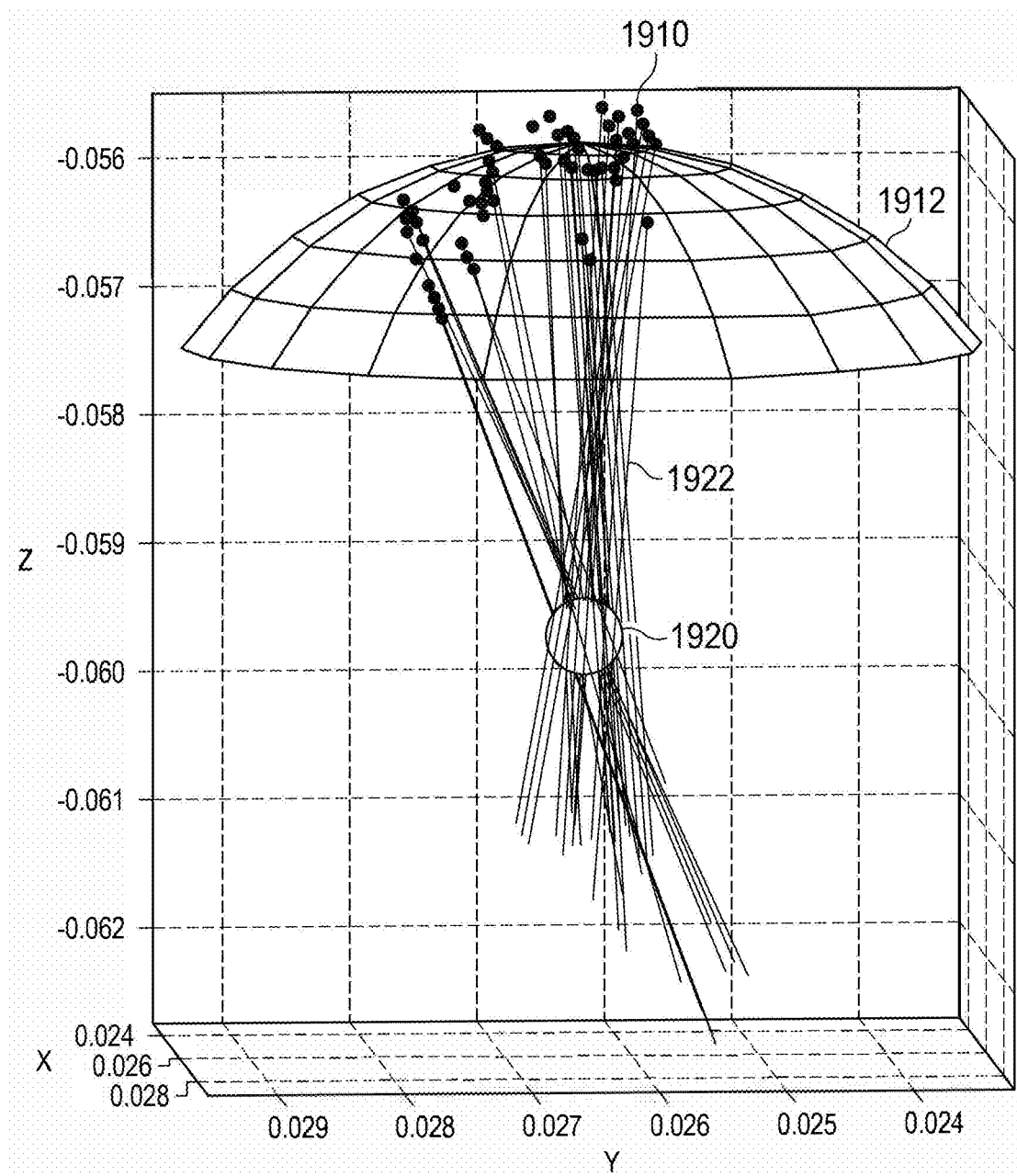

In various implementations, the module 724 may select a portion of estimated cornea centers 1910 to determine a CoR. FIGS. 19A-1 and 19A-2 illustrate an example surface 1912 fit to a portion of estimated cornea centers 1910 that may be selected using a data reduction process. FIGS. 19B-1 and 19B-2 shows example vectors 1916 that may be normal to the surface 1912. The vectors 1916 may originate at the selected estimated cornea centers 1910. FIGS. 19C-1 and 19C-2 illustrate an estimated CoR region 1920 based on points of or a region convergence or intersection of the vectors 1916. As shown in FIGS. 19D-1 and 19D-2, where the module 724 does not select cornea centers 1910 to fit a surface 1912, many of the vectors 1922 may not converge or intersect within the region 1920.

In various implementations, the module 724 may select estimated cornea centers 1910 based on a determined region of convergence of normal vectors 1916. For example, the module 724 may determine a large region in which the normal vectors 1922 intersect. In some implementations, if the large region has a volume greater than a threshold volume, the module 724 may determine a smaller set of the cornea centers 1910 with which to determine the CoR. In certain implementations, the threshold volume can include a suitable volume for determining a CoR associated with a threshold accuracy of gaze tracking based on that CoR. For example, a volume of 30 percent of the volume of the user's eye could be associated with an 80% decrease in accuracy in gaze tracking. Where the determined volume is greater than the threshold volume, the module 724 may select a smaller set of cornea centers 1910 based on any number of suitable data selection criteria, as described below.

Additionally or alternatively, the module 724 may select estimated cornea centers 1910 for analysis using any number of data reduction processes, such as a machine learning algorithm or a filtration process. For example, the module 724 may filter the data to eliminate outliers. The filter may include determining a confidence score associated with a given cornea center 1910 and selecting cornea centers 1910 based on their confidence scores. In some examples, the confidence scores may be determined based on a cornea center(s) of curvature 1910 deviation from a secondary calculation or determination of the cornea center(s) of curvature 1910 or surface 1912. In some examples, confidence scores may be based on the location of the cornea centers of curvature 1910 in relation to a fit surface 1912 (e.g., a deviation of the cornea centers 1910 from the fit surface 1912). In some examples, the confidence scores may be determined based on a calculated error in the glint extraction utilized to determine the cornea centers of curvature 1910. For example, the glint extraction may have a high error if there is error in the eye image(s) analyzed to extract the glint (e.g., due to blur, obstruction in the image, distortion, or other sources of noise).

Figure 20:
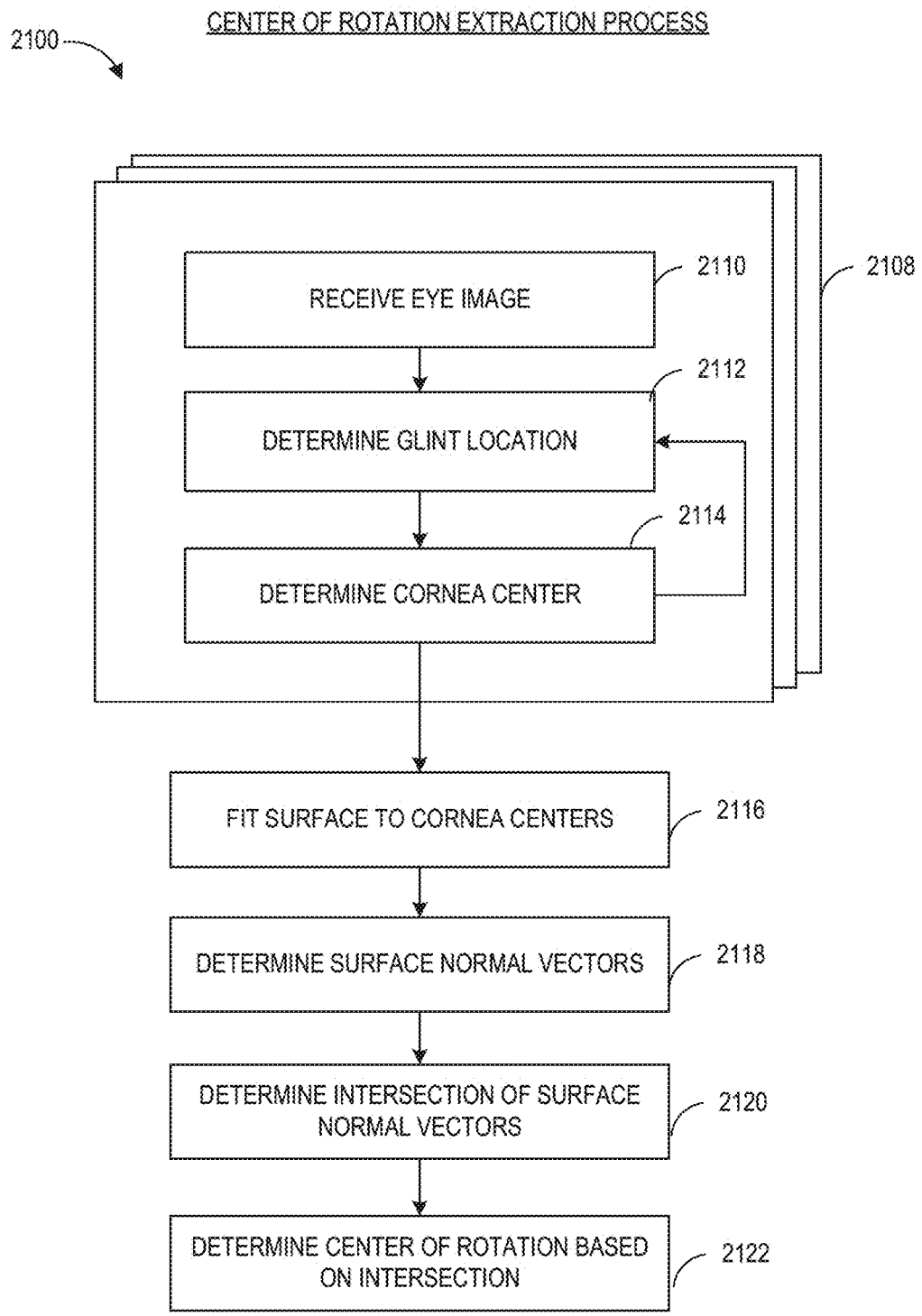
FIG. 20 illustrates an example center of rotation extraction process that may be implemented by an eye tracking module.

Q. Example Application of Center of Corneal Curvature of Rotation Extraction FIG. 20 illustrates an example center of rotation extraction process 2100 that may be implemented by eye tracking module 614. For example, the center of rotation extraction process 2100 can include one or more cornea center estimation processes 2108, a fitting block 2116, a vector determination block 2118, a converges or intersection determination block 2120, and a center of rotation determination block 2122.

The module 614 can perform a number of blocks as part of the one or more cornea center estimation processes 2108. For example, a cornea center estimation process 2108 can include an image receiving block 2110, a glint determination block 2112, and a cornea center determination block 2114.

At an image receiving block 2110, the module 614 can receive one or more images of a user's eye. The images can be obtained from an imaging system associated with a wearable device worn by the user. For example, the wearable device can be a head mounted display that includes a left eyepiece 2010A and a right eyepiece 2010B with imaging systems that include inward-facing cameras 2014, 2016, 2018, and 2020 as illustrated in FIGS. 9A-9D. The module 614 can optionally analyze the images for quality. For example, the module 614 can determine if the images pass a quality threshold. The threshold can include metrics for quality of the image relating to blur, obstruction, unwanted glints, or other quality metrics that may affect the accuracy of the center of rotation analysis. If the module 614 determines that the image passes the image quality threshold, the module 614 may use the image in further analysis.

At a glint determination block 2112, the module 614 may analyze the image(s) received from block 2110 to determine a location of one or more glints within the image(s). As described above with reference to FIGS. 12A-16C, the glint locations can correspond to a location of one or more glints produced by one or more illumination sources in an image plane. Additionally or alternatively, the glint locations can correspond to a location of one or more glints produced by one or more illumination sources in the coordinate frame of the user's eye. Glints can also be obtained for different camera and/or different camera locations.

At a cornea center determination block 2114, the module 614 can analyze the glint locations to determine an estimated cornea center of curvature. As described above with reference to FIGS. 12A-16C, the determination can involve determining a vector along which the cornea center of curvature is located based on glint, illumination source, and camera locations. The determination can also involve determining an estimated cornea center of curvature based on an intersection location of one or more of those vectors.

Additionally or alternatively, the module 614 can perform blocks 2110, 2112, and 2114 multiple times. For example, the module 614 may perform 2112 and 2114 multiple times for each eye image or set of eye images from block 2110 in order to calculate one or more cornea centers of curvature. In another example, the module 614 may perform blocks 2110, 2112, and 2114 for multiple eye poses or conditions. For example, the module 614 can receive images of a user's eye(s) in different eye poses or different gaze directions. Additionally or alternatively, the module 614 can receive images of a user's eye(s) with different camera conditions, such as camera distance from the user's eye, vertical or horizontal location with respect to the user's eye, or any combination thereof, which may provide different camera perspectives and/or for different cameras having different locations and/or perspectives. As described above, a wearable device can prompt the user to engage in different eye poses by causing the display of gaze targets in different regions of the display. For example, the wearable device can display five gaze targets corresponding to an upper center region of a display, a lower center region of the display, a central region of the display, a left of center region of the display, and a right of center region of the display. The five gaze targets may correspond to five different eye poses of the user. Additionally or alternatively, the wearable system may capture different eye poses that occur during a natural movement of the user's eyes during use of the wearable system.

The module 614 may continue to collect data until a threshold criteria is met. For example, the threshold criteria can include a margin of error, a number of data points, or a minimum, threshold, or target diversity of eye poses. In some examples, the margin of error can correspond to a minimum, threshold, or target number of calculated cornea centers of curvature, a minimum, threshold, or target error level is achieved in a calculated center of rotation or deviation of cornea centers of curvature from a fitted surface, some combination thereof or the like. Other approaches are possible.

At block 2116, the module 614 may fit a surface to the one or more cornea centers output from processes 2108. As described above with reference to FIGS. 17A and 17B, the module 614 may perform a regression analysis to generate a fitted surface. For example, the module 614 may perform a polynomial regression to generate a low order polynomial 3D surface to the cornea centers. Other techniques, however, may be used.

At block 2118, the module 614 may determine surface normal vectors from the surface fit at block 2116. As described above with reference to FIG. 18A, the module 614 may determine surface normal vectors that are normal to the fitted surface that originate at or go through the cornea centers of curvature. Additionally or alternatively, the module 614 may determine surface normal vectors originating from any point on the fitted surface. Other approaches are also possible.

At block 2120, the module 614 may determine a region of convergence of the surface normal vectors determined at block 2118. As described above with reference to FIGS. 19A-19E, the module 614 may determine a point or region of convergence of the surface normal vectors. The region of convergence may be a volume of space in which a substantial portion of the surface normal vectors converge and/or intersect. The point or region of convergence may approximately correspond to or assist in estimating a center of rotation of the user's eye.

At block 2122, the module 614 may determine a center of rotation based on the determined region of convergence from block 2120. The center of rotation may for example, be at, within, or on the region of convergence. Other locations may also be determined for the center of rotation based on the region of convergence. In some implementations, as described above, the module 614 may analyze the region of convergence for a threshold criteria (e.g., a error). If the module 614 determines that the region of convergence does not meet a threshold criteria (e.g., for error and/or volume), the module 614 may not output a center of rotation. If the module 614 determines that the region of convergence meets the threshold criteria, then the module 614 may determine that the center of rotation is a center of the region of convergence.

Figure 21:
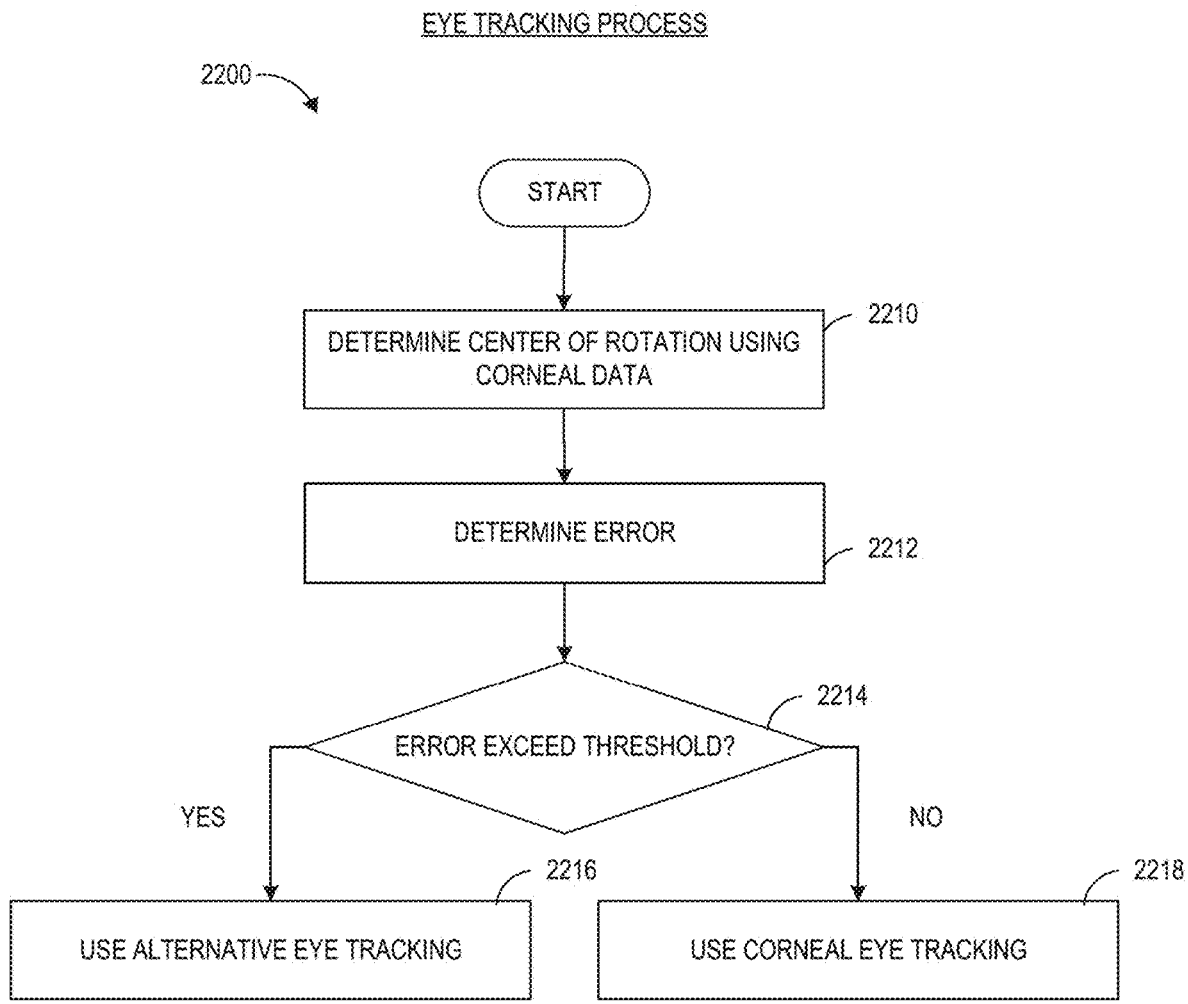
FIG. 21 illustrates an example eye tracking process that may use the process of FIG. 20 for determining estimated of centers of rotation using centers of corneal curvature.

R. Example Eye Tracking Process Using Center of Corneal Curvature for Center of Rotation Extraction FIG. 21 illustrates an example eye tracking process 2200 that may use a process 2100 of determining the center of corneal curvature for center of rotation extraction (e.g., as described above with reference to FIG. 20). The process 2200 in this example can include a center of rotation determination block 2210, an error determination block 2212, a threshold determination block 2214, an alternative eye tracking block 2216, and a corneal eye tracking block 2218.

At the center of rotation determination block 2210, the module 614 can determine a center of rotation using corneal data. For example, the module 614 may determine a center of rotation using a process 2100 described above with reference to FIG. 21. At the error determination block 2212, the module 614 can determine an error associated with the center of rotation from block 2210. At the block 2214, the module 614 can analyze the error from block 2212 to determine if it exceeds a threshold error value. In some implementations, the threshold error value can correspond to a value associated with a deviation (e.g., heighted or threshold deviation) of the center of rotation from an expected value. In some implementations, the expected value can include a location of the center of rotation based on a different center of rotation determination process, an expected center of rotation based on an eye geometry, an average center of rotation across a population of users, or another suitable center of rotation value. Other threshold values may be used. If the error exceeds the threshold, the module 614 may utilize an alternate eye tracking or center of rotation estimation method at block 2216. If the error does not exceed the threshold, then the module 614 may utilize the calculated center of rotation from block 2210 at block 2218.

Figure 22A:
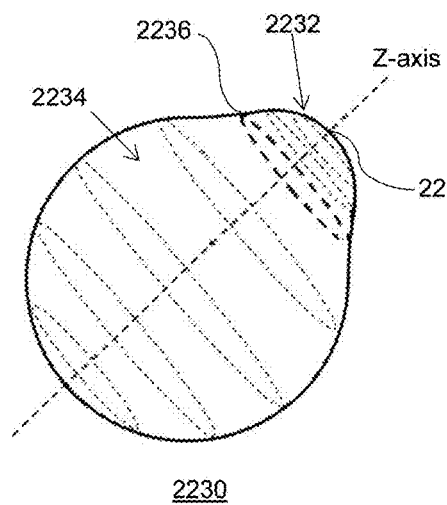
FIG. 22A schematically illustrates a perspective view of eyeball.
Figure 22B:
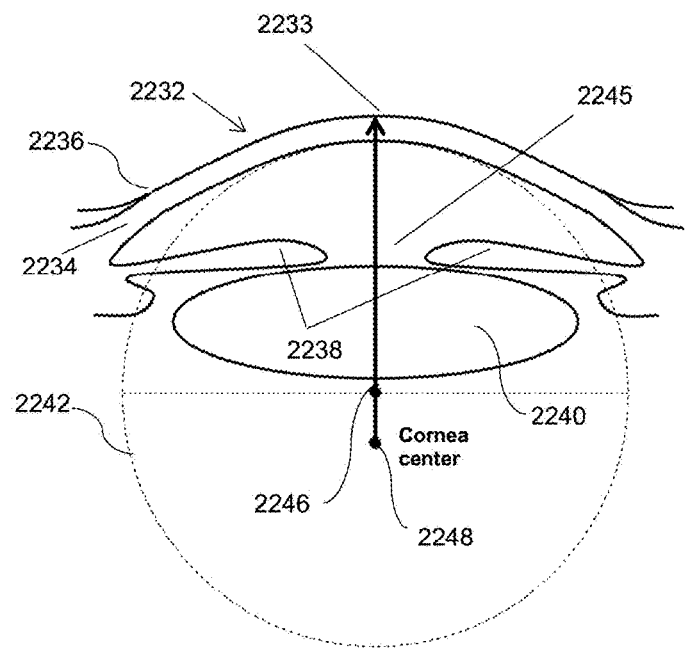
FIG. 22B schematically illustrates a 2D cross-sectional view of the cornea of an eye.

S. Determining the 3D Position of the Center of the Cornea Using Aspherical Cornea Models In most eyes, the cornea is not perfectly spherical in shape, but is rather more spheroidal. FIG. 22A illustrates a schematic perspective view of an eyeball 2230. As illustrated, the cornea 2232 has an aspheric surface with a curvature that gradually decreases (e.g., the radius of curvature increases) from the corneal apex 2233 towards the margin 2236 between the cornea 2232 and the sclera 2234. FIG. 22B illustrates a 2D cross-sectional view of an eye showing the cornea 2232, sclera 2234, iris 2238, pupil 2245 and natural lens 2240. While a spherical surface 2242 may be a fairly accurate approximation for the curvature of the corneal surface 2232 near the corneal apex 2233, toward the boundary 2236 between sclera 2234 and the cornea 2232, the actual curvature of the cornea becomes noticeably less than the curvature of the spherical surface that is used in some spherical corneal models. As discussed above, in various implementations, the corneal center of curvature (cornea center) may be one of the input parameters to the Light-Field Render Controller 618 (see FIGS. 7A and 7B)

and therefore its accuracy may directly affect the orientation and/or location of the images rendered by the head mounted display (HMD). Moreover, the cornea center is a parameter that may be used in estimating the optical axis and/or the pupil center of the eye. In various methods and systems, the optical axis and/or the pupil center may be potentially used for estimating the center of rotation (CoR) of the eyeball, which may in some cases be one of the input parameters to the Light-Field Render Controller 618. As such, a difference between the estimated and actual location of cornea center, may potentially result in rendering an image that is not perceived by the wearer of the HMD the way intended.

In some implementations, the center of curvature of the cornea (corneal center of curvature) or the center of the cornea refers to the center of curvature of a portion of the cornea or the center of curvature of a spherical surface that coincides with a portion of the surface of the cornea. For example, in some implementations such as possibly for aspheric models such as spheroidal models of the eye discussed below, the center of curvature of the cornea or the center of the cornea refers to the center of curvature at the corneal apex or the center of curvature of a spherical surface that coincides with a portion of the surface at the corneal apex 2233. The cornea center may also refer to a center of an surface such as a sphere that coincides, e.g., approximately, with the shape of the cornea, the shape of a surface of the cornea, the shape of a portion of the cornea, or the shape of a portion of the surface of the cornea. Similarly, the corneal center may also refer to a center of an aspheric surface such as an aspheric spheroid that coincides, e.g., approximately, with the shape of the cornea, the shape of a surface of the cornea, the shape of a portion of the cornea, or the shape of a portion of the surface of the cornea.

As discussed above, the cornea center may be estimated using the location of two or more glints on one or more images captured by one or more eye cameras (eye tracking cameras). The glints may be generated by specular reflections of light generated by two or more light sources (e.g., IR LEDs) affixed on the HMD frame. Using the known position of the light sources and measured position of one or more glints with respect to a coordinate system (e.g., coordinate system of the eye camera) as inputs, a processing module may estimate the cornea center based on a corneal model through a set of instructions stored in a non-transitory memory of the HMD. In some methods described above, a spherical cornea model is used to estimate the cornea center.

Some methods may use the location of the glints, the eye camera and the light sources, to generate two or more cornea vectors pointing to a cornea center and then determine an intersection or region of convergence of the generated cornea vectors, to estimate the center of corneal curvature. For example, the cornea vectors may be generated using the images captured by one camera and the two light sources based on the procedure described above with reference to FIG. 11 to FIG. 14. In other examples, the cornea vectors may be generated using the images captured by two eye cameras and four sources based on the procedure described with reference to FIG. 15. In yet other examples, the cornea vectors may be estimated using the images captured by two cameras and two shared slight sources based on the procedure described with reference to FIG. 16. In various implementation, the methods used to calculate the cornea vectors provide an estimation value for the location of a cornea center based on the assumption that the glints are generated by specular reflection off of a spherical corneal surface.

Some additional methods may also use the location of glints on captured images of the eye to estimate the cornea center based on a spherical corneal model. For example, an algorithm may be used to find the center of a reflective spherical surface that upon illumination by the light sources with known locations, generates the glints images overlapping with those appearing on a captured image. An example of a cornea center estimation procedure based on such method that may use two or more light sources and one camera is described above with respect to FIGS. 8A-8E as well as in US 2019/0243448A1, which is incorporated herein by reference in its entirety.

Figure 22C:
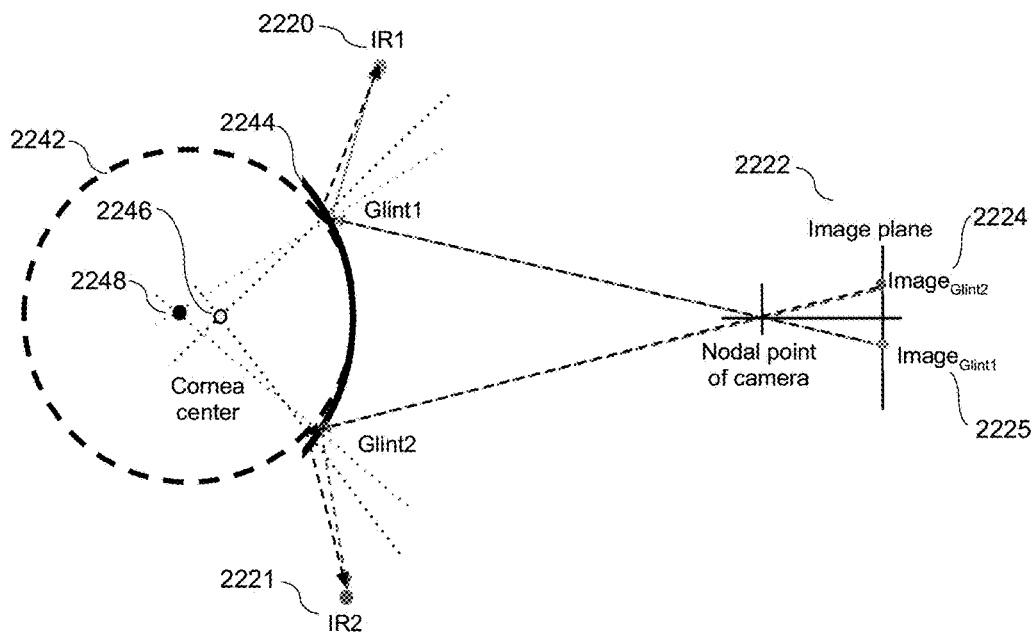
FIG. 22C schematically illustrates a 2D cross-sectional view of specular reflection of light from two light sources off of spherical and spheroidal reflecting surfaces.

However, using any of these methods that assume the cornea has spherical shape, may potentially result in an erroneous estimation or at least partially erroneous or less accurate estimation of the cornea center (center of corneal curvature). FIG. 22C, for example, illustrates how laws of reflection may be used to calculate the center of curvature for an axially symmetric reflecting surface (e.g., surface of cornea) based on the locations of two light sources 2220/2221 and the locations of the resulting glints 2224/2225 on the image plane 2222 of an eye camera. In this example, the two light sources are equidistant from the axis of symmetry of the cornea surface. As illustrated by the figure, if it is assumed that the surface of the cornea has a spherical shape 2242, the estimated location of the cornea center 2246 is different from the cornea center 2248 estimated assuming that the surface of cornea has an aspheric spheroidal shape 2244. In other words, if two images 2224/225 are generated as a result of two light sources 2220/2221 illuminating an axially symmetric reflective surface, the estimated center of curvature (e.g., the intersection between normal to the surface at the point of incidence and the symmetrical axis of the surface) for at least a particular portion of the surface possibly depend on the assumed surface shape (e.g., spherical or aspheric spheroidal or other aspheric shape). In the example shown in FIG. 22C, the magnitude of the difference between the two estimated values of the center of corneal curvature 2246/2248 is larger when the glints are generated from specular reflection off of regions of the cornea farther from the corneal apex 2233. Given the fixed location of the light sources and the eye cameras on the HMD frame, and the fact that the gaze direction of the wearer is constantly changing, it may not be practical to maintain a configuration that always provides glint images generated from specular reflection off of the regions of the cornea close to its apex (to reduce or minimize the estimation error). As a result, in many configurations and scenarios (e.g., measurements at different gaze directions and using different combinations of the available light sources and cameras), the estimated locations of cornea center that are based on a method that relies solely on a spherical eye model, may not provide as accurate an estimation for the cornea center as a method the employs an aspheric model of the cornea.

Using a model that takes into account the aspherical shape of the cornea may improve the accuracy of the estimated eye parameters and therefore the overall accuracy of the eye tracker. Specifically, estimations based on an aspherical model (e.g., aspheric spheroidal model) may improve the accuracy of the gaze tracking, center of cornea and CoR calculations. Advantageously, in some implementations, such models may improve accuracy of the eye tracker possibly without the need for user specific calibration. However, some various implementations include user specific calibration, possibly further improving the accuracy.

Unlike spherical cornea models, various aspherical models of the cornea, such as the aspheric spheroidal model of the cornea, do not offer the benefit of yielding closed-form solutions to the center of cornea determination problem.

Various methodologies discussed herein employ approaches and procedures for estimating the 3D position of cornea center based on aspherical models resulting in enhanced accuracy. The disclosed methodologies described below may include computationally efficient procedures for estimating the 3D position of cornea center in HMD systems that use single eye camera as well as that use two eye cameras such as those described above. See also US 2019/0243448A1, which is incorporated herein by reference in its entirety.

Spheroidal Eye Model

In some examples methods and systems discussed herein, the spheroidal eye model may use a surface of revolution described, for example, by one or both of the following equations as an estimation for the shape of the user's cornea:

$$X^2 + Y^2 + (1+Q)Z^2 = 2ZR \quad (1A)$$

$$Z = \frac{\frac{X^2}{R} + \frac{Y^2}{R}}{1 + \sqrt{1 - (1+Q)*\left(\frac{X^2}{R^2} + \frac{Y^2}{R^2}\right)}} \quad (1B)$$

where R is the radius at the corneal apex 2303/2233, Z-axis is the axis of revolution of the spheroid and also the optical axis of the cornea, Q is the asphericity or the conic parameter that alters the shape of the ellipsoid in X-Z or Y-Z plane). The magnitude of R may have an average of 7.8 mm (e.g., for an average adult user) although may be different from this value. The distribution of the magnitude of R may, for example, approach a normal distribution with a mean value of 7.8 mm and a standard deviation of 0.26 mm for adults with emmetropic vision.

Figure 23A:
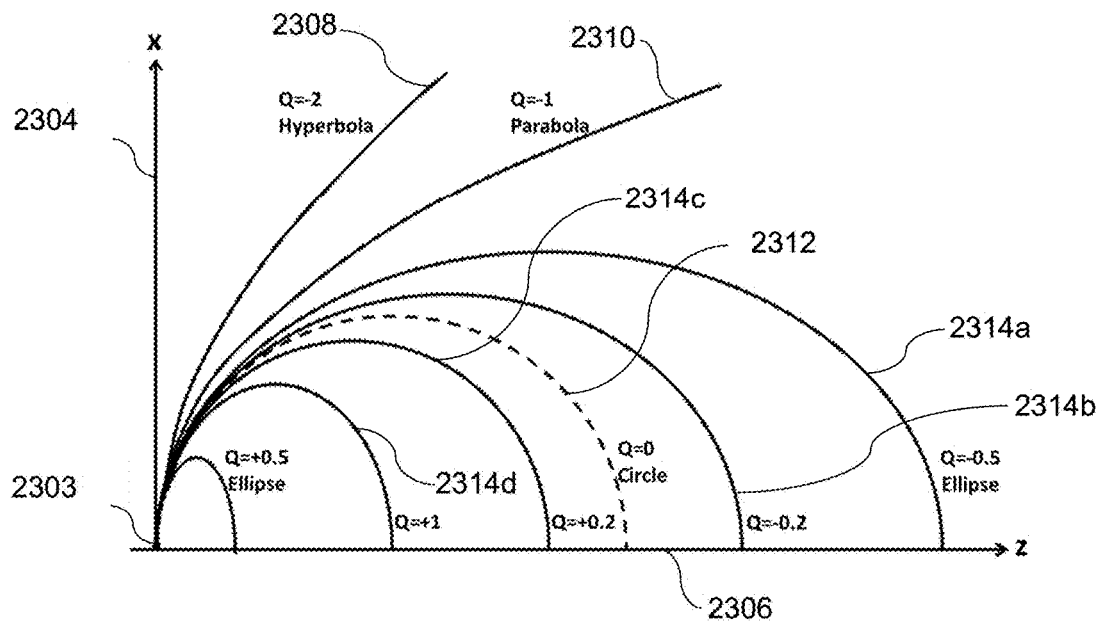
FIG. 23A shows 2D cross-sectional profiles of axially symmetric spheroidal surfaces plotted in the X-Z plane for the different values of the conic parameters.
Figure 23B:
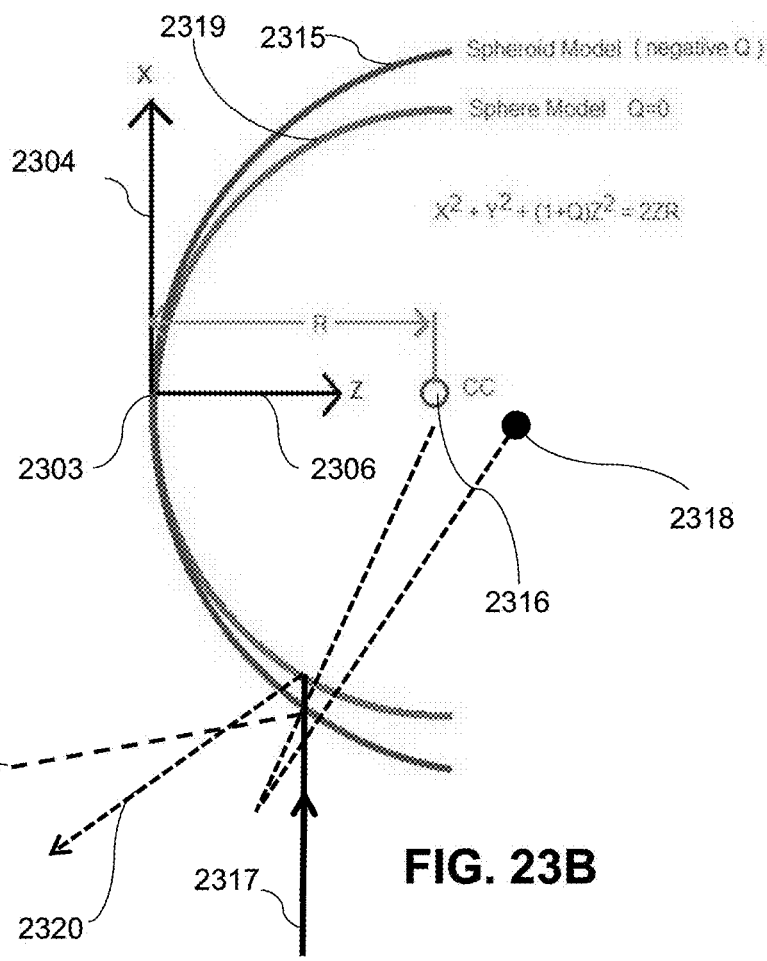
FIG. 23B shows a 2D cross-section of two axially symmetric spheroids plotted in X-Z plane; one with a conic parameter of zero (a sphere), and the other with conic parameter of −0.25 (Arizona eye model spheroid). The specular reflection of a light ray off of each one of these surfaces is also shown.

FIG. 23A shows Equation (1A) plotted in the X-Z plane (where Y=0) for several values of Q. The surface defined by Equation (1A) is rotationally symmetric (a spheroid) around Z-axis 2306, so for a given value of R and different vales of Q, the profile of such surface in Y-Z plane will be similar to those shown in FIG. 23A. Additionally, cross-sections of the surface formed by Equation (1A) in the X-Y plane will be circular. Values of Q between 0 and −1 (e.g., 0>Q>−1) results in an elliptical shaped cross-sections 2314a and 2314b such as from prolate spheroids whereas values of Q between 0 and +1 (e.g., 0<Q<+1) result in elliptical shaped cross-sections 2314c and 2314d such as from oblate spheroids. In FIG. 23A, a value for Q of +1.0 is shown as yielding a parabolic 2310 cross-section while a value for Q of +2.0 produces a hyperbolic 2308 cross-section. When Q is equal to zero, Equation (1A) describes a sphere 2312 with radius R centered at Z=R, and the spheroidal model is reduced to the spherical model. A circular cross-section is thus shown in FIG. 23A for Q=0. The parameters R and Q may vary for different spheroidal models resulting in different values for the distance between cornea center 2218 to the corneal vertex 2233, and different profiles (e.g., spherical, prolate or oblate elliptical profiles). For example, in the well-known Arizona eye model, the cornea shape is based on a prolate spheroid with R=0.78 mm, and Q=−0.25. FIG. 23B shows Equation (1A) plotted in the X-Z plane (where Y=0) for Q=0 and Q=−0.25 to provide a comparison between the cross-sectional profile of the cornea based on the spherical model and the more realistic aspheric spheroidal model (the Arizona spheroidal model in this case). In FIGS. 23A and 23B, the origin of the coordinate axes 2303 is at the vertex 2233 of the cornea 2232 (for both values of Q). As shown in FIG. 23B, a spherical cornea 2319 and an aspheric spheroidal cornea 2315 reflect a single incident beam 2317 into two different directions (assuming that the vertex of differently shapes corneas overlap). A comparison between the trajectories of the reflected ray 2320 from the spherical cornea and the reflected ray 2322 from the aspheric spheroidal cornea, shows that given the distance between the eye ball and the eye camera, the difference between the positions of the glints images generated by these rays can be measurably different. As a result, the cornea center 2316 estimated based on the glints generated by reflection off of the spherical cornea will likely be different from the cornea center 2318 estimated based on the glints generated by refection off of the aspheric spheroidal cornea. As discussed herein for a given corneal radius R, the aspheric spheroidal model may be used to estimate the cornea center using one camera and at least two light sources. Additionally, with two cameras, however, the cornea center can be estimated using two light sources without knowing the value of the corneal radius R.

As normal corneas often show astigmatism (e.g., the radius of curvature of cornea is larger at the horizontal than at the vertical meridian), in some examples, the aspherical model may also take into account that the surface representing the cornea, may not be rotationally symmetric about the Z-axis. For example, an astigmatic corneal surface may be a biconic surface having a conical profile in the X-Y plane and also a conical profile in the Y-Z plane different and independent than the conical profile in the X-Z. An equation for such a biconic surface may be written as:

$$Z = \frac{\frac{X^2}{R_x} + \frac{Y^2}{R_y}}{1 + \sqrt{1 - (1+Q_x)*\frac{X^2}{R_x^2} - (1+Q_y)*\frac{Y^2}{R_y^2}}} \quad (1C)$$

Equation 1C represents a general biconic surface, which can be used to model the corneal shape for most eyes that are emmetropic, myopic, hyperopic, or astigmatic. ($R_x$, $Q_x$) and ($R_y$, $Q_y$) specify the radius and conic parameter of the corneal surface in the horizontal and vertical dimension respectively. The distributions of $R_x$ and $R_y$ measured for different eyes may be the same distribution as R (used in equation 1A or 1B) measured for different eyes, which for example may have a mean value of 7.8 mm and a standard deviation of 0.26 mm. The distributions of $Q_x$ and $Q_y$ measured for different eyes may be the same distribution as Q (used in equation 1A or 1B), which may for example have a mean of −0.26 and a standard deviation of 0.18. When the model is used to represent an astigmatic corneal surface, the surface defined by equation 1C, may be rotated (e.g., between 0 to 180 degrees) around the optical axis (Z-axis) to be aligned with the astigmatic axis of the corneal surface. As such, 4 independent t parameters may be required to the define the shape of a general biconic surface an fifth independent may be required to align the biconic surface with the astigmatic axes of a cornea.

In yet other examples, an astigmatic corneal surface may be modeled as a non-revolution ellipsoid having a conical profile in the X-Y plane and also a conical profile in the Y-Z plane different (which potentially may not be independent of the conical profile in the X-Z). An equation for such an ellipsoidal surface may be written as:

$$(X^2/Q_1^2) + (Y^2/Q_2^2) + [(Z-Q_3)^2/Q_3^2] = 1 \quad (1D)$$

that defines an ellipsoid that has one of its vertices located at Z=0 (the apex of cornea). Here, $Q_1$, $Q_2$ and $Q_3$, are the semi-axes of ellipsoid that determine the shape of the ellipsoid, and their values may be provided by an eye model.

Note that equation 1B (or 1A) and 1D may be special surfaces for the general bioconic surface defined by equation 1C. The general biconic surface becomes a spheroidal surface when $R_x=R_y=R$ and $Q_x=Q_y=Q$ and an ellipsoidal surface when $R_x=Q_1^2/Q_3$, $R_y=Q_2^2/Q_3$, $Q_x=(Q_1^2/Q_3^2)-1$ and $Q_y=(Q_2^2/Q_3^2)-1$. In some examples, the fact that a non-revolution ellipsoid has only three independent parameters, may reduce the complexity of calculations when estimating the center of an astigmatic the cornea.

Determining the 3D Position of the Cornea Center Using a Single Eye Camera and an Aspheric Model In some examples, an aspheric eye model can be used to estimate the cornea center based on the measured position of several glints on one or more images captured by one eye camera. The glints may be produced by specular reflection of light emitted by several light sources affixed on the HMD frame. The light sources may have known locations, for example, known coordinates associated with the position of the light emitters in a coordinate system (e.g., eye camera coordinate system). FIG. 11, for example, illustrates two glints 1104A/1104B on an image 1110 generated by two light sources.

In some such examples, the number (e.g., minimum number) of glints and therefore light sources for providing estimations of the cornea center may be calculated using the number of unknown parameters in the model and the number of constraints imposed by the aspheric (e.g., aspheric spheroidal) model, the location of the camera and the locations of the light sources. Assuming that the radius of the cornea at the vertex (R) and conic parameter (Q) of the specific eye model (e.g., from the Arizona eye model) are known, determining the three-dimensional position of the cornea center (e.g., the position coordinates of the cornea center) in a given coordinate system (e.g., eye camera coordinate system) may involve calculation of three parameters: CX, CY and CZ (coordinates of the cornea center); however, the intermediate steps in the corresponding calculations may also involve the orientation of the spheroid defined by pitch and yaw parameters for its axis of symmetry (e.g., Z-axis in FIG. 23) measured with respect to the same coordinate system. These two intermediate parameters are used because the relation between the locations of the glints on an image and the cornea center (for given values of R, Q, coordinates of the light sources), may be defined based on specular reflections of light rays generated by the light sources off of the corneal surface (therefore may be affected by it orientation). In some examples, the value of R may be 7.8 mm and the value of Q can be −0.25 (e.g. from the Arizona eye model). In addition, the three-dimensional location of the glints on the cornea surface (GX, GY and GZ, corresponding to the points at which light is reflected on the corneal surface) may be estimated as well.

Therefore, using each glint in the estimation can add three more unknown parameters. As a result, the total number of unknowns may be (5+3)×NG, where NG is the total number of glints used in the estimation. In some examples, the constraints are determined by three relations: 1) The relation between the location of the glints (GX, GY, and GZ), the location of the camera and the location of light sources. This relation may result in two constraints: 2) the relation between the location of the glints (GX, GY, and GZ) and the location of the cornea center (CX, CY, and CZ). This relation may result in one constraint. 3) The relation between the location of the glints (GX, GY, and GZ) and the location of the camera. This relation results in two constraints. In conclusion, 5×NG constraints could be used to estimate (5+3)×NG unknowns resulting in the number of glints to be three or more in some implementations. Other variations, however, are possible. For example, the number of glints and the number of light sources may be more or less.

Figure 24:
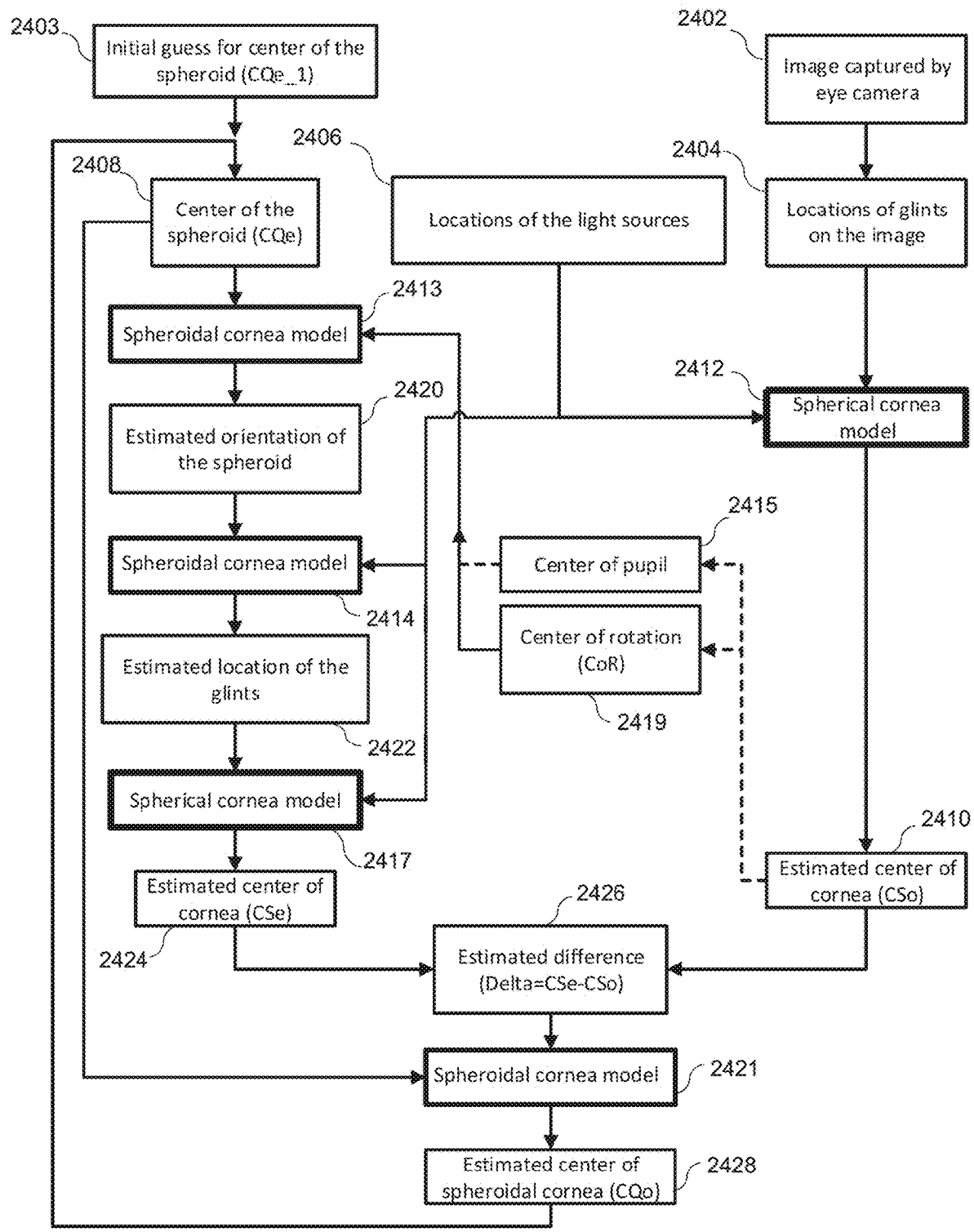
FIG. 24 is a block diagram illustrating an example procedure that may be used for estimating the location of center of the cornea using one eye camera and based on a spheroidal cornea model.

FIG. 24 is a bock diagram illustrating an iterative procedure that may be used for estimating the location of the center of the cornea (e.g., a three-dimensional location such as an x, y, z location described by one or more coordinates such as x, y, z or r, θ, φ, etc., with respect to a reference frame), based on an aspheric spheroidal cornea model using one or more images captured by possibly only one eye camera while one or more, potentially a plurality of light sources, affixed on the head-mounted display frame, generate three or more glints on the image plane of the eye camera. The position of the eye camera and the position of the light sources, with respect to the eye camera, may be known values stored in the system memory. In some implementations, the location of the center of curvature of the cornea may be determined with respect to reference frame or coordinate system of the eye camera or a fixed reference frame with a respect a head-mounted display.

In some examples, this procedure may follow the estimation of the location of the center of the cornea using the spherical cornea model as described above, for example, with respect to FIGS. 8A-8E, or described in US 2019/0243448A1, which is incorporated herein by reference in its entirety. In some other examples, the CoR may be determined as part of the procedure. In some implementations, the corneal radius of curvature (used in the calculations based on the spherical and aspheric spheroidal models) and/or the Q parameter(s) (used in calculations based on the aspheric spheroidal model) may be known values of the model or may be estimated using known eye models. In some examples, the values for radius of the curvature of the cornea (R) and the Q parameter(s) of the spheroid may be the values of these parameters in known eye models (e.g., Arizona eye model).

In some examples, each iteration of the procedure may be broken down into five steps described below:

Step 1: An image is captured by the eye camera (eye tracking camera) in block 2402 while a plurality of, for example, three or more light sources, affixed on the frame, are outputting light resulting in the appearance of three or more glints on the captured image. The positions of the glints on the image plane of the eye camera may be determined in block 2404. The glint detection and labeling module 714 shown in FIG. 7A may possibly be used, for example. A cornea center of the eye (CSo) based on the spherical model of the eye is determined. For example, using the spherical cornea model referenced in block 2412, the known locations of the light sources represented by block 2406 and the measured values of glint locations determined in block 2404 in the image captured in block 2402, the cornea center of the eye (CSo) may be calculated in block 2410. In some example methods, the CSo may correspond to corneal center of curvature 816c and/or 1008 in FIGS. 8E and/or FIG. 10 of U.S. Patent Application No. 2019/0243448A1, respectively. Some operations that may be performed for this calculation are discussed, for example, in connection with one or more of FIGS. 8B-8E above and in U.S. Patent Application 2019/0243448A1, which is incorporated herein by reference in its entirety. In some processes, CSo may be estimated in block 2410 using only two light sources such as, for example, using the procedure described in with reference to FIGS. 11-14 above. Other approaches and other numbers of light sources area also possible.

As illustrated with reference to block 2419, the CoR may be determined from the estimated center of the cornea CSo value(s) arrived at in block 2410 based on the spherical model. As illustrated with reference to block 2415, the center of the pupil may be determined, possibly from the estimated center of the cornea CSo arrived at in block 2410 based on the spherical model.

Step 2: Assuming the cornea is represented by an aspheric spheroidal model and aspheric spheroidal surface, an initial value for the center of the spheroid (CQe_1) is selected in block 2403. In the first iteration of the procedure, this initial value may be selected based on an educated guess that may take into account, for example, the fact that the center of the spheroid is within some fixed distance behind the center of cornea (CSo) that is estimated based on the spherical model in step 1. In some examples, the initial value for the center of a spheroid (CQe_1) used, for example, in block 2413 can be assumed to be equal to CSo such as determined in block 2410 using a spherical model. In the subsequent iterations, the value used in block 2408 may be the output value generated in the previous iteration (e.g., shown being provided by block 2428). Using the value for the center of an aspheric spheroid (CQe_1) from block 2408 and the center of rotation of the eye (CoR) previously determined in block 2419, the orientation of the spheroid can be determined in block 2420 using the aspheric spheroidal model as referenced in block 2413. As illustrated by the connection between blocks 2019 and 2015 and block 2013, the center of rotation (CoR) and/or the center of the pupil may be used in the spheroidal model of block 2013.

In some examples, the CoR (e.g., from block 2419) may be estimated by the modules used for CoR estimation (see FIG. 7A) possibly using the image(s) captured in block 2402 in step-1 and/or the one or more procedures described in US 2019/0243448A1 which is incorporated herein by reference in its entirety. In some examples, the CoR (e.g., referenced in block 2419) may be estimated using the image(s) captured in step-1 and the procedure described above.

In some implementations, instead of using the CoR from block 2419, the center of the pupil from block 2415 may be used to determine the orientation of the spheroid in block 2420. In these implementations, center of the pupil from block 2415, may be estimated by 3D pupil center locator module possibly using the image(s) captured in block 2402 in step-1 and the procedure described above.

Figure 25A:
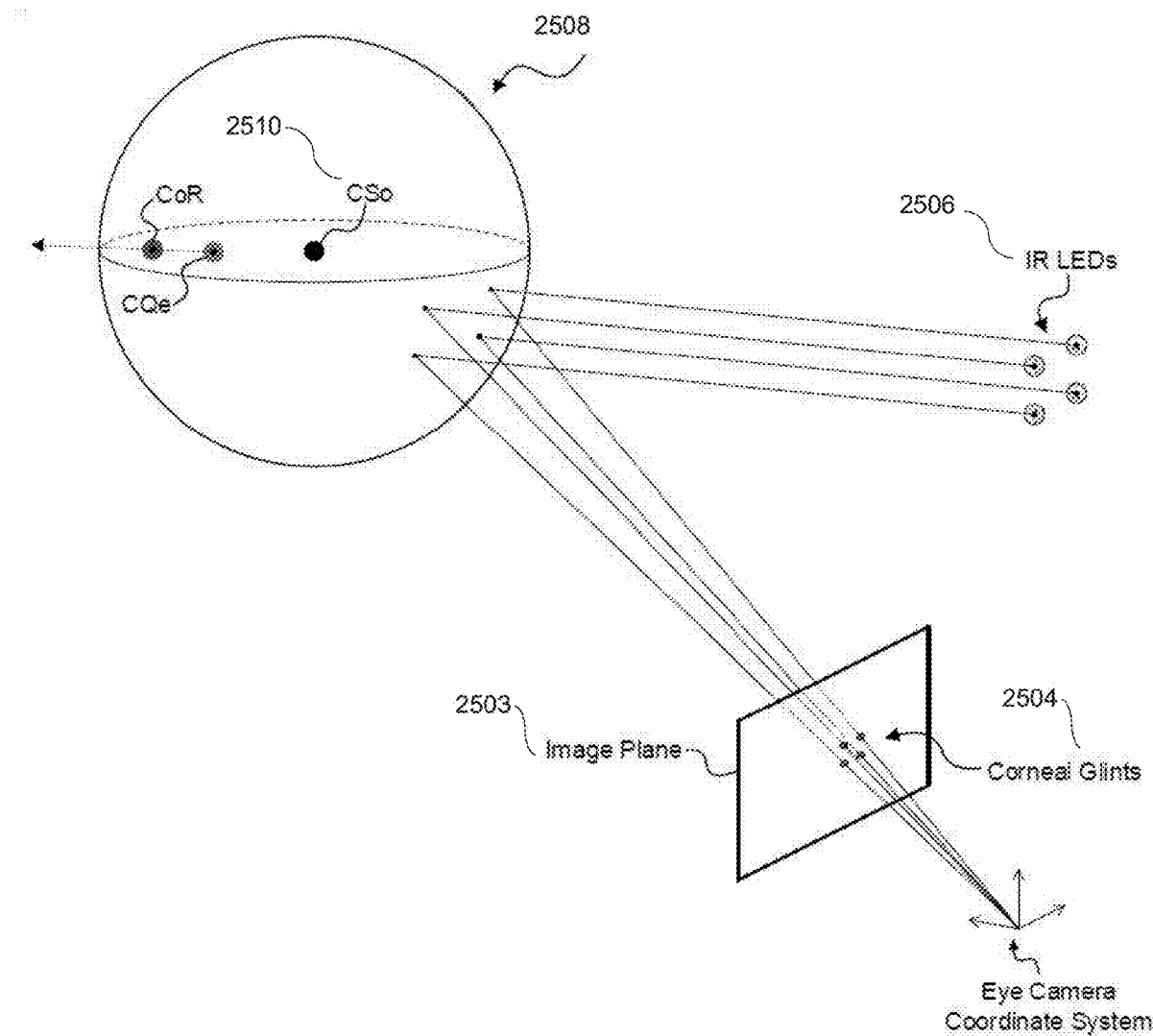
FIGS. 25A-25D illustrate example steps in an example determination of the cornea center based on the procedure illustrated in FIG. 24.
Figure 25B:
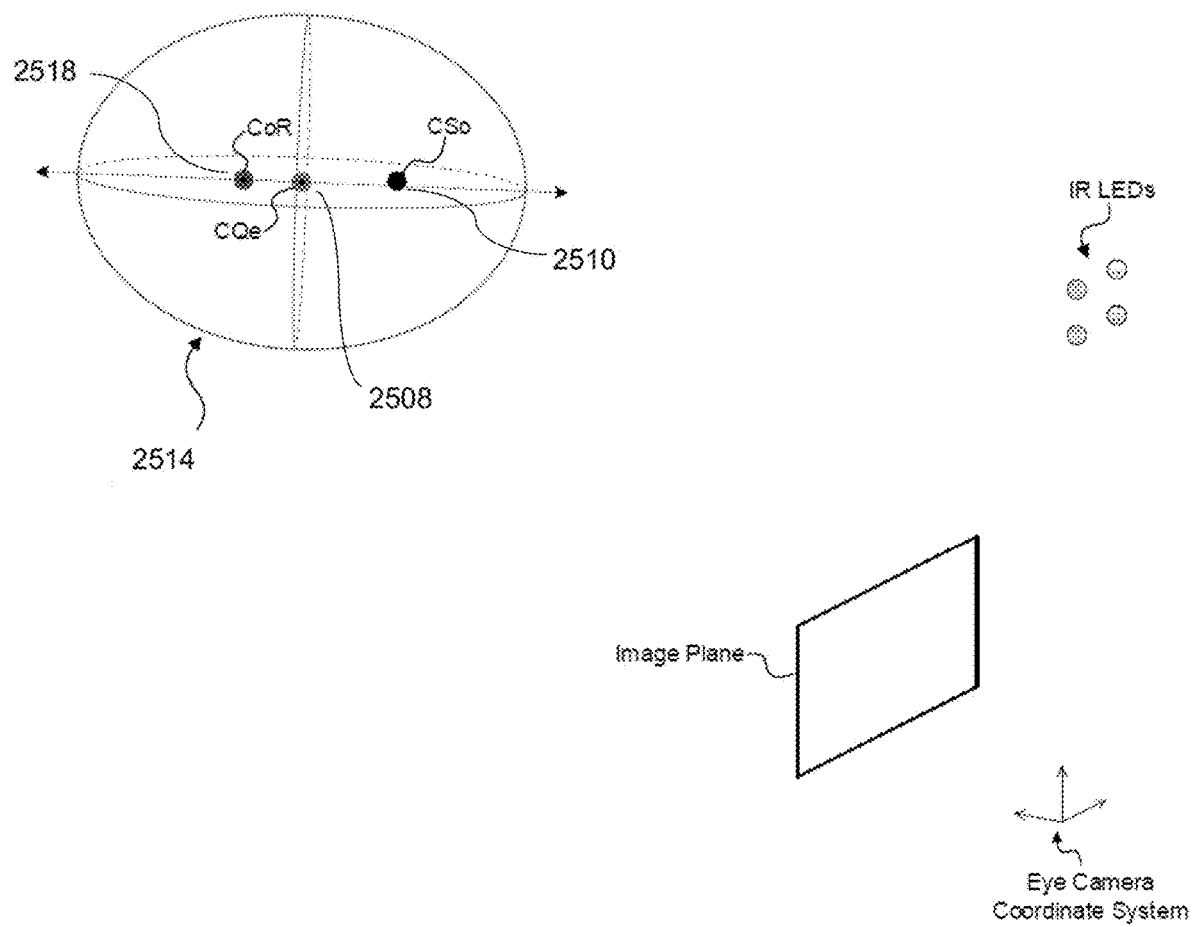

FIG. 25A illustrates the specular reflection of four light rays generated by four light sources 2506 (e.g., four IR LEDs) off of a spherical corneal surface 2508 centered at the center calculated based on the spherical model CSo 2510. These rays generate four glints images 2504, on the image plane 2503 of an eye camera (e.g., on a detector array of a camera). FIG. 25B illustrates an example of an aspheric spheroid 2514 centered at CQe 2508 and oriented in a direction determined using CoR 2518 possibly initially determined from the spheroidal model. As discussed above, the initial value of spheroidal center CQe 2508 may be estimated based on the cornea center calculated based on the spherical model CSo 2510 and thus may be calculated or determined based on the spherical model.

Figure 25C:
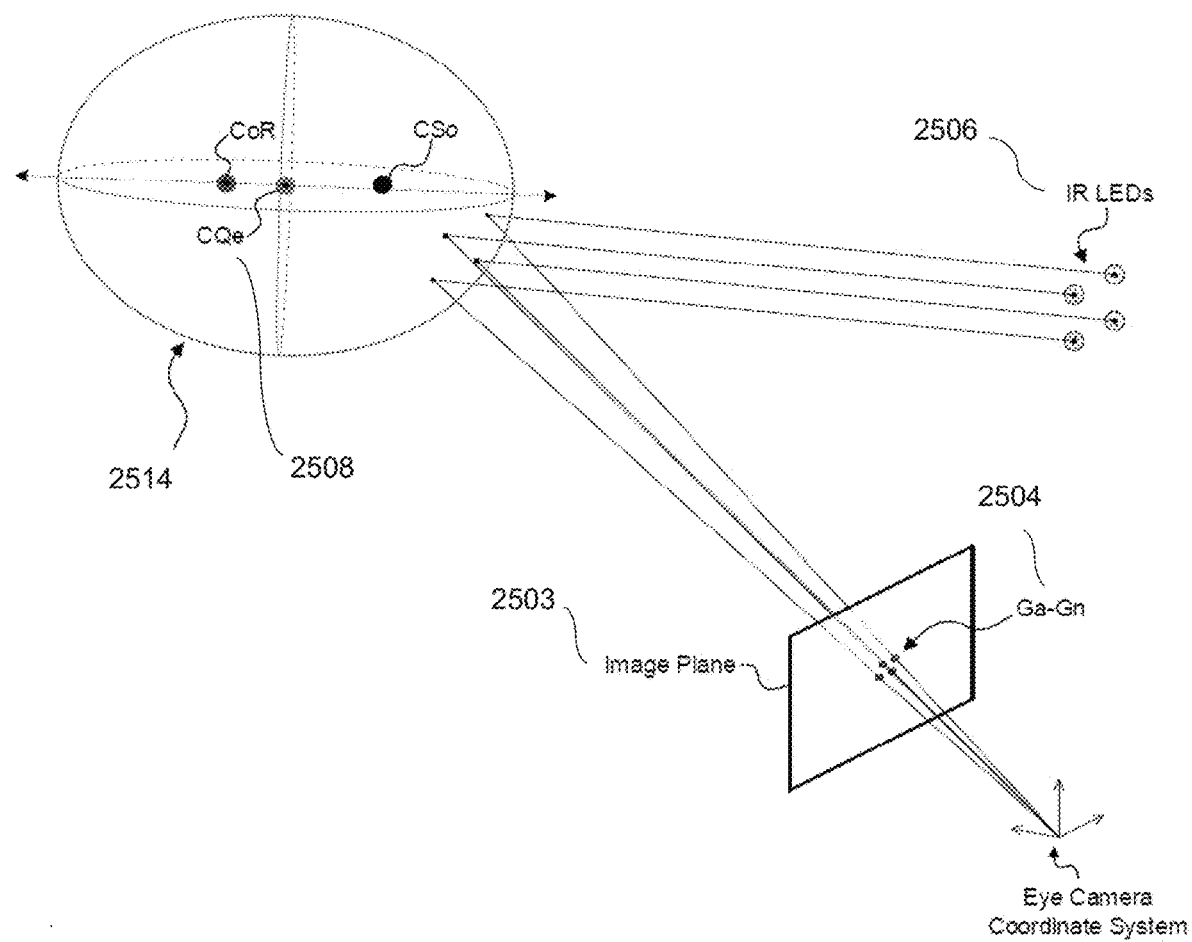

Step 3: In various implementations, using the known location of the light sources 2406 and applying the spheroidal model as referenced in block 2414, the expected locations of the glint images in the image plane (e.g., with respect to the eye camera reference frame) are estimated in block 2422. The aspheric spheroidal surface representing the cornea of the eye is assumed to be centered at CQe and oriented with respect to a coordinate system (e.g., eye camera coordinate system), according to the estimated value of the spheroid orientation calculated in step-2 (e.g., block 2420). FIG. 25C illustrates an example of estimation of the location of four glint images 2504 on the image plane 2503 based on the location of four light sources 2506 (e.g., four IR LEDs) and specular reflection off of a spheroidal reflecting surface 2514 whose center CQe 2508 and orientation are calculated in step 2.

Figure 25D:
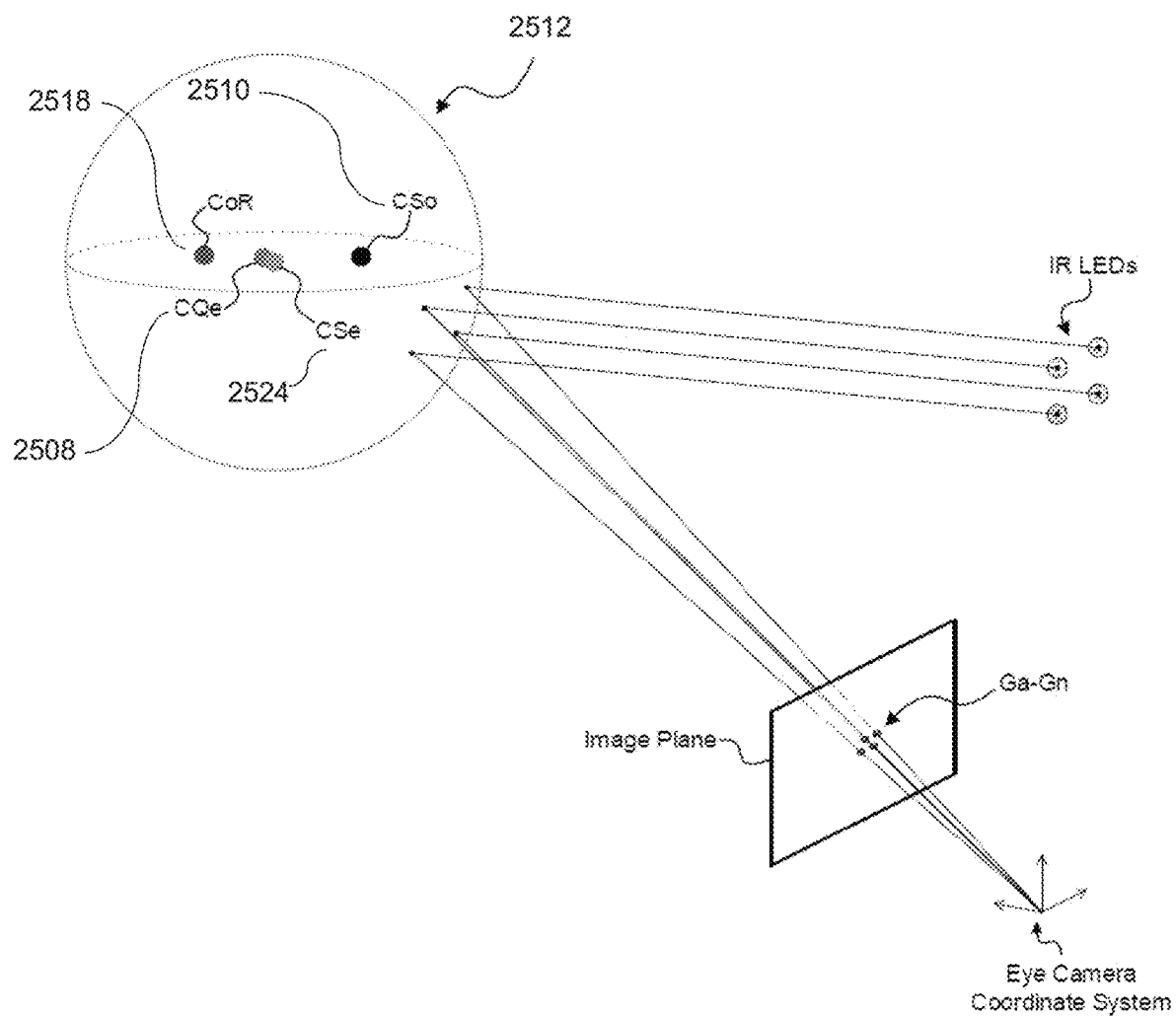

Step 4: Using the expected location of the glints determined in step-3 (block 2422), the known location of the light sources 2406 and applying the spherical cornea model referenced in block 2417, the center of a spherical cornea (CSe) that would generate the glint images at the expected locations 2422 estimated in step-3, is determined in block 2424. The center of this spherical cornea (CS), in part determined using the aspheric spheroidal model, and the cornea center (CSo) that was determined using the spherical model and not the spheroidal model, may differ from each other by Δ. For example, Δ may be determined by subtracting CSo and CSe and may correspond to the absolute value of CSo-Cse in some implementations. FIG. 25D illustrates the relative location of the CoR 2518, CQe 2508, CSo 2510 and CSe 2524. In various implementations, CQe, CSo and CSe may be 3-element vectors or vectors comprising three components or terms defining the vector.

Step 5: Using the difference A and the previously estimated value of CQe, in the aspheric spheroidal model of block 2421, a new value for center of the aspheric spheroid (CQo_1) is determined in block 2428 completing the first iteration of the procedure in various implementations. In some examples, CQo_1 may be estimated using a simplified version of Newton's Method. For example, in some implementations, the process may employ the following relationship:

$$X(j+1) = CQo = X(j) - (J(X))^{-1} * F(X) \quad (2)$$

where F(X)=CSe−CSo, J(X)=Jacobian of F(X), and X=CQe. With convergence of the values of CSe and CSo, the difference between CSe and CSo (e.g., CSe−CSo) approaches zero. As indicated by Equation (2), as the difference between CSe and CSo approaches zero, the difference between X(j) and X(j+1) will also be smaller. Accordingly, in various implementations, equation F(X)=0 is solved, e.g., numerically. Newton's method may, for example, be used to solve the equations F(X)=0, where F(X)=CSe−CSo.

The Jacobian VF(X) may be assumed to be a unity matrix for the single iteration, for example, where the values of CSo and CSe are close to each other. Equation (2) may, in some cases, therefore, be considered to be $$CQe\_updated = CQe + K * (CSo - CSe) \quad (3)$$

where $K=(J(X))^{-1}$ equals the unity matrix and J(X) is a 3×3 Jacobian matrix. The elements of this matrix can vary from the unity matrix to within a standard deviation of up to about 30%. In some examples, a single iteration of the method described above may provide a reasonable solution that reduces the error associated with cornea center estimation by as much as 60%. Additional iterations may further reduce the error although one iteration may be used in some cases.

In some examples, two or more iterations may be used to improve the accuracy of the cornea center estimation possibly by a desired percentage (e.g., larger than 60%). In such examples, the final value of the center of the spheroid (CQo_1) generated in the last (fifth) step of the first iteration, will be used as the initial value of the center of the spheroid (CQe_2) in step-2 of the second iteration. Similarly, in the subsequent iterations, the initial value for the center of a spheroid needed in step-2 of each iteration (CQe_n) will be the final value of the center of the spheroid (CQo_n−1) generated in the last (fifth) step. In some examples, CQo_n in a given iteration, may be estimated using a simplified Newton's Method.

In some other examples, CQo_n in a given iteration may be determined, for example, in block 2428, by reducing or minimizing a function of $\Delta$ (e.g., $\Delta^2$), for example, using the gradient descent method.

In various implementations, for example, to solve for F(X)=0, a cost function such as H(x) may be reduced or minimized.

$$H(X) = (CSe - CSo)^2 \quad (4)$$

The gradient descent method may be used in some implementations. For example, the relationship $$X(j+1) = X(J) + K * \nabla H(X) \quad (5)$$

where K is the step size which may be constant or change, for example, adaptively over steps, may be employed. In some implementations, the step size K may change with different steps (e.g., for multiple steps or with each step). Various forms of gradient descent methods may be used and/or various step sizes may be selected.

In some implementations, the step size may be the Newton step which can lead back to Equation (3) since $$\nabla H(X) \propto CSe - CSo = F(X) \quad (6)$$

For example, substituting Equation (6) into Equation (5) leads to Equation (3).

Other methods besides a Newton's method-based approach or a gradient descent method and variations thereof may be employed.

In some examples, a new image or images, e.g., to obtain glints, may be captured and used for different iterations, e.g., possibly each iteration or multiple iterations. In some such examples, the values of CoR or the pupil center may be recalculated based on the new image or images. In some other examples, the values of CoR and/or the pupil center may be fixed and predetermined values in multiple iterations (e.g., all iterations, all iterations in a series, or otherwise).

The cornea center estimated based on the above procedure and using a aspheric spheroidal cornea model, may be used by the optical axis determination module of the wearable display system (see, e.g., FIG. 7A and associated discussion) to provide more accurate values for various eye parameters (e.g., vergence depth, CoR, center of perspective, or other parameters). Such parameters may, for example, be provided to the light-field render controller module 618. The cornea center may be used in other ways in different implementations.

In some examples, different variations of the method described above may be used to estimate the center of cornea based on an aspheric cornea model. In some variations, one or more steps may be added, omitted, changed or substituted by other steps. In some other variations, the order and/or arrangement of the steps may be different. Likewise, different variations of the procedure represented by the block diagram in FIG. 24, may be implemented without departing from the principal aspects of the procedure. For example, blocks may be added, omitted, altered, or substituted by other blocks, blocks may be reordered or rearranged or any combination of any of these.

Figure 26:
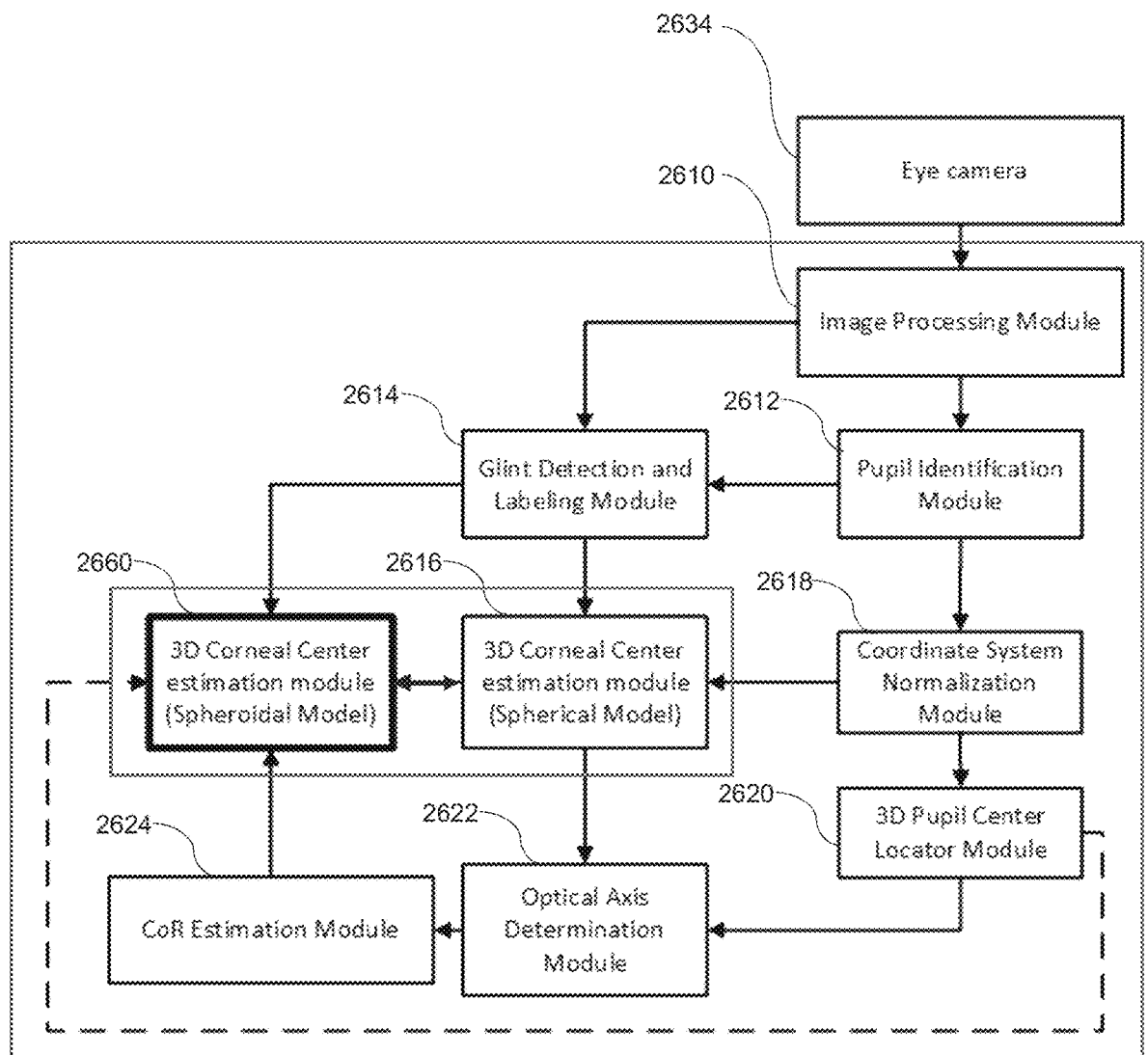
FIG. 26 is a block diagram illustrating a subset of interconnected submodules of an example eye tracking module, that may be combined with a 3D spheroidal cornea center estimation module to estimate the cornea center using a spheroidal cornea model based on the procedure illustrated in FIG. 24.

The above procedure may be performed by one or more processors and one or more non-transitory memories that may store the related instructions in conjunction with the modules of the HMD system (see, e.g., FIG. 7A). FIG. 26 is a block diagram illustrating a subset of submodules used in an example eye tracking module (e.g., the eye tracking module 614 shown in FIG. 7A) that may be combined with a second 3D cornea center estimation submodule 2660 configured for 3D cornea center estimation based on a aspheric spheroidal corneal model and using, for example, the a numerical procedure such as an iterative procedure that may, in some implementations be similar to the procedure described above. Eye camera 2634, image processing module 2610, pupil identification module 2612 and glint detection module 2614 together may provide the location of glints that may be used by the first 2616 and second 2660 3D cornea center estimation modules. The coordinate system normalization module 2618, 3D pupil center locator module 2620 and the first 3D cornea center estimation module 2616 may provide the parameters for estimating the orientation of the optical axis of the eye to the optical axis determination module 2622. The CoR estimation module 2624 can use the orientation of optical axis estimated by the optical axis determination module 2622 to estimate CoR. In some examples, the CoR provided by the CoR estimation module 2624 and the glint locations provided by the glint detection and labeling module 2614, may be used by the first 2616 and second 2660 3D cornea center estimation modules to estimate the center of an aspheric spheroidal cornea. In some examples, one or more of the aforementioned modules may be implemented using a set of shared non-transitional memories and processors. In some examples, different subset of modules comprising one or more modules may share a set of non-transitional memories and processors. In some examples, one or more of the modules can be algorithms written in a specific programing language, stored in a non-transitional memory and executed by one or more processors. In certain implementations, one or more subsets of these modules, comprising one or more modules, may be implemented on a separate hardware (e.g., an FPGA).

Simulations were performed to estimate the cornea center using a single iteration of the procedure described above with J(X) equal to the unity matrix for a spheroid model with R=7.8 mm and Q=−0.25. Results were obtained from simulations of 1000 random eye gazes within +/−20 degrees in horizontal and vertical directions using 4 glints. Table 1 shows the RMS error (in mm) for the three coordinates defining the location of the estimated cornea centers. The total RMS error for the three coordinates is also shown. The RMS errors for center of curvature calculated using both the sphere model as well as the aspheric spheroid model are shown.

TABLE 1

| RMS errors (mm) | X | Y | Z | Total |
|---|---|---|---|---|
| Sphere Model CC | 0.141 | 0.470 | 0.471 | 0.680 |
| Spheroid Model CC (single iteration estimate) | 0.058 | 0.205 | 0.191 | 0.287 |

A comparison between the data points calculated using the aspheric spheroidal model and those calculated using the spherical model show an error reduction of about 60% when the spheroidal model is used.

Determining the 3D Position of the Cornea Center Using Two Eye Cameras and a Spheroidal Model As discussed above, different procedures may utilize an aspheric model such as an aspheric spheroidal model and a wide range of variations may be included in such procedures. In some processes, for example, two cameras may be employed. The two cameras may image glints on the eye to provide information regarding the position and/or orientation of the eye.

Figure 27:
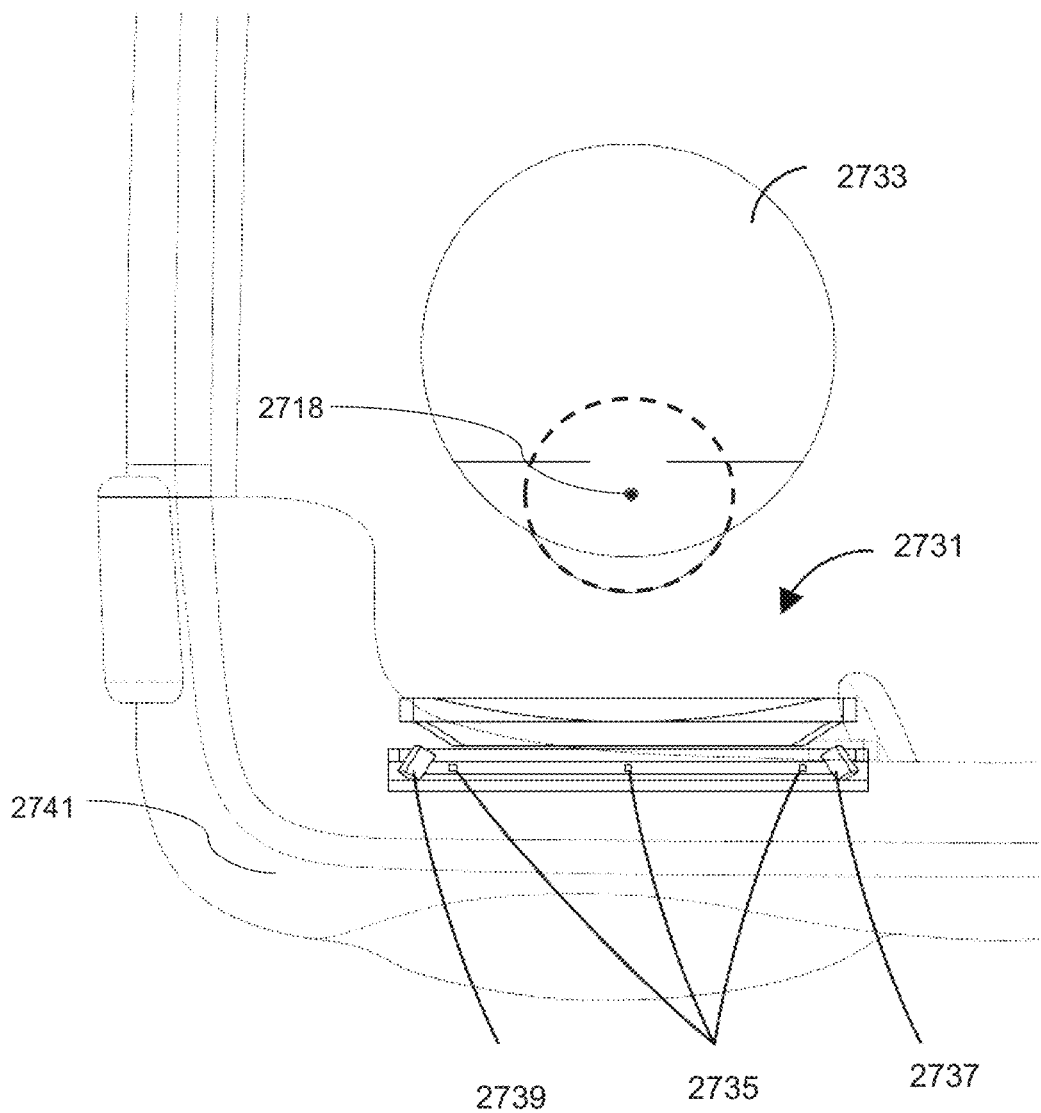
FIG. 27 is an example configuration wherein two cameras are disposed on an eye piece of a head-mounted display frame to capture the images of the glints generated by three light sources also disposed on the frame.

FIG. 27 is an example configuration wherein two cameras 2739/2737 are disposed on an eye piece 2731 of a head-mounted display frame 2741 to capture the images of the glints generated by three light sources 2735 also disposed on the frame 2741. These images may be used to estimate the location of the center of the cornea 2718 of an eyeball 2733 using the method described below.

Figure 28:
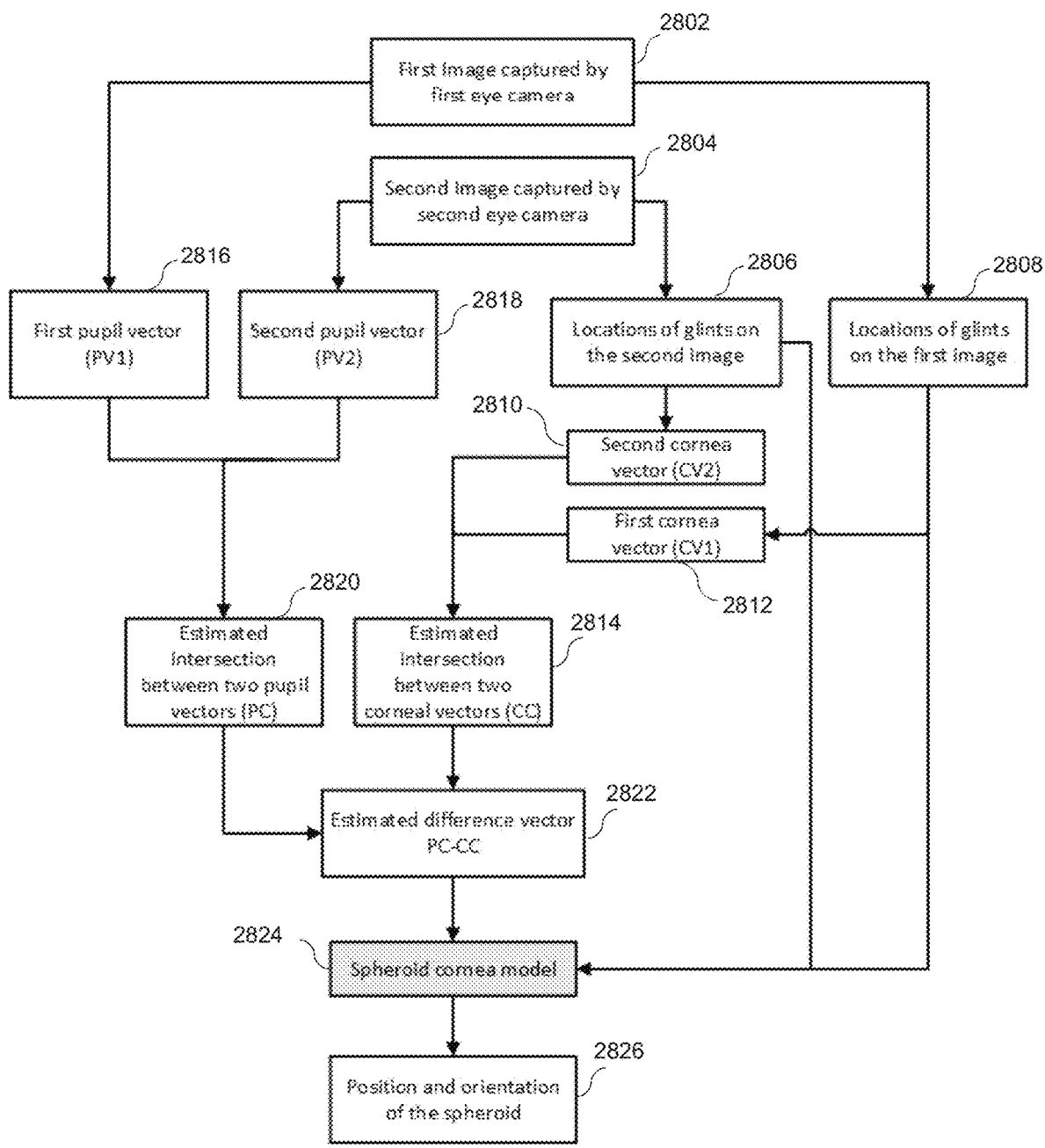
FIG. 28 is a block diagram illustrating an example procedure for estimating the location of center of the cornea based on a spheroidal cornea model using images captured by two eye cameras.

FIG. 28 is a block diagram illustrating procedure for estimating the location of the center of the cornea (e.g., a three-dimensional location such as an x, y, z location described by one or more coordinates such as x, y, z or r, θ, φ, etc., with respect to a reference frame), based on an aspherical spheroidal cornea model using images captured by two eye cameras while a plurality of light sources, affixed on the head-mounted display frame, generate two or more, e.g., four or more, glints on the image plane of each eye camera. A different number of light sources may be used in other implementations. The positions of the eye cameras and the positions of the light sources, with respect to a coordinate system (e.g., coordinate system of the eye cameras), may be known values stored in a non-transitory memory of the HMD system. In some implementations, however, the usage of two eye cameras enables a determination of the corneal center of the eye without knowing the radius of the cornea (R). In some implementations, the location of the center of curvature of the cornea may be determined with respect to reference frame or coordinate system of the eye camera or a fixed reference frame with a respect a head-mounted display.

Advantageously, using images captured by two cameras and the procedure described below, may reduce the time to estimate the cornea center based on an aspheric model (e.g., aspheric spheroidal model) compared to methods that use one eye camera (e.g., the method described above). In some cases, the procedure is non-iterative.

In some examples, this procedure may include some or part of the estimation of the cornea and/or pupil vectors (based on a spherical model) described above (e.g., with reference to FIGS. 9, 11, 13, 14, 15 and 16). In some examples, the cornea and/or pupil vectors may be determined as part of the procedure.

Figure 29A:
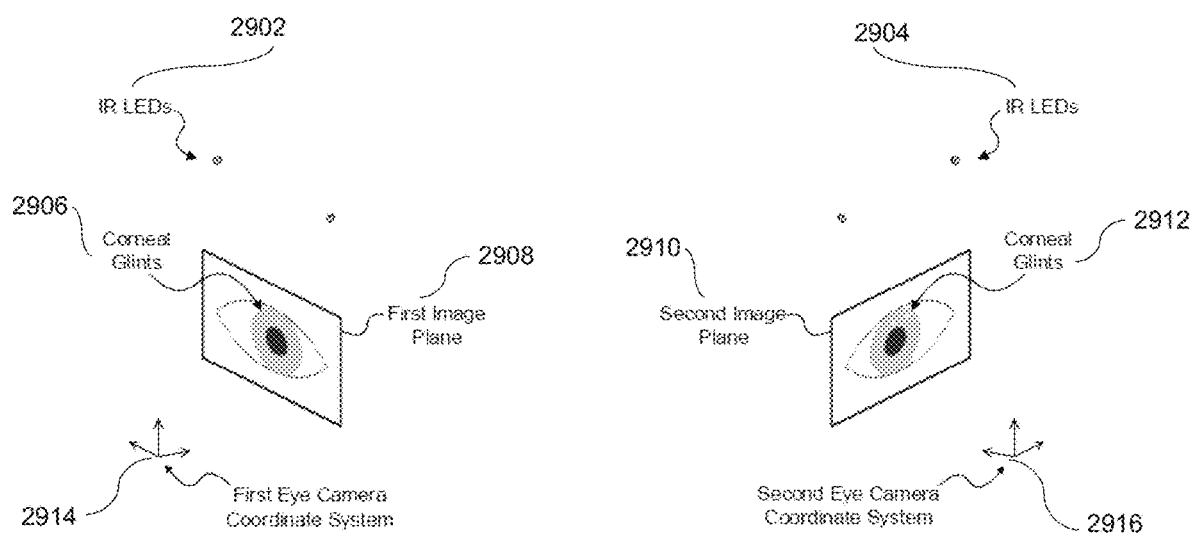
FIGS. 29A-29D illustrate example steps in an example determination of the cornea center based on the procedure illustrated in FIG. 28.

For some implementations, the procedure may include the seven steps described below or one or more portions thereof:

Step 1: A first image is captured by a first eye camera (eye tracking camera) and a second image is captured by a second eye camera (eye tracking camera) as referenced by the first and second block 2802 and 2804, respectively, shown in FIG. 28. Two or more light sources, affixed on the frame, are configured to output light resulting in the appearance of two or more glints on each captured image. In some implementations, the first and second cameras may correspond to cameras 2014 and 2016 or cameras 2018 and 2020 in FIG. 9B-9E. The positions of the glints with respect to the image plane of the first and second eye cameras may be determined (see blocks 2808 and 2806, respectively). This determination of the glint positions may be performed by the image preprocessing module 710 and glint detection and labeling module 714. In some examples, a pair of light sources may generate two glints on the first and second images captured by the first and second eye cameras, respectively. See, e.g., FIG. 29A. In some examples, a first pair of light sources may generate two glints on the first image captured by the first camera and a second pair of light sources may generate two glints on the second image captured by the second camera. A different number of light sources may be employed in other implementations.

Figure 29B:
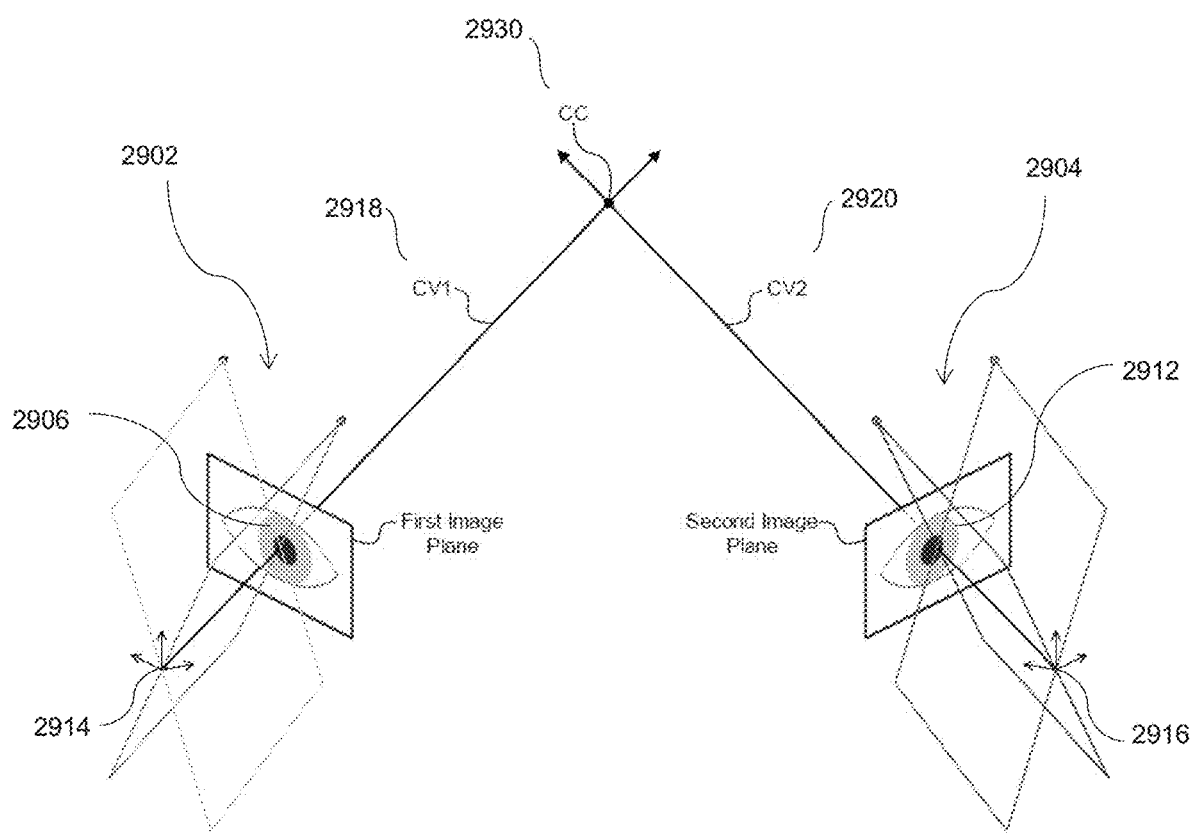

Step 2: FIG. 29B illustrates how the glints can be employed to determine vectors directed toward the eye, e.g., toward the cornea center of curvature. Using the positions of the two glints on the first image captured by the first camera, a first cornea vector CV1 is determined in block 2812. Using the positions of the two glints on the second image captured by the second camera, a second cornea vector CV2 is determined in block 2810.

In some examples, CV1 and CV2 may be determined using two glints in the first captured image and two glints in the second captured image generated by a first and second pairs of light sources, respectively, based on procedure described above—with reference to FIGS. 15A and 15B. The first and second cornea vectors CV1 and CV2 may, for example, correspond to vectors 1510 and 1530 in FIGS. 15A and 15B. In these examples, CV1 is determined in block 2812 using the location of the first camera, the locations of the first pair of light sources, and the locations of the two glints in the first captured image. Similarly, CV2 is determined in block 2810 using the location of the second camera, the locations of the second pair of light sources, and the locations of the two glints on the second captured image.

In some other examples, CV1 and CV2 may be determined using only two light sources that generate two glints on each one of the captured images based on procedure described above with reference to FIG. 16A-16C possibly based on the assumption of a spherical corneal shape. The first and second cornea vectors CV1 and CV2 may correspond to vectors 1610 and 1630 in FIG. 16A-16C. In these examples, CV1 may be determined 2812 using the location of the first camera, the locations of the two light sources, and the locations of the two glints on the first captured image. Similarly, CV2 is determined 2810 using the location of the second camera, the locations of the two light sources, and the location of the two glints on the second captured image. In some implementations, CV1 and CV2 are additionally transformed into the coordinate system of the wearable device by the coordinate system normalization module 718 (see FIG. 7).

Step 3: Using the cornea vectors CV1 and CV2 determined in step-2, the three-dimensional coordinates of the cornea center (CC) may be identified with respect to a coordinate system of the wearable device (since in step-2, CV1 and CV2 are transformed into the coordinate system of the wearable device in various implementations), as represented by block 2814. In some examples, such as in FIG. 29B, the three-dimensional coordinates of the cornea center or region thereabout may be determined by finding the point or region at which vectors CV1 and CV2 intersect. This intersection may correspond to point 1520 or 1620 in FIGS. 15A-16C, and may be determined using the procedure described in paragraph 172 (or 179). In some cases, the vectors do not intersect at a point, however, the vectors may converge. Accordingly, in various implementations a location exists where the vectors converge or where the distance between the vectors is reduced or is a minimum. In some other examples, the cornea center may be estimated using one or more estimation techniques, such as root mean square estimation techniques.

Figure 29C:
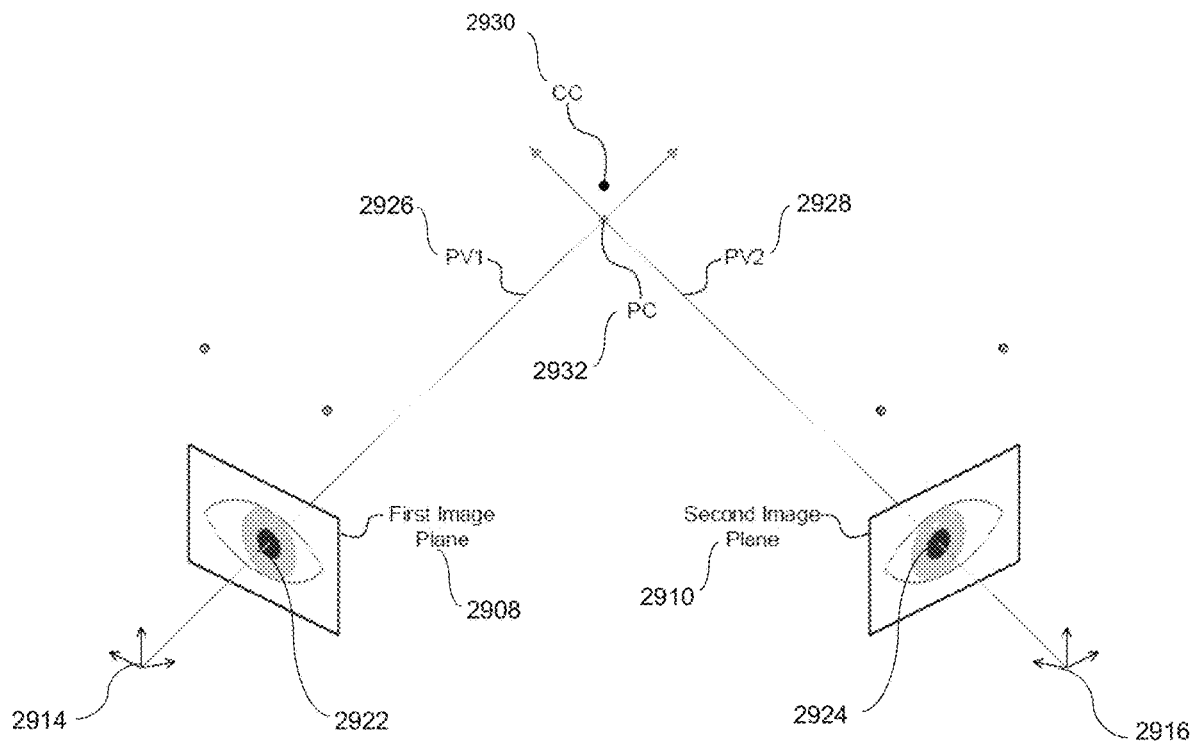

Step 4: Additionally, using the first image captured by the first eye camera, a first pupil vector PV1 may be determined 2816. Similarly, using the second image captured by the second eye camera, a second pupil vector PV2 may be determined 2818. In some examples, the first and second pupil vectors PV1 and PV2 may extend from the origins of the first and second eye cameras coordinate systems through the locations of the centers of the pupils in the first and second image planes, respectively as illustrated in FIG. 29C. In some examples, the first 2816 and second 2818 pupil vectors PV1 and PV2, may be similar to the first and second cornea vectors CV1 and CV2.

Step 5: the three-dimensional coordinates of the point at which PV1 2816 and PV2 2818 intersect (PC) is determined 2820 with respect to the same coordinate systems used in step-3 (e.g., coordinate system of the wearable device). In some cases, the vectors do not intersect at a point, however, the vectors may converge. Accordingly, in various implementations a location exists where the vectors converge or where the distance between the vectors is reduced or is a minimum. In such cases, a location associated with, e.g., within, this region may correspond to PC. In some examples, the point PC may be approximated using one or more estimation techniques, such as root mean square estimation techniques.

Step 6: Using the intersection or convergence location CC determined in step-3 (block 2814 of FIG. 28) and the intersection point or convergence region PC determined in step 5 (block 2820), a vector PC-CC, extending through points PC and CC, is determined in block 2822. The points CC and PC, and the vector PC-CC may be determined with respect to the coordinate system of the wearable device in various implementations. In some examples, the vector PC-CC may roughly correspond to the optical axis of the user's eye. In some examples, the cornea center may be located along the estimated vector PC-CC.

Step 7: Using the aspherical spheroidal corneal model 2824 (e.g., with a given Q value), the locations of glints on the first and second images (block 2806 and 2808), the point CC, determined in step-3 (block 2814) and the vector PC-CC, determined in step 6 (block 2822), the position and the orientation of the aspheric spheroid in three-dimensional space can be estimated as referenced in block 2826. The orientation of the spheroidal may be determined from PC-CC, for example, the axis of the spheroid may be parallel to and/or along PC-CC. The position of the center of the spheroid can also be estimated knowing the PC-CC vector. The position of the spheroidal center may be assumed to be along the PC-CC vector in various implementations. In some embodiments, the spherical model is used to estimate the position of the aspheric spheroid, e.g., along the PC-CC vector. In these embodiments, for example, using the intersection point CC determined in block 2814, the location information of cameras and light sources, and the locations of glints on the first and second images, the location of the center of a spherical reflecting surface associated with the spherical model is calculated. For example, based at least in part a given conic parameter of Q associated with the aspheric spheroidal corneal model, a shift value is calculated and the location of the center of the aspheric spheroid is determined using the shift value, for example, to determine the shift from the CC point. In particular, in some examples, the center of the aspheric spheroid is determined by shifting the center of the spherical reflecting surface along the PC-CC vector by the shift value, which may be calculated based on the shape of the spheroid, e.g., based on the Q value. In some cases, the shift value is calculated based at least in part on the location information of cameras and light sources, and the locations of glints on the first and second images. In some examples, the given value of the Q may be an average value of the Q based on a specific eye model (e.g., −0.25 for Arizona eye model or −0.26 for Navarro eye model), a published value of the Q (e.g., published in a research paper or text book), or a user specific value of the Q parameter.

In addition or in alternative, the position of the center of the spheroid may be determined iteratively. For example, the center of the aspheric spheroid may be assumed to be located somewhere along the PC-CC vector, for example, at the CC point or at a fixed distance from CC such as at the shifted location referenced above where the shift is based on the shape of the spheroid (e.g., the Q value). Knowing the location of the light emitter, locations of the glints can be calculated, for example, by ray tracing rays of light from the light emitters reflected off the aspheric spheroidal surface. These calculated glints can be compared to measured glint locations. The aspheric spheroid can be shifted along the PC-CC vector, for example, by shifting the center of the spheroid along the PC-CC vector. Again, knowing the location of the light emitter, locations of the glints can be calculated by ray tracing rays of light from the light emitters reflected off the aspheric spheroidal surface. These calculated glints can be compared to measured glint locations. This process can be repeated, for example, until a location of the spheroid (and the center of the spheroid) along the PC-CC vector is identified wherein the calculate glint locations are close, for example, sufficiently close with respect to a threshold, to the measured locations of the glints. In some implementations, the location of the spheroid that produces, for example, a reduced or minimum distance may be selected. Accordingly, in some designs, the position of the aspheric spheroid in three-dimensional space is estimated such as referenced in block 2826.

As referenced above, in some examples, the orientation of the spheroid in three-dimensional space may correspond to an orientation of the PC-CC vector 2822, for example, the orientation of the spheroid in three-dimensional space may correspond to the orientation at which vector PC-CC 2822 passes through the center of the aspheric spheroid and both vertices/poles of the spheroid. In some such examples, the orientation of the aspheric spheroid may be sufficient for estimating direction of a user's gaze vector. In these examples, estimating a large collection of gaze vectors, based on images captured at different gaze directions of a user, may be used to estimate the CoR with reduced computational expense. For example, as discussed above and in U.S. Patent Publication US 2019/0243448A1 titled "Eye Center of Rotation Determination, Depth Plane Selection, and Render Camera Positioning in Display Systems," which is incorporated herein by reference in its entirety, multiple gaze vectors or optical axes may be evaluated for different gaze directions to identify an intersection or convergence of the gaze vectors or optical axes, which can be used as an estimate of the center of rotation of the eye. Accordingly, in some embodiments, the eye tracking module 614 may use the orientation of the aspheric spheroid without determining the position of the corneal center or center of curvature of the cornea. In these embodiments, a significant amount of computation time may potentially be saved by not calculating the center of curvature of the cornea, while enabling tracking of the eye gaze direction.

In some implementations, all the above-mentioned steps may be performed by module 716 (see FIG. 7A).

FIGS. 29A-29D schematically illustrate the procedure for determination of the vector PC-CC 2836 based on the procedure discussed above with regard to FIG. 28, for example, wherein two pairs of light sources are used to generate a pair of glints on two separate images generated by two respective eye cameras. As shown, a first pair of light sources 2902 generate a first pair of glints 2905 on the image plane 2908 of the first eye camera. A second pair of light sources 2904 produce a second pair of glints 2912 on the image plane 2910 of the second eye camera (see FIG. 29A). Using the coordinates of: the first eye camera 2914, the first pair of glints 2906 and the first pair of light sources 2902, a first cornea vector CV1 2918 is determined. Using the coordinates of: the second eye camera 2916, the second pair of glints 2912 and the second pair of light sources 2904, a second cornea vector CV2 2920 is determined. As discussed above, a single pair of light sources can be used to produce two glints that are imaged by both the first and second camera in some implementations. In some examples, wherein the two corneal vectors CV1 2918 and CV2 2920 intercept or converge, the coordinates of the interception or convergence point CC 3330 are determined (see FIG. 29B as well as FIG. 16A-16C discussed above).

As discussed above, using the location of the pupil 2922 on the image plane 2908 and the origin of the coordinate system 2914 of the first eye camera, a first pupil vector PV1 2926 is determined. Using the location of the pupil 2924 on the second image plane 2910 and the origin of the coordinate system 2916 of the second eye camera, a second pupil vector PV2 2928 is determined. In some examples, wherein the two corneal vectors PV1 2926 and CV2 2928 intercept or converge, the coordinates of the interception or convergence point or region PC 2932 may be determined with respect to the same coordinate system used to determine the coordinates of the estimated center of curvature of the cornea location CC 2930 in FIG. 29C.

Figure 29D:
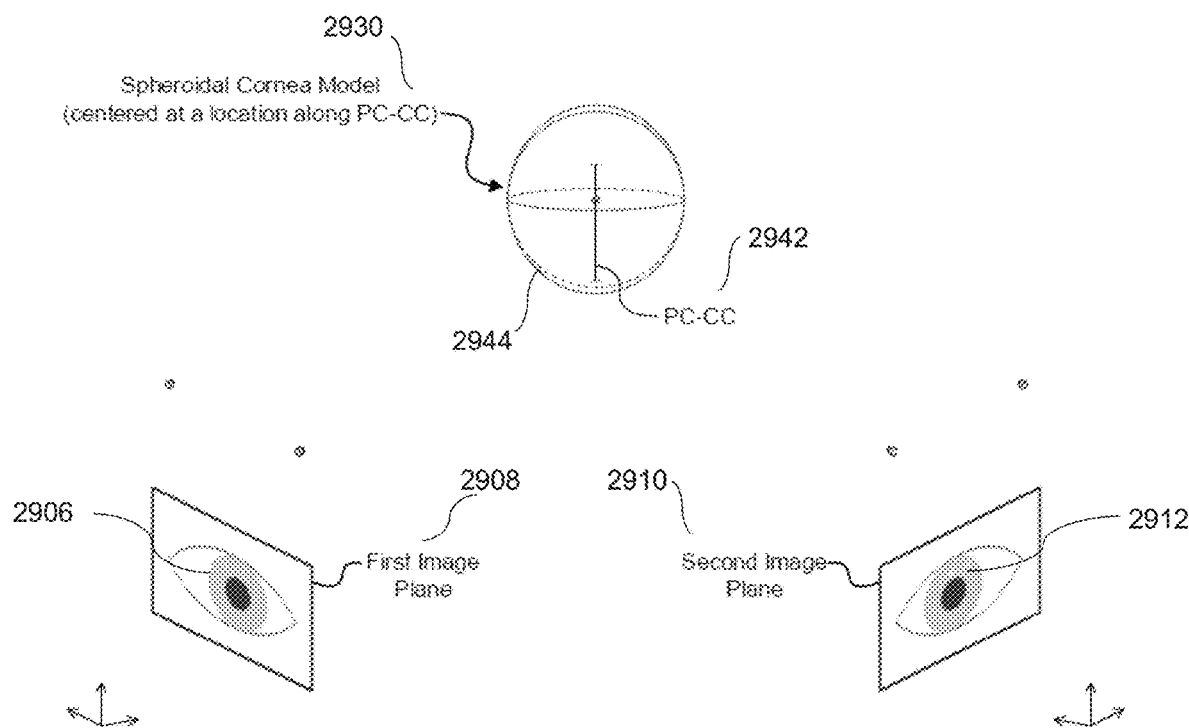

Also, as discussed above, the orientation of the aspheric spheroid 2944, representing the cornea is determined using the vector PC-CC 2942 (defined as the vector connecting CC 2930 and PC 2932) (see FIG. 29D). In some examples, the orientation of the spheroid may be determined by assuming that the vector PC-CC 2942 passes through the center of the aspheric spheroid and both vertices/poles of the spheroid.

Additionally, in some examples, the location of the center of the aspheric spheroid along the vector PC-CC 2942 may be estimated by matching the measured locations of the glints 2906/2912 on the first and second image planes 2908/2910, and the calculated location of the glints on each image plane 2908/2910 based on specular reflection of light rays (generated by the light sources at known locations) off of a spheroid whose center is a point along the vector PC-CC 2942. Other methods may be used.

In some examples, different variations of the method described above may be used to estimate the center and orientation of the cornea based on an aspherical spheroidal cornea model. In some variations, one or more steps may be added, omitted, changed, substituted by other steps or any combination thereof. In some other variations, the order of the steps may be changed or the steps otherwise rearranged. Likewise, different variations of the procedure represented by the block diagram in FIG. 28, may be implemented without departing from the principal aspects of the procedure. For example, certain blocks may be added, omitted, changed rearranged, substituted by other blocks or any combination thereof. Other changes are possible.

Figure 30:
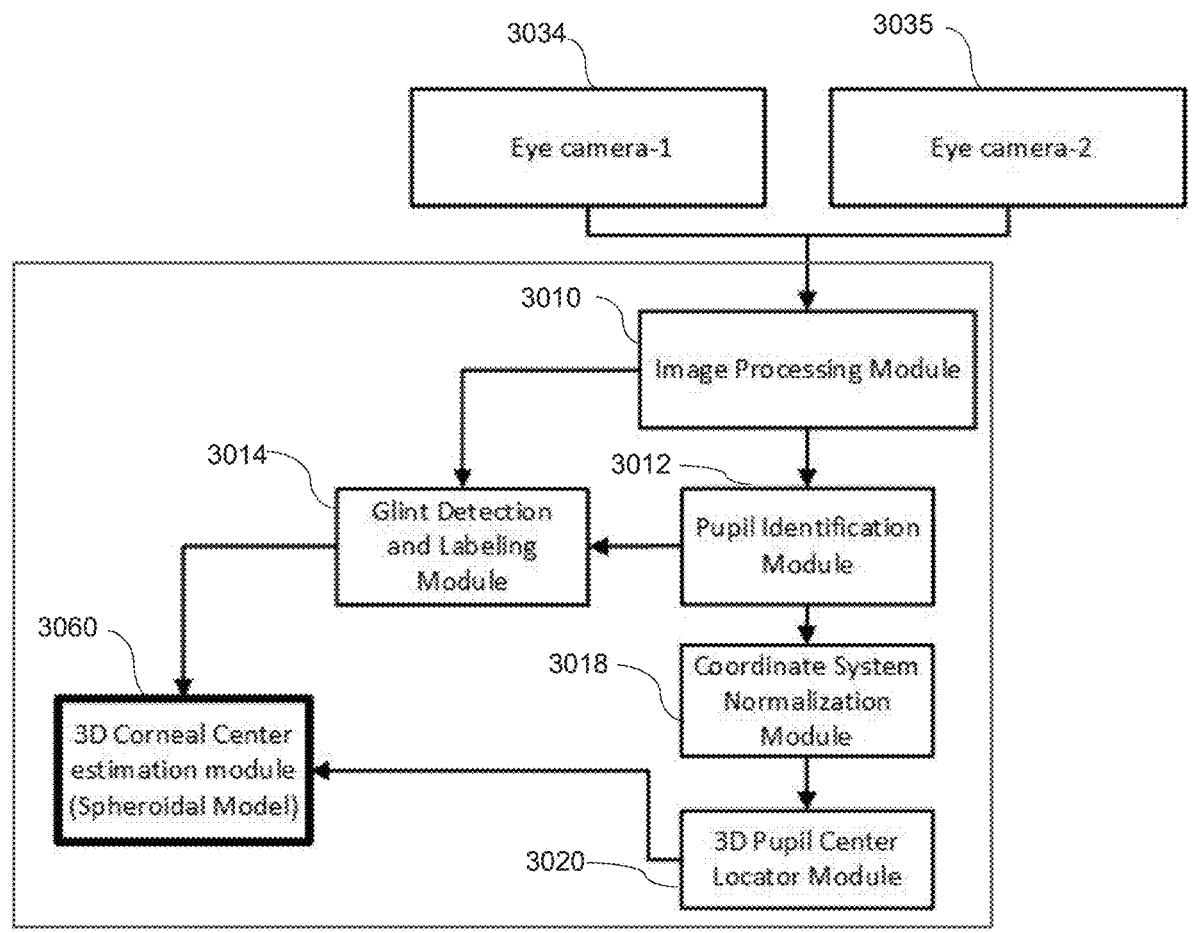
FIG. 30 is a block diagram illustrating a subset of interconnected submodules of an example eye tracking module that may be combined with a 3D spheroidal cornea center estimation module to estimate the cornea center based on a spheroidal cornea model and the procedure illustrated in FIG. 28.

The above-mentioned procedure may be performed by one or more processors and one or more non-transitional memories that may store the related instructions in conjunction with the modules of the HMD system (FIG. 7A). FIG. 30 is a block diagram illustrating a subset of submodules that may be used in an example eye tracking module (e.g., the eye tracking module 614 shown in FIG. 7A), and that may be combined with a new 3D cornea center estimation submodule 3060 configured for 3D cornea center estimation based on an aspheric spheroidal corneal model. In some implementations, the process may employ, for example, the procedure described above with regard to FIG. 28. Note that, in some implementations of the procedure described above with regard to FIG. 28, the two eye cameras 3034/3035, the image processing module 3010, pupil identification module 3012 and glint detection module 3014 together may provide the location of glints to the 3D cornea center of curvature estimation module 3060. Glint locations may be used by the 3D cornea center estimation module 3060, to determine the cornea vectors 2918/2920 (CV1 and CV2) that may be used by the 3D cornea center estimation module 3060 to estimate the center and/or orientation of the aspheric spheroid representing the cornea as explained in step-7. The coordinate system module 3018 and the 3D pupil center locator module 3020 may provide the pupil locations needed to determine the pupil vectors 2926/2928 (PV1 and PV2). Using the cornea vectors, pupil vectors and the location of the glints, the 3D cornea center estimation module 3060, can estimate the center and orientation of the aspheric spheroid representing the cornea. Other methods and/or configurations are possible.

In various implementations, estimating a location of a corneal center of the user's eye based on the location of the glint reflections in images produced by one or more eye tracking camera, includes numerical calculations to determine a value (e.g., a three-dimensional location such as an x, y, z location described by one or more coordinates such as x, y, z or r, θ, φ, etc., with respect to a reference frame) or an estimate or a location of a center of curvature of the cornea based on the location of the glint reflections in images produced by said one or more cameras, locations of the one or more tracking cameras and the locations of the emitters that produced said respective glint reflections.

In some examples, the aforementioned modules may be implemented using a set of shared non-transitory memories and processors, however, other configurations are possible. In some examples, subsets of modules comprising one or more modules may share a set of non-transitory memories and processors. In some examples, one or more of the modules can comprises algorithms written in a specific programing language, stored in a non-transitory memory and executed by one or more processors. In certain implementations, one or more subsets of these modules, comprising one or more submodules, may be implemented using a separate hardware (e.g., an FPGA or a dedicated processor).

In some implementations, the center and orientation of the cornea of an eye may be estimated using an aspherical eye model wherein the cornea is represented by a non-rotationally symmetric surface. The aspheric eye model may for example employ a biconic or an ellipsoidal surface which are not rotationally symmetric round any axis. These shapes may be used to capture the different curvatures of the cornea in different planes (e.g., horizontal or vertical). Sec, for example, Equation (1C) and (1D) above and discussion thereof. Accordingly, in various implementations such non-rotationally symmetrical models that use a non-rotationally symmetric surface such as a biconic or an ellipsoidal surface to model the cornea may be used with the methods described herein.

In some such implementations, for example, a non-revolution ellipsoid may be used to model the surface of the cornea (e.g., the surface defined by equation 1D). In such case, a third known parameter (in addition to Q and R) may be used to estimate the position and/or the orientation of the ellipsoidal surface modelling the cornea. In some examples, the value of the third parameter may be provided by the eye model. Methods comprising the same or modified versions of the procedures described with reference to FIG. 24, FIG. 28 or elsewhere herein may be used with non-rotationally symmetric models such as non-revolution ellipsoid eye models of the cornea in place of the aspheric spheroid model of the cornea.

In some other implementations, the aspherical corneal model may be a biconic model wherein the surface of the cornea is represented by a general biconic surface (e.g., the biconic surface defined by the equation 1C). As mentioned above, a biconic model may be used to model the corneal shape for large variety eye shapes associated with, for example, emmetropic, myopic, hyperopic, or astigmatic eyes. In some such examples, the biconic surface may be specified using five parameters. With reference to Equation 1C, $(R_x, Q_x)$ and $(R_y, Q_y)$ may specify the radius and conic parameter of the corneal surface in the horizontal and vertical dimension respectively. Additionally, the orientation of the biconic surface with respect to the astigmatic axis of the cornea, may be specified by an angle (the fifth parameter) ranging from 0 to 180 degrees. In some examples, the value of these parameters may be obtained from known eye models or average values reported in the literature. Methods comprising the same or modified version of the procedures described with reference to FIG. 24, FIG. 28 or elsewhere herein may be used with biconic eye models of the cornea in place of the aspheric spheroid model of the cornea.

In some such examples, the five parameters of a biconic spheroidal model may be estimated based on an extended version of procedures described with reference to FIG. 24 and FIG. 28, wherein additional steps may be added to estimate the one or more unknown parameters in the model. In some cases, additional glints and possibly additional light sources and/or images may be employed. In some such examples, four or more glints may be used to estimate the cornea center, the gaze direction, and the eye ball center.

In some other examples, some constraints on the range or statistical distribution of one or more parameters in the eye models, can be used to facilitate the computation. (e.g., reduce the additional steps in the extended procedures). For example, the statistical distributions of $R_x$ and $R_y$ may be the same as R; thus they may have the same mean value (e.g., of 7.8 mm) and the same standard deviation (e.g., 0.26 mm).

The distributions of $Q_x$ and $Q_y$ may be the same as Q, thus, they may have the same mean value (e.g., −0.26 or −0.25) and the same standard deviation (e.g., 0.18). Most astigmatic corneas may have an astigmatic axis closer to the vertical or horizontal axes, for example, defined based on the coordinate system of the eye wear. Additionally, many eye parameters are often similar in right and left eye pairs. In some examples, if an eye (cornea of an eye) is not astigmatic, $R_x$ may be equal to and $R_y$ and equal to R. Similarly for a non-astigmatic eye, $Q_x$ may be equal to $Q_y$ and equal to Q; in such cases, the biconic ellipsoidal eye model may be reduced to a spheroidal eye model.

As discussed above, the cornea center and the gaze direction may be estimated using the glint images captured by one or more eye cameras.

In some embodiments, the user specific value of the Q parameter may be estimated using a Q calibration process. In some embodiments, during the Q calibration process one or more procedures described herein such as with respect to FIG. 24 and FIG. 28 or a portion thereof may be used or methods described elsewhere may be employed to determine the user specific value of the Q parameter for an aspheric spheroidal model used to estimate the cornea center of an eye of the user wearing the HMD. For example, as described above and shown in FIG. 7A, the cornea center (e.g., estimated at block 716) and the corresponding center of rotation (CoR) of the eye (e.g., estimated at block 724 based on the cornea center) may be input parameters to, for example, the Light-Field Render Controller 618. As such, the estimated cornea center, can affect the characteristics of the image rendered by HMD. Advantageously, the user specific value of the Q parameter may be used by the light-field render controller 618 and/or one or more other modules that feed parameter values to the light-field render controller 618 (e.g., the CoR estimation module 732 and the CoP estimation module 724), to render an image that is perceived by the user closer to the way intended.

In some embodiments, a user specific value of Q parameter may be estimated using a process comprising measurement/data collection and analysis/estimation. The measurement and data collection may be a repetitive procedure comprising providing a target for the user to look at while one or more light emitters illuminate the user's eye to form a glint thereon and capturing one or more images of the eye using one or more eye tracking cameras wherein the one or more images are associated with a gaze direction determined by a location of the target. In some cases, this process can be repeated with the target location being changed to alter the gaze direction of the user.

Using these procedures a plurality of images of the eye may be collected where, for example, different images captured by one eye camera or different pairs of images captured by two eye tracking cameras are associated with a different respective gaze directions. In some cases, an image captured by one eye camera or a pair of images captured by two eye tracking cameras may include glint reflections associated with one or more light emitters. The plurality of images may be stored, for example, in a memory of the eye tracking module 614 or a memory of HMD.

In the analysis and estimation step, the plurality of images of the eye may be used to determine a user specific value of the Q parameter. In some implementations, the analysis and estimation may be an iterative process. In some implementations, an iteration may comprise estimating a plurality of CoR values using one or more procedures/methods described herein (e.g., one or more procedures described with respect to FIG. 24, or FIG. 28) or other methods.

Estimation of the CoR may possibly employ a plurality of images of the eye, locations of the emitters that produced glints, an initial value of the Q parameter or a value of the Q parameter generated in a previous iteration or any one or more of these. A statistical parameter or metric (e.g., variance, standard deviation), for example, associated with the estimated CoR values for the different predetermined Q values may be calculated. The statistical metric may be a measure or otherwise indicate variation, instability, uncertainty, or error in the CoR for the particular Q value. The statistical parameter or metric (e.g., variance, standard deviation) may be calculated using the plurality of the estimated CoR values or the process of determining the CoR values. The statistical metric may, for example, correlate to the size of the region of convergence 1824 in FIG. 18B or estimated CoR region 1920 in FIG. 19C-1, 19C-2, 19C-3, 19C-4 or region of converge of optical axes calculated for different gaze direction such as described in U.S. Patent Publication US 2019/0243448A1, which is incorporated herein by reference in its entirety, from which the CoR may be determined. A new value of Q parameter may be generated based at least in part on the calculated statistical parameter or metric. For example, the statistical metric may be monitored and selection of the Q may be based on the value of the statistical metric. For instance, a Q value may be selected that corresponds to a reduced or minimum statistical metric or a statistical metric below a threshold value. In some cases, the Q value may be modified as well (e.g., averaged, scaled etc.), possibly based on other Q values and/or the statistical metric or values based thereon.

In some embodiments, a first iteration may use the initial value of the Q parameter. Subsequent iterations may, in some implementations, use the value of Q parameter generated in the iteration performed just before each subsequent iteration although other approaches are possible. The initial value of the Q parameter may be an estimated value based on, for example, measured data collected from several subjects, one or more eye models, and the like. In some examples, the initial value of the Q parameter may be −0.25±0.1.

In some implementations, the analysis and estimation may be a non-iterative process. For example, the estimation may comprise selection of one or more Q values from a plurality of predetermined values of the Q parameter. In some examples, the non-iterative process may comprise estimating a plurality of CoR values for the different Q values. As described above, the CoR may be determined using methods described herein (e.g., one or more methods described with respect to FIG. 24, or FIG. 28) or other methods. Estimation of the COR may possibly employ a plurality of images of the eye, locations of the emitters that produced glints, a plurality of predetermined values of the Q parameter or one or more of these. A statistical parameter or metric (e.g., variance, standard deviation), for example, associated with the estimated CoR values for the different predetermined Q values may be calculated. The statistical metric may be a measure or otherwise indicate variation, instability, uncertainty, or error in the CoR for the particular Q value. (As discussed above, the statistical metric may, for example, correlate to the size of the region of convergence 1824 in FIG. 18B or estimated CoR region 1920 in FIG. 19C-1, 19C-2, 19C-3, 19C-4 or region of converge of optical axes calculated for different gaze direction such as described in the such as described in U.S. Patent Publication US 2019/0243448A1 which is incorporated herein by reference in its entirety from which the COR may be determined. Accordingly, a Q parameter that yields a desired or improved, e.g., the reduced, minimal or othered more desirable or best statistical parameter or metric may be selected. In some cases, the Q value may be modified as well (e.g., averaged, scaled etc.), possibly based on other Q values and/or the statistical metric or values based thereon.

In some examples, the plurality of the predetermined values of the Q parameter may be values published in the literature (e.g., research papers, text books, reference books and the like). In some other examples, the plurality of the predetermined values of the Q parameter may be a plurality of calculated values of the Q parameter for a population. For example, a corneal topographer may be used to measure corneal shapes of eyes of a group of subjects (e.g., 10, 50, 100, subjects or more), and values of the Q parameter may be calculated using the measured corneal shapes. Other methods of obtaining Q values are also possible.

Accordingly, in various implementations, the statistical metric calculated may be a measure of variation, for example, of a statistical distribution of the estimated CoR values for different gaze directions. In some implementations, a new value of the Q parameter may be selected to reduce or minimize the variance. Alternatively, the metric may be determined for multiple Q values and the Q value is selected based on the metric, for example, to reduce the value of the metric, such as to reduce the variation, uncertainty, error, etc., in the CoR values obtained for different gaze directions.

In some implementations, the process described above may be performed by the eye tracking module 614 of the HMD. In some other configurations, the measurement and data collection may be performed by the eye tracking module and the analysis and estimation may be performed by another module of the HMD (e.g., a processing module comprising a processor and a memory).

In some embodiments, three or more eye cameras may be used to capture eye images for estimating a parameter such as the center of cornea. The parameter, for example, center a cornea may be estimated using a spherical model and/or an aspheric spheroidal model. In some such embodiments, the eye-tracking module 614 may select a pair of eye cameras from the three or more eye cameras and use the pair of cameras to estimate the parameter, e.g., 3D cornea center, 3D pupil center CoR or other parameter. For example, a pair of eye cameras of the three or more eye cameras can be selected to capture two (or more) images of the eye of a user (e.g., a user wearing the HMD) from which a parameter can be estimated, for example, using methods described above. A different pair of eye cameras of the three or more eye cameras can be selected to capture two (or more) images of the eye of a user (e.g., a user wearing the HMD) and the parameter can be estimated again based on the images from this pair of cameras. This process can possibly be repeated selecting another different pair of cameras. For example, a first and second camera can be initially selected, followed by the second and third cameras followed by the first and third cameras. The order or procedure may vary. The values obtained with the different camera pairs may be statistically combined, e.g., averaged, or otherwise used together to determine an estimate of the parameter. This parameter may comprise a physical, optical, and/or structural feature of the eye of the user such as an estimate of the corneal center, center of rotation, center of perspective, or intermediate value for obtaining such parameters. In some implementations, such values may be employed in rendering an image based on the estimated center of cornea and/or other parameter(s). In various embodiment described above, the location (e.g., three dimensional location) of various eye parameters (e.g., cornea center, pupil center, center of rotation and the like) may be calculated with respect to one or more normalized coordinate systems. In some cases, the eye camera coordinate system may be a normalized coordinate system and the location of the image plane may be determined with respect to the eye camera coordinate system. Normalized coordinate systems may be determined, for example, by the coordinate system normalization module 718 of the eye tracking module 614 (see FIG. 7A), using, for example, methods discussed in U.S. Patent Publication US 2019/0243448A1 titled "Eye Center of Rotation Determination, Depth Plane Selection, and Render Camera Positioning in Display Systems," which is incorporated herein by reference in its entirety, however, other variations or approaches may be employed to normalize or otherwise transform the coordinates/locations, for example, to another system such as another coordinate system.

T. Examples for When Eye Tracking is Unavailable

In some embodiments, eye tracking may not be provided or may be temporarily unavailable. As examples, the eye tracking camera 324 or light sources 326 may be obscured, damaged, or disabled by a user, the environmental lighting conditions may make eye tracking prohibitively difficult, the wearable system may be improperly fitted in a manner that prevents eye tracking, the user may be squinting or have eyes that are not easily tracked, etc. At such times, the wearable system may be configured to fall back upon various strategies for positioning the render camera and selecting depth planes in the absence of eye tracking data.

For example, with respect to the render camera, the wearable system may position the render camera to a default position if the user's pupils are not detected for longer than a predetermined threshold, such as a few seconds or longer than a typical blink. The wearable system may possibly move the render camera to the default position in a smooth movement, which may, e.g., follow an over-damped oscillator model. In some implementations, the default position may be determined as part of a calibration process of the wearable system to a particular user. However, the default position may be a user's left and right eyes' centers of rotation. These are merely illustrative examples.

U. Computer Vision to Detect Objects in Ambient Environment

As discussed above, the display system may be configured to detect objects in or properties of the environment surrounding the user. The detection may be accomplished using a variety of techniques, including various environmental sensors (e.g., cameras, audio sensors, temperature sensors, etc.), as discussed herein.

In some embodiments, objects present in the environment may be detected using computer vision techniques. For example, as disclosed herein, the display system's forward-facing camera may be configured to image the ambient environment and the display system may be configured to perform image analysis on the images to determine the presence of objects in the ambient environment. The display system may analyze the images acquired by the outward-facing imaging system to perform scene reconstruction, event detection, video tracking, object recognition, object pose estimation, learning, indexing, motion estimation, or image restoration, etc. As other examples, the display system may be configured to perform face and/or eye recognition to determine the presence and location of faces and/or human eyes in the user's field of view. One or more computer vision algorithms may be used to perform these tasks. Non-limiting examples of computer vision algorithms include: Scale-invariant feature transform (SIFT), speeded up robust features (SURF), oriented FAST and rotated BRIEF (ORB), binary robust invariant scalable keypoints (BRISK), fast retina keypoint (FREAK), Viola-Jones algorithm, Eigenfaces approach, Lucas-Kanade algorithm, Horn-Schunk algorithm, Mean-shift algorithm, visual simultaneous location and mapping (vSLAM) techniques, a sequential Bayesian estimator (e.g., Kalman filter, extended Kalman filter, etc.), bundle adjustment, Adaptive thresholding (and other thresholding techniques), Iterative Closest Point (ICP), Semi Global Matching (SGM), Semi Global Block Matching (SGBM), Feature Point Histograms, various machine learning algorithms (such as e.g., support vector machine, k-nearest neighbors algorithm, Naive Bayes, neural network (including convolutional or deep neural networks), or other supervised/unsupervised models, etc.), and so forth.

One or more of these computer vision techniques may also be used together with data acquired from other environmental sensors (such as, e.g., microphone) to detect and determine various properties of the objects detected by the sensors.

As discussed herein, the objects in the ambient environment may be detected based on one or more criteria. When the display system detects the presence or absence of the criteria in the ambient environment using a computer vision algorithm or using data received from one or more sensor assemblies (which may or may not be part of the display system), the display system may then signal the presence of the object.

V. Machine Learning

A variety of machine learning algorithms may be used to learn to identify the presence of objects in the ambient environment. Once trained, the machine learning algorithms may be stored by the display system. Some examples of machine learning algorithms may include supervised or non-supervised machine learning algorithms, including regression algorithms (such as, for example, Ordinary Least Squares Regression), instance-based algorithms (such as, for example, Learning Vector Quantization), decision tree algorithms (such as, for example, classification and regression trees), Bayesian algorithms (such as, for example, Naive Bayes), clustering algorithms (such as, for example, k-means clustering), association rule learning algorithms (such as, for example, a-priori algorithms), artificial neural network algorithms (such as, for example, Perceptron), deep learning algorithms (such as, for example, Deep Boltzmann Machine, or deep neural network), dimensionality reduction algorithms (such as, for example, Principal Component Analysis), ensemble algorithms (such as, for example, Stacked Generalization), and/or other machine learning algorithms. In some embodiments, individual models may be customized for individual data sets. For example, the wearable device may generate or store a base model. The base model may be used as a starting point to generate additional models specific to a data type (e.g., a particular user), a data set (e.g., a set of additional images obtained), conditional situations, or other variations. In some embodiments, the display system may be configured to utilize a plurality of techniques to generate models for analysis of the aggregated data. Other techniques may include using pre-defined thresholds or data values.

The criteria for detecting an object may include one or more threshold conditions. If the analysis of the data acquired by the environmental sensor indicates that a threshold condition is passed, the display system may provide a signal indicating the detection the presence of the object in the ambient environment. The threshold condition may involve a quantitative and/or qualitative measure. For example, the threshold condition may include a score or a percentage associated with the likelihood of the reflection and/or object being present in the environment. The display system may compare the score calculated from the environmental sensor's data with the threshold score. If the score is higher than the threshold level, the display system may detect the presence of the reflection and/or object. In some other embodiments, the display system may signal the presence of the object in the environment if the score is lower than the threshold. In some embodiments, the threshold condition may be determined based on the user's emotional state and/or the user's interactions with the ambient environment.

In some embodiments, the threshold conditions, the machine learning algorithms, or the computer vision algorithms may be specialized for a specific context. For example, in a diagnostic context, the computer vision algorithm may be specialized to detect certain responses to the stimulus. As another example, the display system may execute facial recognition algorithms and/or event tracing algorithms to sense the user's reaction to a stimulus, as discussed herein.

It will be appreciated that each of the processes, methods, and algorithms described herein and/or depicted in the figures may be embodied in, and fully or partially automated by, code modules executed by one or more physical computing systems, hardware computer processors, application-specific circuitry, and/or electronic hardware configured to execute specific and particular computer instructions. For example, computing systems may include general purpose computers (e.g., servers) programmed with specific computer instructions or special purpose computers, special purpose circuitry, and so forth. A code module may be compiled and linked into an executable program, installed in a dynamic link library, or may be written in an interpreted programming language. In some embodiments, particular operations and methods may be performed by circuitry that is specific to a given function.

Further, certain embodiments of the functionality of the present disclosure are sufficiently mathematically, computationally, or technically complex that application-specific hardware or one or more physical computing devices (utilizing appropriate specialized executable instructions) may be necessary to perform the functionality, for example, due to the volume or complexity of the calculations involved or to provide results substantially in real-time. For example, a video may include many frames, with each frame having millions of pixels, and specifically programmed computer hardware is necessary to process the video data to provide a desired image processing task or application in a commercially reasonable amount of time.

Code modules or any type of data may be stored on any type of non-transitory computer-readable medium, such as physical computer storage including hard drives, solid state memory, random access memory (RAM), read only memory (ROM), optical disc, volatile or non-volatile storage, combinations of the same and/or the like. In some embodiments, the non-transitory computer-readable medium may be part of one or more of the local processing and data module (140), the remote processing module (150), and remote data repository (160). The methods and modules (or data) may also be transmitted as generated data signals (e.g., as part of a carrier wave or other analog or digital propagated signal) on a variety of computer-readable transmission mediums, including wireless-based and wired/cable-based mediums, and may take a variety of forms (e.g., as part of a single or multiplexed analog signal, or as multiple discrete digital packets or frames). The results of the disclosed processes or process steps may be stored, persistently or otherwise, in any type of non-transitory, tangible computer storage or may be communicated via a computer-readable transmission medium.

Any processes, blocks, states, steps, or functionalities in flow diagrams described herein and/or depicted in the attached figures should be understood as potentially representing code modules, segments, or portions of code which include one or more executable instructions for implementing specific functions (e.g., logical or arithmetical) or steps in the process. The various processes, blocks, states, steps, or functionalities may be combined, rearranged, added to, deleted from, modified, or otherwise changed from the illustrative examples provided herein. In some embodiments, additional or different computing systems or code modules may perform some or all of the functionalities described herein. The methods and processes described herein are also not limited to any particular sequence, and the blocks, steps, or states relating thereto may be performed in other sequences that are appropriate, for example, in serial, in parallel, or in some other manner. Tasks or events may be added to or removed from the disclosed example embodiments. Moreover, the separation of various system components in the embodiments described herein is for illustrative purposes and should not be understood as requiring such separation in all embodiments. It should be understood that the described program components, methods, and systems may generally be integrated together in a single computer product or packaged into multiple computer products.

W. Other Considerations

Each of the processes, methods, and algorithms described herein and/or depicted in the attached figures may be embodied in, and fully or partially automated by, code modules executed by one or more physical computing systems, hardware computer processors, application-specific circuitry, and/or electronic hardware configured to execute specific and particular computer instructions. For example, computing systems can include general purpose computers (e.g., servers) programmed with specific computer instructions or special purpose computers, special purpose circuitry, and so forth. A code module may be compiled and linked into an executable program, installed in a dynamic link library, or may be written in an interpreted programming language. In some implementations, particular operations and methods may be performed by circuitry that is specific to a given function.

Further, certain implementations of the functionality of the present disclosure are sufficiently mathematically, computationally, or technically complex that application-specific hardware or one or more physical computing devices (utilizing appropriate specialized executable instructions) may be necessary to perform the functionality, for example, due to the volume or complexity of the calculations involved or to provide results substantially in real-time. For example, animations or video may include many frames, with each frame having millions of pixels, and specifically programmed computer hardware is necessary to process the video data to provide a desired image processing task or application in a commercially reasonable amount of time.

Code modules or any type of data may be stored on any type of non-transitory computer-readable medium, such as physical computer storage including hard drives, solid state memory, random access memory (RAM), read only memory (ROM), optical disc, volatile or non-volatile storage, combinations of the same and/or the like. The methods and modules (or data) may also be transmitted as generated data signals (e.g., as part of a carrier wave or other analog or digital propagated signal) on a variety of computer-readable transmission mediums, including wireless-based and wired/cable-based mediums, and may take a variety of forms (e.g., as part of a single or multiplexed analog signal, or as multiple discrete digital packets or frames). The results of the disclosed processes or process steps may be stored, persistently or otherwise, in any type of non-transitory, tangible computer storage or may be communicated via a computer-readable transmission medium.

Any processes, blocks, states, steps, or functionalities in flow diagrams described herein and/or depicted in the attached figures should be understood as potentially representing code modules, segments, or portions of code which include one or more executable instructions for implementing specific functions (e.g., logical or arithmetical) or steps in the process. The various processes, blocks, states, steps, or functionalities can be combined, rearranged, added to, deleted from, modified, or otherwise changed from the illustrative examples provided herein. In some embodiments, additional or different computing systems or code modules may perform some or all of the functionalities described herein. The methods and processes described herein are also not limited to any particular sequence, and the blocks, steps, or states relating thereto can be performed in other sequences that are appropriate, for example, in serial, in parallel, or in some other manner. Tasks or events may be added to or removed from the disclosed example embodiments. Moreover, the separation of various system components in the implementations described herein is for illustrative purposes and should not be understood as requiring such separation in all implementations. It should be understood that the described program components, methods, and systems can generally be integrated together in a single computer product or packaged into multiple computer products. Many implementation variations are possible.

The processes, methods, and systems may be implemented in a network (or distributed) computing environment. Network environments include enterprise-wide computer networks, intranets, local area networks (LAN), wide area networks (WAN), personal area networks (PAN), cloud computing networks, crowd-sourced computing networks, the Internet, and the World Wide Web. The network may be a wired or a wireless network or any other type of communication network.

The systems and methods of the disclosure each have several innovative aspects, no single one of which is solely responsible or required for the desirable attributes disclosed herein. The various features and processes described above may be used independently of one another, or may be combined in various ways. All possible combinations and subcombinations are intended to fall within the scope of this disclosure. Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. No single feature or group of features is necessary or indispensable to each and every embodiment.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y and at least one of Z to each be present.

Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one more example processes in the form of a flowchart. However, other operations that are not depicted can be incorporated in the example methods and processes that are schematically illustrated. For example, one or more additional operations can be performed before, after, simultaneously, or between any of the illustrated operations. Additionally, the operations may be rearranged or reordered in other implementations. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

X. Examples

Examples of display systems configured for a user to display virtual image content in a vision field of said user are described herein such as the examples enumerated below:

Part-A

Example 1: A display system configured to project light to an eye of a user to display virtual image content in a vision field of said user, said display system comprising: a frame configured to be supported on a head of the user; a head-mounted display disposed on the frame, said display configured to project light into said user's eye to display virtual image content to the user's vision field; first and second eye tracking cameras configured to image the user's eye; a plurality of light emitters; and processing electronics in communication with the display and the first and second eye tracking cameras, the processing electronics configured to: receive images of the user's eye captured by the first and second eye tracking cameras, glint reflections of the different light emitters observable in said images of the eye captured by the first and second eye tracking cameras; and estimate a location of said center of corneal curvature of the user's eye based on the location of the glint reflections in said images produced by both said first and second eye tracking camera and based on the location of both the first and second eye tracking cameras and the locations of the emitters that produced said respective glint reflections.

Example 2: The display system of Example 1, wherein said processing electronics is configured to: based on the location of the glint reflections in one or more images produced by said first eye tracking camera and based on the location of the first eye tracking camera and the location of the emitters that produced said glint reflections, determine a first direction toward the center of corneal curvature of the user's eye; and based on the location of the glint reflections in one or more images produced by said second eye tracking camera and based on the location of the second eye tracking camera and the location of the emitters that produced said glint reflections, determine a second direction toward the center of corneal curvature of the user's eye.

Example 3: The display system of Example 2, wherein said processing electronics is configured to determine the first direction by: defining a first plane that includes the first eye tracking camera, a location of a first glint reflection and a location of the light emitter corresponding to said first glint reflection; defining a second plane that includes the first eye tracking camera, a location of a second glint reflection and a location of the light emitter corresponding to said second glint reflection; and determining a region of convergence of the first plane and the second plane, the region of convergence extending along the first direction.

Example 4: The display system of Example 3, said processing electronics are configured to determine the second direction by: defining a third plane that includes the second eye tracking camera, the location of a third glint reflection, and a location of the light emitter corresponding to said third glint reflection; defining a fourth plane that includes the second eye tracking camera, the location of a fourth glint reflection, and a location of the light emitter corresponding to said fourth glint reflection; and determining a region of convergence of the third plane and the fourth plane, the region of convergence extending along the second direction.

Example 5: The display system of any of the examples above, wherein said processing electronics is configured to estimate a location of said center of corneal curvature of the user's eye based on said first and second directions toward the center of the corneal curvature of the user's eye.

Example 6: The display system of any of the examples above, wherein said processing electronics is configured to: determine said first direction along which the center of corneal curvature of the user's eye is estimated to be located based on at least one first image received from the first eye tracking camera; and determine said second direction along which the center of corneal curvature of the user's eye is estimated to be located based on at least one second image received from the second eye tracking camera, said first and second directions converging toward a region.

Example 7: The display system of any of the examples above, wherein said processing electronics is configured to: obtain an estimate of a center of corneal curvature of the user's eye based on the convergence of the first and second directions.

Example 8: The display system of any of the examples above, wherein said processing electronics is configured to estimate a location of said center of corneal curvature of the user's eye by identifying a region of convergence of said first and second directions toward the center of the corneal curvature of the user's eye.

Example 9: The display system of any of the examples above, wherein said processing electronics is configured to obtain an estimate of a center of rotation of the user's eye based on multiple determinations of the center of corneal curvature of the user's eye for different eye poses.

Example 10: The display system of any of the examples above, wherein said processing electronics is configured to determine a locus of points corresponding to estimates of the center of corneal curvature of the user's eye for different eye poses.

Example 11: The display system of Example 10, wherein said processing electronics is configured to obtain an estimate of a center of rotation of the user's eye based on said locus of points corresponding to estimates of the center of corneal curvature of the user's eye for different eye poses.

Example 12: The display system of Examples 10 or 11, wherein said processing electronics is configured to determine a surface based on said locus of points and to obtain an estimate of a center of rotation of the user's eye.

Example 13: The display system of Examples 10 or 11, wherein said processing electronics is configured to determine a surface based on said locus of points and to obtain an estimate of a center of rotation of the user's eye by estimating a center of curvature of said surface.

Example 14: The display system of Examples 10 or 11, wherein said processing electronics is configured to determine a surface based on said locus of points and to obtain an estimate of a center of rotation of the user's eye by determining a region where a plurality of normals to said surface converge.

Example 15: The display system of any of Examples 12, 13, or 14, wherein said processing electronics is configured to fit said surface to said locus of points to obtain said surface.

Example 16: The display system of any of the examples above, wherein said processing electronics is configured to use a render camera to render virtual images to be presented to the eye of the user, said render camera having a position determined by said center of rotation.

Example 17: The display system of any of the examples above, wherein said display is configured to project light into said user's eye to display virtual image content to the user's vision field at different amounts of at least one of divergence and collimation and thus the displayed virtual image content appears to originate from different depths at different periods of time.

Example 18: A display system configured to project light to an eye of a user to display virtual image content in a vision field of said user, said display system comprising: a frame configured to be supported on a head of the user; a head-mounted display disposed on the frame, said display configured to project light into said user's eye to display virtual image content to the user's vision field; first and second eye tracking cameras configured to image the user's eye; a plurality of light emitters; and processing electronics in communication with the display and the first and second eye tracking cameras, the processing electronics configured to: receive images of the user's eye captured by the first and second eye tracking cameras, glint reflections of the different light emitters observable in said images of the eye captured by the first and second eye tracking cameras; and estimate a location of said center of rotation of the user's eye based on the location of the glint reflections in said images produced by both said first and second eye tracking camera and based on said the location of both the first and second eye tracking cameras and the locations of the emitters that produced said glint reflections for multiple eye poses.

Example 19: The system of example 18, wherein to obtain an estimate of the center of rotation of said eye, the processing electronics are configured to: determine a plurality of estimates of the center of corneal curvature of the user's eye based a plurality of glint reflections for multiple eye poses; and determine the estimate of the center of rotation of the user's eye based on the plurality of estimates of the center of corneal curvature of the user's eye for said multiple eye poses.

Example 20: The system of example 19, wherein to determine said plurality of estimates of the corneal curvature of the user's eye, the processing electronics are configured to: determine a first direction toward the center of corneal curvature based on the respective locations of at least a portion of said plurality of emitters and a first camera of the eye tracking cameras; determine a second direction toward the center of corneal curvature based on the respective locations of at least a portion of said plurality of emitters and a second camera of the eye tracking cameras; and determine an estimate of the center of corneal curvature of the user's eye based on said the first and second directions.

Example 21: The display system of Example 20, wherein said processing electronics is configured to determine the first direction by: defining a first plane that includes the first eye tracking camera, a location of a first glint reflection and a location of the light emitter corresponding to said first glint reflection; defining a second plane that includes the first eye tracking camera, a location of a second glint reflection and a location of the light emitter corresponding to said second glint reflection; and determining a region of convergence of the first plane and the second plane, the region of convergence extending along the first direction.

Example 22: The display system of Example 21, said processing electronics are configured to determine the second direction by: defining a third plane that includes the second eye tracking camera, the location of a third glint reflection, and a location of the light emitter corresponding to said third glint reflection; defining a fourth plane that includes the second eye tracking camera, the location of a fourth glint reflection, and a location of the light emitter corresponding to said fourth glint reflection; and determining a region of convergence of the third plane and the fourth plane, the region of convergence extending along the second direction.

Example 23: The system of any of Examples 20-22, wherein to determine said plurality of estimates of the corneal curvature of the user's eye, the processing electronics are configured to: determine a region of convergence between the first direction and second direction to determine an estimate of the center of corneal curvature of the user's eye.

Example 24: The system of any of Examples 19-23, wherein to obtain an estimate of the center of rotation of said eye, the processing electronics are configured to: generate a three-dimensional surface associated with the plurality of estimates of the center of the corneal curvature; and determine the estimate of the center of rotation of the user's eye based on the three-dimensional surface.

Example 25: The system of example 24, wherein to generate a three-dimensional surface associated with the plurality of estimates of the center of the corneal curvature, the processing electronics are configured to fit a surface to the plurality of estimates of the center of the corneal curvature.

Example 26: The system of example 24, wherein to generate a three-dimensional surface associated with the plurality of estimates of the center of the corneal curvature, the processing electronics are configured to fit a sphere to the plurality of estimates of the center of the corneal curvature.

Example 27: The system of any of Example 24-26, wherein to determine the estimate of the center of rotation of the user's eye, the processing electronics are configured to: determine two or more normals to the three-dimensional surface; and determine a region of convergence of the two or more normals, wherein the region of convergence comprises the estimate of the center of rotation of the user's eye.

Example 28: The system of any of Examples 21-27, wherein the one or more images of the user's eye comprise one or more images associated with different gaze vectors of the user's eye.

Example 29: The system of any of Examples 21-28, wherein the processing electronics are configured to map the cornea of the user's eye using a gaze target.

Example 30: The display system of any of Examples 18-29, wherein said processing electronics is configured to use a render camera to render virtual images to be presented to the eye of the user, said render camera having a position determined by said center of rotation.

Example 31: The display system of any of Examples 18-30, wherein said display is configured to project light into said user's eye to display virtual image content to the user's vision field at different amounts of at least one of divergence and collimation and thus the displayed virtual image content appears to originate from different depths at different periods of time.

Example 32: A method of determining one or more parameters associated with an eye for rendering virtual image content in a display system configured to project light to an eye of a user to display the virtual image content in a vision field of said user, said eye having a cornea, said method comprising: with a plurality of eye tracking cameras configured to image the eye of the user and a plurality of light emitters disposed with respect to said eye to form glints thereon, capturing a plurality of images of the eye of the user, said images comprising a plurality of glints; and obtaining an estimate of a center of rotation of said eye based on the plurality of glints, wherein obtaining an estimate of the center of rotation of said eye comprises: determining a plurality of estimates of the center of corneal curvature of the user's eye based on the plurality of glints; generating a three-dimensional surface from the plurality of estimates of the center of the corneal curvature; and determining the estimate of the center of rotation of the user's eye using the three-dimensional surface.

Example 33: The method of Example 32, wherein determining the plurality of estimates of the corneal curvature of the user's eye comprises: determining a first vector directed toward the center of corneal curvature based on the locations of at least a portion of the plurality of light emitters and the location of a first camera of the plurality of eye tracking cameras; determining a second vector directed toward the center of corneal curvature based on locations of at least a portion of the plurality of light emitters and the location of a second camera of the plurality of eye tracking cameras; and determining a region of convergence between the first vector and second vector to determine an estimate of the center of corneal curvature of the user's eye.

Example 34: The method of Example 33, wherein the first direction is determined by: defining a first plane that includes the first eye tracking camera, a location of a first glint reflection and a location of the light emitter corresponding to said first glint reflection, defining a second plane that includes the first eye tracking camera, a location of a second glint reflection and a location of the light emitter corresponding to said second glint reflection; and determining a region of convergence of the first plane and the second plane, the region of convergence extending along the first direction.

Example 35: The method of Example 33, wherein the second direction is determined by: defining a third plane that includes the second eye tracking camera, the location of a third glint reflection, and a location of the light emitter corresponding to said third glint reflection; defining a fourth plane that includes the second eye tracking camera, the location of a fourth glint reflection, and a location of the light emitter corresponding to said fourth glint reflection; and determining a region of convergence of the third plane and the fourth plane, the region of convergence extending along the second direction.

Example 36: The method of any of Examples 32-35, wherein generating a three-dimensional surface from the plurality of estimates of the center of the corneal curvature comprises fitting a surface to the plurality of estimates of the center of the corneal curvature.

Example 37: The method of any of Examples 32-35, wherein generating a three-dimensional surface from the plurality of estimates of the center of the corneal curvature comprises fitting a sphere to the plurality of estimates of the center of the corneal curvature.

Example 38: The method of any of Examples 32-37, wherein determining the estimate of the center of rotation of the user's eye comprises: determining two or more vectors normal to the three-dimensional surface; and determining a region of convergence of the two or more vectors normal to the three-dimensional surface, wherein the region of convergence comprises the estimate of the center of rotation of the user's eye.

Example 39: The method of any of Examples 32-38, wherein the plurality of images of the user's eye comprise images associated with different gaze directions of the user's eye.

Example 40: The method of any of Examples 32-39, further comprising mapping the cornea of the user's eye using a gaze target.

Example 41: A display system configured to project light to an eye of a user to display virtual image content in a vision field of said user, said display system comprising: a frame configured to be supported on a head of the user; a head-mounted display disposed on the first and second eye tracking cameras configured to image the user's eye; and processing electronics in communication with the display and the first and second eye tracking cameras, the processing electronics configured to: receive multiple pairs of captured images of the user's eye from the first and second eye tracking cameras; for pairs of images received from the first and second eye tracking cameras, respectively, obtain an estimate of a center of corneal curvature of the user's eye based at least in part on the respective pair of captured images; determine a three-dimensional surface based on the estimated centers of corneal curvature of the user's eye obtained based on the multiple pairs of captured images of the user's eye received from the respective first and second eye tracking cameras; and identify a center of curvature of the 3D surface to obtain an estimate of a center of rotation of the user's eye.

Example 42: The display system of Example 41, wherein said processing electronics is configured to fit a three-dimensional surface to the estimated centers of corneal curvature of the user's eye obtained based on the multiple pairs of captured images of the user's eye received from the respective first and second eye tracking cameras.

Example 43: The display system of Examples 41 or 42, wherein to obtain the estimate of the center of corneal curvature of the user's eye based at least in part on the respective pair of captured images, the processing electronics are configured to: determine a first vector along which the center of corneal curvature of the user's eye is estimated to be located based on a first image received from the first eye tracking camera; determine a second vector along which the center of corneal curvature of the user's eye is estimated to be located based on a second image received from the second eye tracking camera, the first and second images corresponding to one of said pairs of images; and identify a region of convergence between paths extending in the direction of the first vector and the second vector to obtain an estimate of a center of corneal curvature of the user's eye.

Example 44: The display system of Example 43, further comprising: a plurality of light emitters configured to illuminate the user's eye to form glint reflections thereon, wherein to determine the first vector based on the first image of the pair of captured images, the processing electronics are configured to: define a first plane that includes the first eye tracking camera, a location of a first glint reflection and a location of the light emitter corresponding to said first glint reflection; define a second plane that includes the first eye tracking camera, a location of a second glint reflection and a location of the light emitter corresponding to said second glint reflection; and identify a region of convergence of the first plane and the second plane, the region of convergence extending along the direction of the first vector.

Example 45: The display system of Example 44, wherein to determine the second vector based on the second image in each pair of captured images, the processing electronics are configured to: define a third plane that includes the second eye tracking camera, the location of a third glint reflection, and a location of the light emitter corresponding to said third glint reflection; define a fourth plane that includes the second eye tracking camera, the location of a fourth glint reflection, and a location of the light emitter corresponding to said fourth glint reflection; and determine a region of convergence of the third plane and the fourth plane, the region of convergence extending along the direction of the second vector.

Example 46: The display system of any of Examples 41-45, wherein said processing electronics is configured to use a render camera to render virtual images to be presented to the eye of the user, said render camera having a position determined by said center of rotation.

Example 47: The display system of any of Examples 41-46, wherein said display is configured to project light into said user's eye to display virtual image content to the user's vision field at different amounts of at least one of divergence and collimation and thus the displayed virtual image content appears to originate from different depths at different periods of time.

Example 48: The display system of any of the examples above, wherein at least a portion of said display is transparent and disposed at a location in front of the user's eye when the user wears said head-mounted display such that said transparent portion transmits light from a portion of the environment in front of the user and said head-mounted display to the user's eye to provide a view of said portion of the environment in front of the user and said head-mounted display.

Example 49: A display system configured to project light to an eye of a user to display virtual image content in a vision field of said user, said display system comprising: a frame configured to be supported on a head of the user; a head-mounted display disposed on the frame, said display configured to project light into said user's eye to display virtual image content to the user's vision field; an eye tracking camera configured to image the user's eye; a plurality of light emitters; and processing electronics in communication with the display and the eye tracking camera, the processing electronics configured to: receive images of the user's eye captured by the eye tracking camera at a first and second location, glint reflections of the different light emitters observable in said images of the eye captured by the eye tracking camera; and estimate a location of said center of corneal curvature of the user's eye based on the location of the glint reflections in said images produced by said eye tracking camera and based on the location of the eye tracking camera and the locations of the emitters that produced said respective glint reflections.

Example 50: The display system of Example 49, wherein said processing electronics is configured to: based on the location of the glint reflections in one or more images produced by said eye tracking camera and based on the first location of the eye tracking camera and the location of the emitters that produced said glint reflections, determine a first direction toward the center of corneal curvature of the user's eye; and based on the location of the glint reflections in one or more images produced by said eye tracking camera and based on the second location of the eye tracking camera and the location of the emitters that produced said glint reflections, determine a second direction toward the center of corneal curvature of the user's eye.

Example 51: The display system of Example 50, wherein said processing electronics is configured to determine the first direction by: defining a first plane that includes the first location of the eye tracking camera, a location of a first glint reflection and a location of the light emitter corresponding to said first glint reflection; defining a second plane that includes the first location of the eye tracking camera, a location of a second glint reflection and a location of the light emitter corresponding to said second glint reflection; and determining a region of convergence of the first plane and the second plane, the region of convergence extending along the first direction.

Example 52: The display system of Example 51, said processing electronics are configured to determine the second direction by: defining a third plane that includes the second location of the eye tracking camera, the location of a third glint reflection, and a location of the light emitter corresponding to said third glint reflection; defining a fourth plane that includes the second location of the eye tracking camera, the location of a fourth glint reflection, and a location of the light emitter corresponding to said fourth glint reflection; and determining a region of convergence of the third plane and the fourth plane, the region of convergence extending along the second direction.

Example 53: The display system of any of the examples above, wherein said processing electronics is configured to estimate a location of said center of corneal curvature of the user's eye based on said first and second directions toward the center of the corneal curvature of the user's eye.

Example 54: The display system of any of the examples above, wherein said processing electronics is configured to: determine said first direction along which the center of corneal curvature of the user's eye is estimated to be located based on at least one first image received from the first location of the eye tracking camera; and determine said second direction along which the center of corneal curvature of the user's eye is estimated to be located based on at least one second image received from the second location of the eye tracking camera, said first and second directions converging toward a region.

Example 55: The display system of any of the examples above, wherein said processing electronics is configured to: obtain an estimate of a center of corneal curvature of the user's eye based on the convergence of the first and second directions.

Example 56: The display system of any of the examples above, wherein said processing electronics is configured to estimate a location of said center of corneal curvature of the user's eye by identifying a region of convergence of said first and second directions toward the center of the corneal curvature of the user's eye.

Example 57: The display system of any of the examples above, wherein said processing electronics is configured to obtain an estimate of a center of rotation of the user's eye based on multiple determinations of the center of corneal curvature of the user's eye for different eye poses.

Example 58: The display system of any of the examples above, wherein said processing electronics is configured to determine a locus of points corresponding to estimates of the center of corneal curvature of the user's eye for different eye poses.

Example 59: The display system of Example 58, wherein said processing electronics is configured to obtain an estimate of a center of rotation of the user's eye based on said locus of points corresponding to estimates of the center of corneal curvature of the user's eye for different eye poses.

Example 60: The display system of Examples 58 or 59, wherein said processing electronics is configured to determine a surface based on said locus of points and to obtain an estimate of a center of rotation of the user's eye.

Example 61: The display system of Examples 58 or 59, wherein said processing electronics is configured to determine a surface based on said locus of points and to obtain an estimate of a center of rotation of the user's eye by estimating a center of curvature of said surface.

Example 62: The display system of Examples 58 or 59, wherein said processing electronics is configured to determine a surface based on said locus of points and to obtain an estimate of a center of rotation of the user's eye by determining a region where a plurality of normals to said surface converge.

Example 63: The display system of any of Examples 60, 61, or 62, wherein said processing electronics is configured to fit said surface to said locus of points to obtain said surface.

Example 64: The display system of any of the examples above, wherein said processing electronics is configured to use a render camera to render virtual images to be presented to the eye of the user, said render camera having a position determined by said center of rotation.

Example 65: The display system of any of the examples above, wherein said display is configured to project light into said user's eye to display virtual image content to the user's vision field at different amounts of at least one of divergence and collimation and thus the displayed virtual image content appears to originate from different depths at different periods of time.

Example 66: A display system configured to project light to an eye of a user to display virtual image content in a vision field of said user, said display system comprising: a frame configured to be supported on a head of the user; a head-mounted display disposed on the frame, said display configured to project light into said user's eye to display virtual image content to the user's vision field; an eye tracking camera configured to image the user's eye; a plurality of light emitters; and processing electronics in communication with the display and the eye tracking camera, the processing electronics configured to: receive images of the user's eye captured by the eye tracking camera at a first camera and second location, glint reflections of the different light emitters observable in said images of the eye captured by the eye tracking camera; and estimate a location of said center of rotation of the user's eye based on the location of the glint reflections in said images produced by said eye tracking camera and based on said first and second location of the eye tracking camera and the locations of the emitters that produced said glint reflections for multiple eye poses.

Example 67: The system of example 66, wherein to obtain an estimate of the center of rotation of said eye, the processing electronics are configured to: determine a plurality of estimates of the center of corneal curvature of the user's eye based a plurality of glint reflections for multiple eye poses; and determine the estimate of the center of rotation of the user's eye based on the plurality of estimates of the center of corneal curvature of the user's eye for said multiple eye poses.

Example 68: The system of example 67, wherein to determine said plurality of estimates of the corneal curvature of the user's eye, the processing electronics are configured to: determine a first direction toward the center of corneal curvature based on at least a respective location of a portion of said plurality of emitters and a first location of the eye tracking camera; determine a second direction toward the center of corneal curvature based on at least a respective location of at least a portion of said plurality of emitters and a second location of the eye tracking camera; and determine an estimate of the center of corneal curvature of the user's eye based on said the first and second directions.

Example 69: The display system of Example 68, wherein said processing electronics is configured to determine the first direction by: defining a first plane that includes the first location of the eye tracking camera, a location of a first glint reflection and a location of the light emitter corresponding to said first glint reflection; defining a second plane that includes the first location of the eye tracking camera, a location of a second glint reflection and a location of the light emitter corresponding to said second glint reflection; and determining a region of convergence of the first plane and the second plane, the region of convergence extending along the first direction.

Example 70: The display system of Example 69, said processing electronics are configured to determine the second direction by: defining a third plane that includes the second location of the eye tracking camera, the location of a third glint reflection, and a location of the light emitter corresponding to said third glint reflection; defining a fourth plane that includes the second location of the eye tracking camera, the location of a fourth glint reflection, and a location of the light emitter corresponding to said fourth glint reflection; and determining a region of convergence of the third plane and the fourth plane, the region of convergence extending along the second direction.

Example 71: The system of any of Examples 68-70, wherein to determine said plurality of estimates of the corneal curvature of the user's eye, the processing electronics are configured to: determine a region of convergence between the first direction and second direction to determine an estimate of the center of corneal curvature of the user's eye.

Example 72: The system of any of Examples 19-71, wherein to obtain an estimate of the center of rotation of said eye, the processing electronics are configured to: generate a three-dimensional surface associated with the plurality of estimates of the center of the corneal curvature; and determine the estimate of the center of rotation of the user's eye based on the three-dimensional surface.

Example 73: The system of example 72, wherein to generate a three-dimensional surface associated with the plurality of estimates of the center of the corneal curvature, the processing electronics are configured to fit a surface to the plurality of estimates of the center of the corneal curvature.

Example 74: The system of example 73, wherein to generate a three-dimensional surface associated with the plurality of estimates of the center of the corneal curvature, the processing electronics are configured to fit a sphere to the plurality of estimates of the center of the corneal curvature.

Example 75: The system of any of Examples 72-74, wherein to determine the estimate of the center of rotation of the user's eye, the processing electronics are configured to: determine two or more normals to the three-dimensional surface; and determine a region of convergence of the two or more normals, wherein the region of convergence comprises the estimate of the center of rotation of the user's eye.

Example 76: The system of any of Examples 69-75, wherein the one or more images of the user's eye comprise one or more images associated with different gaze vectors of the user's eye.

Example 77: The system of any of Examples 69-76, wherein the processing electronics are configured to map the cornea of the user's eye using a gaze target.

Example 78: The display system of any of Examples 66-77, wherein said processing electronics is configured to use a render camera to render virtual images to be presented to the eye of the user, said render camera having a position determined by said center of rotation.

Example 79: The display system of any of Examples 66-78, wherein said display is configured to project light into said user's eye to display virtual image content to the user's vision field at different amounts of at least one of divergence and collimation and thus the displayed virtual image content appears to originate from different depths at different periods of time.

Example 80: A method of determining one or more parameters associated with an eye for rendering virtual image content in a display system configured to project light to an eye of a user to display the virtual image content in a vision field of said user, said eye having a cornea, said method comprising: with an eye tracking camera configured to image the eye of the user and a plurality of light emitters disposed with respect to said eye to form glints thereon, capturing a plurality of images of the eye of the user, said images comprising a plurality of glints; and obtaining an estimate of a center of rotation of said eye based on the plurality of glints, wherein obtaining an estimate of the center of rotation of said eye comprises: determining a plurality of estimates of the center of corneal curvature of the user's eye based on the plurality of glints; generating a three-dimensional surface from the plurality of estimates of the center of the corneal curvature; and determining the estimate of the center of rotation of the user's eye using the three-dimensional surface.

Example 81: The method of Example 80, wherein determining the plurality of estimates of the corneal curvature of the user's eye comprises: determining a first vector directed toward the center of corneal curvature based on the locations of at least a portion of the plurality of light emitters and a first location of the eye tracking camera; determining a second vector directed toward the center of corneal curvature based on locations of at least a portion of the plurality of light emitters and a second location of the eye tracking camera; and determining a region of convergence between the first vector and second vector to determine an estimate of the center of corneal curvature of the user's eye.

Example 82: The method of Example 81, wherein the first direction is determined by: defining a first plane that includes the first location of the eye tracking camera, a location of a first glint reflection and a location of the light emitter corresponding to said first glint reflection, defining a second plane that includes the first location of the eye tracking camera, a location of a second glint reflection and a location of the light emitter corresponding to said second glint reflection; and determining a region of convergence of the first plane and the second plane, the region of convergence extending along the first direction.

Example 83: The method of Example 82, wherein the second direction is determined by: defining a third plane that includes the second location of the eye tracking camera, the location of a third glint reflection, and a location of the light emitter corresponding to said third glint reflection; defining a fourth plane that includes the second location of the eye tracking camera, the location of a fourth glint reflection, and a location of the light emitter corresponding to said fourth glint reflection; and determining a region of convergence of the third plane and the fourth plane, the region of convergence extending along the second direction.

Example 84: The method of any of Examples 81-83, wherein generating a three-dimensional surface from the plurality of estimates of the center of the corneal curvature comprises fitting a surface to the plurality of estimates of the center of the corneal curvature.

Example 85: The method of any of Examples 81-83, wherein generating a three-dimensional surface from the plurality of estimates of the center of the corneal curvature comprises fitting a sphere to the plurality of estimates of the center of the corneal curvature.

Example 86: The method of any of Examples 81-85, wherein determining the estimate of the center of rotation of the user's eye comprises: determining two or more vectors normal to the three-dimensional surface; and determining a region of convergence of the two or more vectors normal to the three-dimensional surface, wherein the region of convergence comprises the estimate of the center of rotation of the user's eye.

Example 87: The method of any of Examples 81-86, wherein the plurality of images of the user's eye comprise images associated with different gaze directions of the user's eye.

Example 88: The method of any of Examples 81-87, further comprising mapping the cornea of the user's eye using a gaze target.

Example 89: A display system configured to project light to an eye of a user to display virtual image content in a vision field of said user, said display system comprising: a frame configured to be supported on a head of the user; a head-mounted display disposed on the an eye tracking camera configured to image the user's eye; and processing electronics in communication with the display and the eye tracking camera, the processing electronics configured to: receive multiple pairs of captured images of the user's eye from the eye tracking camera; for pairs of images received from the eye tracking camera, respectively, obtain an estimate of a center of corneal curvature of the user's eye based at least in part on the respective pair of captured images; determine a three-dimensional surface based on the estimated centers of corneal curvature of the user's eye obtained based on the multiple pairs of captured images of the user's eye received from the eye tracking camera; and identify a center of curvature of the 3D surface to obtain an estimate of a center of rotation of the user's eye.

Example 90: The display system of Example 89, wherein said processing electronics is configured to fit a three-dimensional surface to the estimated centers of corneal curvature of the user's eye obtained based on the multiple pairs of captured images of the user's eye received from the eye tracking camera.

Example 91: The display system of Examples 89 or 90, wherein to obtain the estimate of the center of corneal curvature of the user's eye based at least in part on the respective pair of captured images, the processing electronics are configured to: determine a first vector along which the center of corneal curvature of the user's eye is estimated to be located based on a first image received from a first location of the eye tracking camera; determine a second vector along which the center of corneal curvature of the user's eye is estimated to be located based on a second image received from a second location of the eye tracking camera, the first and second images corresponding to one of said pairs of images; and identify a region of convergence between paths extending in the direction of the first vector and the second vector to obtain an estimate of a center of corneal curvature of the user's eye.

Example 92: The display system of Example 91, further comprising: a plurality of light emitters configured to illuminate the user's eye to form glint reflections thereon, wherein to determine the first vector based on the first image of the pair of captured images, the processing electronics are configured to: define a first plane that includes the first location of the eye tracking camera, a location of a first glint reflection and a location of the light emitter corresponding to said first glint reflection; define a second plane that includes the first location of the eye tracking camera, a location of a second glint reflection and a location of the light emitter corresponding to said second glint reflection; and identify a region of convergence of the first plane and the second plane, the region of convergence extending along the direction of the first vector.

Example 93: The display system of Example 92, wherein to determine the second vector based on the second image in each pair of captured images, the processing electronics are configured to: define a third plane that includes the second location of the eye tracking camera, the location of a third glint reflection, and a location of the light emitter corresponding to said third glint reflection; define a fourth plane that includes the second location of the eye tracking camera, the location of a fourth glint reflection, and a location of the light emitter corresponding to said fourth glint reflection; and determine a region of convergence of the third plane and the fourth plane, the region of convergence extending along the direction of the second vector.

Example 94: The display system of any of Examples 89-93, wherein said processing electronics is configured to use a render camera to render virtual images to be presented to the eye of the user, said render camera having a position determined by said center of rotation.

Example 95: The display system of any of Examples 89-94, wherein said display is configured to project light into said user's eye to display virtual image content to the user's vision field at different amounts of at least one of divergence and collimation and thus the displayed virtual image content appears to originate from different depths at different periods of time.

Example 96: The display system of any of the examples above, wherein at least a portion of said display is transparent and disposed at a location in front of the user's eye when the user wears said head-mounted display such that said transparent portion transmits light from a portion of the environment in front of the user and said head-mounted display to the user's eye to provide a view of said portion of the environment in front of the user and said head-mounted display.

Example 97: A display system configured to project light to an eye of a user to display virtual image content in a vision field of said user, said display system comprising: a frame configured to be supported on a head of the user; a head-mounted display disposed on the frame, said display configured to project light into said user's eye to display virtual image content to the user's vision field; at least one eye tracking camera configured to image the user's eye; a plurality of light emitters; and processing electronics in communication with the display and the eye tracking camera, the processing electronics configured to: receive images of the user's eye captured by the at least one eye tracking camera at a first and second location, glint reflections of the different light emitters observable in said images of the eye captured by the eye tracking camera; and estimate a location of said center of corneal curvature of the user's eye based on the location of the glint reflections in said images produced by said at least one eye tracking camera and based on the location of the at least one eye tracking camera and the locations of the emitters that produced said respective glint reflections.

Example 98: The display system of Example 97, wherein said processing electronics is configured to: based on the location of the glint reflections in one or more images produced by said at least one eye tracking camera and based on the first location of the at least one eye tracking camera and the location of the emitters that produced said glint reflections, determine a first direction toward the center of corneal curvature of the user's eye; and based on the location of the glint reflections in one or more images produced by said at least one eye tracking camera and based on the second location of the at least one eye tracking camera and the location of the emitters that produced said glint reflections, determine a second direction toward the center of corneal curvature of the user's eye.

Example 99: The display system of Example 98, wherein said processing electronics is configured to determine the first direction by: defining a first plane that includes the first location of the at least one eye tracking camera, a location of a first glint reflection and a location of the light emitter corresponding to said first glint reflection; defining a second plane that includes the first location of the at least one eye tracking camera, a location of a second glint reflection and a location of the light emitter corresponding to said second glint reflection; and determining a region of convergence of the first plane and the second plane, the region of convergence extending along the first direction.

Example 100: The display system of Example 99, said processing electronics are configured to determine the second direction by: defining a third plane that includes the second location of the at least one eye tracking camera, the location of a third glint reflection, and a location of the light emitter corresponding to said third glint reflection; defining a fourth plane that includes the second location of the at least one eye tracking camera, the location of a fourth glint reflection, and a location of the light emitter corresponding to said fourth glint reflection; and determining a region of convergence of the third plane and the fourth plane, the region of convergence extending along the second direction.

Example 101: The display system of any of the examples above, wherein said processing electronics is configured to estimate a location of said center of corneal curvature of the user's eye based on said first and second directions toward the center of the corneal curvature of the user's eye.

Example 102: The display system of any of the examples above, wherein said processing electronics is configured to: determine said first direction along which the center of corneal curvature of the user's eye is estimated to be located based on at least one first image received from the first location of the at least one eye tracking camera; and determine said second direction along which the center of corneal curvature of the user's eye is estimated to be located based on at least one second image received from the second location of the at least one eye tracking camera, said first and second directions converging toward a region.

Example 103: The display system of any of the examples above, wherein said processing electronics is configured to:
obtain an estimate of a center of corneal curvature of the user's eye based on the convergence of the first and second directions.

Example 104: The display system of any of the examples above, wherein said processing electronics is configured to estimate a location of said center of corneal curvature of the user's eye by identifying a region of convergence of said first and second directions toward the center of the corneal curvature of the user's eye.

Example 105: The display system of any of the examples above, wherein said processing electronics is configured to obtain an estimate of a center of rotation of the user's eye based on multiple determinations of the center of corneal curvature of the user's eye for different eye poses.

Example 106: The display system of any of the examples above, wherein said processing electronics is configured to determine a locus of points corresponding to estimates of the center of corneal curvature of the user's eye for different eye poses.

Example 107: The display system of Example 106, wherein said processing electronics is configured to obtain an estimate of a center of rotation of the user's eye based on said locus of points corresponding to estimates of the center of corneal curvature of the user's eye for different eye poses.

Example 108: The display system of Examples 106 or 107, wherein said processing electronics is configured to determine a surface based on said locus of points and to obtain an estimate of a center of rotation of the user's eye.

Example 109: The display system of Examples 106 or 107, wherein said processing electronics is configured to determine a surface based on said locus of points and to obtain an estimate of a center of rotation of the user's eye by estimating a center of curvature of said surface.

Example 110: The display system of Examples 106 or 107, wherein said processing electronics is configured to determine a surface based on said locus of points and to obtain an estimate of a center of rotation of the user's eye by determining a region where a plurality of normals to said surface converge.

Example 111: The display system of any of Examples 108, 109, or 110, wherein said processing electronics is configured to fit said surface to said locus of points to obtain said surface.

Example 112: The display system of any of the examples above, wherein said processing electronics is configured to use a render camera to render virtual images to be presented to the eye of the user, said render camera having a position determined by said center of rotation.

Example 113: The display system of any of the examples above, wherein said display is configured to project light into said user's eye to display virtual image content to the user's vision field at different amounts of at least one of divergence and collimation and thus the displayed virtual image content appears to originate from different depths at different periods of time.

Example 114: The display system of any of the examples above, further comprising a third camera configured to image the user's eye, said processing electronics in communication with said third eye tracking camera, glint reflections of light emitters observable in the images of the eye captured by the third eye tracking camera.

Example 115: The display system of any of the examples above, wherein said processing electronics is configured to estimate a location of a corneal center of the user's eye based on the location of the glint reflections in said images produced by said first, second and third eye tracking cameras.

Example 116: The display system of any of the examples above, wherein said processing electronics is configured to estimate a location of a corneal center of the user's eye based on the location of the glint reflections in said images produced by both said first and third eye tracking camera and based on the location of both the first and third eye tracking cameras and the locations of the emitters that produced said respective glint reflections.

Example 117: The display system of any of the examples above, wherein said processing electronics is configured to estimate a location of a corneal center of the user's eye based on the location of the glint reflections in said images produced by both said second and third eye tracking camera and based on the location of both the second and third eye tracking cameras and the locations of the emitters that produced said respective glint reflections.

Example 118: The display system of any of the examples above, wherein said processing electronics is configured to estimate a location of a corneal center of the user's eye based on a location of a corneal center of the user's eye determined by said first and third eye tracking camera and a location of a corneal center of the user's eye determined by said first and second eye tracking camera.

Example 119: The display system of any of the examples above, wherein said processing electronics is configured to estimate a location of a corneal center of the user's eye based on a location of a corneal center of the user's eye determined by said second and third eye tracking camera and a location of a corneal center of the user's eye determined by said first and second eye tracking camera.

Example 118: The display system of any of the examples above, wherein said processing electronics is configured to estimate a location of a corneal center of the user's eye based on an average of a location of a corneal center of the user's eye determined by said first and third eye tracking camera and a location of a corneal center of the user's eye determined by said first and second eye tracking camera.

Example 119: The display system of any of the examples above, wherein said processing electronics is configured to estimate a location of a corneal center of the user's eye based on an average of a location of a corneal center of the user's eye determined by said second and third eye tracking camera and a location of a corneal center of the user's eye by determined said first and second eye tracking camera.

Example 120: The display system of any of the examples above, wherein said corneal center of the user's eye comprises a center of curvature of the cornea of the user's eye.

Example 121: The display system of any of the examples above, wherein said corneal center of the user's eye comprises a center of curvature of the corneal apex of the cornea of the user's eye.

Example 122: A display system configured to project light to an eye of a user to display virtual image content in a vision field of said user, said display system comprising: a frame configured to be supported on a head of the user; a head-mounted display disposed on the frame, said display configured to project light into said user's eye to display virtual image content to the user's vision field; first and second eye tracking cameras configured to image the user's eye; a plurality of light emitters; and processing electronics in communication with the display and the first and second eye tracking cameras, the processing electronics configured to: receive images of the user's eye captured by the first and second eye tracking cameras, glint reflections of the different light emitters observable in said images of the eye captured by the first and second eye tracking cameras; and estimate a parameter of the user's eye based on the location of the glint reflections in said images produced by both said first and second eye tracking camera Example 123: The display system of Example 122, wherein said processing electronics is configured to estimate said parameter of the user's eye based on the location of the glint reflections in said images produced by both said first and second eye tracking camera and based on the location of both the first and second eye tracking cameras and the locations of the emitters that produced said respective glint reflections.

Example 124: The display system of Example 122 or 123, wherein said processing electronics is configured to: based on the location of the glint reflections in one or more images produced by said first eye tracking camera and based on the location of the first eye tracking camera and the location of the emitters that produced said glint reflections, determine a first direction toward a corneal center of the user's eye; and based on the location of the glint reflections in one or more images produced by said second eye tracking camera and based on the location of the second eye tracking camera and the location of the emitters that produced said glint reflections, determine a second direction toward the corneal center of the user's eye.

Example 125: The display system of Example 124, wherein said processing electronics is configured to determine the first direction by: defining a first plane that includes the first eye tracking camera, a location of a first glint reflection and a location of the light emitter corresponding to said first glint reflection; defining a second plane that includes the first eye tracking camera, a location of a second glint reflection and a location of the light emitter corresponding to said second glint reflection; and determining a region of convergence of the first plane and the second plane, the region of convergence extending along the first direction.

Example 126: The display system of Example 125, said processing electronics are configured to determine the second direction by: defining a third plane that includes the second eye tracking camera, the location of a third glint reflection, and a location of the light emitter corresponding to said third glint reflection; defining a fourth plane that includes the second eye tracking camera, the location of a fourth glint reflection, and a location of the light emitter corresponding to said fourth glint reflection; and determining a region of convergence of the third plane and the fourth plane, the region of convergence extending along the second direction.

Example 127: The display system of any of Examples 122-126, wherein said processing electronics is configured to estimate a location of said corneal center the user's eye based on said first and second directions toward the corneal center of the user's eye.

Example 128: The display system of any of the Examples 122-127, wherein said processing electronics is configured to: determine said first direction along which the corneal center of the user's eye is estimated to be located based on at least one first image received from the first eye tracking camera; and determine said second direction along which the corneal center of the user's eye is estimated to be located based on at least one second image received from the second eye tracking camera, said first and second directions converging toward a region.

Example 129: The display system of any of the Examples 122-128, wherein said processing electronics is configured to: obtain an estimate of a corneal center of the user's eye based on the convergence of the first and second directions.

Example 130: The display system of any of the Examples 122-129, wherein said processing electronics is configured to estimate a location of said corneal center of the user's eye by identifying a region of convergence of said first and second directions toward the corneal center of the user's eye.

Example 131: The display system of any of the Examples 122-130, wherein said processing electronics is configured to obtain an estimate of a center of rotation of the user's eye based on multiple determinations of the corneal center of the user's eye for different eye poses.

Example 132: The display system of any of the Examples 122-131, wherein said processing electronics is configured to determine a locus of points corresponding to estimates of the corneal center of the user's eye for different eye poses.

Example 133: The display system of Example 132, wherein said processing electronics is configured to obtain an estimate of a center of rotation of the user's eye based on said locus of points corresponding to estimates of the corneal center of the user's eye for different eye poses.

Example 134: The display system of Examples 132 or 133, wherein said processing electronics is configured to determine a surface based on said locus of points and to obtain an estimate of a center of rotation of the user's eye.

Example 135: The display system of Examples 132 or 133, wherein said processing electronics is configured to determine a surface based on said locus of points and to obtain an estimate of a center of rotation of the user's eye by estimating a center of curvature of said surface.

Example 136: The display system of Examples 132 or 133, wherein said processing electronics is configured to determine a surface based on said locus of points and to obtain an estimate of a center of rotation of the user's eye by determining a region where a plurality of normals to said surface converge.

Example 137: The display system of any of Examples 134, 135, or 136, wherein said processing electronics is configured to fit said surface to said locus of points to obtain said surface.

Example 138: The display system of any of Examples 122 to 137, wherein said parameter comprises the center of rotation of the eye.

Example 139: The display system of any of Examples 131 to 138, wherein said processing electronics is configured to use a render camera to render virtual images to be presented to the eye of the user, said render camera having a position determined by the center of rotation.

Example 140: The display system of any of the Examples 122 to 139, wherein said display is configured to project light into said user's eye to display virtual image content to the user's vision field at different amounts of at least one of divergence and collimation and thus the displayed virtual image content appears to originate from different depths at different periods of time.

Example 141: The display system of any of the examples above, further comprising a third camera configured to image the user's eye, said processing electronics in communication with said third eye tracking camera, glint reflections of light emitters observable in the images of the eye captured by the third eye tracking camera.

Example 142: The display system of any of the examples above, wherein said processing electronics is configured to estimate said parameter of the user's eye based on the location of the glint reflections in said images produced by said first, second and third eye tracking cameras.

Example 143: The display system of any of the examples above, wherein said processing electronics is configured to estimate said parameter of the user's eye based on the location of the glint reflections in said images produced by both said first and third eye tracking camera and based on the location of both the first and third eye tracking cameras and the locations of the emitters that produced said respective glint reflections.

Example 144: The display system of any of the examples above, wherein said processing electronics is configured to estimate said parameter of the user's eye based on the location of the glint reflections in said images produced by both said second and third eye tracking camera and based on the location of both the second and third eye tracking cameras and the locations of the emitters that produced said respective glint reflections.

Example 145: The display system of any of the examples above, wherein said processing electronics is configured to estimate said parameter based on a parameter of the user's eye determined by said first and third eye tracking camera and a parameter of the user's eye determined said first and second eye tracking camera.

Example 146: The display system of any of the examples above, wherein said processing electronics is configured to estimate said parameter of the user's eye based on a parameter of the user's eye determined by said second and third eye tracking camera and a parameter of the user's eye determined said first and second eye tracking camera.

Example 147: The display system of any of the examples above, wherein said processing electronics is configured to estimate said parameter of the user's eye based on an average of a parameter of the user's eye determined by said first and third eye tracking camera and a parameter of the user's eye determined said first and second eye tracking camera.

Example 148: The display system of any of the examples above, wherein said processing electronics is configured to estimate said parameter of the user's eye based on an average of a parameter of the user's eye determined by said second and third eye tracking camera and a parameter of a corneal center of the user's eye determined said first and second eye tracking camera.

Example 149: The display system of any of the examples above, wherein said parameter said processing electronics is configured to estimate comprise a corneal center.

Example 150: The display system of any of the examples above, wherein said corneal center of the user's eye comprises a center of curvature of the cornea of the user's eye.

Example 151: The display system of any of the examples above, wherein said corneal center of the user's eye comprises a center of curvature of the corneal apex of the cornea of the user's eye.

Example 152: The display system of any of the examples above, wherein said parameter said processing electronics is configured to estimate comprises a center of rotation of the eye.

Part-B

Example 1: A display system configured to project light to an eye of a user to display virtual image content in a vision field of said user, said eye having a cornea and a pupil, said display system comprising: a frame configured to be supported on a head of the user; a head-mounted display disposed on the frame, said display configured to project light into said user's eye to display virtual image content to the user's vision field; one or more eye tracking cameras configured to image the user's eye; a plurality of light emitters; and processing electronics in communication with the display and the one or more eye tracking cameras, the processing electronics configured to: receive images of the user's eye captured by the one or more eye tracking cameras, glint reflections of the different light emitters observable in said images of the eye captured by the one or more tracking cameras; and estimate a location of a center of curvature of said cornea of the user's eye based at least in part on the location of the glint reflections in said images produced by said one or more eye tracking camera, wherein said processing electronics uses an aspheric model of said cornea in numerical calculations to estimate said location of said center of corneal curvature of the user's eye.

Example 2: The display system of example 1, wherein said processing electronics additionally employs a spherical model of said cornea in numerical calculations to estimate a value of said center of curvature of said cornea.

Example 3: The display system of example 2, wherein said spherical model of said cornea is used in numerical calculations to determine a value of said center of curvature of said cornea based on the location of the glint reflections in said images produced by one or more eye tracking camera and on the location of one or more tracking cameras and the locations of the emitters that produced said respective glint reflections.

Example 4: The display system of examples 2 or 3, wherein said estimate of said center of curvature of said cornea determined from a spherical model of said cornea is applied to said aspheric model in numerical calculations to determine a value of said center of curvature of said cornea.

Example 5: The display system of any of the examples above, wherein said processing electronics is configured to determine an estimate of said center of curvature of said cornea using an iterative process.

Example 6: The display system of any of the examples above, wherein said processing electronics is configured to determine an estimate of said center of curvature of said cornea using an iterative process including repeatedly evaluating said estimate of the center of curvature and using said estimate to recalculate another different estimate of said center of curvature using said aspheric model.

Example 7: The display system of any of the examples above, wherein said processing electronics is configured to determine an estimate of said center of curvature of said cornea using an iterative process repeatedly evaluating said estimate of the center of curvature and using said estimate to recalculate another different estimate of said center of curvature using said spherical model and said aspheric model.

Example 8: The display system of examples 2 or 3, wherein said estimate of said center of curvature of said cornea determined from a spherical model of said cornea is used to estimate a center of curvature for said aspheric model in numerical calculations to determine a value of said center of curvature of said cornea.

Example 9: The display system of examples 2, 3 or 8, wherein said estimate of said center of curvature of said cornea determined from a spherical model of said cornea is used to estimate an orientation of an aspheric spheroid determined from said aspheric model in numerical calculations to determine a value of said center of curvature of said cornea.

Example 10: The display system of examples 1-9, wherein a center of rotation of said eye or a center of pupil for said eye is estimated and used to estimate an orientation of an aspheric spheroid determined from said aspheric model in numerical calculations to determine a value of said center of curvature of said cornea.

Example 11: The display system of any of the examples above, wherein said aspheric model is used to predict the location of a plurality of glints based on locations of light sources.

Example 12: The display system of examples 2, 3, or 8-10, wherein said aspheric model is used to predict the location of a plurality of glints based on locations of light sources.

Example 13: The display system of example 12, wherein said location of said glints predicted based on said aspheric model are used to determine a spherical model.

Example 14: The display system of example 13, wherein said processing electronics are configured to determine a center of curvature of said spherical model determined based on said location of said glints predicted based on said aspheric model.

Example 15: The display system of example 14, wherein said processing electronics are configured to compare said center of curvature of said spherical model determined based on said location of said glints predicted based on said aspheric model with said center of curvature determined using said spherical model that was used to determine the center of said aspheric model.

Example 16: The display system of any of the examples above, wherein said processing electronics are configured to use a comparison between two centers of curvatures obtained from two spherical models to determine an updated aspherical model.

Example 17: The display system of any of the examples above, wherein said processing electronics are configured to use a comparison between two centers of curvatures obtained from two spherical models, one of said spherical models determined based on an aspherical model, to determine an updated aspherical model.

Example 18: The display system of example 15, wherein said processing electronics are configured to use said comparison to determine an updated center of curvature of said aspheric model.

Example 19: The display system of any of the examples above, wherein said processing electronics are configured to use a spherical model to determine one or more parameters of an aspherical model.

Example 20: The display system of any of the examples above, wherein said processing electronics are configured to use an aspherical model to determine one or more parameters of a spherical model.

Example 21: The display system of any of the examples above, wherein said processing electronics are configured to use an aspherical model to determine one or more parameters of a spherical model to determine one or more parameters of an updated aspherical model.

Example 22: The display system of any of the examples above, wherein said processing electronics are configured to use said updated aspherical model to determine one or more parameters of a further updated aspherical model.

Example 23: The display system of any of the examples above, wherein said processing electronics are configured to use said updated aspherical model to determine one or more parameters of a spherical model.

Example 24: The display system of any of the examples above, wherein said processing electronics are configured to use said updated aspherical model to determine one or more parameters of a spherical model to determine one or more parameters of a further updated aspherical model.

Example 25: The display system of any of the examples above, wherein said processing electronics are configured to use a comparison of one or more parameters of a spherical model determined based on said updated aspherical model with one or more parameters of another spherical model to determine one or more parameters of a further updated aspherical model.

Example 26: The display system of any of the examples above, wherein said aspheric model comprises an aspheric surface that is rotationally symmetric.

Example 27: The display system of any of the examples above, wherein said aspheric model comprises a spheroid.

Example 28: The display system of any of the examples above, wherein an equation representing a spheroid is used in numerical calculations for determining a value of said center of curvature of said cornea.

Example 29: The display system of any of examples 1-25, wherein said aspheric model comprises a surface that is non-rotationally symmetric.

Example 30: The display system of any of examples 1-25, wherein said aspheric model comprises a surface that has a different curvature along two orthogonal cross-sections.

Example 31: The display system of any of examples 1-25, wherein said aspheric model has a first curvature along a horizontal direction and a second curvature along a vertical direction, said second curvature different than said first curvature; and the aspheric model is not rotationally symmetric.

Example 32: The display system of any of examples 1-25, wherein said aspheric model comprises an ellipsoid.

Example 33: The display system of any of examples 1-25, wherein said aspheric model comprises a prolate ellipsoid.

Example 34: The display system of any of the examples above, wherein an equation representing an aspheric surface is used in said numerical calculations for determining a value of said center of curvature of said cornea.

Example 35: The display system of example 34, wherein said equation includes three variables defining position on said aspheric surface and two constants determining the shape of the aspheric surface.

Example 36: The display system of Example 34 or 35, wherein said equation is the same or equivalent to $X^2+Y^2+(1+Q)Z^2=2ZR$, where X, Y, and Z define position on said aspheric surface and Q and R determine the shape of the aspheric surface.

Example 37: The display system of any of examples 34, wherein said equation includes three variables defining position on said aspheric surface and three constants determining the shape of the aspheric surface.

Example 38: The display system of any of examples 1-34 and 37, wherein an equation representing an ellipsoid surface is used in numerical calculations for determining a value of said center of curvature of said cornea.

Example 39: The display system of any of examples 1-33 and 37, wherein an equation representing a prolate ellipsoid surface is used in numerical calculations for determining a value of said center of curvature of said cornea.

Example 40: The display system of any of the examples above, wherein an equation representing a spherical surface and an equation representing an aspheric surface is used in numerical calculations for determining a value of said center of curvature of said cornea.

Example 41: The display system of any of the examples above, wherein said one or more eye tracking cameras configured to image the user's eye comprises first and second eye tracking cameras.

Example 42: The display system of example 41, wherein said processing electronics is configured to: based on the location of the glint reflections in one or more images produced by said first eye tracking camera and based on the location of the first eye tracking camera and the location of the emitters that produced said glint reflections, determine a first direction toward the center of corneal curvature of the user's eye; and based on the location of the glint reflections in one or more images produced by said second eye tracking camera and based on the location of the second eye tracking camera and the location of the emitters that produced said glint reflections, determine a second direction toward the center of corneal curvature of the user's eye.

Example 43: The display system of Example 42, wherein said processing electronics is configured to determine the first direction by: defining a first plane that includes the first eye tracking camera, a location of a first glint reflection and a location of the light emitter corresponding to said first glint reflection; defining a second plane that includes the first eye tracking camera, a location of a second glint reflection and a location of the light emitter corresponding to said second glint reflection; and determining a region of convergence of the first plane and the second plane, the region of convergence extending along the first direction.

Example 44: The display system of Example 43, said processing electronics are configured to determine the second direction by: defining a third plane that includes the second eye tracking camera, the location of a third glint reflection, and a location of the light emitter corresponding to said third glint reflection; defining a fourth plane that includes the second eye tracking camera, the location of a fourth glint reflection, and a location of the light emitter corresponding to said fourth glint reflection; and determining a region of convergence of the third plane and the fourth plane, the region of convergence extending along the second direction.

Example 45: The display system of any of Examples 42-44, wherein said processing electronics is configured to estimate a location of said center of corneal curvature of the user's eye based on said first and second directions toward the center of the corneal curvature of the user's eye.

Example 46: The display system of any of Examples 42-45, wherein said processing electronics is configured to: determine said first direction along which the center of corneal curvature of the user's eye is estimated to be located based on at least one first image received from the first eye tracking camera; and determine said second direction along which the center of corneal curvature of the user's eye is estimated to be located based on at least one second image received from the second eye tracking camera, said first and second directions converging toward a region.

Example 47: The display system of any of Examples 42-46, wherein said processing electronics is configured to: obtain an estimate of a center of corneal curvature of the user's eye based on the convergence of the first and second directions.

Example 48: The display system of any of Examples 41-47, wherein said processing electronics is configured to estimate a location of said center of corneal curvature of the user's eye by identifying a region of convergence of first and second directions toward the center of the corneal curvature of the user's eye.

Example 49: The display system of any of Examples 41-48, wherein said processing electronics is configured to obtain an estimate of a center of rotation of the user's eye based on multiple determinations of the center of corneal curvature of the user's eye for different eye poses.

Example 50: The display system of any of Examples above, wherein said processing electronics is configured to obtain an estimate of the orientation of the aspheric model using the center of corneal curvature.

Example 51: The display system of any of Examples 41-50, wherein said processing electronics is configured to obtain an estimate of the orientation of the aspheric model based on an estimate of a center of corneal curvature and an estimate of the convergence of multiple vectors that pass through centers of the pupil determined from images obtained by the first and second eye tracking cameras.

Example 52: The display system of Example 51, wherein said processing electronics is configured to obtain an estimate of the position of the aspheric model having a center along a line that includes said center of corneal curvature and an estimate of the convergence of multiple vectors that pass through centers of the pupil.

Example 53: The display system of Example 51 or 52, wherein said processing electronics is configured to use triangulation to determine the position of said aspheric model.

Example 54: The display system of any of the Examples above, wherein said display is configured to project light into said user's eye to display virtual image content to the user's vision field such that the displayed virtual image content appears to originate from different depths.

Example 55: The display system of any of the Examples above, wherein said display is configured to project light into said user's eye to display virtual image content to the user's vision field at different amounts of at least one of divergence such that the displayed virtual image content appears to originate from different depths.

Example 56: The display system of any of the Examples above, wherein said display is configured to project light into said user's eye that divergences and to project light into said user's eye that is collimated to display virtual image content to the user's vision field that appears to originate from different depths.

Example 57: A method of determining one or more parameters associated with an eye for rendering virtual image content in a display system configured to project light to an eye of a user to display the virtual image content in a vision field of said user, said eye having a cornea, said method comprising: with one or more eye tracking cameras configured to image the eye of the user and a plurality of light emitters disposed with respect to said eye to form glints thereon, capturing a plurality of images of the eye of the user, said images comprising a plurality of glints reflections of the different light emitters; and estimating a location of a center of curvature of said cornea of the user's eye based on the location of the glint reflections in said images produced by one or more eye tracking camera, wherein an aspheric model of said cornea is used in numerical calculations to estimate said location of said center of corneal curvature of the user's eye.

Example 58: The method of Example 57, wherein both a spherical model and an aspherical model are used in determining a value of said center of curvature of said cornea.

Example 59 The method of Example 57, wherein both a spherical model and an aspherical model are used in numerical calculations for determining a value of said center of curvature of said cornea.

Example 60: The method of any of Examples 57-59, wherein said aspheric model is rotationally symmetric.

Example 61: The method of any of Examples 57-60, wherein said aspheric model comprises a spheroid.

Example 62: The method of any of Examples 57-59, wherein said aspheric model is non-rotationally symmetric.

Example 63: The method of any of Examples 57-59 or 62, wherein said aspheric model has a different curvature along two orthogonal cross-sections.

Example 64: The method of any of Examples 57-59 or 62, wherein said aspheric model has a first curvature along a horizontal direction and a second curvature along a vertical direction, said second curvature different than said first curvature; and the aspheric model is not rotationally symmetric.

Example 65: The method of any of Examples 57-59 or 62-64, wherein said aspheric model comprises an ellipsoid.

Example 66: The method of any of Examples 57-59 or 62-64, wherein said aspheric model comprises a prolate ellipsoid.

Example 67: The method of any of Examples 57-66, wherein said estimating said location of said center of curvature of said cornea comprises estimating a location of a center of curvature of said cornea of the user's eye based on the location of the glint reflections in said images produced by said one or more eye tracking camera and based on the location of one or more tracking cameras and the locations of the emitters that produced said respective glint reflections.

Example 68: The display system of Examples 56-66, wherein said processing electronics are configured to use a comparison between two centers of curvatures to determine an updated aspherical model.

Example 69: The display system of any of Examples 1-56, wherein said electronic processor is configured to estimate a location of a center of curvature of said cornea of the user's eye based on the location of the glint reflections in said images produced by said one or more eye tracking camera and based on the location of one or more tracking cameras and the locations of the emitters that produced said respective glint reflections.

Example 70: The method of any of Examples 41-64, wherein said electronic processor is configured to estimate a location of a center of curvature of said cornea of the user's eye based on the location of the glint reflections in said images produced by said one or more eye tracking camera and based on the location of one or more tracking cameras and the locations of the emitters that produced said respective glint reflections.

Example 71: A computer-implemented method of estimating the location of the center of corneal curvature of a user's eye, said eye having a cornea and a pupil, the method comprising: by a computing system of a display system configured to project light to an eye of a user to display virtual image content in a vision field of said user: receiving images of the user's eye captured by the one or more eye tracking cameras, glint reflections of one or more light emitters observable in said images of the eye captured by the one or more tracking cameras, wherein one or more eye tracking cameras configured to image the user's eye; and estimating a location of a center of curvature of said cornea of the user's eye based on the location of the glint reflections in said images produced by said one or more eye tracking camera, wherein an aspheric model of said cornea is used to numerically estimate said location of said center of corneal curvature of the user's eye.

Example 72: The computer-implemented method of Example 71, wherein a spherical model of said cornea is used to estimate a value of said center of curvature of said cornea.

Example 73: The computer-implemented method of Example 72, wherein said spherical model of said cornea is used in numerical calculations to determine a value of said center of curvature of said cornea based on the location of the glint reflections in said images produced by one or more eye tracking camera and on the location of one or more tracking cameras and the locations of the emitters that produced said respective glint reflections.

Example 74: The computer-implemented method of Example 72 or 73, wherein said estimate of said center of curvature of said cornea determined from a spherical model of said cornea is applied to said aspheric model in numerical calculations to determine a value of said center of curvature of said cornea.

Example 75: The computer-implemented method of any of the Examples above, wherein an iterative process is used to determine an estimate of said center of curvature of said cornea.

Example 76: The computer-implemented method of any of the Examples above, wherein an iterative process including repeatedly evaluating said estimate of the center of curvature and using said estimate to recalculate another different estimate of said center of curvature using said aspheric model, is used to determine an estimate of said center of curvature of said cornea.

Example 77: The computer-implemented method of any of the Examples above, wherein an iterative process repeatedly evaluating said estimate of the center of curvature and using said estimate to recalculate another different estimate of said center of curvature using said spherical model and said aspheric model, is used to determine an estimate of said center of curvature of said cornea.

Example 78: The computer-implemented method of any of the Examples above, wherein said estimate of said center of curvature of said cornea determined from a spherical model of said cornea is used to estimate a center of curvature for said aspheric model in numerical calculations to determine a value of said center of curvature of said cornea.

Example 79: The computer-implemented method of any of Examples 72, 73 or 78, wherein said estimate of said center of curvature of said cornea determined from a spherical model of said cornea is used to estimate an orientation a spheroid determined from said aspheric model in numerical calculations to determine a value of said center of curvature of said cornea.

Example 80: The computer-implemented method of Examples 71-79, wherein a center of rotation of said eye or a center of pupil for said eye is estimated and used to estimate an orientation of a spheroid determined from said aspheric model in numerical calculations to determine a value of said center of curvature of said cornea.

Example 81: The computer-implemented method of any of the Examples above, wherein said aspheric model is used to predict the location of a plurality of glints based on locations of light sources.

Example 82: The computer-implemented method of Examples 72, 73, or 78-80, wherein said aspheric model is used to predict the location of a plurality of glints based on locations of light sources.

Example 83: The computer-implemented method of Example 82, wherein said location of said glints predicted based on said aspheric model are used to determine a spherical model.

Example 84: The computer-implemented method of Example 83, wherein a center of curvature of said spherical model determined based on said location of said glints predicted based on said aspheric model, is determined.

Example 85: The computer-implemented method of Example 84, wherein said center of curvature of said spherical model determined based on said location of said glints predicted based on said aspheric model is compared with said center of curvature determined using said spherical model that was used to determine the center of said aspheric model.

Example 86: The computer-implemented method of any of the Examples above, wherein a comparison between two centers of curvatures obtained from two spherical models is used to determine an updated aspherical model.

Example 87: The computer-implemented method of any of the Examples above, wherein a comparison between two centers of curvatures obtained from two spherical models, one of said spherical models determined based on an aspherical model, is used to determine an updated aspherical model.

Example 88: The computer-implemented method of Example 85, wherein the said comparison is used to determine an updated center of curvature of for an aspheric model.

Example 89: The computer-implemented method of any of the Examples above, wherein a spherical model is used to determine one or more parameters of an aspherical model.

Example 90: The computer-implemented method of any of the Examples above, wherein an aspherical model is used to determine one or more parameters of a spherical model.

Example 91: The computer-implemented method of the Examples above, wherein an aspherical model is used to determine one or more parameters of a spherical model to determine one or more parameters of an updated aspherical model.

Example 92: The computer-implemented method of the Examples above, wherein said updated aspherical model is used to determine one or more parameters of a further updated aspherical model.

Example 93: The computer-implemented method of the Examples above, wherein said updated aspherical model is used to determine one or more parameters of a spherical model.

Example 94: The computer-implemented method of the Examples above, wherein said updated aspherical model to determine one or more parameters of a spherical model is used to determine one or more parameters of a further updated aspherical model.

Example 95: The computer-implemented method of the Examples above, wherein a comparison of one or more parameters of a spherical model determined based on said updated aspherical model with one or more parameters of another spherical model is used to determine one or more parameters of a further updated aspherical model.

Example 96: The computer-implemented method of the Examples above, wherein said aspheric model comprises an aspheric surface that is rotationally symmetric.

Example 97: The computer-implemented method of the Examples above, wherein said aspheric model comprises a spheroid.

Example 98: The computer-implemented method of the Examples above, wherein an equation representing a spheroid is used in numerical calculations for determining a value of said center of curvature of said cornea.

Example 99: The computer-implemented method of any of Examples 71-95, wherein said aspheric model comprises a surface that is non-rotationally symmetric.

Example 100: The computer-implemented method of any of Examples 71-95, wherein said aspheric model comprises a surface that has a different curvature along two orthogonal cross-sections.

Example 101: The computer-implemented method of any of Examples 71-95, wherein said aspheric model has a first curvature along a horizontal direction and a second curvature along a vertical direction, said second curvature different than said first curvature; and the aspheric model is not rotationally symmetric.

Example 102: The computer-implemented method of Examples 71-95, wherein said aspheric model comprises an ellipsoid.

Example 103: The computer-implemented method of Examples 71-95, wherein said aspheric model comprises a prolate ellipsoid.

Example 104: The computer-implemented method of any of the Examples above, wherein an equation representing an aspheric surface is used in said numerical calculations for determining a value of said center of curvature of said cornea.

Example 105: The computer-implemented method of Example 104, wherein said equation includes three variables defining position on said aspheric surface and two constants determining the shape of the aspheric surface.

Example 106: The computer-implemented method of Example 104 or 105, wherein said equation is the same or equivalent to $X^2+Y^2+(1+Q)Z^2=2ZR$, where X, Y, and Z define position on said aspheric surface and Q and R determine the shape of the aspheric surface.

Example 107: The computer-implemented method of Examples 104, wherein said equation includes three variables defining position on said aspheric surface and three constants determining the shape of the aspheric surface.

Example 108: The computer-implemented method of Examples 71-104 and 107, wherein an equation representing an ellipsoid surface is used in numerical calculations for determining a value of said center of curvature of said cornea.

Example 109: The computer-implemented method of Examples 71-103 and 107, wherein an equation representing a prolate ellipsoid surface is used in numerical calculations for determining a value of said center of curvature of said cornea.

Example 110: The computer-implemented method of any of the Examples above, wherein an equation representing a spherical surface and an equation representing an aspheric surface is used in numerical calculations for determining a value of said center of curvature of said cornea.

Example 111: The computer-implemented method of any of the Examples above, wherein said one or more eye tracking cameras configured to image the user's eye comprises first and second eye tracking cameras.

Example 112: The computer-implemented method of Example 111, wherein a first direction toward the center of corneal curvature of the user's eye is determined, based on the location of the glint reflections in one or more images produced by said first eye tracking camera and based on the location of the first eye tracking camera and the location of the emitters that produced said glint reflections; and a second direction toward the center of corneal curvature of the user's eye is determined, based on the location of the glint reflections in one or more images produced by said second eye tracking camera and based on the location of the second eye tracking camera and the location of the emitters that produced said glint reflections.

Example 113: The computer-implemented method of Example 112, wherein the first direction is determined by: defining a first plane that includes the first eye tracking camera, a location of a first glint reflection and a location of the light emitter corresponding to said first glint reflection; defining a second plane that includes the first eye tracking camera, a location of a second glint reflection and a location of the light emitter corresponding to said second glint reflection; and determining a region of convergence of the first plane and the second plane, the region of convergence extending along the first direction.

Example 114: The computer-implemented method of Example 113, wherein the second direction is determined by: defining a third plane that includes the second eye tracking camera, the location of a third glint reflection, and a location of the light emitter corresponding to said third glint reflection; defining a fourth plane that includes the second eye tracking camera, the location of a fourth glint reflection, and a location of the light emitter corresponding to said fourth glint reflection; and determining a region of convergence of the third plane and the fourth plane, the region of convergence extending along the second direction.

Example 115: The computer-implemented method of Examples 112-114, wherein a location of said center of corneal curvature of the user's eye is determined based on said first and second directions toward the center of the corneal curvature of the user's eye.

Example 116: The computer-implemented method of Examples 112-115, wherein in said first direction along which the center of corneal curvature of the user's eye is estimated to be located based on at least one first image received from the first eye tracking camera, is determined; and; said second direction along which the center of corneal curvature of the user's eye is estimated to be located based on at least one second image received from the second eye tracking camera, said first and second directions converging toward a region.

Example 117: The computer-implemented method of any of Examples 112-116, wherein an estimate of a center of corneal curvature of the user's eye is obtained based on the convergence of the first and second directions.

Example 118: The computer-implemented method of any of Examples 111-117, wherein location of said center of corneal curvature of the user's eye is estimated by identifying a region of convergence of first and second directions toward the center of the corneal curvature of the user's eye.

Example 119: The computer-implemented method of any of Examples 111-118, wherein an estimate of a center of rotation of the user's eye is obtained based on multiple determinations of the center of corneal curvature of the user's eye for different eye poses.

Example 120: The computer-implemented method of any of Examples above, wherein an estimate of the orientation of the aspheric model using the center of corneal curvature is obtained.

Example 121: The computer-implemented method of any of Examples 111-120, wherein an estimate of the orientation of the aspheric model is obtained based on an estimate of a center of corneal curvature and an estimate of the convergence of multiple vectors that pass through centers of the pupil determined from images obtained by the first and second eye tracking cameras.

Example 122: The computer-implemented method of Example 121, wherein an estimate of the position of the aspheric model having a center along a line that includes said center of corneal curvature and an estimate of the convergence of multiple vectors that pass through centers of the pupil, are obtained.

Example 123: The computer-implemented method of Example 121 or 122, wherein triangulation method to is determine the position of said aspheric model.

Example 124: The computer-implemented method of any of the Examples above, wherein said display is configured to project light into said user's eye to display virtual image content to the user's vision field such that the displayed virtual image content appears to originate from different depths.

Part-C

Example 1: A display system configured to project light to an eye of a user to display virtual image content in a vision field of said user, said eye having a cornea and a pupil, said display system comprising: a frame configured to be supported on a head of the user; a head-mounted display disposed on the frame, said display configured to project light into said user's eye to display virtual image content to the user's vision field; one or more eye tracking cameras configured to image the user's eye; a plurality of light emitters; and processing electronics in communication with the display and the one or more eye tracking cameras, the processing electronics configured to: receive images of the user's eye captured by the one or more eye tracking cameras, glint reflections of the different light emitters observable in said images of the eye captured by the one or more tracking cameras; and estimate a first parameter of the user's eye based at least in part on the location of the glint reflections in said images produced by said one or more eye tracking camera, wherein said processing electronics uses an aspheric model of said cornea in numerical calculations to estimate said first parameter of the user's eye.

Example 2: The display system of example 1, wherein said processing electronics additionally employs a spherical model of said cornea in numerical calculations to estimate a value of said first parameter.

Example 3: The display system of examples 2, wherein said spherical model of said cornea is used in numerical calculations to determine a value of said first parameter based on the location of the glint reflections in said images produced by one or more eye tracking camera and on the location of one or more tracking cameras and the locations of the emitters that produced said respective glint reflections.

Example 4: The display system of examples 2 or 3, wherein said estimate of said first parameter determined from a spherical model of said cornea is applied to said aspheric model in numerical calculations to determine a value of said first parameter.

Example 5: The display system of any of the examples above, wherein said processing electronics is configured to determine an estimate of said first parameter using an iterative process.

Example 6: The display system of any of the examples above, wherein said processing electronics is configured to determine an estimate of said first parameter using an iterative process including repeatedly evaluating said first parameter and using said estimate to recalculate another different estimate of said first parameter using said aspheric model.

Example 7: The display system of any of the examples above, wherein said processing electronics is configured to determine an estimate of said first parameter using an iterative process repeatedly evaluating said estimate of said first parameter and using said estimate to recalculate another different estimate of said first parameter using said spherical model and said aspheric model.

Example 8: The display system of examples 2 or 3, wherein said estimate of said first parameter determined from a spherical model of said cornea is used to estimate a value of said first parameter for said aspheric model in numerical calculations to determine a value of said first parameter.

Example 9: The display system of any of the examples above, wherein said aspheric model comprises an aspheric surface that is rotationally symmetric.

Example 10: The display system of any of the examples above, wherein said aspheric model comprises a spheroid.

Example 11: The display system of any of the examples above, wherein an equation representing a spheroid is used in numerical calculations for determining a value of said center of curvature of said cornea.

Example 12: The display system of any of examples 1-8, wherein said aspheric model comprises a surface that is non-rotationally symmetric.

Example 13: The display system of any of examples 1-8, wherein said aspheric model comprises a surface that has a different curvature along two orthogonal cross-sections.

Example 14: The display system of any of examples 1-8, wherein said aspheric model has a first curvature along a horizontal direction and a second curvature along a vertical direction, said second curvature different than said first curvature; and the aspheric model is not rotationally symmetric.

Example 15: The display system of any of examples 1-8, wherein said aspheric model comprises an ellipsoid.

Example 16: The display system of any of examples 1-8, wherein said aspheric model comprises a prolate ellipsoid.

Example 17: The display system of any of examples 1-8, wherein an equation representing an aspheric surface is used in said numerical calculations for determining a value of said first parameter.

Example 18: The display system of example 17, wherein said equation includes three variables defining position on said aspheric surface and two constants determining the shape of the aspheric surface.

Example 19: The display system of example 17 or 18, wherein said equation is the same or equivalent to $X+Y+(1+Q)Z=2ZR$, where X, Y, and Z define position on said aspheric surface and Q and R determine the shape of the aspheric surface.

Example 20: The display system of any of examples 17, wherein said equation includes three variables defining position on said aspheric surface and three constants determining the shape of the aspheric surface.

Example 21: The display system of any of examples 1-17 and 20, wherein an equation representing an ellipsoid surface is used in numerical calculations for determining a value of said first parameter.

Example 22: The display system of any of examples 1-17 and 20, wherein an equation representing a prolate ellipsoid surface is used in numerical calculations for determining a value of said first parameter.

Example 23: The display system of any of the examples above, wherein an equation representing a spherical surface and an equation representing an aspheric surface is used in numerical calculations for determining a value of said first parameter.

Example 24: The display system of any of the examples above, wherein said display is configured to project light into said user's eye to display virtual image content to the user's vision field such that the displayed virtual image content appears to originate from different depths.

Example 25: The display system of any of the examples above, wherein said display is configured to project light into said user's eye to display virtual image content to the user's vision field at different amounts of at least one of divergence such that the displayed virtual image content appears to originate from different depths.

Example 26: The display system of any of the examples above, wherein said display is configured to project light into said user's eye that divergences and to project light into said user's eye that is collimated to display virtual image content to the user's vision field that appears to originate from different depths.

Example 27: The display system of any of the examples above, wherein said electronic processor is configured to estimate said parameter of the user's eye based on the location of the glint reflections in said images produced by said one or more eye tracking camera and based on the location of one or more tracking cameras and the locations of the emitters that produced said respective glint reflections.

Example 28: A method of determining one or more parameters associated with an eye for rendering virtual image content in a display system configured to project light to an eye of a user to display the virtual image content in a vision field of said user, said eye having a cornea, said method comprising: with one or more eye tracking cameras configured to image the eye of the user and a plurality of light emitters disposed with respect to said eye to form glints thereon, capturing a plurality of images of the eye of the user, said images comprising a plurality of glints reflections of the different light emitters; and estimating a first parameter of the user's eye based on the location of the glint reflections in said images produced by one or more eye tracking camera, wherein an aspheric model of said cornea is used in numerical calculations to estimate said location of said first parameter of the user's eye.

Example 29: The method of example 28, wherein both a spherical model and an aspherical model are used in determining a value of said first parameter.

Example 30: The method of example 28, wherein both a spherical model and an aspherical model are used in numerical calculations for determining a value of said first parameter.

Example 31: The method of any of examples 28-30, wherein said aspheric model is rotationally symmetric.

Example 32: The method of any of examples 28-31, wherein said aspheric model comprises a spheroid.

Example 33: The method of any of examples 28-30, wherein said aspheric model is non-rotationally symmetric.

Example 34: The method of any of examples 28-30 or 33, wherein said aspheric model has a different curvature along two orthogonal cross-sections.

Example 35: The method of any of examples 28-30 or 33, wherein said aspheric model has a first curvature along a horizontal direction and a second curvature along a vertical direction, said second curvature different than said first curvature; and the aspheric model is not rotationally symmetric.

Example 36: The method of any of examples 28-30 or 31-35, wherein said aspheric model comprises an ellipsoid.

Example 37: The method of any of examples 28-30 or 31-35, wherein said aspheric model comprises a prolate ellipsoid.

Example 38: The method of any of examples 28-37, wherein said estimating said first parameter comprises estimating said first parameter of the user's eye based on the location of the glint reflections in said images produced by said one or more eye tracking camera and based on the location of one or more tracking cameras and the locations of the emitters that produced said respective glint reflections.

Example 39: The method of any of examples 28-38, wherein said electronic processor is configured to estimate a value of said first parameter of the user's eye based on the location of the glint reflections in said images produced by said one or more eye tracking camera and based on the location of one or more tracking cameras and the locations of the emitters that produced said respective glint reflections.

Example 40: The method of any of the examples above, wherein the first parameter comprises a location of a center of curvature of said cornea.

Example 41: The method of any of the examples above, wherein the first parameter comprises a parameter associated with the position and/or orientation of the eye.

Example 42: The method of any of the examples above, wherein the first parameter comprises a parameter with the position of the eye.

Example 43: The method of any of the examples above, wherein the first parameter comprises a parameter dependent on the position of the eye.

Example 44: The method of any of the examples above, wherein the first parameter comprises a parameter that can be used to determine the position of the eye.

Example 45: The display of any of examples 1-27, wherein the first parameter comprises a parameter associated with the position and/or orientation of the eye.

Example 46: The display of any of examples 1-27, wherein the first parameter comprises a parameter associated with the position of the eye.

Example 47: The display of any of examples 1-27, wherein the first parameter comprises a parameter dependent on with the position of the eye.

Example 48: The display of any of examples 1-27, wherein the first parameter comprises a parameter that can be used to determine the position of the eye.

Example 49: The display of any of examples 1-27, wherein the first parameter comprises a location of a center of curvature of said cornea.

Example 50: The display system of any of the examples above, wherein said processing electronics is further configured to update a parameter affecting the shape of said aspheric model based on at least one iteration.

Example 51: The display system of any of the examples above, wherein said processing electronics is further configured to update a constant characterizing the shape of said aspheric model based on at least one iteration.

Example 52: The display system of any of the examples above, wherein said processing electronics is further configured to update a constant characterizing the shape of an aspheric spheroidal model based on at least one iteration.

Example 53: The display system of any of the examples above, wherein said processing electronics is further configured to update a value of, Q, characterizing the shape of an aspheric spheroidal model based on at least one iteration.

Example 54: The display system of any of the examples above, wherein said processing electronics is further configured to update a parameter affecting the shape of said aspheric model over multiple iterations.

Example 55: The display system of any of the examples above, wherein said processing electronics is further configured to update a constant characterizing the shape of said aspheric model over multiple iterations.

Example 56: The display system of any of the examples above, wherein said processing electronics is further configured to update a constant characterizing the shape of an aspheric spheroidal model over multiple iterations.

Example 57: The display system of any of the examples above, wherein said processing electronics is further configured to update a value of, Q, characterizing the shape of an aspheric spheroidal model over multiple iterations.

Example 58: The display system of any of the examples above, wherein said processing electronics is further configured to update said value, constant, or parameter by determining a value, constant, or parameter that reduces variation, uncertainty, or error in calculated values of the center of rotation.

Example 59: The display system of any of the examples above, wherein said processing electronics is further configured to update said value, constant, or parameter by determining a value, constant, or parameter that reduces variation, uncertainty, or error in calculated values of the center of rotation for different eye gazes.

Example 60: The display system of any of the examples above, wherein said processing electronics is further configured to update said value, constant, or parameter by determining a value, constant, or parameter that reduces variation, uncertainty, or error in calculated values of the center of rotation for different eye gazes during a calibration process.

Example 61: The display system of any of the examples above, wherein said processing electronics is further configured to update said value, constant, or parameter by determining a value, constant, or parameter that reduces variation, uncertainty, or error in calculated values of the center of rotation for different eye gazes during a calibration process where fixation targets are provided to the viewer on said display to alter the gaze of the user.

Example 62: The display system of any of the examples above, wherein said processing electronics is further configured to use said value, constant, or parameter affecting the shape of said aspheric model until an additional calibration is performed.

Example 63: The display system of any of the examples above, wherein said processing electronics is further configured to use said value, constant, or parameter affecting the shape of said aspheric model until an additional calibration is performed for determining a parameter of the user's eye.

Example 64: The display system of any of the examples above, wherein said processing electronics is further configured to use said value, constant, or parameter affecting the shape of said aspheric model until an additional calibration is performed for determining a corneal center of the user's eye.

Example 65: The display system of any of the examples above, wherein said processing electronics is further configured use said value, constant, or parameter affecting the shape of said aspheric model until an additional calibration is performed for determining a corneal center of the user's eye.

Example 66: The display system of any of the examples above, wherein said processing electronics is further configured use said value, constant, or parameter affecting the shape of said aspheric model until an additional calibration is performed for determining a center of rotation of the user's eye.

Example 67: The display system of any of the examples above, wherein said at least one eye tracking camera comprises first, second and third eye tracking camera configured to image the user's eye, said processing electronics in communication with said first, second and third eye tracking camera, glint reflections of light emitters observable in the images of the eye captured by the first, second and third eye tracking camera.

Example 68: The display system of any of the examples above, wherein said processing electronics is configured to estimate said first parameter of the user's eye based on the location of the glint reflections in said images produced by said first, second and third eye tracking cameras.

Example 69: The display system of any of the examples above, wherein said processing electronics is configured to estimate said first parameter of the user's eye based on the location of the glint reflections in said images produced by said first, second, and third eye tracking camera and based on the location of said first, second, and third eye tracking cameras and the locations of the emitters that produced said respective glint reflections.

Example 70: The display system of any of the examples above, wherein said processing electronics is configured to estimate said parameter of the user's eye based on a parameter of the user's eye determined by said first and third eye tracking camera and a parameter of the user's eye determined by said first and second eye tracking camera.

Example 71: The display system of any of the examples above, wherein said processing electronics is configured to estimate said parameter of the user's eye based on a parameter of the user's eye determined by said second and third eye tracking camera and a parameter of the user's eye determined by said first and second eye tracking camera.

Example 72: The display system of any of the examples above, wherein said processing electronics is configured to estimate said first parameter of the user's eye based on an average of a parameter of the user's eye determined by said first and third eye tracking camera and a parameter of the user's eye determined by said first and second eye tracking camera.

Example 73: The display system of any of the examples above, wherein said processing electronics is configured to estimate said first parameter of the user's eye based on an average of a parameter of the user's eye determined by said second and third eye tracking camera and a parameter of the user's eye determined by said first and second eye tracking camera.

Example 74: The display system of any of the examples above, wherein said first parameter said processing electronics is configured to estimate comprise a corneal center.

Example 75: The display system of any of the examples above, wherein said corneal center of the user's eye comprises a center of curvature of the cornea of the user's eye.

Example 76: The display system of any of the examples above, wherein said corneal center of the user's eye comprises a center of curvature of the corneal apex of the cornea of the user's eye.

Example 77: The display system of any of the examples above, wherein said first parameter said processing electronics is configured to estimate comprises a center of rotation of the eye.

Example 78: The display system of any of the examples above, wherein said processing electronics is further configured to determine a user specific value of a parameter affecting the shape of said aspheric model using a plurality of images of the user's eye captured by the one or more eye tracking cameras.

Example 79: The display system of example 78, wherein said user specific value of the parameter is associated with said user's eye.

Example 80: The display system of example 78, wherein different images of said plurality of images of the user's eye are captured at different gaze directions associated with respective target locations, wherein the target location is determined by the display system and wherein the target location is different for different images of said plurality of images of the user's eye.

Example 81: The display system of example 78, wherein different pairs of images of said plurality of images of the user's eye is captured at different gaze directions associated with respective target locations, wherein the target location is determined by the display system and wherein the target location is different for different pair of images of said plurality of images of the user's eye.

Example 82: The display system of any of the examples 80 or 81, wherein processing electronics determines said user specific value of said parameter affecting the shape of said aspheric model based on an iterative process wherein an iteration comprises: estimating a plurality of center of rotations of the user's eye based at least in part on a value of the parameter affecting the shape of said aspheric model; calculating a value of a statistical metric associated with the estimated plurality of the plurality of center of rotations the user's eye; generating a modified value of said parameter affecting the shape of said aspheric model based at least in part on the calculated statistical metric.

Example 83: The display system of example 82, wherein the value of the parameter affecting the shape of said aspheric model is the modified value of said parameter affecting the shape of said aspheric model based generated in a previous iteration.

Example 84: The display system of example 82, wherein the value of the parameter affecting the shape of said aspheric model used in the first iteration of the iterative process is an initial value determined by an eye model.

Example 85: The display system of example 84, wherein the eye model is the Arizona eye model and the initial value of the parameter affecting the shape of said aspheric model is −0.26.

Example 86: The display system of example 82, wherein the modified value of said parameter affecting the shape of said aspheric model reduces the value of the statistical metric.

Example 87: The display system of example 86, wherein the statistical metric comprises a variation of a statistical distribution of the plurality of center of rotations.

Example 88: The display system of example 87, wherein the statistical metric comprises a variance or standard deviation.

Example 89: The display system of example 82, wherein the plurality of center of rotations of the user's eye are estimated based at least in part on said aspheric model, the location of one or more tracking cameras and the locations of the emitters that produced said respective glint reflections.

Example 90: The display of any of examples above, wherein the first parameter comprises a location of a corneal center.

Example 91: The method of any of the examples above, wherein the first parameter comprises a location of a corneal center.

Example 92: The method of any of the examples above, wherein the first parameter comprises a location of a center of rotation of the eye.

Part-D

Example 1: A display system configured to project light to an eye of a user to display virtual image content in a vision field of said user, said eye having a cornea and a pupil, said display system comprising: a frame configured to be supported on a head of the user; a head-mounted display disposed on the frame, said display configured to project light into said user's eye to display virtual image content to the user's vision field; one or more eye tracking cameras configured to image the user's eye; a plurality of light emitters; and processing electronics in communication with the display and the one or more eye tracking cameras, the processing electronics configured to: receive images of the user's eye captured by the one or more eye tracking cameras, glint reflections of the different light emitters observable in said images of the eye captured by the one or more tracking cameras; and estimate a location of a center of curvature of said cornea of the user's eye based at least in part on the location of the glint reflections in said images produced by said one or more eye tracking camera, wherein said processing electronics uses an aspheric model of said cornea in numerical calculations to estimate said location of said center of corneal curvature of the user's eye.

Example 2: The display system of example 1, wherein said processing electronics additionally employs a spherical model of said cornea in numerical calculations to estimate a value of said center of curvature of said cornea.

Example 3: The display system of examples 2, wherein said spherical model of said cornea is used in numerical calculations to determine a value of said center of curvature of said cornea based on the location of the glint reflections in said images produced by one or more eye tracking camera and on the location of one or more tracking cameras and the locations of the emitters that produced said respective glint reflections.

Example 4: The display system of examples 2 or 3, wherein said estimate of said center of curvature of said cornea determined from a spherical model of said cornea is applied to said aspheric model in numerical calculations to determine a value of said center of curvature of said cornea.

Example 5: The display system of any of the examples above, wherein said processing electronics is configured to determine an estimate of said center of curvature of said cornea using an iterative process.

Example 6: The display system of any of the examples above, wherein said processing electronics is configured to determine an estimate of said center of curvature of said cornea using an iterative process including repeatedly evaluating said estimate of the center of curvature and using said estimate to recalculate another different estimate of said center of curvature using said aspheric model.

Example 7: The display system of any of the examples above, wherein said processing electronics is configured to determine an estimate of said center of curvature of said cornea using an iterative process repeatedly evaluating said estimate of the center of curvature and using said estimate to recalculate another different estimate of said center of curvature using said spherical model and said aspheric model.

Example 8: The display system of examples 2 or 3, wherein said estimate of said center of curvature of said cornea determined from a spherical model of said cornea is used to estimate a center of curvature of an aspheric surface for application of said aspheric model in numerical calculations to determine a value of said center of curvature of said cornea.

Example 9: The display system of examples 2, 3 or 8, wherein said estimate of said center of curvature of said cornea determined from a spherical model of said cornea is used to estimate an orientation of an aspheric surface for application of said aspheric model in numerical calculations to determine a value of said center of curvature of said cornea.

Example 10: The display system of examples 1-9, wherein a center of rotation of said eye or a center of pupil for said eye is estimated and used to estimate an orientation of an aspheric surface for application of said aspheric model in numerical calculations to determine a value of said center of curvature of said cornea.

Example 11: The display system of any of the examples above, wherein said aspheric model is used to predict the location of a plurality of glints based on locations of light sources.

Example 12: The display system of examples 2, 3, or 8-10, wherein said aspheric model is used to predict the location of a plurality of glints based on locations of light sources.

Example 13: The display system of example 12, wherein said location of said glints predicted based on said aspheric model are used to determine a center of curvature a spherical surface.

Example 14: The display system of example 13, wherein said processing electronics are configured to determine a center of curvature of a spherical surface based on said location of said glints predicted based on said aspheric model.

Example 15: The display system of example 14, wherein said processing electronics are configured to compare said center of curvature of said spherical surface determined based on said location of said glints predicted based on said aspheric model with said center of curvature determined using said spherical model that was used to determine the center of curvature of said aspheric surface.

Example 16: The display system of any of the examples above, wherein said processing electronics are configured to use a comparison between two centers of curvatures for two spherical surfaces to determine an updated center of curvature of said aspherical surface.

Example 17: The display system of any of the examples above, wherein said processing electronics are configured to use a comparison between two centers of curvatures of two spherical surfaces obtained from application of the spherical model, one of said spherical surfaces determined based on an aspherical model, to determine an updated center of curvature of said aspherical surface.

Example 18: The display system of example 15, wherein said processing electronics are configured to use said comparison to determine a updated center of curvature of said aspheric surface.

Example 19: The display system of any of the examples above, wherein said processing electronics are configured to use a spherical model to determine one or more parameters of an aspheric surface.

Example 20: The display system of any of the examples above, wherein said processing electronics are configured to use an aspherical model to determine one or more parameters of a spherical surface.

Example 21: The display system of any of the examples above, wherein said processing electronics are configured to use an aspherical model to determine one or more parameters of a spherical surface to determine one or more parameters of an aspherical surface.

Example 22: The display system of any of the examples above, wherein said processing electronics are configured to use said updated center of curvature of said aspherical surface for application of said aspherical model to further update said center of curvature of said aspherical surface.

Example 23: The display system of any of the examples above, wherein said processing electronics are configured to use said updated center of curvature of said aspherical surface for application of the aspherical model to determine one or more parameters of a spherical surface.

Example 24: The display system of any of the examples above, wherein said processing electronics are configured to use said updated center of curvature of said aspherical surface to determine one or more parameters of a spherical surface for application of a spherical model to further update the center of curvature of said aspherical surface.

Example 25: The display system of any of the examples above, wherein said processing electronics are configured to use a comparison of one or more parameters of a spherical surface determined based on said updated aspherical surface with one or more parameters of another spherical surface to update one or more parameters of said aspherical surface.

Example 26: The display system of any of the examples above, wherein said aspheric model comprises an aspheric surface that is rotationally symmetric.

Example 27: The display system of any of the examples above, wherein said aspheric model comprises a spheroid.

Example 28: The display system of any of the examples above, wherein an equation representing a spheroid is used in numerical calculations for determining a value of said center of curvature of said cornea.

Example 29: The display system of any of examples 1-25, wherein said aspheric model comprises a surface that is non-rotationally symmetric.

Example 30: The display system of any of examples 1-25, wherein said aspheric model comprises a surface that has a different curvature along two orthogonal cross-sections.

Example 31: The display system of any of examples 1-25, wherein said aspheric model has a first curvature along a horizontal direction and a second curvature along a vertical direction, said second curvature different than said first curvature; and the aspheric model is not rotationally symmetric.

Example 32: The display system of any of examples 1-25, wherein said aspheric model comprises an ellipsoid.

Example 33: The display system of any of examples 1-25, wherein said aspheric model comprises a prolate ellipsoid.

Example 34: The display system of any of the examples above, wherein an equation representing an aspheric surface is used in said numerical calculations for determining a value of said center of curvature of said cornea.

Example 35: The display system of example 34, wherein said equation includes three variables defining position on said aspheric surface and two constants determining the shape of the aspheric surface.

Example 36: The display system of example 34 or 35, wherein said equation is the same or equivalent to $X+Y+(1+Q)Z=2ZR$, where X, Y, and Z define position on said aspheric surface and Q and R determine the shape of the aspheric surface.

Example 37: The display system of any of examples 34, wherein said equation includes three variables defining position on said aspheric surface and three constants determining the shape of the aspheric surface.

Example 38: The display system of any of examples 1-34 and 37, wherein an equation representing an ellipsoid surface is used in numerical calculations for determining a value of said center of curvature of said cornea.

Example 39: The display system of any of examples 1-33 and 37, wherein an equation representing a prolate ellipsoid surface is used in numerical calculations for determining a value of said center of curvature of said cornea.

Example 40: The display system of any of the examples above, wherein an equation representing a spherical surface and an equation representing an aspherical surface is used in numerical calculations for determining a value of said center of curvature of said cornea.

Example 41: The display system of any of the examples above, wherein said one or more eye tracking cameras configured to image the user's eye comprises first and second eye tracking cameras.

Example 42: The display system of example 41, wherein said processing electronics is configured to: based on the location of the glint reflections in one or more images produced by said first eye tracking camera and based on the location of the first eye tracking camera and the location of the emitters that produced said glint reflections, determine a first direction toward the center of corneal curvature of the user's eye; and based on the location of the glint reflections in one or more images produced by said second eye tracking camera and based on the location of the second eye tracking camera and the location of the emitters that produced said glint reflections, determine a second direction toward the center of corneal curvature of the user's eye.

Example 43: The display system of example 42, wherein said processing electronics is configured to determine the first direction by: defining a first plane that includes the first eye tracking camera, a location of a first glint reflection and a location of the light emitter corresponding to said first glint reflection; defining a second plane that includes the first eye tracking camera, a location of a second glint reflection and a location of the light emitter corresponding to said second glint reflection; and determining a region of convergence of the first plane and the second plane, the region of convergence extending along the first direction.

Example 44: The display system of example 43, said processing electronics are configured to determine the second direction by: defining a third plane that includes the second eye tracking camera, the location of a third glint reflection, and a location of the light emitter corresponding to said third glint reflection; defining a fourth plane that includes the second eye tracking camera, the location of a fourth glint reflection, and a location of the light emitter corresponding to said fourth glint reflection; and determining a region of convergence of the third plane and the fourth plane, the region of convergence extending along the second direction.

Example 45: The display system of any of examples 42-44, wherein said processing electronics is configured to estimate a location of said center of corneal curvature of the user's eye based on said first and second directions toward the center of the corneal curvature of the user's eye.

Example 46: The display system of any of examples 42-45, wherein said processing electronics is configured to: determine said first direction along which the center of corneal curvature of the user's eye is estimated to be located based on at least one first image received from the first eye tracking camera; and determine said second direction along which the center of corneal curvature of the user's eye is estimated to be located based on at least one second image received from the second eye tracking camera, said first and second directions converging toward a region.

Example 47: The display system of any of examples 42-46, wherein said processing electronics is configured to: obtain an estimate of a center of corneal curvature of the user's eye based on the convergence of the first and second directions.

Example 48: The display system of any of examples 41-47, wherein said processing electronics is configured to estimate a location of said center of corneal curvature of the user's eye by identifying a region of convergence of first and second directions toward the center of the corneal curvature of the user's eye.

Example 49: The display system of any of examples 41-48, wherein said processing electronics is configured to obtain an estimate of a center of rotation of the user's eye based on multiple determinations of the center of corneal curvature of the user's eye for different eye poses.

Example 50: The display system of any of examples above, wherein said processing electronics is configured to obtain an estimate of the orientation of an aspheric surface for application of the aspheric model using the center of corneal curvature.

Example 51: The display system of any of examples 41-50, wherein said processing electronics is configured to obtain an estimate of the orientation of an aspheric surface for application of the aspheric model based on an estimate of a center of corneal curvature and an estimate of the convergence of multiple vectors that pass through centers of the pupil determined from images obtained by the first and second eye tracking cameras.

Example 52: The display system of example 51, wherein said processing electronics is configured to obtain an estimate of the position of an aspheric surface for application of the aspheric model having a center along a line that includes said center of corneal curvature and an estimate of the convergence of multiple vectors that pass through centers of the pupil.

Example 53: The display system of example 51 or 52, wherein said processing electronics is configured to use triangulation to determine the position of said aspheric surface.

Example 54: The display system of any of the examples above, wherein said display is configured to project light into said user's eye to display virtual image content to the user's vision field such that the displayed virtual image content appears to originate from different depths.

Example 55: The display system of any of the examples above, wherein said display is configured to project light into said user's eye to display virtual image content to the user's vision field at different amounts of at least one of divergence such that the displayed virtual image content appears to originate from different depths.

Example 56: The display system of any of the examples above, wherein said display is configured to project light into said user's eye that divergences and to project light into said user's eye that is collimated to display virtual image content to the user's vision field that appears to originate from different depths.

Example 57: A method of determining one or more parameters associated with an eye for rendering virtual image content in a display system configured to project light to an eye of a user to display the virtual image content in a vision field of said user, said eye having a cornea, said method comprising: with one or more eye tracking cameras configured to image the eye of the user and a plurality of light emitters disposed with respect to said eye to form glints thereon, capturing a plurality of images of the eye of the user, said images comprising a plurality of glints reflections of the different light emitters; and estimating a location of a center of curvature of said cornea of the user's eye based on the location of the glint reflections in said images produced by one or more eye tracking camera, wherein an aspheric model of said cornea is used in numerical calculations to estimate said location of said center of corneal curvature of the user's eye.

Example 58: The method of example 57, wherein both a spherical model and an aspherical model are used in determining a value of said center of curvature of said cornea.

Example 59: The method of example 57, wherein both a spherical model and an aspherical model are used in numerical calculations for determining a value of said center of curvature of said cornea.

Example 60: The method of any of examples 57-59, wherein said aspheric model is rotationally symmetric.

Example 61: The method of any of examples 57-60, wherein said aspheric model comprises a spheroid.

Example 62: The method of any of examples 57-59, wherein said aspheric model is non-rotationally symmetric.

Example 63: The method of any of examples 57-59 or 62, wherein said aspheric model has a different curvature along two orthogonal cross-sections.

Example 64: The method of any of examples 57-59 or 62, wherein said aspheric model has a first curvature along a horizontal direction and a second curvature along a vertical direction, said second curvature different than said first curvature; and the aspheric model is not rotationally symmetric.

Example 65: The method of any of examples 57-59 or 62-64, wherein said aspheric model comprises an ellipsoid.

Example 66: The method of any of examples 57-59 or 62-64, wherein said aspheric model comprises a prolate ellipsoid.

Example 67: The method of any of examples 56-66, wherein said estimating said location of said center of curvature of said cornea comprises estimating a location of a center of curvature of said cornea of the user's eye based on the location of the glint reflections in said images produced by said one or more eye tracking camera and based on the location of one or more tracking cameras and the locations of the emitters that produced said respective glint reflections.

Example 68: The display system of examples 56-66, wherein said processing electronics are configured to use a comparison between two centers of curvatures of spherical surfaces to determine an updated center of curvature of an aspheric surface.

Example 69: The display system of any of examples 1-56, wherein said electronic processor is configured to estimate a location of a center of curvature of said cornea of the user's eye based on the location of the glint reflections in said images produced by said one or more eye tracking camera and based on the location of one or more tracking cameras and the locations of the emitters that produced said respective glint reflections.

Example 70: The method of any of examples 41-64, wherein said electronic processor is configured to estimate a location of a center of curvature of said cornea of the user's eye based on the location of the glint reflections in said images produced by said one or more eye tracking camera and based on the location of one or more tracking cameras and the locations of the emitters that produced said respective glint reflections.

Part-E

Example 1: A display system configured to project light to an eye of a user to display virtual image content in a vision field of said user, said eye having a cornea and a pupil, said display system comprising: a frame configured to be supported on a head of the user; a head-mounted display disposed on the frame, said display configured to project light into said user's eye to display virtual image content to the user's vision field; one or more eye tracking cameras configured to image the user's eye; a plurality of light emitters; and processing electronics in communication with the display and the one or more eye tracking cameras, the processing electronics configured to: receive images of the user's eye captured by the one or more eye tracking cameras, glint reflections of the different light emitters observable in said images of the eye captured by the one or more tracking cameras; and estimate a location of a corneal center of the user's eye based at least in part on the location of the glint reflections in said images produced by said one or more eye tracking camera, wherein said processing electronics uses an aspheric model of said cornea in numerical calculations to estimate said location of said corneal center of the user's eye.

Example 2: The display system of example 1, wherein said processing electronics additionally employs a spherical model of said cornea in numerical calculations to estimate a value of said corneal center.

Example 3: The display system of examples 2, wherein said spherical model of said cornea is used in numerical calculations to determine a value of said corneal center based on the location of the glint reflections in said images produced by one or more eye tracking camera and on the location of one or more tracking cameras and the locations of the emitters that produced said respective glint reflections.

Example 4: The display system of examples 2 or 3, wherein said estimate of said corneal center determined from a spherical model of said cornea is applied to said aspheric model in numerical calculations to determine a value of said corneal center.

Example 5: The display system of any of the examples above, wherein said processing electronics is configured to determine an estimate of said corneal center using an iterative process.

Example 6: The display system of any of the examples above, wherein said processing electronics is configured to determine an estimate of said corneal center using an iterative process including repeatedly evaluating said estimate of the corneal center and using said estimate to recalculate another different estimate of said corneal center using said aspheric model.

Example 7: The display system of any of the examples above, wherein said processing electronics is configured to determine an estimate of said corneal center using an iterative process repeatedly evaluating said estimate of the corneal center and using said estimate to recalculate another different estimate of said corneal center using said spherical model and said aspheric model.

Example 8: The display system of examples 2 or 3, wherein said estimate of said corneal center determined from a spherical model of said cornea is used to estimate a corneal center of an aspheric surface for application of said aspheric model in numerical calculations to determine a value of said corneal center.

Example 9: The display system of examples 2, 3 or 8, wherein said estimate of said corneal center determined from a spherical model of said cornea is used to estimate an orientation of an aspheric surface for application of said aspheric model in numerical calculations to determine a value of said corneal center.

Example 10: The display system of examples 1-9, wherein a center of rotation of said eye or a center of pupil for said eye is estimated and used to estimate an orientation of an aspheric surface for application of said aspheric model in numerical calculations to determine a value of said corneal center.

Example 11: The display system of any of the examples above, wherein said aspheric model is used to predict the location of a plurality of glints based on locations of light emitters.

Example 12: The display system of examples 2, 3, or 8-10, wherein said aspheric model is used to predict the location of a plurality of glints based on locations of light emitters.

Example 13: The display system of example 12, wherein said location of said glints predicted based on said aspheric model are used to determine a center of curvature of a spherical surface.

Example 14: The display system of example 13, wherein said processing electronics are configured to determine a center of curvature of a spherical surface based on said location of said glints predicted based on said aspheric model.

Example 15: The display system of example 14, wherein said processing electronics are configured to compare said center of curvature of said spherical surface determined based on said location of said glints predicted based on said aspheric model with said center of curvature determined using said spherical model that was used to determine the center of said aspheric surface.

Example 16: The display system of any of the examples above, wherein said processing electronics are configured to use a comparison between two centers of curvatures for two spherical surfaces to determine an updated center of said aspherical surface.

Example 17: The display system of any of the examples above, wherein said processing electronics are configured to use a comparison between two centers of curvatures of two spherical surfaces obtained from application of the spherical model, one of said spherical surfaces determined based on an aspherical model, to determine an updated center of said aspherical surface.

Example 18: The display system of example 15, wherein said processing electronics are configured to use said comparison to determine a updated center of said aspheric surface.

Example 19: The display system of any of the examples above, wherein said processing electronics are configured to use a spherical model to determine one or more parameters of an aspheric surface.

Example 20: The display system of any of the examples above, wherein said processing electronics are configured to use an aspherical model to determine one or more parameters of a spherical surface.

Example 21: The display system of any of the examples above, wherein said processing electronics are configured to use an aspherical model to determine one or more parameters of a spherical surface to determine one or more parameters of an aspherical surface.

Example 22: The display system of any of the examples above, wherein said processing electronics are configured to use said updated center of said aspherical surface for application of said aspherical model to further update said center of said aspherical surface.

Example 23: The display system of any of the examples above, wherein said processing electronics are configured to use said updated center of said aspherical surface for application of the aspherical model to determine one or more parameters of a spherical surface.

Example 24: The display system of any of the examples above, wherein said processing electronics are configured to use said updated center of said aspherical surface to determine one or more parameters of a spherical surface for application of a spherical model to further update the center of said aspherical surface.

Example 25: The display system of any of the examples above, wherein said processing electronics are configured to use a comparison of one or more parameters of a spherical surface determined based on said updated aspherical surface with one or more parameters of another spherical surface to update one or more parameters of said aspherical surface.

Example 26: The display system of any of the examples above, wherein said aspheric model comprises an aspheric surface that is rotationally symmetric.

Example 27: The display system of any of the examples above, wherein said aspheric model comprises a spheroid.

Example 28: The display system of any of the examples above, wherein an equation representing a spheroid is used in numerical calculations for determining a value of said corneal center of said cornea.

Example 29: The display system of any of examples 1-25, wherein said aspheric model comprises a surface that is non-rotationally symmetric.

Example 30: The display system of any of examples 1-25 or 29, wherein said aspheric model comprises a surface that has a different curvature along two orthogonal cross-sections.

Example 31: The display system of any of examples 1-25, 29 or 30, wherein said aspheric model has a first curvature along a horizontal direction and a second curvature along a vertical direction, said second curvature different than said first curvature; and the aspheric model is not rotationally symmetric.

Example 32: The display system of any of examples 1-25 or 29-31, wherein said aspheric model comprises an ellipsoid.

Example 33: The display system of any of examples 1-25 or 29-32, wherein said aspheric model comprises a prolate ellipsoid.

Example 34: The display system of any of the examples above, wherein an equation representing an aspheric surface is used in said numerical calculations for determining a value of said corneal center of said cornea.

Example 35: The display system of example 34, wherein said equation includes three variables defining position on said aspheric surface and two constants determining the shape of the aspheric surface.

Example 36: The display system of example 34 or 35, wherein said equation is the same or equivalent to $X+Y+(1+Q)Z=2ZR$, where X, Y, and Z define position on said aspheric surface and Q and R determine the shape of the aspheric surface.

Example 37: The display system of any of examples 34, wherein said equation includes three variables defining position on said aspheric surface and three constants determining the shape of the aspheric surface.

Example 38: The display system of any of examples 1-34 and 37, wherein an equation representing an ellipsoid surface is used in numerical calculations for determining a value of said corneal center of said cornea.

Example 39: The display system of any of examples 1-33 and 37, wherein an equation representing a prolate ellipsoid surface is used in numerical calculations for determining a value of said corneal center of said cornea.

Example 40: The display system of any of the examples above, wherein an equation representing a spherical surface and an equation representing an aspheric surface is used in numerical calculations for determining a value of said corneal center of said cornea.

Example 41: The display system of any of the examples above, wherein said one or more eye tracking cameras configured to image the user's eye comprises first and second eye tracking cameras.

Example 42: The display system of example 41, wherein said processing electronics is configured to: based on the location of the glint reflections in one or more images produced by said first eye tracking camera and based on the location of the first eye tracking camera and the location of the emitters that produced said glint reflections, determine a first direction toward the center of corneal curvature of the user's eye; and based on the location of the glint reflections in one or more images produced by said second eye tracking camera and based on the location of the second eye tracking camera and the location of the emitters that produced said glint reflections, determine a second direction toward the corneal center of the user's eye.

Example 43: The display system of example 42, wherein said processing electronics is configured to determine the first direction by: defining a first plane that includes the first eye tracking camera, a location of a first glint reflection and a location of the light emitter corresponding to said first glint reflection; defining a second plane that includes the first eye tracking camera, a location of a second glint reflection and a location of the light emitter corresponding to said second glint reflection; and determining a region of convergence of the first plane and the second plane, the region of convergence extending along the first direction.

Example 44: The display system of example 43, said processing electronics are configured to determine the second direction by: defining a third plane that includes the second eye tracking camera, the location of a third glint reflection, and a location of the light emitter corresponding to said third glint reflection; defining a fourth plane that includes the second eye tracking camera, the location of a fourth glint reflection, and a location of the light emitter corresponding to said fourth glint reflection; and determining a region of convergence of the third plane and the fourth plane, the region of convergence extending along the second direction.

Example 45: The display system of any of examples 42-44, wherein said processing electronics is configured to estimate a location of said corneal center of the user's eye based on said first and second directions toward the corneal center of the user's eye.

Example 46: The display system of any of examples 42-45, wherein said processing electronics is configured to: determine said first direction along which the corneal center of the user's eye is estimated to be located based on at least one first image received from the first eye tracking camera; and determine said second direction along which the corneal center of the user's eye is estimated to be located based on at least one second image received from the second eye tracking camera, said first and second directions converging toward a region.

Example 47: The display system of any of examples 42-46, wherein said processing electronics is configured to: obtain an estimate of a corneal center of the user's eye based on the convergence of the first and second directions.

Example 48: The display system of any of examples 41-47, wherein said processing electronics is configured to estimate a location of said corneal center of the user's eye by identifying a region of convergence of first and second directions toward the corneal center of the user's eye.

Example 49: The display system of any of examples 41-48, wherein said processing electronics is configured to obtain an estimate of a corneal center of the user's eye based on multiple determinations of the corneal center of the user's eye for different eye poses.

Example 50: The display system of any of examples above, wherein said processing electronics is configured to obtain an estimate of the orientation of an aspheric surface for application of the aspheric model using the corneal center.

Example 51: The display system of any of examples 41-50, wherein said processing electronics is configured to obtain an estimate of the orientation of an aspheric surface for application of the aspheric model based on an estimate of a corneal center and an estimate of the convergence of multiple vectors that pass through centers of the pupil determined from images obtained by the first and second eye tracking cameras.

Example 52: The display system of example 51, wherein said processing electronics is configured to obtain an estimate of the position of an aspheric surface for application of the aspheric model having a center along a line that includes said corneal center and an estimate of the convergence of multiple vectors that pass through centers of the pupil.

Example 53: The display system of example 51 or 52, wherein said processing electronics is configured to use triangulation to determine the position of said aspheric surface.

Example 54: The display system of any of the examples above, wherein said display is configured to project light into said user's eye to display virtual image content to the user's vision field such that the displayed virtual image content appears to originate from different depths.

Example 55: The display system of any of the examples above, wherein said display is configured to project light into said user's eye to display virtual image content to the user's vision field at different amounts of at least one of divergence such that the displayed virtual image content appears to originate from different depths.

Example 56: The display system of any of the examples above, wherein said display is configured to project light into said user's eye that divergences and to project light into said user's eye that is collimated to display virtual image content to the user's vision field that appears to originate from different depths.

Example 57: A method of determining one or more parameters associated with an eye for rendering virtual image content in a display system configured to project light to an eye of a user to display the virtual image content in a vision field of said user, said eye having a cornea, said method comprising: with one or more eye tracking cameras configured to image the eye of the user and a plurality of light emitters disposed with respect to said eye to form glints thereon, capturing a plurality of images of the eye of the user, said images comprising a plurality of glints reflections of the different light emitters; and estimating a location of a corneal center of the user's eye based on the location of the glint reflections in said images produced by one or more eye tracking camera, wherein an aspheric model of said cornea is used in numerical calculations to estimate said location of said corneal center of the user's eye.

Example 58: The method of example 57, wherein both a spherical model and an aspherical model are used in determining a value of said corneal center.

Example 59: The method of example 57, wherein both a spherical model and an aspherical model are used in numerical calculations for determining a value of said corneal center.

Example 60: The method of any of examples 57-59, wherein said aspheric model is rotationally symmetric.

Example 61: The method of any of examples 57-60, wherein said aspheric model comprises a spheroid.

Example 62: The method of any of examples 57-59, wherein said aspheric model is non-rotationally symmetric.

Example 63: The method of any of examples 57-59 or 62, wherein said aspheric model has a different curvature along two orthogonal cross-sections.

Example 64: The method of any of examples 57-59 or 62, wherein said aspheric model has a first curvature along a horizontal direction and a second curvature along a vertical direction, said second curvature different than said first curvature; and the aspheric model is not rotationally symmetric.

Example 65: The method of any of examples 57-59 or 62-64, wherein said aspheric model comprises an ellipsoid.

Example 66: The method of any of examples 57-59 or 62-64, wherein said aspheric model comprises a prolate ellipsoid.

Example 67: The method of any of examples 56-66, wherein said estimating said location of said corneal center comprises estimating a location of a corneal center of the user's eye based on the location of the glint reflections in said images produced by said one or more eye tracking camera and based on the location of one or more tracking cameras and the locations of the emitters that produced said respective glint reflections.

Example 68: The display system of examples 56-66, wherein said processing electronics are configured to use a comparison between two centers of curvatures of spherical surfaces to determine an updated center of an aspheric surface.

Example 69: The display system of any of examples 1-56, wherein said electronic processor is configured to estimate a location of a corneal center of said cornea of the user's eye based on the location of the glint reflections in said images produced by said one or more eye tracking camera and based on the location of one or more tracking cameras and the locations of the emitters that produced said respective glint reflections.

Example 70: The method of any of examples 41-64, wherein said electronic processor is configured to estimate a location of a corneal center of the user's eye based on the location of the glint reflections in said images produced by said one or more eye tracking camera and based on the location of one or more tracking cameras and the locations of the emitters that produced said respective glint reflections.

Example 71: The display system of any of the examples above, wherein said processing electronics is further configured to update a parameter affecting the shape of said aspheric model based on at least one iteration.

Example 72: The display system of any of the examples above, wherein said processing electronics is further configured to update a constant characterizing the shape of said aspheric model based on at least one iteration.

Example 73: The display system of any of the examples above, wherein said processing electronics is further configured to update a constant characterizing the shape of an aspheric spheroidal model based on at least one iteration.

Example 74: The display system of any of the examples above, wherein said processing electronics is further configured to update a value of, Q, characterizing the shape of an aspheric spheroidal model based on at least one iteration.

Example 75: The display system of any of the examples above, wherein said processing electronics is further configured to update a parameter affecting the shape of said aspheric model over multiple iterations.

Example 76: The display system of any of the examples above, wherein said processing electronics is further configured to update a constant characterizing the shape of said aspheric model over multiple iterations.

Example 77: The display system of any of the examples above, wherein said processing electronics is further configured to update a constant characterizing the shape of an aspheric spheroidal model over multiple iterations.

Example 78: The display system of any of the examples above, wherein said processing electronics is further configured to update a value of, Q, characterizing the shape of an aspheric spheroidal model over multiple iterations.

Example 79: The display system of any of the examples above, wherein said processing electronics is further configured to update said value, constant, or parameter by determining a value, constant, or parameter that reduces variation, uncertainty, or error in calculated values of the center of rotation.

Example 80: The display system of any of the examples above, wherein said processing electronics is further configured to update said value, constant, or parameter by determining a value, constant, or parameter that reduces variation, uncertainty, or error in calculated values of the center of rotation for different eye gazes.

Example 81: The display system of any of the examples above, wherein said processing electronics is further configured to update said value, constant, or parameter by determining a value, constant, or parameter that reduces variation, uncertainty, or error in calculated values of the center of rotation for different eye gazes during a calibration process.

Example 82: The display system of any of the examples above, wherein said processing electronics is further configured to update said value, constant, or parameter by determining a value, constant, or parameter that reduces variation, uncertainty, or error in calculated values of the center of rotation for different eye gazes during a calibration process where fixation targets are provided to the viewer on said display to alter the gaze of the user.

Example 83: The display system of any of the examples above, wherein said processing electronics is further configured to use said value, constant, or parameter affecting the shape of said aspheric model until an additional calibration is performed.

Example 84: The display system of any of the examples above, wherein said processing electronics is further configured to use said value, constant, or parameter affecting the shape of said aspheric model until an additional calibration is performed for determining a parameter of the user's eye.

Example 85: The display system of any of the examples above, wherein said processing electronics is further configured to use said value, constant, or parameter affecting the shape of said aspheric model until an additional calibration is performed for determining a corneal center of the user's eye.

Example 86: The display system of any of the examples above, wherein said processing electronics is further configured use said value, constant, or parameter affecting the shape of said aspheric model until an additional calibration is performed for determining a corneal center of the user's eye.

Example 87: The display system of any of the examples above, wherein said processing electronics is further configured use said value, constant, or parameter affecting the shape of said aspheric model until an additional calibration is performed for determining a center of rotation of the user's eye.

Example 88: The display system of any of the examples above, wherein said at least one eye tracking camera comprises first, second and third eye tracking cameras configured to image the user's eye, said processing electronics in communication with said first, second and third eye tracking camera, glint reflections of light emitters observable in the images of the eye captured by the first, second and third eye tracking camera.

Example 89: The display system of any of the examples above, wherein said processing electronics is configured to estimate said corneal center of the user's eye based on the location of the glint reflections in said images produced by said first, second and third eye tracking cameras.

Example 90: The display system of any of the examples above, wherein said processing electronics is configured to estimate said corneal center of the user's eye based on the location of the glint reflections in said images produced by said first, second, and third eye tracking cameras and based on the location of said first, second, and third eye tracking cameras and the locations of the emitters that produced said respective glint reflections.

Example 91: The display system of any of the examples above, wherein said processing electronics is configured to estimate said corneal center of the user's eye based on a parameter of the user's eye determined by said first and third eye tracking cameras and a parameter of the user's eye determined by said first and second eye tracking cameras.

Example 92: The display system of any of the examples above, wherein said processing electronics is configured to estimate said corneal center of the user's eye based on a parameter of the user's eye determined by said second and third eye tracking cameras and a parameter of the user's eye determined by said first and second eye tracking cameras.

Example 93: The display system of any of the examples above, wherein said processing electronics is configured to estimate said corneal center of the user's eye based on an average of a parameter of the user's eye determined by said first and third eye tracking cameras and a parameter of the user's eye determined by said first and second eye tracking cameras.

Example 94: The display system of any of the examples above, wherein said processing electronics is configured to estimate said corneal center of the user's eye based on an average of a parameter of the user's eye determined by said second and third eye tracking camera and a parameter of the user's eye determined by said first and second eye tracking cameras.

Example 95: The display system of any of the examples above, wherein said corneal center of the user's eye comprises a center of curvature of the cornea of the user's eye.

Example 96: The display system of any of the examples above, wherein said corneal center of the user's eye comprises a center of curvature of the corneal apex of the cornea of the user's eye.

Example 97: The display system of any of the examples above, wherein said processing electronics is further configured to determine a user specific value of a parameter affecting the shape of said aspheric model using a plurality of images of the user's eye captured by the one or more eye tracking cameras.

Example 98: The display system of example 97, wherein said user specific value of the parameter is associated with said user's eye.

Example 99: The display system of example 97, wherein different images of said plurality of images of the user's eye are captured at different gaze directions associated with respective target locations, wherein the target location is determined by the display system and wherein the target location is different for different images of said plurality of images of the user's eye.

Example 100: The display system of example 97, wherein different pairs of images of said plurality of images of the user's eye is captured at different gaze directions associated with respective target locations, wherein the target location is determined by the display system and wherein the target location is different for different pair of images of said plurality of images of the user's eye.

Example 101: The display system of any of the examples 99 or 100, wherein processing electronics determines said user specific value of said parameter affecting the shape of said aspheric model based on an iterative process wherein an iteration comprises: estimating a plurality of center of rotations of the user's eye based at least in part on a value of the parameter affecting the shape of said aspheric model; calculating a value of a statistical metric associated with the estimated plurality of the plurality of center of rotations the user's eye; generating a modified value of said parameter affecting the shape of said aspheric model based at least in part on the calculated statistical metric.

Example 102: The display system of example 101, wherein the value of the parameter affecting the shape of said aspheric model is the modified value of said parameter affecting the shape of said aspheric model based generated in a previous iteration.

Example 103: The display system of example 101, wherein the value of the parameter affecting the shape of said aspheric model used in the first iteration of the iterative process is an initial value determined by an eye model.

Example 104: The display system of example 103, wherein the eye model is the Arizona eye model and the initial value of the parameter affecting the shape of said aspheric model is −0.26.

Example 105: The display system of example 101, wherein the modified value of said parameter affecting the shape of said aspheric model reduces the value of the statistical metric.

Example 106: The display system of example 105, wherein the statistical metric comprises a variation of a statistical distribution of the plurality of center of rotations.

Example 107: The display system of example 106, wherein the statistical metric comprises a variance or standard deviation.

Example 108: The display system of example 101, wherein the plurality of center of rotations of the user's eye are estimated based at least in part on said aspheric model, the location of one or more tracking cameras and the locations of the emitters that produced said respective glint reflections.

Example 109: The display system of any of the examples above, wherein said processing electronics is further configured to change a parameter affecting the shape of said aspheric model.

Example 110: The display system of any of the examples above, wherein said processing electronics is further configured to change a constant characterizing the shape of said aspheric model.

Example 111: The display system of any of the examples above, wherein said processing electronics is further configured to change a constant characterizing the shape of an aspheric spheroidal model.

Example 112: The display system of any of the examples above, wherein said processing electronics is further configured to change a value of, Q, characterizing the shape of an aspheric spheroidal model.

Example 113: The display system of any of the examples above, wherein said processing electronics is further configured to select said value, constant, or parameter by determining a value, constant, or parameter that reduces variation, uncertainty, or error in calculated values of the center of rotation.

Example 114: The display system of any of the examples above, wherein said processing electronics is further configured to select said value, constant, or parameter by determining a value, constant, or parameter that reduces variation, uncertainty, or error in calculated values of the center of rotation for different eye gazes.

Example 115: The display system of any of the examples above, wherein said processing electronics is further configured to select said value, constant, or parameter by determining a value, constant, or parameter that reduces variation, uncertainty, or error in calculated values of the center of rotation for different eye gazes during a calibration process.

Example 116: The display system of any of the examples above, wherein said processing electronics is further configured to select said value, constant, or parameter by determining a value, constant, or parameter that reduces variation, uncertainty, or error in calculated values of the center of rotation for different eye gazes during a calibration process where fixation targets are provided to the viewer on said display to alter the gaze of the user.

Any of the above Examples or Additional Examples can be combined. Additionally, any of the above Examples or Additional Examples can be integrated with a head mounted display. In addition, any of the above Examples or Additional Examples can be implemented with a single depth plane and/or with one or more variable depth planes (e.g., one or more elements with variable focusing power that provide accommodation cues that vary over time).

Furthermore, apparatus and methods for determining a variety of values, parameters, etc., such as, but not limited to, anatomical, optical, and geometric features, locations, and orientations, etc., are disclosed herein. Examples of such parameters include, for example, the center of rotation of the eye, the center of curvature of the cornea, the center of the pupil, the boundary of the pupil, the center of the iris, the boundary of the iris, the boundary of the limbus, the optical axis of the eye, the visual axis of the eye, the center of perspective, but are not limited to these. Determinations of such values, parameters, etc., as recited herein include estimations thereof and need not necessarily coincide precisely with the actual values. For example, determinations of the center of rotation of the eye, the center of curvature of the cornea, the center or boundary of the pupil or iris, the boundary of the limbus, the optical axis of the eye, the visual axis of the eye, the center of perspective, etc., may be estimations, approximations, or values close to, but not the same as, the actual (e.g., anatomical, optical, or geometric) values or parameters. In some cases, for example, root mean square estimation techniques may be used to obtain estimates of such values. As an example, certain techniques described herein relate to identifying a location or point at which rays or vectors intersect. Such rays or vectors, however, may not intersect. In this example, the location or point may be estimated. For example, the location or point may be determined based on root mean square, or other, estimation techniques (e.g., the location or point may be estimated to be close to or the closest to the rays or vectors). Other processes may also be used to estimate, approximate or otherwise provide a value that may not coincide with the actual value. Accordingly, the term determining and estimating, or determined and estimated, are used interchangeably herein. Reference to such determined values may therefore include estimates, approximations, or values close to the actual value. Accordingly, reference to determining a parameter or value above, or elsewhere herein should not be limited precisely to the actual value but may include estimations, approximations or values close thereto.

What is claimed is:

1. A display system configured to project light to an eye of a user to display virtual image content in a vision field of said user, said eye having a cornea and a pupil, said display system comprising:
   a frame configured to be supported on a head of the user;
   a head-mounted display disposed on the frame, said display configured to project light into said user's eye to display virtual image content to the user's vision field;
   one or more eye tracking cameras configured to image the user's eye;
   a plurality of light emitters; and
   processing electronics in communication with the display and the one or more eye tracking cameras, the processing electronics configured to:
      receive images of the user's eye captured by the one or more eye tracking cameras, wherein glint reflections of the different light emitters are observable in said images of the eye captured by the one or more eye tracking cameras; and
      estimate a location of a corneal center of the user's eye based at least in part on the locations of the glint reflections in said images captured by said one or more eye tracking camera,
      wherein said processing electronics employ an aspheric model of said cornea in numerical calculations to estimate said location of said corneal center of the user's eye, and wherein said aspheric model comprises an aspheric surface that is rotationally symmetric.

2. The display system of claim 1, wherein said processing electronics additionally employ a spherical model of said cornea in numerical calculations to estimate said location of said corneal center.

3. The display system of claim 2, wherein said spherical model of said cornea is used in numerical calculations to determine a location of said corneal center based on the location of the glint reflections in said images produced by the one or more eye tracking cameras, and further based on the location of the one or more eye tracking cameras and the locations of the emitters that produced said respective glint reflections.

4. The display system of claim 2, wherein said estimate of said corneal center determined from the spherical model of said cornea is applied to said aspheric model in numerical calculations to determine the location of said corneal center.

5. The display system of claim 1, wherein said processing electronics are further configured to determine the estimate of said corneal center using an iterative process.

6. The display system of claim 1, wherein said aspheric model is used to predict the locations of the glint reflections based on locations of the light emitters.

7. The display system of claim 6, wherein said locations of said glint reflections predicted based on said aspheric model are used to determine a center of curvature of a spherical surface.

8. The display system of claim 1, wherein said processing electronics are configured to use a spherical model to determine one or more parameters of an aspheric surface.

9. The display system of claim 1, wherein said processing electronics are configured to use an aspherical model to determine one or more parameters of a spherical surface.

10. The display system of claim 1, wherein said aspheric model comprises a surface that is non-rotationally symmetric.

11. The display system of claim 1, wherein said one or more eye tracking cameras configured to image the user's eye comprise first and second eye tracking cameras.

12. The display system of claim 11, wherein said processing electronics are further configured to:
   based on the location of the glint reflections in one or more images produced by said first eye tracking camera and based on the location of the first eye tracking camera and the location of the emitters that produced said glint reflections, determine a first direction toward the center of corneal curvature of the user's eye; and
   based on the location of the glint reflections in one or more images produced by said second eye tracking camera and based on the location of the second eye tracking camera and the location of the emitters that produced said glint reflections, determine a second direction toward the corneal center of the user's eye.

13. The display system of claim 12, wherein said processing electronics are further configured to estimate the location of said corneal center of the user's eye based on said first and second directions toward the corneal center of the user's eye.

14. The display system of claim 12, wherein said processing electronics are further configured to:
   obtain an estimate of a corneal center of the user's eye based on the convergence of the first and second directions.

15. The display system of claim 1, wherein said processing electronics are further configured to obtain an estimate of the corneal center of the user's eye based on multiple determinations of the corneal center of the user's eye for different eye poses.

16. The display system of claim 1, wherein said processing electronics are further configured to obtain an estimate of the orientation of an aspheric surface for application of the aspheric model using the corneal center.

17. The display system of claim 11, wherein said processing electronics are further configured to obtain an estimate of the orientation of an aspheric surface for application of the aspheric model based on an estimate of a corneal center and an estimate of a convergence of multiple vectors that pass through centers of the pupil determined from images obtained by the first and second eye tracking cameras.

18. The display system of claim 1, wherein said one or more eye tracking cameras comprise first, second and third eye tracking cameras configured to image the user's eye, wherein said processing electronics are in communication with said first, second and third eye tracking cameras, and wherein the glint reflections of the light emitters are observable in the images of the eye captured by the first, second and third eye tracking camera.

19. The display system of claim 18, wherein said processing electronics are further configured to estimate said corneal center of the user's eye based on a parameter of the user's eye determined by said first and third eye tracking cameras and a parameter of the user's eye determined by said first and second eye tracking cameras.

* * * * *